US011332499B2

(12) United States Patent
Haskell-Luevano et al.

(10) Patent No.: US 11,332,499 B2
(45) Date of Patent: May 17, 2022

(54) CYCLIC PEPTIDES AND METHODS OF USE THEREOF

(71) Applicant: Regents of the University of Minnesota, Minneapolis, MN (US)

(72) Inventors: Carrie Haskell-Luevano, Minneapolis, MN (US); Mark Ericson, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/542,006

(22) Filed: Aug. 15, 2019

(65) Prior Publication Data

US 2020/0115416 A1 Apr. 16, 2020

Related U.S. Application Data

(60) Provisional application No. 62/764,884, filed on Aug. 16, 2018.

(51) Int. Cl.
*C07K 7/64* (2006.01)
*A61P 3/04* (2006.01)
*A61K 38/00* (2006.01)

(52) U.S. Cl.
CPC .................. *C07K 7/64* (2013.01); *A61P 3/04* (2018.01); *A61K 38/00* (2013.01)

(58) Field of Classification Search
CPC .. C07K 7/64; C07K 14/47; A61P 3/04; A61K 38/00
See application file for complete search history.

(56) References Cited

U.S. PATENT DOCUMENTS 4,559,157 A 12/1985 Smith et al.
4,608,392 A 8/1986 Jacquet et al.
4,612,302 A 9/1986 Szabo et al.
4,684,620 A 8/1987 Hruby et al.
4,820,508 A 4/1989 Wortzman
4,853,371 A 8/1989 Coy et al.
4,938,949 A 7/1990 Borch et al.
4,992,478 A 2/1991 Geria
6,500,934 B1 12/2002 Lerner et al.
8,455,617 B2 6/2013 Dodd et al.
8,703,139 B2 4/2014 Hofbauer et al.
8,946,265 B2 2/2015 Zhang et al.
9,040,663 B2 5/2015 Dodd et al.
10,899,793 B2 1/2021 Haskell-Luevano et al.
10,954,268 B2 3/2021 Tartaglia et al.
2004/0224901 A1 11/2004 Chaturvedula et al.
2011/0009341 A1 1/2011 Sharma et al.
2017/0342107 A1 11/2017 Haskell-Luevano et al.
2018/0118789 A1 5/2018 Haskell-Luevano et al.
2018/0360972 A1 12/2018 Haskell-Luevano et al.
2019/0255142 A1 8/2019 Hruby et al.
2021/0179666 A1 6/2021 Haskell-Luevano et al.

FOREIGN PATENT DOCUMENTS

WO 2002018437 A2 3/2002
WO 2003006604 A2 1/2003
WO 2007123839 A2 11/2007
WO 2009061411 A2 5/2009
WO 2011153817 A1 12/2011
WO 2020131282 A1 6/2020
WO 2020257662 A1 12/2020

OTHER PUBLICATIONS

Betts et al. (Bioinformatics for Geneticists, 2003, chapter 14, Ed. Michael Barnes and Ian Gray, John Wiley & Sons, Ltd.) (Year: 2003).*
Feng et al (BioMol Concepts, 2016, 7(3), 179-187) (Year: 2016).*
Friedmann (Chemistry & Biodiversity, 2010, 7, 1491-1530) (Year: 2010).*
Sela et al (The FASEB Journal, May 1997, 11,449-456) (Year: 1997).*
Handl, H L , et al., "Synthesis and Evaluation of Bivalent NDP-α-MSH(7) Peptide Ligands for Binding to the Human Melanocortin Receptor 4 (hMC4R)", Bioconjug Chem 18(4), 1101-1109 (2007).
Hano, K , et al., "Evaluation of the physiological properties of d-histidyl-d-phenylalanyl-d-arginyl-d-tryptophyl-glycine in frog melanocyte", Biochimica et Biophysica Acta 9BBA)—General Subjects 90(1), 201-204 (1964).
Haskell-Luevano, C , et al., "Characterization of Melanocortin NDP-MSH Agonist Peptide Fragments at the Mouse Central and Peripheral Melanocortin Receptors ", J Med Chem 44(13), 2247-2252 (2001).
Haskell-Luevano, C , et al., "Characterization of the Neuroanatomical Distribution of Agouti-Related Protein Immunoreactivity in the Rhesus Monkey and the Rat.", Endocrinology 140, 1408-1415 (1999).

(Continued)

*Primary Examiner* — Sudhakar Katakam
(74) *Attorney, Agent, or Firm* — Viksnins Harris Padys Malen LLP

(57) ABSTRACT

Certain embodiments of the invention provide a cyclic compound of formula I:

$$\underbrace{\text{Pro-X}^1\text{-X}^2\text{-X}^3\text{-X}^4\text{-X}^5\text{-X}^6\text{-DPro}} \qquad \text{I}$$

wherein: Pro is a residue of L-proline; $X^1$ is a residue of Arg or DArg; $X^2$ is a residue of Phe or DPhe; $X^3$ is a residue of Phe, DPhe or hPhe; $X^4$ is a residue of a natural or unnatural amino acid; $X^5$ is a residue of Ala, Asp, Glu, Lys, His, Phe, Ser, Leu or Gly; $X^6$ is a residue of Phe, Ala, Gly, Ser, Lys, Asp, Leu, Nle, Trp, Tyr, Cha or hPhe; and DPro is a residue of D-proline; or a salt thereof. Certain embodiments also provide compositions comprising such compounds, as well as methods of using such compounds and compositions.

21 Claims, 28 Drawing Sheets

Specification includes a Sequence Listing.

(56) References Cited

OTHER PUBLICATIONS

Haskell-Luevano, C , et al., "Discovery of Prototype Peptidomimetic Agonists at the Human Melanocortin Receptors MC1R and MC4R ", J Med Chem 40(14), 2133-2139 (1997).
Haskell-Luevano, C , et al., "Structure Activity Studies of the Melanocortin-4 Receptor by in Vitro Mutagenesis: Identification of Agouti-Related Protein (AGRP), Melanocortin Agonist and Synthetic Peptide Antagonist Interaction Determinants", Biochemistry 40(20), 6164-6179 (2001).
Haskell-Luevano, C , et al., "Truncation studies of alpha-melanotropin peptides identify tripeptide analogues exhibiting prolonged agonist bioactivity.". Peptides 17(6), 995-1002 (1996).
Haslach, E M , et al., "Identification of Tetrapeptides from a Mixture Based Positional Scanning Library That Can Restore nM Full Agonist Function of the L106P, I69T, I102S, A219V, C271Y, and C271R Human Melanocortin-4 Polymorphic Receptors (hMC4Rs)", J. Med. Chem. 57(11), 4615-4628 (2014).
Haynes, R C , et al., "Studies on the mechanism of action of the adrenocorticotropic hormone ", J Biol Chem 225, 115-124 (1957).
Haynes, RC Jr., "The activation of adrenal phosphorylase by the adrenocorticotropic hormone", J. Biol. Chem 233 (5), 1220-1222 (1958).
Hess , et al., "Backbone cyclic peptidomimetic melanocortin-4 receptor agonist as a novel orally administrated drug lead for treating obesity", J Med Chem 51(4), 1026-1034 (2008).
Higgins, DG , et al., "CLUSTAL: a package for performing multiple sequence alignment on a microcomputer.", Gene 73(1), 237-244 (1988).
Higgins, D , et al., "Fast and sensitive multiple sequence alignments on a microcomputer.", CABIOS 5(2), 151-153 (1989).
Hiller, C , et al., "Class A G-Protein-Coupled Receptor (GPCR) Dimers and Bivalent Ligands ", J Med Chem 56, 6542-6559 (2013).
Hlavackova, V , et al., "Evidence for a single heptahelical domain being turned on upon activation of a dimeric GPCR.", EMBO J 24, 499-509 (2005).
Holder, J , et al., "Characterization of aliphatic, cyclic, and aromatic N-terminally "capped" His-d-Phe-Arg-Trp-NH2 tetrapeptides at the melanocortin receptors", European Journal fo Pharmacology 462, 41-52 (2003).
Holder, J , et al., "Design and pharmacology of peptoids and peptide-peptoid hybrids based on the melanocortin agonists core tetrapeptide sequence", Bioorg. Med. Chem. Lett. 13(24), 4505-4509 (2003).
Holder, J R , et al., "Structure-Activity Relationships of the Melanocortin Tetrapeptide Ac-His-DPhe-Arg-Trp-NH2 at the Mouse Melanocortin Receptors. 1. Modifications at the His Position", J. Med. Chem. 45(13), 2801-2810 (2002).
Holder, J R , et al., "Structure-Activity Relationships of the Melanocortin Tetrapeptide Ac-His-d-Phe-Arg-Trp-NH2 at the Mouse Melanocortin Receptors. 4. Modifications at the Trp Position", J. Med. Chem. 45(26), 5736-5744 (2002).
Holder, J , et al., "Structure-Activity Relationships of the Melanocortin Tetrapeptide Ac-His-DPhe-Arg-Trp-NH2 at the Mouse Melanocortin Receptors: Part 2 Modifications at the Phe Position ", J Med Chem 45(14), 3073-3081 (2002).
Holder, J , et al., "Structure-activity relationships of the melanocortin tetrapeptide Ac-His-DPhe-Arg-Trp-NH2 at the mouse melanocortin receptors. Part 3: modifications at the Arg position", Peptides 24(1), 73-82 (2003).
Houghten, R , "General method for the rapid solid-phase synthesis of large numbers of peptides: specificity of antigen-antibody interaction at the level of individual amino acids", Proc. Natl. Acad. Sci. U.S.A 82(15), 5131-5135 (1985).
Houghten, R , et al., "Mixture-Based Synthetic Combinatorial Libraries", J. Med. Chem. 42(19), 3743-3778 (1999).
Houghten, R , et al., "Simplified procedure for carrying out simultaneous multiple hydrogen fluoride cleavages of protected peptide resins", Int. J. Pept. Protein Res. 27(6), 673-678 (1986).
Houghten, R , et al., "Strategies for the Use of Mixture-Based Synthetic Combinatorial Libraries: Scaffold Ranking, Direct Testing In Vivo, and Enhanced Deconvolution by Computational Methods", J. Comb. Chem. 10(1), 3-19 (2008).
Hruby, V , et al., "Cyclic lactam .alpha.-melanotropin analogs of Ac-Nle4-cyclo[Asp5,D-Phe7,Lys10]-.alpha.-melanocyte-stimulating hormone-(4-10)-NH2 with bulky aromatic amino acids at position 7 show high antagonist potency and selectivity at specific melanocortin receptors", J. Med. Chem. 38(18), 3454-3461 (1995).
Hruby, V , et al., "α-Melanotropin: the minimal active sequence in the frog skin bioassay", J. Med. Chem. 30(11), 2126-2130 (1987).
Huang, X , et al., "Parallelization of a local similarity algorithm.", CABIOS 8(2), 155-165 (1992).
Hunter, W , et al., "Preparation of lodine-131 Labelled Human Growth Hormone of High Specific Activity", Nature 194(4827), 495-496 (1962).
Huszar, D , et al., "Targeted disruption of the melanocortin-4 receptor results in obesity in mice ", Cell 88(1), 131-141 (1997).
Iglesias, A , et al., "Serotonin-2A homodimers are needed for signalling via both phospholipase A2 and phospholipase C in transfected CHO cells ", Eur J Pharmacol 800, 63-69 (2017).
Irani, B , et al., "Implication of the melanocortin-3 receptor in the regulation of food intake.", Eur J Pharmacol 660(1), 80-87 (2011).
Irani, B , et al., "Progress in the development of melanocortin receptor selective ligands", Current Pharmaceutical Design 10(28), 3443-3479 (2004).
Jackson, P J , et al., "Chimeras of the agouti-related protein: Insights into agonist and antagonist selectivity of melanocortin receptors ", Peptides 26, 1978-1987 (2005).
Jackson, P J , et al., "Design, Pharmacology, and NMR Structure of a Minimized Cystine Knot with Agouti-Related Protein Activity ", Biochemistry 41, 7565-7572 (2002).
Jagadish, B , et al., "Squalene-derived Flexible Linkers for Bioactive Peptides.", Bioorg Med Chem Lett 17(12), 3310-3313 (2007).
Joppa, M A , et al., "Central administration of peptide and small molecule MC4 receptor antagonists induce hyperphagia in mice and attenuate cytokine-induced anorexia.", Peptides 26, 2294-2301 (2005).
Josan, J , et al., "Cell-Specific Targeting by Heterobivalent Ligands ", Bioconjugate Chem 22(7), 1270-1278 (2011).
Josan, J S , et al., "Solid-Phase Synthesis of Heterobivalent Ligands Targeted to Melanocortin and Cholecystokinin Receptors ", Int J Pept Res Ther 14, 293-300 (2008).
Joseph, C , et al., "Chimeric NDP-MSH and MTII melanocortin peptides with agouti-related protein (AGRP) Arg-Phe-Phe amino acids possess agonist melanocortin receptor activity ", Peptides 24(12), 1899-1908 (2003).
Joseph, C , et al., "Elongation studies of the human agouti-related protein (AGRP) core decapeptide (Yc [CRFFNAFC]Y) results in antagonism at the mouse melanocortin-3 receptor", Peptides 24, 263-270 (2003).
Joseph, C , et al., "Modified melanocortin tetrapeptide Ac-His-dPhe-Arg-Trp-NH at the arginine side chain with ureas and thioureas", J Pept Res 66(5), 297-307 (2005).
Joseph, C , et al., "Stereochemical Studies of the Monocyclic Agouti-Related Protein (103-122) Arg-Phe-Phe Residues: Conversion of a Melanocortin-4 Receptor Antagonist into an Agonist and Results in the Discovery of a Potent and Selective Melanocortin-1 Agonist", J. Med. Chern. 47(27), 6702-6710 (2004).
Joseph, C , et al., "γ2-Melanocyte stimulation hormone (γ2- MSH) truncation studies results in the cautionary note that γ2-MSH is not selective for the mouse MC3R over the mouse MC5R", Peptides 31 (12), 2304-2313 (2010).
Journe, A S , et al., "N1-linked melatonin dimers as bivalent ligands targeting dimeric melatonin receptors.", Medchemcomm 5, 792-796 (2014).
Kaiser, E , et al., "Color test for detection of free terminal amino groups in the solid-phase synthesis of peptides.", Anal Biochem 34(2), 595-598 (1970).
Karlin, S , et al., "Applications and statistics for multiple high-scoring segments in molecular sequences", Proc Natl Acad Sci 90, 5873-5877 (1993).
Karlin, S , et al., "Methods for assessing the statistical significance of molecular sequence features by using general scoring schemes", Proc Natl Acad Sci 87(6), 2264-2268 (1990).

(56) References Cited

OTHER PUBLICATIONS

Kavarana, M , et al., "Novel Cyclic Templates of α-MSH Give Highly Selective and Potent Antagonists/Agonists for Human Melanocortin-3/4 Receptors", J. Med. Chem. 45(12), 2644-2650 (2002).
Kiefer, L , et al., "Melanocortin Receptor Binding Determinants in the Agouti Protein", Biochemistry 37(4), 991-997 (1998).
Zhao, H , et al., "Drug Conjugates with Poly(Ethylene Glycol).", Drug Delivery in Oncology, 627-656 (2012).
Zheng, Y , et al., "Induced association of mu opioid (MOP) and type 2 cholecystokinin (CCK2) receptors by novel bivalent ligands", J Am Chem 52(2), 247-258 (2009).
Zylbergold, P , et al., "A division of labor: asymmetric roles for GPCR subunits in receptor dimers", Nat Chem Biol 5(9), 608-609 (2009).
Pinilla, C , et al., "Advances in the use of synthetic combinatorial chemistry: mixture-based libraries", Nat. Med. 9(1), 118-122 (2003).
Pinilla, C , et al., "Rapid identification of high affinity peptide ligands using positional scanning synthetic peptide combinatorial libraries", BioTechniques 13(6), 901-905 (1992).
Poggioli, R , et al., "ACTH-(1-24) and alpha-MSH antagonize feeding behavior stimulated by kappa opiate agonists ", Peptides 7, 843-848 (1986).
Portoghese, P , et al., "Heteromer Induction: An Approach to Unique Pharmacology?", ACS Chem Neurosci 8, 426-428 (2017).
Portoghese, P , et al., "Opioid Agonist and Antagonist Bivalent Ligands as Receptor Probes.", Life Sciences, 31 (12 & 13), 1283-1286 (1982).
Proneth, B , et al., "Melanocortin Tetrapeptide Ac-His-DPhe-Arg-Trp-NH2 Modified at the Para Position of the Benzyl Side Chain (DPhe): Importance for Mouse Melanocortin-3 Receptor Agonist versus Antagonist Activity", J. Med. Chem. 51(18), 5585-5593 (2008).
Prusis, P , et al., "Design of new small cyclic melanocortin receptor-binding peptides using molecular modelling: Role of the His residue in the melanocortin peptide core", Eur J Med Chem 36, 137-146 (2001).
Rask-Andersen, M , et al., "Trends in the exploitation of novel drug targets.", Nat Rev Drug Discov 10, 579-590 (2011).
Roselli-Rehfuss, L , et al., "Identification of a receptor for gamma melanotropin and other proopiomelanocortin peptides in the hypothalamus and limbic system.", Proc Natl Acad Sci USA 90(19), 8856-8860 (1993).
Russo, O , et al., "Synthesis of specific bivalent probes that functionally interact with 5-HT(4) receptor dimers.", J Med Chem 50(18), 4482-4492 (2007).
Santos, R , et al., "A comprehensive map of molecular drug targets.", Nat Rev Drug Discov 16, 19-34 (2017).
Santos, R , et al., "Use and Implications of the Harmonic Mean Model on Mixtures for Basic Research and Drug Discovery", ACS Comb. Sci. 13(3), 337-344 (2011).
Sartania, N , et al., "Agonist occupancy of a single monomeric element is sufficient to cause internalization of the dimeric β2-adrenoceptor.", Cell Signal 19, 1928-1938 (2007).
Sawyer, T , et al., "4—Norleucine, 7-D-phenylalanine-α-melanocyte-stimulating Hormone: A Highly Potent α-melanotropin with Ultralong Biological Activity ", Proc Natl Acad Sci USA 77(10), 5754-5758 (1980).
Schild, H O , "pA, A New Scale for the Measurement of Drug Antagonism", British Journal of Pharmacology 2(3), 189-206 (1947).
Schiöth, H , et al., "Major pharmacological distinction of the ACTH receptor from other melanocortin receptors", Life Sci. 59(10), 797-801 (1996).
Shinyama, H , et al., "Regulation of Melanocortin-4 Receptor Signaling: Agonist-Mediated Desensitization and Internalization ", Endocrinology 144, 1301-1314 (2003).
Singh, A , et al., "Incorporation of a Bioactive Reverse-Turn Heterocycle into a Peptide Template Using Solid-Phase Synthesis To Probe Melanocortin Receptor Selectivity and Ligand Conformations by 2D 1H NMR.", J Med Chem 54, 1379-1390 (2011).
Singh, A , et al., "Synthesis and pharmacology of α/β3-peptides based on the melanocortin agonist Ac-His-d Phe-Arg-Trp-NH2 sequence ", ACS Med Chem Lett 6(5), 568-572 (2015).
Smeester, BA , et al., "Targeting putative mu opioid/metabotropic glutamate receptor-5 heteromers produces potent antinociception in a chronic murine bone cancer model ", Eur J Pharmacol 743, 48-52 (2014).
Smith, N J , et al., "Allostery at G Protein-Coupled Receptor Homo- and Heteromers: Uncharted Pharmacological Landscapes.", Pharmacol Rev 62, 701-725 (2010).
Smith, T , et al., "Comparison of biosequences", Adv Appl Math 2(4), 482-489 (1981).
Smith, P E , "Experimental Ablation of the Hypophysis in the Frog Embryo", Science 44(1130), 280-282 (1916).
Stephenson, R P , "A Modification of Receptor Theory", Br J Pharmacol Chemother 11, 379-393 (1956).
Szalai, B , "Allosteric interactions within the AT1 angiotensin receptor homodimer: Role of the conserved DRY motif.", Biochem Pharmacol 84, 477-485 (2012).
Tabor, A , et al., "Visualization and ligand-induced modulation of dopamine receptor dimerization at the single molecule level.", Sci Rep 6, 33233 (2016).
Takeyasu, K , et al., "Experimental evidence and dynamic aspects of spare receptor.", Life Sci 25(20), 1761-1771 (1979).
Tala, S , et al., "Microwave-assisted solid-phase synthesis of side-chain to side-chain lactam-bridge cyclic peptides.", Bioorg Med Chem Lett 25(24), 5708-5711 (2015).
Tam, J , et al., "SN2 deprotection of synthetic peptides with a low concentration of HF in dimethyl sulfide: evidence and application in peptide synthesis", J Am. Chem. Soc 105(21), 6442-6455 (1983).
Tanner, J M , et al., "Fasting-induced reductions in cardiovascular and metabolic variables occur sooner in obese vs. lean mice ", Exp Biol Med (Maywood) 235(12), 1489-1497 (2010).
Teitler, M , et al., "A new approach for studying GPCR dimers: drug-induced inactivation and reactivation to reveal GPCR dimer function in vitro, in primary culture, and in vivo.", Pharmacol Ther 133, 205-217 (2012).
Todorovic, A , et al., "N-Terminal Fatty Acylated His-dPhe-Arg-Trp-NH2 Tetrapeptides: Influence of Fatty Acid Chain Length on Potency and Selectivity at the Mouse Melanocortin Receptors and Human Melanocytes", J. Med. Chem. 48(9), 3328-3336 (2005).
Todorovic, A , et al., "Synthesis and activity of the melanocortin Xaa-d-Phe-Arg-Trp-NH tetrapeptides with amide bond modifications", J Peptide Res 63, 270-278 (2004).
Topiol, S , "A Surprising Recipe for Designing Biased Ligands", J Med Chem 62, 141-143 (2019).
Tota, M R , et al., "Molecular Interaction of Agouti Protein and Agouti-Related Protein with Human Melanocortin Receptors ", Biochemistry 38(3), 897-904 (1999).
Uckert, S , et al., "Melanocortin receptor agonists in the treatment of male and female sexual dysfunctions: results from basic research and clinical studies ", Expert Opin Invest Drugs 23(11), 1477-1483 (2014).
Vagner, J , et al., "Novel targeting strategy based on multimeric ligands for drug delivery and molecular imaging: homooligomers of α-MSH.", Bioorg Med Chem Lett 14, 211-215 (2004).
Van Der Ploeg, L , et al., "A role for the melanocortin 4 receptor in sexual function ", Proc Natl Acad Sci USA 99 (17), 11381-11386 (2002).
Violin, J , et al., "Biased ligands at G-protein-coupled receptors: promise and progress", Trends Pharmacol Sci 35, 308-316 (2014).
Weeden, T , et al., "A retro-inverso α-melanocyte stimulating hormone analog with MC1R-binding selectivity", J. Pept. Sci. 17(1), 47-55 (2011).
Wessells, H , et al., "Synthetic melanotropic peptide initiates erections in men with psychogenic erectile dysfunction: double-blind, placebo controlled crossover study", J. Urol. 160(2), 389-393 (1998).
Wilczynski, A , et al., "Identification of Putative Agouti-Related Protein(87-132)-Melanocortin-4 Receptor Interactions by Homology Molecular Modeling and Validation Using Chimeric Peptide Ligands.", J Med Chem 47(9), 2194-2207 (2004).

(56) References Cited

OTHER PUBLICATIONS

Wilczynski, A , et al., "Structure-Activity Relationships of the Unique and Potent Agouti-Related Protein (AGRP)-Melanocortin Chimeric Tyr-c[å-Asp-His-DPhe-Arg-Trp-Asn-Ala-Phe-Dpr]-Tyr-NH2 Peptide Template.", J Med Chem 48, 3060-3075 (2005).
Xiang, Z M , et al., "Peptide and Small Molecules Rescue the Functional Activity and Agonist Potency of Dysfunctional Human Melanocortin-4 Receptor Polymorphisms", Biochemistry 46, 8273-8287 (2007).
Xiang, Z , et al., "Pharmacological Characterization of 30 Human Melanocortin-4 Receptor Polymorphisms with the Endogenous Proopiomelanocortin Derived Agonists, Synthetic Agonists, and the Endogenous Agouti-Related Protein (AGRP) Antagonist.", Biochemistry 49(22), 4583-4600 (2010).
Xiang, Z , et al., "Pharmacological Characterization of 40 Human Melanocortin-4 Receptor Polymorphisms with the Endogenous Proopiomelanocortin-Derived Agonists and the Agouti-Related Protein (AGRP) Antagonist.", Biochemistry 45, 7277-7288 (2006).
Xu, L , et al., "Heterobivalent ligands target cell-surface receptor combinations in vivo.", Proc Natl Acad Sci USA 109, 21295-21300 (2012).
Yang, Z , et al., "Biased signaling initiated by agouti-related peptide through human melanocortin-3 and -4 receptors", Biochim Biophys Acta 1862, 1485-1494 (2016).
Yang, Y K , et al., "Characterization of Agouti-Related Protein Binding to Melanocortin Receptors.", Mol Endocrinol 13, 148-155 (1999).
Ye, Z , et al., "Structure-activity relationship of linear tetrapeptides Tic-DPhe-Arg-Trp-NH2 at the human melanocortin-4 receptor and effects on feeding behaviors in rat", Peptides 26(10), 2017-2025 (2005).
U.S. Appl. No. 15/605,213, 2017-0342107.
U.S. Appl. No. 15/786,005, 2018-0118789.
U.S. Appl. No. 15/969,670, 2018-0360972.
Dehigaspitiya, D C , et al., "Linear scaffolds for multivalent targeting of melanocortin receptors.", Org Biomol Chem 13, 11507-11517 (2015).
Dehigaspitiya, D C , et al., "Synthesis and bioactivity of MSH4 oligomers prepared by an A2 + B2 strategy.", Tetrahedron Lett 56(23), 3060-3065 (2015).
Doering, S , et al., "Discovery of Mixed Pharmacology Melanocortin-3 Agonists and Melanocortin-4 Receptor Tetrapeptide Antagonist Compounds (TACOs) Based on the Sequence Ac-Xaa1-Arg-(pl)DPhe-Xaa4-NH2", J Med Chem 60(10), 4342-4357 (2017).
Doering, S , "Discovery of Peptide and Peptidomimetic Based Ligands Targeting the Melanocortin Receptors: A campaign in mixture-based positional scanning, chemical topology, and structure-activity relationships", Dissertation Submitted to the Faculty of the University of Minnesota, In Partial Fulfillment of the Requirements for the Degree of Doctor of Philosophy, 181 pages (Jul. 2016).
Doering, S , et al., "Melanocortin Antagonist Tetrapeptides with Minimal Agonist Activity at the Mouse Melanocortin-3 Receptor ", ACS Med Chem Lett 6(2), 123-127 (2015).
Dooley, C T, et al., "Selective Ligands for the μ, δ, and κ Opioid Receptors Identified from a Single Mixture Based Tetrapeptide Positional Scanning Combinatorial Library", J. Biol. Chem. 273(30), 18848-18856 (1998).
Dooley, C T , et al., "The use of positional scanning synthetic peptide combinatorial libraries for the rapid determination of opioid receptor ligands", Life Sci. 52(18), 1509-1517 (1993).
Durroux, T, "Principles: A model for the allosteric interactions between ligand binding sites within a dimeric GPCR.", Trends Pharmacol Sci 26, 376-384 (2005).
Ebihara, K , et al., "Involvement of Agouti-Related Protein, an Endogenous Antagonist of Hypothalamic Melanocortin Receptor, in Leptin Action ", Diabetes 48, 2028-2033 (1999).
Echalier, C , et al., "Heating and microwave assisted SPPS of C-terminal acid peptides on trityl resin: the truth behind the yield.", Amino Acids 45, 1395-1403 (2013).
Ellacott, K , et al., "Assessment of feeding behavior in laboratory mice.", Cell Metab 12(1), 10-17 (2010).
Elshan, N G R , et al., "Trigonal scaffolds for multivalent targeting of melanocortin receptors.", Org Biomol Chem 13 (6), 1778-1791 (2015).
Elster, L , et al., "Bioluminescence Resonance Energy Transfer as a Screening Assay: Focus on Partial and Inverse Agonism.", J Biomol Screen 12, 41-49 (2007).
Emmerson , "Melanocortin-4 receptor agonists for the treatment of obesity", Current Topics in Medicinal Chemistry 7 (11), 1121-1130 (2007).
Erez, M , et al., "Narcotic Antagonistic Potency of Bivalent Ligands Which Contain β-Naltrexamine. Evidence for Bridging between Proximal Recognition Sites.", J Med Chem 25, 847-849 (1982).
Ericson, M , et al., "A fragment of the *Escherichia coli* ClpB heat-shock protein is a micromolar melanocortin 1 teceptor agonist ", Bioorg Med Chem Lett 25(22), 5306-5308 (2015).
Ericson, M , et al., "A Macrocyclic Agouti-Related Protein/[Nle4, DPhe7]α-Melanocyte Stimulating Hormone Chimeric Scaffold Produces Sub-nanomolar Melanocortin Receptor Ligands", J Med Chem 60(2), 805-813 (2017).
Ericson, M , et al., "Arg-Phe-Phe D-Amino Acid Stereochemistry Scan in the Macrocyclic Agouti-Related Protein Antagonist Scaffold c[Pro- Arg-Phe-Phe-Xaa-Ala-Phe-DPro] Results in Unanticipated Melanocortin-1 Receptor Agonist Profiles", ACS Chem Neurosci 9(12), 3015-3023 (2018).
Ericson, M D , et al., "Bench-top to clinical therapies: A review of melanocortin ligands from 1954 to 2016.", Biochim Biophys Acta Mol Basis Dis 1863, 2414-2435 (2017).
Ericson, M , et al., "Discovery of a β-Hairpin Octapeptide, c[Pro-Arg-Phe-Phe-Dap-Ala-Phe-DPro], Mimetic of Agouti-Related Protein(87-132) [AGRP(87-132)] with Equipotent Mouse Melanocortin-4 Receptor (mMC4R) Antagonist Pharmacology.", J Med Chem 58(11), 4638-4647 (2015).
Ericson, M , et al., "Structure-Activity Relationship Studies on a Macrocyclic Agouti-Related Protein (AGRP) Scaffold Reveal Agouti Signaling Protein (ASP) Residue Substitutions Maintain Melanocortin-4 Receptor Antagonist Potency and Result in Inverse Agonist Pharmacology at . . ", J Med Chem 60, 8103-8114 (2017).
Fan, W , et al., "Role of melanocortinergic neurons in feeding and the agouti obesity syndrome.", Nature 385(6612), 165-168 (1997).
Farooqi, I S , et al., "Clinical Spectrum of Obesity and Mutations in the Melanocortin 4 Receptor Gene", N Engl J Med 348(12), 1085-1095 (2003).
Fernandes, S M , et al., "Synthesis and evaluation of bivalent ligands for binding to the human melanocortin-4 receptor.", Bioorg Med Chem 22, 6360-6365 (2014).
Ferre, S , "G Protein-Coupled Receptor Oligomerization Revisited: Functional and Pharmacological Perspectives ", Pharmacol Rev 66, 413-434 (2014).
Ferre, S , et al., "The GPCR Heterotetramer: Challenging Classical Pharmacology ", Trends Pharmacol Sci 36(3), 145-152 (2015).
Fields, G , et al., "Solid phase peptide synthesis utilizing 9-fluorenylmethoxycarbonyl amino acids", Int. J. Pept. Protein Res. 35(3), 161-214 (1990).
Filpula, D , et al., "Releasable PEGylation of proteins with customized linkers.", Advanced Drug Delivery 60, 29-49 (2008).
Finan, B , et al., "A rationally designed monomeric peptide triagonist corrects obesity and diabetes in rodents", Nat. Med. 21(1), 27-36 (2015).
Finan, B , et al., "Unimolecular Dual Incretins Maximize Metabolic Benefits in Rodents, Monkeys, and Humans", Science Translational Medicine 5(209), 209ra151-209ra151 (2013).
Fleming, K , et al., "Structure-Activity Relationship Studies of a Macrocyclic AGRP-Mimetic Scaffold c[Pro-Arg-Phe-Phe-Asn-Ala-Phe-DPro] Yield Potent and Selective Melanocortin-4 Receptor Antagonists and Melanocortin-5 Receptor Inverse Agonists that Increase Food Intake in Mice", ACS Chem Neurosci 9(5), 1141-1151 (2018).
Fleming, K , et al., "Synergistic Multi-Residue Substitutions of a Macrocyclic c[Pro-Arg-Phe-Phe-Asn-Ala-Phe-DPro] Agouti-Related Protein (AGRP) Scaffold Yield Potent and >600-Fold

(56) References Cited

OTHER PUBLICATIONS

MC4R versus MC3R Selective Melanocortin Receptor Antagonists", J Med Chem 61(17), 7729-7740 (2018).
Gantz, I , et al., "Molecular cloning of a novel melanocortin receptor.", J Biol Chem 268(11), 8246-8250 (1993).
Gantz, 1 , et al., "Molecular cloning, expression, and characterization of a fifth melanocortin receptor.", Biochem Biophys Res Commun 200(3), 1214-1220 (1994).
Gantz, I , et al., "Molecular cloning, expression, and gene localization of a fourth melanocortin receptor.", J Biol Chem 268(20), 15174-15179 (1993).
Gao, Z , et al., "Agonist-Dependent Internalization of the Human Melanocortin-4 Receptors in Human Embryonic Kidney 293 Cells. ", J Pharmacol Exp Ther 307, 870-877 (2003).
Ghamari-Langroudi, M , et al., "G-protein-independent coupling of MC4R to Kir7.1 in hypothalamic neurons", Nature 520(7545), 94-98 (2015).
Giuliani, D , et al., "Melanocortins protect against progression of Alzheimer's disease in tripletransgenic mice by targeting multiple pathophysiological pathways ", Neurobiol Aging 35, 537-547 (2014).
Giuliani, D , et al., "NDP-α-MSH induces intense neurogenesis and cognitive recovery in Alzheimer transgenic mice through activation of melanocortin MC4 receptors.", Mol Cell Neurosci 67, 13-21 (2015).
Goodman, M , et al., "On the concept of linear modified retropeptide structures", Acc. Chem. Res. 12(1), 1-7 (1979).
Gracia, E , et al., "Homodimerization of adenosine A1 receptors in brain cortex explains the biphasic effects of caffeine.". Neuropharmacology 71, 56-69 (2013).
Grant, M , et al., "Agonist-dependent Dissociation of Human Somatostatin Receptor 2 Dimers.", J Biol Chem 279 (35), 36179-36183 (2004).
Greenfield, J R , et al., "Modulation of Blood Pressure by Central Melanocortinergic Pathways.", New Engl J Med 360, 44-52 (2009).
Grieco, P , et al., "D-Amino acid scan of gamma-melanocyte-stimulating hormone: importance of Trp(8) on human MC3 receptor selectivity", J. Med. Chem. 43(26), 4998-5002 (2000).
Grieco, P , et al., "Further structure-activity studies of lactam derivatives of MT-II and SHU-9119: Their activity and selectivity at human melanocortin receptors 3, 4 and 5", Peptides 28(6), 1191-1196 (2007).
Grieco, P , et al., "Structure-Activity Studies of the Melanocortin Peptides: Discovery of Potent and Selective Affinity Antagonists for the hMC3 and hMC4 Receptors", J. Med. Chem. 45(24), 5287-5294 (2002).
Griffon, N , et al., "Molecular cloning and characterization of the rat fifth melanocortin receptor", Biochem Biophys Res Commun 200(2), 1007-1014 (1994).
Hadley, M E , "Discovery that a melanocortin regulates sexual functions in male and female humans", Peptides 26 (10), 1687-1689 (2005).
Hahn, T , et al., "Coexpression of Agrp and NPY in fasting-activated hypothalamic neurons.", Nat Neurosci 1, 271-272 (1998).
Han, Y , et al., "Allosteric communication between protomers of dopamine Class A GPCR dimers modulates activation ", Nat Chem Biol 5, 688-695 (2009).
Akgun, E , et al., "Inhibition of Inflammatory and Neuropathic Pain by Targeting a Mu Opioid Receptor/Chemokine Receptor5 Heteromer (MOR-CCR5).", J Med Chem 58(21), 8647-8657 (2015).
Albizu, L , et al., "Time-resolved FREI between GPCR ligands reveals oligomers in native tissues.", Nat Chem Biol 6 (8), 587-594 (2010).
Allen, B M , "The Results of Extirpation of the Anterior Lobe of the Hypophysis and of the Thyroid of Rana Pipiens Larvae", Science 44, 755-758 (1916).
Altschul, S , et al., "Basic local alignment search tool", J Mol Biol 215, 403-410 (1990).
Altschul, S , et al., "Gapped BLAST and PSI-BLAST: a new generation of protein database search programs.", Nucleic Acids Res 25(17), 3389-3402 (1997).
Atalayer, D , et al., "Food demand and meal size in mice with single or combined disruption of melanocortin type 3 and 4 receptors", Am. J. Physiol. Intergr. Comp. Physiol. 298(6), R1667-R1674 (2010).
Ballet, S , et al., "Novel selective human melanocortin-3 receptor ligands: Use of the 4-amino-1,2,4,5-tetrahydro-2-benzazepin-3-one (Aba) scaffold", Bioorg. Med Chem. Lett. 17(9), 2492-2498 (2007).
Barkey, N M , et al., "Development of melanoma-targeted polymer micelles by conjugation of a Melanocortin 1 Receptor (MC1R) specific ligand ", J Med Chem 54, 8078-8084 (2011).
Barnea, G , et al., "The genetic design of signaling cascades to record receptor activation.", PNAS 105(1), 64-69 (2008).
Barrett, C E , et al., "Neonatal melanocortin receptor agonist treatment reduces play fighting and promotes adult attachment in prairie voles in a sex-dependent manner.", Neuropharmacology 85, 357-366 (2014).
Boeglin, D , et al, "Aza-scanning of the Potent Melanocortin Receptor Agonist Ac-His-d-Phe-Arg-Trp-NH2", Chem Biol Drug Des 67(4), 275-283 (2006).
Bolin, K A , et al., "NMR structure of a minimized human agouti related protein prepared by total chemical synthesis.", FEBS Lett 451, 125-131 (1999).
Bowen, M E , et al., "Design, Synthesis, and Validation of a Branched Flexible Linker for Bioactive Peptides.", J Org Chem 72(5), 1675-1680 (2007).
Brabez, N , et al., "Design, synthesis and biological studies of efficient multivalent melanotropin ligands: tools towards melanoma diagnosis and treatment ", J Med Chem 54(20), 7375-7384 (2011).
Brabez, N , et al., "Multivalent Interactions: Synthesis and Evaluation of Melanotropin Multimers—Tools for Melanoma Targeting.", ACS Med Chem Lett 4, 98-102 (2013).
Breit, A , et al., "Alternative G protein-coupling and biased agonism: new insights into melanocortin-4 receptor signalling", Mol Cell Endocrinol 331, 232-240 (2010).
Brock, C , et al., "Activation of a Dimeric Metabotropic Glutamate Receptor by Intersubunit Rearrangement.", J Biol Chem 282, 33000-33008 (2007).
Broussard, J A , et al., "Fluorescence resonance energy transfer microscopy as demonstrated by measuring the activation of the serine/ threonine kinase Akt ", Nat Protoc 8(2), 265-281 (2013).
Brown, K S , et al., "Central injection in rats of a-melanocyte-stimulating hormone analog: effects on food intake and brain Fos", Regul Peptides 78, 89-94 (1998).
Büch, T , et al., "Pertussis Toxin-sensitive Signaling of Melanocortin-4 Receptors in Hypothalamic GT1-7 Cells Defines Agouti-related Protein as a Biased Agonist", J. Biol. Chem. 284(39), 26411-26420 (2009).
Bultman, S J , et al., "Molecular characterization of the mouse agouti locus", Cell 71(7), 1195-1204 (1992).
Butler, A A , et al., "A unique metabolic syndrome causes obesity in the melanocortin-3 receptor-deficient mouse.", Endocrinol 141(9), 3518-3521 (2000).
Cai, M , et al., "Cell Signaling and Trafficking of Human Melanocortin Receptors in Real Time Using Two-photon Fluorescence and Confocal Laser Microscopy: Differentiation of Agonists and Antagonists.", Chem Biol Drug Des 68 (4), 183-193 (2006).
Carotenuto , et al., "Discovery of Novel Potent and Selective Agonists at the Melanocortin-3 Receptor", J. Med. Chem. 58(24), 9773-9778 (2015).
Carpino, L , et al., "The 9-Fluorenylmethoxycarbonyl Amino-Protecting Group.", J Org Chem 37(22), 3404-3409 (1972).
Carpino, L A , et al., "The 9-Fluorenylmethoxycarbonyl Function, a New Base-Sensitive Amino-Protecting Group.", J Am Chem Soc 92, 5748-5749 (1970).
Carrithers, M D , et al., "Synthesis and characterization of bivalent peptide ligands targeted to G-protein-coupled receptors ", Chemistry & Biology 3(7), 537-542 (1996).
Casado, V , et al., "Old and new ways to calculate the affinity of agonists and antagonists interacting with G-protein-coupled monomeric and dimeric receptors: The receptor-dimer cooperativity index ", Pharmacol Ther 116, 343-354 (2007).

(56) References Cited

OTHER PUBLICATIONS

Chapman, K L , et al., "The melanocortin 4 receptor: Oligomer formation, interaction sites and functional significance ", Biochim Biophys Acta 1828, 535-542 (2013).
Chen, W , et al., "A Colorimetric Assay for Measuring Activation of Gs- and Gq-Coupled Signaling Pathways", Anal. Biochem. 226(2), 349-354 (1995).
Chen, C A , et al., "Calcium phosphate-mediated gene transfer: a highly efficient transfection system for stably transforming cells with plasmid DNA ", BioTechniques 6(7), 632-638 (1988).
Chen, W , et al., "Exocrine Gland Dysfunction in MC5-R-Deficient Mice: Evidence for Coordinated Regulation of Exocrine Gland Function by Melanocortin Peptides", Cell 91(6), 789-798 (1997).
Chen, M , et al., "Functional characterization of the modified melanocortin peptides responsible for ligand selectivity at the human melanocortin receptors ", Peptides 27, 2836-2845 (2006).
Chen, A S , et al., "Inactivation of the mouse melanocortin-3 receptor results in increased fat mass and reduced lean body mass ", Nat Genet 26, 97-102 (2000).
Cheung, A , et al., "Structure-Activity relationship of linear peptide Bu-His-DPhe-Arg-Trp-Gly-NH2 at the human melanocortin-1 and -4 receptors: arginine substitution", Bioorg Med. Chem. Lett 12(17), 2407-2410 (2002).
Chhajlani, V , et al., "Molecular cloning and expression of the human melanocyte stimulating hormone receptor eDNA.", FEBS Lett 309(3), 417-420 (1992).
Chhajlani, V , et al., "Molecular cloning of a novel human melanocortin receptor.", Biochem Biophys Res Commun 195, 866-873 (1993).
Chorev, M , et al., "A dozen years of retro-inverso peptidomimetics", Acc. Chem. Res. 26(5), 266-273 (1993).
Chorev, M , et al., "Partially modified retro-inverso-enkephalinamides: topochemical long-acting analogs in vitro and in vivo", Science 204(4398), 1210-1212 (1979).
Christensen, T , "A Qualitative Test for Monitoring Coupling Completeness in Solid Phase Peptide Synthesis Using Chloranil", Acta Chemica Scandinavica B 33, 763-766 (1979).
Clayton, A H , et al., "Bremelanotide for female sexual dysfunctions in premenopausal women: a randomized, placebo-controlled dose-finding trial.", Women's Health 12, 325-337 (2016).
Comps-Agrar, L , et al., "The oligomeric state sets GABAB receptor signalling efficacy.", EMBO J 30, 2336-2349 (2011).
Corpet, F , et al., "Multiple sequence alignment with hierarchical clustering", Nucl Acids Res 16, 10881-10890 (1988).
Cottet, M , et al., "BRET and time-resolved FRET strategy to study GPCR oligomerization: from cell lines toward native tissues ", Front Endocrinol 3, 92 (2012).
Damian, M , et al., "Asymmetric conformational changes in a GPCR dimer controlled by G-proteins.", EMBO J 25(24), 5693-5702 (2006).
Danho , "Highly Selective Cyclic Peptides for Human Melanocortin-4 Receptor (MC-4 R): Design, Synthesis, Bioactive Conformation, and Pharmacological Evaluation as an Anti-Obesity Agent", Peptides: The Wave of the Future, 701-703 (2001).
Danho, W , et al., "Structure-Activity relationship of linear peptide Bu-His6-DPhe7-Arg8-Trp9-Gly10-NH2 at the human melanocortin-1 and -4 receptors: DPhe7 and Trp9 substitution", Bioorg. Med. Chem. Lett. 13(4), 649-652 (2003).
Daniels, D , et al., "Opioid-induced tolerance and dependence in mice is modulated by the distance between pharmacophores in a bivalent ligand series", Proc Natl Acad Sci 102(52), 19208-19213 (2005).
Day, J , et al., "A new glucagon and GIP-1 co-agonist eliminates obesity in rodents", Nat Chem Biol 5(10), 749-757 (2009).
Deboer, M D , et al., "Cachexia: lessons from melanocortin antagonism.", Trends Endocrinol Metab 17, 199-204 (2006).
Kingsberg, S , "Bremelanotide for Hypoactive Sexual Desire Disorder: Analyses from a Phase 2B Does-Ranging Study", 4th International Consultation on Sexual Medicine, J Sex Med 12(suppl 6), 389 (2015).
Kniazeff, J , et al., "Closed state of both binding domains of homodimeric mGlu receptors is required for full activity ", Nat Struct Mol Biol 11, 706-713 (2004).
Kniazeff, J , et al., "Locking the Dimeric GABAB G-Protein-Coupled Receptor in Its Active State.", J Neurosci 24, 370-377 (2004).
Koikov , et al., "Sub-nanomolar hMC1R agonists by end-capping of the melanocortin tetrapeptide His-D-Phe-Arg-Trp-NH(2)", Bioorg. Med. Chem. Lett. 13(16), 2647-2650 (2003).
Kopanchuk, S , et al., "Co-operative regulation of ligand binding to melanocortin receptor subtypes: evidence for interacting binding sites", Eur J Pharmacol 512, 85-95 (2005).
Kopanchuk, S , et al., "Kinetic evidence for tandemly arranged ligand binding sites in melanocortin 4 receptor complexes.", Neurochem Int 49, 533-542 (2006).
Kroeze, W K , et al., "PRESTO-TANGO: an open-source resource for interrogation of the druggable human GPCR-ome.", Nat Struct Mol Biol 22, 362-369 (2015).
Kuhhorn, J , et al., "Development of a Bivalent Dopamine D2 Receptor Agonist.", J Med Chem 54, 7911-7919 (2011).
Langendonk, J G , et al., "Afamelanotide for Erythropoietic Protoporphyria", N Engl J Med 373, 48-59 (2015).
Le Naour, M , et al., "Bivalent Ligands That Target μ Opioid (MOP) and Cannabinoid1 (CB1) Receptors Are Potent Analgesics Devoid of Tolerance.", J Med Chem 56(13), 5505-5513 (2013).
Le Naour, M , et al., "Putative Kappa Opioid Heteromers As Targets for Developing Analgesics Free of Adverse Effects.", J Med Chem 57, 6383-6392 (2014).
Lensing, C J , et al., "A Direct In Vivo Comparison of The Melanocortin Monovalent Agonist Ac-His-DPhe-Arg-Trp-NH2 versus The Bivalent Agonist Ac-His-DPhe-Arg-Trp-PEDG20-His-DPhe-Arg-Trp-NH2: A Bivalent Advantage.", ACS Chem Neurosci 8(6), 1262-1278 (2017).
Lensing, C , et al., "Ac-Trp-DPhe(p-l)-Arg-Trp-NH2, a 250-Fold Selective Melanocortin-4 Receptor (MC4R) Antagonist over the Melanocortin-3 Receptor (MC3R), Affects Energy Homeostasis in Male and Female Mice Differently", ACS Chem Neurosci 8, 1283-1291 (2016).
Lensing, C J , et al., "An in vitro and in vivo investigation of bivalent ligands that display preferential binding and functional activity for different melanocortin receptor homodimers.", J Med Chem 59, 3112-3128 (2016).
Lensing, C , et al., "Bivalent Ligands as Pharmacological Probes for the Melanocortin Receptors: The Bivalent Advantage", Dissertation submitted to the Faculty of University of Minnesota In Partial Fulfillment of the Requirements for the Degree of Doctor of Philosophy, 327 pages, May 2017.
Lensing, C J , et al., "Developing a Biased Unmatched Bivalent Ligand (BUmBL) Design Strategy to Target the GPCR Homodimer Allosteric Signaling (cAMP over β-Arrestin 2 Recruitment) Within the Melanocortin Receptors.", J Med Chem, Just Accepted (2018).
Lensing, C J , et al., "The Ac-Trp-DPhe(p-l)-Arg-Trp-NH2 250-Fold Selective Melanocortin-4 Receptor (MC4R) Antagonist over the Melanocortin-3 Receptor (MC3R) Affects Energy Homeostasis in Male and Female Mice Differently.", ACS Chem Neurosci 7(9), 1283-1291 (2016).
Lu, D , et al., "Agouti protein is an antagonist of the melanocyte-stimulating-hormone receptor.", Nature 371(6500), 799-802 (1994).
Mandrika, I , et al., "Melanocortin receptors form constitutive homo- and heterodimers.", Biochem Biophys Res Commun 326, 349-354 (2005).
Marsh, D J , et al., "Effects of neuropeptide Y deficiency on hypothalamic agouti-related protein expression and responsiveness to melanocortin analogues ", Brain Research 848, 66-77 (1999).
Marsh, D J , et al., "Response of melanocortin-4 receptor-deficient mice to anorectic and orexigenic peptides.", Nat Genet 21,119-122 (1999).
Marti-Solano, M , et al., "Drugging specific conformational states of GPCRs: challenges and opportunities for computational chemistry", Drug Discovery Today 21, 625-631 (2016).
Marvyn, P M , et al., "Data onoxygenconsumptionrate,respiratory exchangeratio,andmovementinC57BL/6J female miceonthethird-dayofconsuming a high-fatdiet.", Data in Brief 7, 472-475 (2016).

(56) References Cited

OTHER PUBLICATIONS

Masman, M , "Synthesis and conformational analysis of his-phe-arg-trp-nh2 and analogues with antifungal properties", Bioorganic and Medicinal Chemistry 14, 7604-7614 (2006).
Mayorov, A , et al., "Solid-phase peptide head-to-side chain cyclodimerization: Discovery of C2-symmetric cyclic lactam hybrid α-melanocyte-stimulating hormone (MSH)/agouti-signaling protein (ASIP) analogues with potent activities at the human melanocortin receptors", Peptides 31(10), 1894-1905 (2010).
McNulty, J C , et al., "High-Resolution NMR Structure of the Chemically-Synthesized Melanocortin Receptor Binding Domain AGRP(87-132) of the Agouti-Related Protein", Biochemistry 40, 15520-15527 (2001).
Merrifield, R , et al., "Solid Phase Peptide Synthesis. I. the Synthesis of a Tetrapeptide", JACS 85, 2149-2154 (1963).
Miller, M , et al., "Cloning of the mouse agouti gene predicts a secreted protein ubiquitously expressed in mice carrying the lethal yellow mutation", Genes. Dev. 7(3), 454-467 (1993).
Mo, XL , et al., "Activation of MAPK by inverse agonists in six naturally occurring constitutively active mutant human melanocortin-4 receptors", Biochim. Biophys. Acta. 1832(12) 1939-1948 (2013).
Mountjoy, K G , et al., "Localization of the melanocortin-4 receptor (MC4-R) in neuroendocrine and autonomic control circuits in the brain", Mol. Endocrinol 8(10), 1298-1308 (1994).
Mountjoy, K G , et al., "The cloning of a family of genes that encode the melanocortin receptors.", Science 257 (5074), 1248-1251 (1992).
Mutulis, F , et al., "Reductive amination products containing naphthalene and indole moieties bind to melanocortin receptors", Bioorg. Med. Chem. Lett. 12(7), 1035-1038 (2002).
Myers, E , et al., "Optimal alignments in linear space", CABIOS 4(1), 11-17 (1988).
Nakanishi, S , et al., "Nucleotide sequence of cloned cDNA for bovine corticotropin-beta-lipotropin precursor.", Nature 278(5703), 423-427 (1979).
Needleman, S , et al., "A General Method Applicable to the Search for Similarities in the Amino Acid Sequence of Two Proteins", J Mol Biol 48, 443-453 (1970).
Nl, XP , et al., "Central receptors mediating the cardiovascular actions of melanocyte stimulating hormones", J. Hypertens. 24(11), 2239-2246 (2006).
Nickolls, S A , et al., "Dimerization of the melanocortin 4 receptor: A study using bioluminescence resonance anergy transfer.", Peptides 27, 380-387 (2006).
Nickolls, S , et al., "Functional Selectivity of Melanocortin 4 Receptor Peptide and Nonpeptide Agonists: Evidence tor Ligand-Specific Conformational States", J Pharmacol Exp Ther 313, 1281-1288 (2005).
Odagami , "Design of cyclic peptides with agonist activity at melanocortin receptor-4", Bioorg Med Chem Lett 16(14), 3723-3726 (2006).
Ollmann, M , et al., "Antagonism of Central Melanocortin Receptors in Vitro and in Vivo by Agouti-Related Protein.", Science 278(5335), 135-138 (1997).
Orcel, H , et al., "Differential Coupling of the Vasopressin V1b Receptor through Compartmentalization within the Plasma Membrane.", Mol Pharmacol 75, 637-647 (2009).
Ostresh, J , et al., "Peptide libraries: Determination of relative reaction rates of protected amino acids in competitive couplings". Biopolymers 34(12), 1681-1689 (1994).
Otsuka, H , et al., "Synthesis of peptides related to the N-terminal structure of corticotropin. III. The synthesis of L-histidyl-L-phenylalanyl-L-tryptophan, the smallest peptideexhibiting the melanocyte-stimulating and the lipolytic activities", Bull. Chem. Soc. Jpn. 37(10), 1465-1471 (1964).
Pearson, W , et al., "Improved tools for biological sequence comparison", Proc Natl Acad Sci 85, 2444-2448 (1988).
Pearson, W , et al., "Using the FASTA program to search protein and DNA sequence databases.", Meth Mol Biol 24, 307-331 (1994).
Pellissier, L , et al., "G Protein Activation by Serotonin Type 4 Receptor Dimers.", J Biol Chem 286, 9985-9997 (2011).
Penagarikano, O , et al., "Exogenous and evoked oxytocin restores social behavior in the Cntnap2 mouse model of autism.", Sci Transl Med 7(271), 271ra8 (2015).
Pfleger, K , et al., "Bioluminescence resonance energy transfer (BRET) for the real-time detection of protein-protein interactions", Nat Protoc 1(1), 337-345 (2006).
Piechowski, C L , et al., "Inhibition of melanocortin-4 receptor dimerization by substitutions in intracellular loop 2.", J Mol Endocrinol 51, 109-118 (2013).
Pin, J P , et al., "Allosteric functioning of dimeric class C G-protein-coupled receptors.", Febs J 272, 2947-2955 (2005).
Ericson, M , et al., "Discovery of Molecular Interactions of the Human Melanocortin-4 Receptor (hMC4R) Asp189 (D189) Amino Acid with the Endogenous G-Protein-Coupled Receptor (GPCR) Antagonist Agouti-Related Protein AGRP) Provides Insights to AGRP's Inverse Agonist . . . ", ACS Neurosci 12, 542-556 (2021).
Bednarek, M , et al., "Potent and Selective Agonists of Human Melanocortin Receptor 5: Cyclic Analogues of r-Melanocyte-Stimulating Hormone", J Med Chem 50, 2520-2526 (2007).
Ericson, M , et al., "Peptoid NPhe 4 in AGRP-Based c[Pro 1-Arg 2-Phe 3-Phe 4-Xxx 5-Ala 6-Phe 7-DPro 8] Scaffolds Maintain Mouse MC4R Antagonist Potency", ACS Med Chem Lett 11(10), 1942-1948 (2020).
Koerperich, Z , "Incorporation of Agouti-Related Protein (AgRP) Human Single Nucleotide Polymorphisms (SNPs) n the AgRP-Derived Macrocyclic Scaffold c[Pro-Arg-Phe-Phe-Asn-Ala-Phe-dPro] Decreases Melanocortin-4 Receptor Antagonist Potency and Results in the Discovery ... ", J Med Chem 63(5), 2194-2208 (2020).
Koerperich, Z , et al., "Incorporation of Agouti-Related Protein (AGRP) Human Single Nucleotide Polymorphisms in the AGRP-Derived Macrocyclic Scaffold c[Pro-Arg-Phe-Phe-Asn-Ala-Phe-DPro] Decreases Melanocortin-4 Receptor Antagonist Potency", 57th Annual MIKI Meeting, Lawrence, Kansas, Poster and Abstract, 2 pages (Apr. 2019).
Sweeney, P , et al., "The melanocortin-3 receptor is a pharmacological target for the regulation of anorexia", Sci Transl Med 13, eabd6434, 1-16 pages, Supplementary Materials 17-71 (2021).
Bednarek, M, et al., "Potent and selective agonists of a-melanotropin (aMSH) action at human melanocortin Yeceptor 5; linear analogs of a-melanotropin", Peptides 28, 1020-1028 (2007).
Chaki, S, et al., "Involvement of the melanocortin MC4 receptor in stress-related behavior in rodents", European Journal of Pharmacology 474, 95-101 (2003).
Ericson, M, et al., "Functional Mixture-Based Positional Scan Identifies a Library of Antagonist Tetrapeptide Sequences (LAtTeS) with Nanomolar Potency for the Melanocortin-4 Receptor and Equipotent with the Endogenous AGRP(86-132) Antagonist", J Med Chem 64(19), 14860-14875 (2021).
Grieco, P, et al., "Design and Synthesis of Highly Potent and Selective Melanotropin Analogues of SHU9119 Modified at Position 6", Biochem Biophys Res Commun 292(4), 1075-1080 (2002).
Lau, Q, et al., "Discovery of an ultra-short linear antibacterial tetrapeptide with anti-MRSA activity from a structureeactivity relationship study", European Journal of Medicinal Chemistry 105, 138-144 (2015).
Nozawa, D, et al., "Identification of Arginine Analogues as Antagonists and Agonists for the Melanocortin-4 Receptor", Chem Pharm Bull 55(8), 1232-1239 (2007).

* cited by examiner

```
AGRP: MLTAAVLSCALLLALPATRGAQMGLAPMEGIRRPDQALLPELPGLGLRAPLKKTTAEQAEEDLLQE---   66
ASP:  MDVTRLLLATLLVFLCFFTANSHLPPEEKLRDDRSLRSNSSVNLLDVPSVSIVALNKKSKQIGRKAAEK   69

AGRP: ---AQALAEVLDLQDREPRSSRRCVRLHESCLGQQVPCCDPCATCYCRFFNAFCYCRKLGTAMNPCSRT 132

ASP:  KRSSKKEASMKKVVRPRTPLSAPCVATRNSCKPPAPACCDPCASCQCRFFRSACSCRVLSLNC       132
```

B

```
hAGRP: CRFFNAFC
mAGRP: CRFFNAFC
 hASP: CRFFRSAC
 mASP: CRFFGSAC
```

C

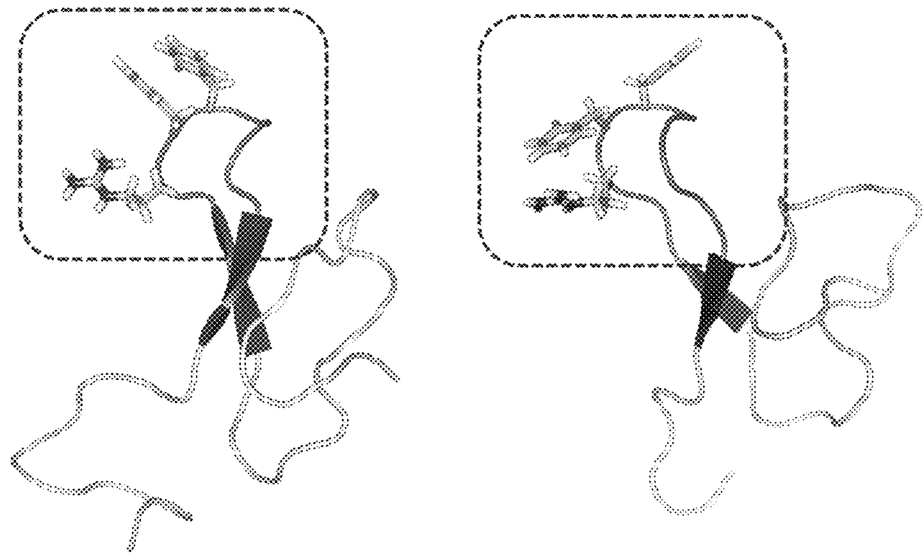

AGRP(87-132)

ASP(80-132: Q115Y, S124Y)

FIGURE 8
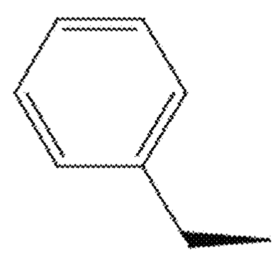
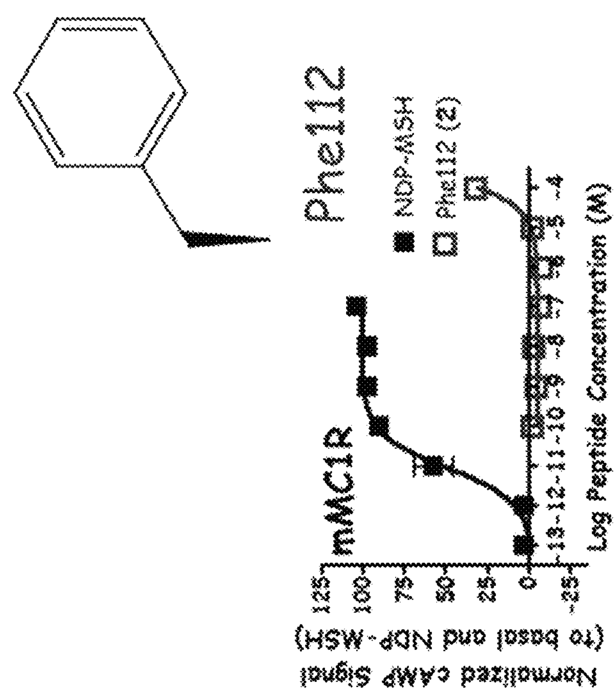
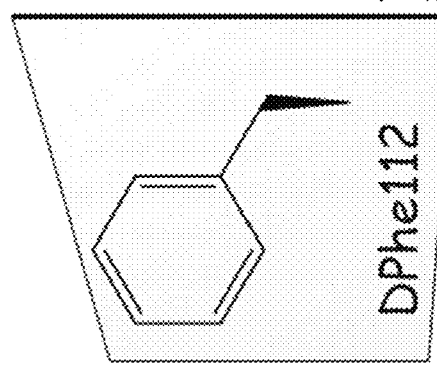
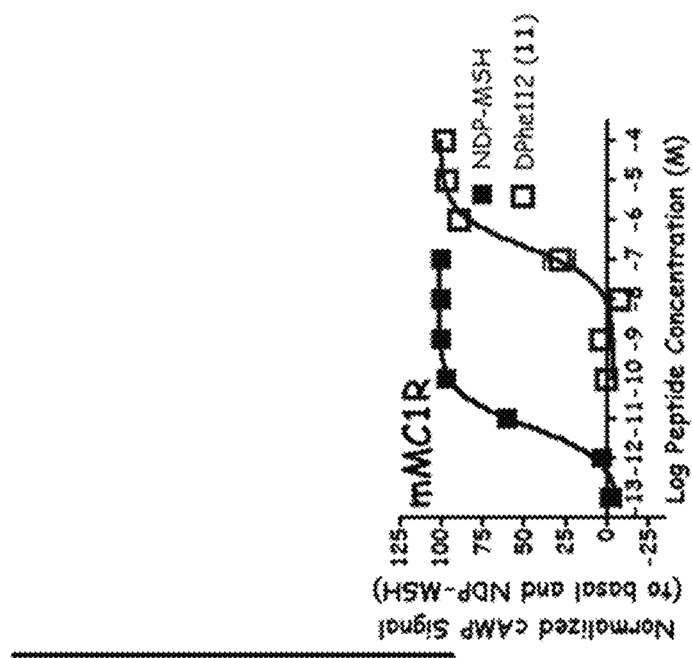

| CMPD | Sequence | mMC3R $pA_2$ |
|---|---|---|
| 21 | c[ Pro Arg Phe hPhe Arg Ala Phe DPro ] | 8.0 |
| 24 | c[ Pro Arg Phe hPhe Arg Ser Nle DPro ] | 7.9 |
| 23 | c[ Pro Arg Phe hPhe Arg Ser Phe DPro ] | 7.7 |
| 22 | c[ Pro Arg Phe hPhe Arg Ala Nle DPro ] | 7.5 |
| 10 | c[ Pro Arg Phe Phe Arg Ala Nle DPro ] | 7.5 |
| 9 | c[ Pro Arg Phe Phe Arg Ala Phe DPro ] | 7.4 |
| 5 | c[ Pro Arg Phe Phe Dap Ala Phe DPro ] | 7.2 |
| 19 | c[ Pro Arg Phe hPhe Dap Ser Phe DPro ] | 7.2 |
| 6 | c[ Pro Arg Phe Phe Dap Ala Nle DPro ] | 7.1 |
| 11 | c[ Pro Arg Phe Phe Arg Ser Phe DPro ] | 7.1 |
| 17 | c[ Pro Arg Phe hPhe Dap Ala Phe DPro ] | 7.1 |
| 12 | c[ Pro Arg Phe Phe Arg Ser Nle DPro ] | 7.1 |
| 7 | c[ Pro Arg Phe Phe Dap Ser Phe DPro ] | 6.8 |
| 18 | c[ Pro Arg Phe hPhe Dap Ala Nle DPro ] | 6.7 |
| 20 | c[ Pro Arg Phe hPhe Dap Ser Nle DPro ] | 6.7 |
| 4 | c[ Pro Arg Phe Phe Asn Ser Nle DPro ] | 6.6 |
| 2 | c[ Pro Arg Phe Phe Asn Ala Nle DPro ] | 6.6 |
| 8 | c[ Pro Arg Phe Phe Dap Ser Nle DPro ] | 6.5 |
| 15 | c[ Pro Arg Phe hPhe Asn Ser Phe DPro ] | 6.5 |
| 1 | c[ Pro Arg Phe Phe Asn Ala Phe DPro ] | 6.3 |
| 16 | c[ Pro Arg Phe hPhe Asn Ser Nle DPro ] | 6.3 |
| 14 | c[ Pro Arg Phe hPhe Asn Ala Nle DPro ] | 6.2 |
| 3 | c[ Pro Arg Phe Phe Asn Ser Phe DPro ] | 6.1 |
| 13 | c[ Pro Arg Phe hPhe Asn Ala Phe DPro ] | 5.6 |

FIGURE 19B

| CMPD | Sequence | mMC4R $pA_2$ |
| --- | --- | --- |
| 12 | c[ProArgPhe Phe Arg Ser Nle DPro] | 9.6 |
| 20 | c[ProArgPhe hPhe Dap Ser Nle DPro] | 9.5 |
| 24 | c[ProArgPhe hPhe Arg Ser Nle DPro] | 9.5 |
| 16 | c[ProArgPhe hPhe Asn Ser Nle DPro] | 9.2 |
| 19 | c[ProArgPhe hPhe Dap Ser Phe DPro] | 9.2 |
| 8 | c[ProArgPhe Phe Dap Ser Nle DPro] | 9.1 |
| 10 | c[ProArgPhe Phe Arg Ala Nle DPro] | 9.1 |
| 17 | c[ProArgPhe hPhe Dap Ala Phe DPro] | 9.1 |
| 18 | c[ProArgPhe hPhe Dap Ala Nle DPro] | 9.1 |
| 7 | c[ProArgPhe Phe Dap Ser Phe DPro] | 9.1 |
| 6 | c[ProArgPhe Phe Dap Ala Nle DPro] | 9.0 |
| 11 | c[ProArgPhe Phe Arg Ser Phe DPro] | 9.0 |
| 21 | c[ProArgPhe hPhe Arg Ala Phe DPro] | 8.9 |
| 2 | c[ProArgPhe Phe Asn Ala Nle DPro] | 8.9 |
| 5 | c[ProArgPhe Phe Dap Ala Phe DPro] | 8.9 |
| 23 | c[ProArgPhe hPhe Arg Ser Phe DPro] | 8.8 |
| 22 | c[ProArgPhe hPhe Arg Ala Nle DPro] | 8.8 |
| 9 | c[ProArgPhe Phe Arg Ala Phe DPro] | 8.7 |
| 14 | c[ProArgPhe hPhe Asn Ala Nle DPro] | 8.6 |
| 15 | c[ProArgPhe hPhe Asn Ser Phe DPro] | 8.6 |
| 4 | c[ProArgPhe Phe Asn Ser Nle DPro] | 8.5 |
| 13 | c[ProArgPhe hPhe Asn Ala Phe DPro] | 8.3 |
| 1 | c[ProArgPhe Phe Asn Ala Phe DPro] | 8.1 |
| 3 | c[ProArgPhe Phe Asn Ser Phe DPro] | 8.1 |

FIGURE 19C

| CMPD | Sequence | Selectivity (MC3R/MC4R) |
|---|---|---|
| 16 | c[Pro Arg Phe hPhe Asn Ser Nle DPro] | 790 |
| 20 | c[Pro Arg Phe hPhe Dap Ser Nle DPro] | 630 |
| 13 | c[Pro Arg Phe hPhe Asn Ala Phe DPro] | 500 |
| 8 | c[Pro Arg Phe Phe Dap Ser Nle DPro] | 430 |
| 12 | c[Pro Arg Phe Phe Arg Ser Nle DPro] | 320 |
| 18 | c[Pro Arg Phe hPhe Dap Ala Nle DPro] | 250 |
| 14 | c[Pro Arg Phe hPhe Asn Ala Nle DPro] | 250 |
| 2 | c[Pro Arg Phe Phe Asn Ala Nle DPro] | 200 |
| 7 | c[Pro Arg Phe Phe Dap Ser Phe DPro] | 170 |
| 15 | c[Pro Arg Phe hPhe Asn Ser Phe DPro] | 130 |
| 19 | c[Pro Arg Phe hPhe Dap Ser Phe DPro] | 120 |
| 17 | c[Pro Arg Phe hPhe Dap Ala Phe DPro] | 100 |
| 3 | c[Pro Arg Phe Phe Asn Ser Phe DPro] | 100 |
| 6 | c[Pro Arg Phe Phe Dap Ala Nle DPro] | 79 |
| 11 | c[Pro Arg Phe Phe Arg Ser Phe DPro] | 79 |
| 4 | c[Pro Arg Phe Phe Asn Ser Nle DPro] | 79 |
| 1 | c[Pro Arg Phe Phe Asn Ala Phe DPro] | 59 |
| 5 | c[Pro Arg Phe Phe Dap Ala Phe DPro] | 47 |
| 10 | c[Pro Arg Phe Phe Arg Ala Nle DPro] | 46 |
| 24 | c[Pro Arg Phe hPhe Arg Ser Nle DPro] | 37 |
| 9 | c[Pro Arg Phe Phe Arg Ala Phe DPro] | 21 |
| 22 | c[Pro Arg Phe hPhe Arg Ala Nle DPro] | 19 |
| 23 | c[Pro Arg Phe hPhe Arg Ser Phe DPro] | 13 |
| 21 | c[Pro Arg Phe hPhe Arg Ala Phe DPro] | 8 |

FIGURES 19D-19E

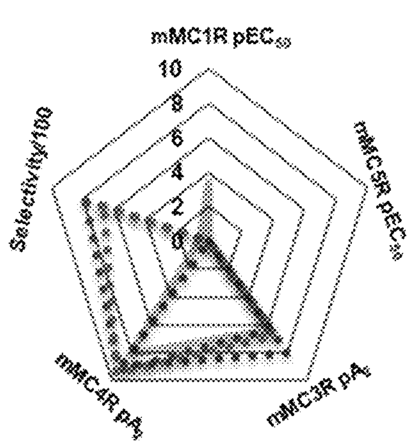

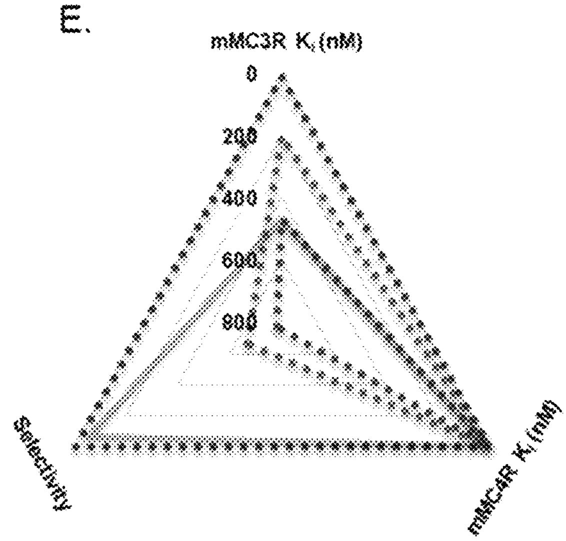

FIGURES 25A-25B
a
| Ligand | Antagonist $K_i$ (nM) | Kir7.1(M125R) Potency (nM) | Antagonist $K_i$/ Kir7.1(M125R) |
|---|---|---|---|
| AGRP | 1.6 | 3.6* | 0.4 |
| MDE3-119-8c | 1.5 | 3.4±0.05 | 0.4 |
| MDE3-119-7c | 2.5 | 9.8±0.02 | 0.3 |
| MDE3-85c | 11 | 0.20±0.08 | 55 |
| MDE3-119-2c | 29 | 0.59±0.06 | 50 |
| MDE3-119-4c | 140 | 0.26±0.07 | 540 |
| MDE3-119-10c | 480 | 0.12±0.07 | 4000 |
b
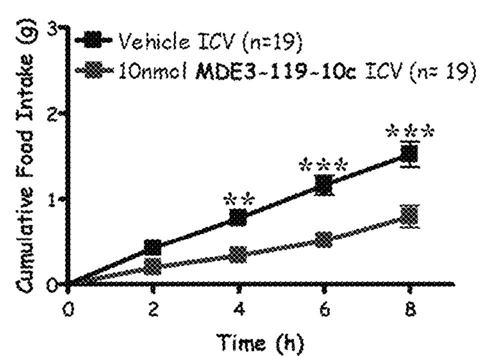
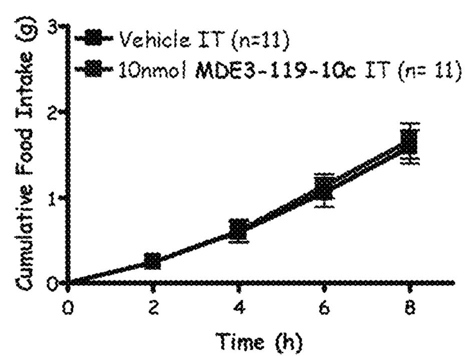
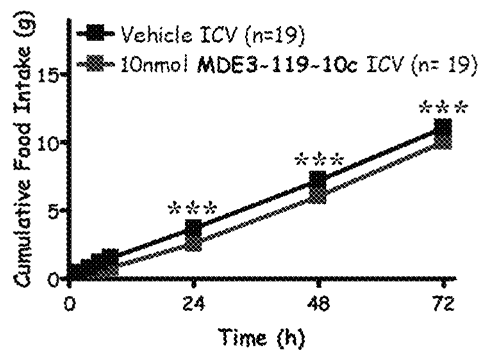
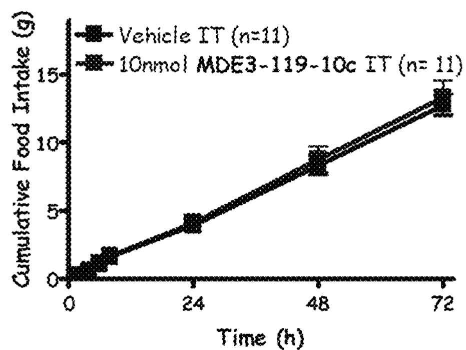

SEQUENCE LISTING

```
<160> NUMBER OF SEQ ID NOS: 163

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 1

Pro Arg Phe Phe Asn Ala Phe Pro
1               5


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
```

<222> LOCATION: (8)..(8)
<223> OTHER INFORMATION: DPro

<400> SEQUENCE: 2

Pro Arg Phe Phe Xaa Ala Phe Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 3

Pro Arg Phe Phe Asn Ala Phe Pro
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 4

Pro Arg Phe Phe Ala Ala Phe Pro
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Abu
<220> FEATURE:
<221> NAME/KEY: MOD_RES
<222> LOCATION: (8)..(8)
<223> OTHER INFORMATION: DPro

<400> SEQUENCE: 5

Pro Arg Phe Phe Xaa Ala Phe Pro
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<221> NAME/KEY: MOD_RES
<222> LOCATION: (8)..(8)
<223> OTHER INFORMATION: DPro

<400> SEQUENCE: 6

Pro Arg Phe Phe Ser Ala Phe Pro
1 5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 7

Pro Arg Phe Phe Thr Ala Phe Pro
1 5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 8

Pro Arg Phe Phe Asp Ala Phe Pro
1 5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 9

Pro Arg Phe Phe Glu Ala Phe Pro
1 5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: DDap
<220> FEATURE:
<221> NAME/KEY: MOD_RES
<222> LOCATION: (8)..(8)
<223> OTHER INFORMATION: DPro

<400> SEQUENCE: 10

Pro Arg Phe Phe Xaa Ala Phe Pro
1 5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 11

Pro Arg Phe Phe His Ala Phe Pro
1 5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 12

Pro Arg Phe Phe Leu Ala Phe Pro
1 5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 13

Pro Arg Phe Phe Leu Ala Phe Pro
1 5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 14

Pro Arg Phe Phe Val Ala Phe Pro
1 5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 15

Pro Arg Phe Phe Phe Ala Phe Pro
1 5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 16

Pro Arg Phe Phe Trp Ala Phe Pro
1 5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 17

Pro Arg Phe Phe Asn Asp Phe Pro
1 5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 18

Pro Arg Phe Phe Asn Glu Phe Pro
1 5

<210> SEQ ID NO 19
<211> LENGTH: 8
<212> TYPE: PRT

<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 19

Pro Arg Phe Phe Asn Lys Phe Pro
1 5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 20

Pro Arg Phe Phe Asn His Phe Pro
1 5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 21

Pro Arg Phe Phe Asn Phe Phe Pro
1 5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 22

Pro Arg Phe Phe Asn Ser Phe Pro
1 5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)

<223> OTHER INFORMATION: DPro

<400> SEQUENCE: 23

Pro Arg Phe Phe Asn Leu Phe Pro
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 24

Pro Arg Phe Phe Asn Gly Phe Pro
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 25

Pro Arg Phe Phe Asn Ala Ala Pro
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (8)..(8)
<223> OTHER INFORMATION: DPro

<400> SEQUENCE: 26

Pro Arg Phe Phe Asn Ala Phe Pro
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 27

Pro Arg Phe Phe Asn Ala Phe Pro
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 28

Pro Arg Phe Phe Asn Ala Phe Pro
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 29

Pro Arg Phe Phe Asn Ala Phe Pro
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 30

Pro Arg Phe Phe Asn Ala Phe Pro
1 5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 31

Pro Arg Phe Phe Asn Ala Phe Pro
1 5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 32

Pro Arg Phe Phe Asn Ala Phe Pro
1 5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 33

Pro Arg Phe Phe Xaa Ala Phe Pro
1 5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 34

Pro Arg Phe Phe Xaa Ala Phe Pro
1 5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 35

Pro Arg Phe Phe Xaa Ala Phe Pro
1 5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:

<221> NAME/KEY: MOD_RES
<222> LOCATION: (8)..(8)
<223> OTHER INFORMATION: DPro

<400> SEQUENCE: 36

Pro Arg Phe Phe Xaa Ala Phe Pro
1 5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 37

Pro Arg Phe Phe Xaa Ala Phe Pro
1 5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 38

Pro Arg Phe Phe Xaa Ala Phe Pro
1 5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 39

Pro Arg Phe Phe Xaa Ala Phe Pro
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 40

Pro Arg Phe Phe Asn Ala Gly Pro
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 41

Pro Arg Phe Phe Asn Ala Ser Pro
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 42

Pro Arg Phe Phe Asn Ala Lys Pro
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 43

Pro Arg Phe Phe Asn Ala Asp Pro
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 44

Pro Arg Phe Phe Asn Ala Leu Pro
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 45

Pro Arg Phe Phe Asn Ala Leu Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 46

Pro Arg Phe Phe Asn Ala Trp Pro
1               5

<210> SEQ ID NO 47
<211> LENGTH: 8
<212> TYPE: PRT

<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 47

Pro Arg Phe Phe Asn Ala Tyr Pro
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (8)..(8)
<223> OTHER INFORMATION: DPro

<400> SEQUENCE: 48

Pro Arg Phe Phe Asn Ala Xaa Pro
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 49

Pro Arg Phe Phe Asn Ala Phe Pro
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 50

Pro Arg Phe Phe Asn Ser Leu Pro
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 51

Pro Arg Phe Phe Xaa Ala Leu Pro
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 52

Pro Arg Phe Phe Xaa Ser Phe Pro
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 53

Pro Arg Phe Phe Xaa Ser Leu Pro
1               5

<210> SEQ ID NO 54
<211> LENGTH: 8
<212> TYPE: PRT

<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 54

Pro Arg Phe Phe Arg Ala Phe Pro
1 5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 55

Pro Arg Phe Phe Arg Ala Leu Pro
1 5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 56

Pro Arg Phe Phe Arg Ser Phe Pro
1 5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 57

Pro Arg Phe Phe Arg Ser Leu Pro
1 5

<210> SEQ ID NO 58
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 58

Pro Arg Phe Phe Asn Ala Leu Pro
1               5


<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 59

Pro Arg Phe Phe Asn Ser Phe Pro
1               5


<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 60

Pro Arg Phe Phe Asn Ser Leu Pro
1               5


<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 61

Pro Arg Phe Phe Xaa Ala Phe Pro
1               5


<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 62

Pro Arg Phe Phe Xaa Ala Leu Pro
1               5


<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 63

Pro Arg Phe Phe Xaa Ser Phe Pro
1               5


<210> SEQ ID NO 64
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 64

Pro Arg Phe Phe Xaa Ser Leu Pro
1               5


<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 65

Pro Arg Phe Phe Arg Ala Phe Pro
1               5


<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 66

Pro Arg Phe Phe Arg Ala Leu Pro
1               5


<210> SEQ ID NO 67
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 67

Pro Arg Phe Phe Arg Ser Phe Pro
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 68

Pro Arg Phe Phe Arg Ser Leu Pro
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Abu
<220> FEATURE:
<221> NAME/KEY: MOD_RES
<222> LOCATION: (8)..(8)
<223> OTHER INFORMATION: DPro

<400> SEQUENCE: 69

Pro Arg Phe Phe Xaa Ala Phe Pro
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 70

Pro Arg Phe Phe Ser Ala Phe Pro
1 5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 71

Pro Arg Phe Phe Thr Ala Phe Pro
1 5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 72

Pro Arg Phe Phe Asp Ala Phe Pro
1 5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 73

Pro Arg Phe Phe Glu Ala Phe Pro
1 5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: DDap
<220> FEATURE:
<221> NAME/KEY: MOD_RES
<222> LOCATION: (8)..(8)
<223> OTHER INFORMATION: DPro

<400> SEQUENCE: 74

Pro Arg Phe Phe Xaa Ala Phe Pro
1 5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 75

Pro Arg Phe Phe His Ala Phe Pro
1 5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 76

Pro Arg Phe Phe Leu Ala Phe Pro
1 5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 77

Pro Arg Phe Phe Leu Ala Phe Pro
1 5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 78

Pro Arg Phe Phe Val Ala Phe Pro
1 5

<210> SEQ ID NO 79
<211> LENGTH: 8

<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 79

Pro Arg Phe Phe Phe Ala Phe Pro
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 80

Pro Arg Phe Phe Trp Ala Phe Pro
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 81

Pro Arg Phe Phe Asn Asp Phe Pro
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 82

Pro Arg Phe Phe Asn Glu Phe Pro
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 83

Pro Arg Phe Phe Asn Lys Phe Pro
1 5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 84

Pro Arg Phe Phe Asn His Phe Pro
1 5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 85

Pro Arg Phe Phe Asn Phe Phe Pro
1 5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 86

Pro Arg Phe Phe Asn Ser Phe Pro
1 5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 87

Pro Arg Phe Phe Asn Leu Phe Pro
1 5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 88

Pro Arg Phe Phe Asn Gly Phe Pro
1 5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 89

Pro Arg Phe Phe Asn Ala Ala Pro
1 5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (8)..(8)
<223> OTHER INFORMATION: DPro

<400> SEQUENCE: 90

Pro Arg Phe Phe Asn Ala Phe Pro
1 5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 91

Pro Arg Phe Phe Asn Ala Phe Pro 1 5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 92

Pro Arg Phe Phe Asn Ala Phe Pro
1 5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 93

Pro Arg Phe Phe Asn Ala Phe Pro
1 5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 94

Pro Arg Phe Phe Asn Ala Phe Pro
1 5

<210> SEQ ID NO 95
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 95

Pro Arg Phe Phe Asn Ala Phe Pro
1               5


<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (8)..(8)
<223> OTHER INFORMATION: DPro

<400> SEQUENCE: 96

Pro Arg Phe Phe Asn Ala Phe Pro
1               5


<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 97

Pro Arg Phe Phe Xaa Ala Phe Pro
1               5
```

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 98

Pro Arg Phe Phe Xaa Ala Phe Pro
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 99

Pro Arg Phe Phe Xaa Ala Phe Pro
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 100

```
Pro Arg Phe Phe Xaa Ala Phe Pro
1               5


<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 101

Pro Arg Phe Phe Xaa Ala Phe Pro
1               5


<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 102

Pro Arg Phe Phe Xaa Ala Phe Pro
1               5


<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DPhe
```

```
<220> FEATURE:
<221> NAME/KEY: MOD_RES
<222> LOCATION: (4)..(4)
<223> OTHER INFORMATION: DPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 103

Pro Arg Phe Phe Xaa Ala Phe Pro
1               5


<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 104

Pro Arg Phe Phe Asn Ala Gly Pro
1               5


<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 105

Pro Arg Phe Phe Asn Ala Ser Pro
1               5


<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: DPro

<400> SEQUENCE: 106

Pro Arg Phe Phe Asn Ala Lys Pro
1               5


<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
```

peptide
<220> FEATURE:
<221> NAME/KEY: MOD_RES
<222> LOCATION: (8)..(8)
<223> OTHER INFORMATION: DPro

<400> SEQUENCE: 107

Pro Arg Phe Phe Asn Ala Asp Pro
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 108

Pro Arg Phe Phe Asn Ala Leu Pro
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 109

Pro Arg Phe Phe Asn Ala Leu Pro
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 110

Pro Arg Phe Phe Asn Ala Trp Pro
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: DPro

<400> SEQUENCE: 111

Pro Arg Phe Phe Asn Ala Tyr Pro
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (8)..(8)
<223> OTHER INFORMATION: DPro

<400> SEQUENCE: 112

Pro Arg Phe Phe Asn Ala Xaa Pro
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 113

Pro Arg Phe Phe Asn Ala Phe Pro
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 114

Pro Arg Phe Phe Asn Ser Leu Pro
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 115

Pro Arg Phe Phe Xaa Ala Leu Pro
1 5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 116

Pro Arg Phe Phe Xaa Ser Phe Pro
1 5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 117

Pro Arg Phe Phe Xaa Ser Leu Pro
1 5

<210> SEQ ID NO 118

<400> SEQUENCE: 118

000

<210> SEQ ID NO 119
<211> LENGTH: 8

<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 119

Pro Arg Phe Phe Arg Ala Leu Pro
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: DPro

<400> SEQUENCE: 120

Pro Arg Phe Phe Arg Ser Phe Pro
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 121

Pro Arg Phe Phe Arg Ser Leu Pro
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 122

Pro Arg Phe Phe Asn Ala Leu Pro
1 5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 123

Pro Arg Phe Phe Asn Ser Phe Pro
1 5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 124

Pro Arg Phe Phe Asn Ser Leu Pro
1 5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 125

Pro Arg Phe Phe Xaa Ala Phe Pro
1 5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 126

Pro Arg Phe Phe Xaa Ala Leu Pro
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 127

Pro Arg Phe Phe Xaa Ser Phe Pro
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 128

Pro Arg Phe Phe Xaa Ser Leu Pro
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 129

Pro Arg Phe Phe Arg Ala Phe Pro
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 130

Pro Arg Phe Phe Arg Ala Leu Pro
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (8)..(8)
<223> OTHER INFORMATION: DPro

<400> SEQUENCE: 131

Pro Arg Phe Phe Arg Ser Phe Pro
1               5

```
<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: hPhe
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: DPro

<400> SEQUENCE: 132

Pro Arg Phe Phe Arg Ser Leu Pro
1               5


<210> SEQ ID NO 133
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DPhe

<400> SEQUENCE: 133

His Phe Arg Trp
1


<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
<222> LOCATION: (9)..(9)
<223> OTHER INFORMATION: DPro

<400> SEQUENCE: 134

Pro His Phe Arg Trp Asn Ala Phe Pro
1               5


<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DPhe
<220> FEATURE:
<221> NAME/KEY: MOD_RES
```

<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: DPro

<400> SEQUENCE: 135

Pro His Phe Arg Trp Xaa Ala Pro
1               5

<210> SEQ ID NO 136
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: DPhe

<400> SEQUENCE: 136

Ser Tyr Ser Leu Glu His Phe Arg Trp Gly Lys Pro Val
1               5                   10

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Asn or Dap
<220> FEATURE:
<221> NAME/KEY: MOD_RES
<222> LOCATION: (8)..(8)
<223> OTHER INFORMATION: DPro

<400> SEQUENCE: 137

Pro Arg Phe Phe Xaa Ala Phe Pro
1               5

<210> SEQ ID NO 138
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Asp Pro Ala Ala Thr Ala Tyr Cys Arg Phe Phe Asn Ala Phe Cys Tyr
1               5                   10                  15

Ala Arg Lys Leu
            20

<210> SEQ ID NO 139
<211> LENGTH: 8
<212> TYPE: PRT
<213> ORGANISM: Homo sapiens

<400> SEQUENCE: 139

Cys Arg Phe Phe Asn Ala Phe Cys
1               5

<210> SEQ ID NO 140
<211> LENGTH: 8
<212> TYPE: PRT
<213> ORGANISM: Mus sp.

<400> SEQUENCE: 140

Cys Arg Phe Phe Gly Ser Ala Cys
1               5

<210> SEQ ID NO 141
<211> LENGTH: 8
<212> TYPE: PRT
<213> ORGANISM: Homo sapiens

<400> SEQUENCE: 141

Cys Arg Phe Phe Arg Ser Ala Cys
1               5

<210> SEQ ID NO 142
<211> LENGTH: 10
<212> TYPE: PRT
<213> ORGANISM: Homo sapiens

<400> SEQUENCE: 142

Tyr Cys Arg Phe Phe Asn Ala Phe Cys Tyr
1               5                   10

<210> SEQ ID NO 143
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Thr Ala Tyr Cys Arg Phe Phe Asn Ala Phe Cys Tyr Ala Arg
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Tyr Cys Arg Phe Phe Asn Ala Phe Cys Tyr Ala Arg Lys Leu
1               5                   10

<210> SEQ ID NO 145
<211> LENGTH: 8
<212> TYPE: PRT
<213> ORGANISM: Unknown
<220> FEATURE:
<223> OTHER INFORMATION: Description of Unknown:
      AGRP peptide

<400> SEQUENCE: 145

Cys Arg Phe Phe Lys Ala Phe Cys
1               5

<210> SEQ ID NO 146
<211> LENGTH: 8
<212> TYPE: PRT
<213> ORGANISM: Unknown
<220> FEATURE:
<223> OTHER INFORMATION: Description of Unknown:
AGRP peptide

<400> SEQUENCE: 146

Cys Arg Phe Phe Asn Ser Phe Cys
1 5

<210> SEQ ID NO 147
<211> LENGTH: 8
<212> TYPE: PRT
<213> ORGANISM: Unknown
<220> FEATURE:
<223> OTHER INFORMATION: Description of Unknown:
AGRP peptide

<400> SEQUENCE: 147

Cys Arg Phe Phe Asn Thr Phe Cys
1 5

<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

His Phe Arg Trp
1

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Dap

<400> SEQUENCE: 149

Tyr Xaa Arg Phe Phe Asn Ala Phe Asp Tyr
1 5 10

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Arg Phe Phe Asn Ala Phe
1 5

<210> SEQ ID NO 151
<211> LENGTH: 8
<212> TYPE: PRT

<213> ORGANISM: Artificial Sequence
<220> FEATURE:
<223> OTHER INFORMATION: Description of Artificial Sequence: Synthetic peptide

<400> SEQUENCE: 151

Cys Arg Phe Phe Asn Ala Phe Cys
1 5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Ser Arg Phe Phe Asn Ala Phe Ser
1 5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: DNal(2')

<400> SEQUENCE: 153

Leu Asp His Xaa Arg Trp Lys
1 5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Cys Arg Phe Phe Asn Ala Phe Cys
1 5

<210> SEQ ID NO 155
<211> LENGTH: 10
<212> TYPE: PRT
<213> ORGANISM: Homo sapiens

<400> SEQUENCE: 155

Tyr Cys Arg Phe Phe Asn Ala Phe Cys Tyr
1 5 10

<210> SEQ ID NO 156
<211> LENGTH: 10
<212> TYPE: PRT
<213> ORGANISM: Homo sapiens

<400> SEQUENCE: 156

```
Tyr Cys Arg Phe Phe Asn Ala Phe Cys Tyr
1               5                   10


<210> SEQ ID NO 157
<211> LENGTH: 132
<212> TYPE: PRT
<213> ORGANISM: Homo sapiens

<400> SEQUENCE: 157

Met Leu Thr Ala Ala Val Leu Ser Cys Ala Leu Leu Leu Ala Leu Pro
1               5                   10                  15

Ala Thr Arg Gly Ala Gln Met Gly Leu Ala Pro Met Glu Gly Ile Arg
            20                  25                  30

Arg Pro Asp Gln Ala Leu Leu Pro Glu Leu Pro Gly Leu Gly Leu Arg
        35                  40                  45

Ala Pro Leu Lys Lys Thr Thr Ala Glu Gln Ala Glu Glu Asp Leu Leu
    50                  55                  60

Gln Glu Ala Gln Ala Leu Ala Glu Val Leu Asp Leu Gln Asp Arg Glu
65                  70                  75                  80

Pro Arg Ser Ser Arg Arg Cys Val Arg Leu His Glu Ser Cys Leu Gly
                85                  90                  95

Gln Gln Val Pro Cys Cys Asp Pro Cys Ala Thr Cys Tyr Cys Arg Phe
            100                 105                 110

Phe Asn Ala Phe Cys Tyr Cys Arg Lys Leu Gly Thr Ala Met Asn Pro
        115                 120                 125

Cys Ser Arg Thr
    130


<210> SEQ ID NO 158
<211> LENGTH: 132
<212> TYPE: PRT
<213> ORGANISM: Homo sapiens

<400> SEQUENCE: 158

Met Asp Val Thr Arg Leu Leu Leu Ala Thr Leu Leu Val Phe Leu Cys
1               5                   10                  15

Phe Phe Thr Ala Asn Ser His Leu Pro Pro Glu Glu Lys Leu Arg Asp
            20                  25                  30

Asp Arg Ser Leu Arg Ser Asn Ser Ser Val Asn Leu Leu Asp Val Pro
        35                  40                  45

Ser Val Ser Ile Val Ala Leu Asn Lys Lys Ser Lys Gln Ile Gly Arg
    50                  55                  60

Lys Ala Ala Glu Lys Lys Arg Ser Ser Lys Lys Glu Ala Ser Met Lys
65                  70                  75                  80

Lys Val Val Arg Pro Arg Thr Pro Leu Ser Ala Pro Cys Val Ala Thr
                85                  90                  95

Arg Asn Ser Cys Lys Pro Pro Ala Pro Ala Cys Cys Asp Pro Cys Ala
            100                 105                 110

Ser Cys Gln Cys Arg Phe Phe Arg Ser Ala Cys Ser Cys Arg Val Leu
        115                 120                 125

Ser Leu Asn Cys
    130


<210> SEQ ID NO 159
<211> LENGTH: 8
<212> TYPE: PRT
<213> ORGANISM: Mus sp.
```

<400> SEQUENCE: 159

Cys Arg Phe Phe Asn Ala Phe Cys
1 5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Phe, Nal(1'), Nal(2'), hPhe, Bip, Tic, Phg or Anc
<220> FEATURE:
<221> NAME/KEY: MOD_RES
<222> LOCATION: (4)..(4)
<223> OTHER INFORMATION: Phe, hPhe, Nal(1'), Nal(2'), Bip, Phg, Tic or Anc
<220> FEATURE:
<221> NAME/KEY: MOD_RES
<222> LOCATION: (5)..(5)
<223> OTHER INFORMATION: Asn, Gly, Dap, Dab, Orn, Lys, Arg, DDap, His, Ala, Abu, Ser, Thr, Asp, Glu, Nle, Leu, Val, Phe or Trp
<220> FEATURE:
<221> NAME/KEY: MOD_RES
<222> LOCATION: (6)..(6)
<223> OTHER INFORMATION: Ala, Ser, Gly, Leu, Phe, His, Lys, Asp or Glu
<220> FEATURE:
<221> NAME/KEY: MOD_RES
<222> LOCATION: (7)..(7)
<223> OTHER INFORMATION: Phe or Ala
<220> FEATURE:
<221> NAME/KEY: MOD_RES
<222> LOCATION: (8)..(8)
<223> OTHER INFORMATION: DPro

<400> SEQUENCE: 160

Pro Arg Xaa Xaa Xaa Xaa Xaa Pro
1 5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Phe, Gly, Ser, Lys, Asp, Leu, Nle, Trp, Tyr, Cha, hPhe or Ala
<220> FEATURE:
<221> NAME/KEY: MOD_RES
<222> LOCATION: (8)..(8)
<223> OTHER INFORMATION: DPro

<400> SEQUENCE: 161

Pro Arg Phe Phe Asn Ala Xaa Pro
1 5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES

```
<222> LOCATION: (3)..(3)
<223> OTHER INFORMATION: Phe, Nal(1'), Nal(2'), hPhe, Bip, Tic, Phg or
      Anc
<220> FEATURE:
<221> NAME/KEY: MOD_RES
<222> LOCATION: (4)..(4)
<223> OTHER INFORMATION: Phe, hPhe, Nal(1'), Nal(2'), Bip, Phg, Tic or
      Anc
<220> FEATURE:
<221> NAME/KEY: MOD_RES
<222> LOCATION: (5)..(5)
<223> OTHER INFORMATION: Asn, Gly, Dap, Dab, Orn, Lys, Arg, DDap, His,
      Ala, Abu, Ser, Thr, Asp, Glu, Nle, Leu, Val, Phe or Trp
<220> FEATURE:
<221> NAME/KEY: MOD_RES
<222> LOCATION: (6)..(6)
<223> OTHER INFORMATION: Ala, Ser, Gly, Leu, Phe, His, Lys, Asp or Glu
<220> FEATURE:
<221> NAME/KEY: MOD_RES
<222> LOCATION: (7)..(7)
<223> OTHER INFORMATION: Phe, Ala, Nle, Trp, Tyr, hPhe, Leu, Cha, Ser,
      Lys, Gly or Asp
<220> FEATURE:
<221> NAME/KEY: MOD_RES
<222> LOCATION: (8)..(8)
<223> OTHER INFORMATION: DPro

<400> SEQUENCE: 162

Pro Arg Xaa Xaa Xaa Xaa Xaa Pro
1               5


<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe or hPhe
<220> FEATURE:
<221> NAME/KEY: MOD_RES
<222> LOCATION: (5)..(5)
<223> OTHER INFORMATION: Asn, Arg or Dap
<220> FEATURE:
<221> NAME/KEY: MOD_RES
<222> LOCATION: (6)..(6)
<223> OTHER INFORMATION: Ala or Ser
<220> FEATURE:
<221> NAME/KEY: MOD_RES
<222> LOCATION: (7)..(7)
<223> OTHER INFORMATION: Phe or Nle
<220> FEATURE:
<221> NAME/KEY: MOD_RES
<222> LOCATION: (8)..(8)
<223> OTHER INFORMATION: DPro

<400> SEQUENCE: 163

Pro Arg Phe Xaa Xaa Xaa Xaa Pro
1               5
```

CYCLIC PEPTIDES AND METHODS OF USE THEREOF

CROSS-REFERENCE APPLICATIONS

This application claims priority to U.S. Provisional Application Ser. No. 62/764,884, filed Aug. 16, 2018. The entire content of the application referenced above is hereby incorporated by reference herein.

GOVERNMENT FUNDING

This invention was made with government support under F32 DK108402, R01 DK091906 and R01 DK064250 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Dec. 23, 2019, is named 09531_471US1_SL.txt and is 53,843 bytes in size.

BACKGROUND OF THE INVENTION

The melanocortin system has been associated with many physiological functions, including skin pigmentation, steroidogenesis, and energy homeostasis. Five melanocortin receptors have been identified to date that are members of the super-family of G protein-coupled receptors (GPCRs). The melanocortin receptors couple to $G_{\alpha s}$ protein subunits and increase intracellular levels of cAMP following agonist stimulation. Naturally occurring ligands for the receptor include peptide agonists derived from the proopiomelanocortin gene transcript and two endogenous antagonists, agouti and agouti-related protein (AGRP). While both the melanocortin-3 receptor (MC3R) and melanocortin-4 receptor (MC4R) have been implicated in food intake and energy homeostasis in mice, polymorphisms in the human MC4R have been directly linked to an obese phenotype. With the worldwide rate of obesity doubling between 1980 and 2014, investigating biological pathways, such as the MC4R associated with food intake and energy homeostasis, may result in new therapeutic agents for weight management.

Accordingly, there is a need for new ligands (e.g., selective ligands) for the melanocortin receptors, as well as for other receptors and ion channels that function within the same pathways as the melanocortin receptors (e.g, Kir7.1). In particular, there is a need for ligands that engage in the MC4R/Kir7.1 K+ ion channel pathway.

SUMMARY OF THE INVENTION

This invention provides new cyclic peptides, which may be used as, e.g., melanocortin ligands and Kir7.1 ligands. Accordingly, certain embodiments of the invention provide a cyclic compound of formula I:

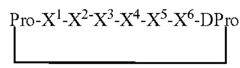

I wherein:

Pro is a residue of L-proline;

$X^1$ is a residue of Arg or DArg;

$X^2$ is a residue of Phe or DPhe;

$X^3$ is a residue of Phe, DPhe or hPhe;

$X^4$ is a residue of a natural or unnatural amino acid;

$X^5$ is a residue of Ala, Asp, Glu, Lys, His, Phe, Ser, Leu or Gly;

$X^6$ is a residue of Phe, Ala, Gly, Ser, Lys, Asp, Leu, Nle, Trp, Tyr, Cha or hPhe; and DPro is a residue of D-proline;

or a salt thereof.

The invention also provides a pharmaceutical composition comprising a compound as described herein (e.g., a compound of formula I), or a pharmaceutically acceptable salt thereof, and a pharmaceutically acceptable carrier.

The invention also provides a method of modulating the activity of a melanocortin receptor or a Kir7.1 ion channel in vitro or in vivo comprising contacting the receptor with an effective amount of a compound as described herein (e.g., a compound of formula I), or a pharmaceutically acceptable salt thereof.

The invention also provides method of modulating metabolic activity and/or modulating appetite in an animal in need thereof, comprising administering an effective amount of a compound as described herein (e.g., a compound of formula I), or a pharmaceutically acceptable salt thereof, to the animal.

The invention also provides a method for treating obesity or a disease associated with obesity in an animal (e.g., a mammal, such as a human) comprising administering a compound as described herein (e.g., a compound of formula I), or a pharmaceutically acceptable salt thereof to the animal.

The invention also provides a compound as described herein (e.g., a compound of formula I), or a pharmaceutically acceptable salt thereof for use in medical therapy.

The invention also provides a compound as described herein (e.g., a compound of formula I), or a pharmaceutically acceptable salt thereof for the prophylactic or therapeutic treatment of obesity or a disease associated with obesity.

The invention also provides the use of a compound as described herein (e.g., a compound of formula I), or a pharmaceutically acceptable salt thereof to prepare a medicament for treating obesity or a disease associated with obesity.

The invention also provides a cyclic peptide, or a salt thereof, as described herein.

The invention also provides a method of using a cyclic peptide, or a salt thereof, as described herein.

The invention also provides processes and intermediates disclosed herein that are useful for preparing a compound of formula I or a salt thereof.

BRIEF DESCRIPTION OF THE FIGURES

FIGS. 1A-1C. FIG. 1A) Sequence alignment of human ASP (SEQ ID NO: 158) and AGRP (SEQ ID NO: 157). The hypothesized Arg-Phe-Phe pharmacophore region is shown. The disulfide pairing is also indicated. FIG. 1B) Sequence alignment of the postulated active loop of human and mouse ASP and AGRP. The conserved Arg-Phe-Phe is shown. FIG. 1B discloses SEQ ID NOS 139, 159, 141 and 140, respectively, in order of appearance. FIG. 1C) NMR solution structures of human AGRP(87-132) (PDB=1HYK) (Bolin, et al. FEBS Lett. 1999, 451, 125-131) and human ASP(80-132: Q115Y, S124Y) (PDB=1Y7K) (McNulty, et al. J. Mol.

Biol. 2005, 346, 1059-1070). The β-hairpin loops are shown in the box. The Arg-Phe-Phe tripeptide side-chains are drawn to illustrate their similar positions within the structures.

Figure 2:
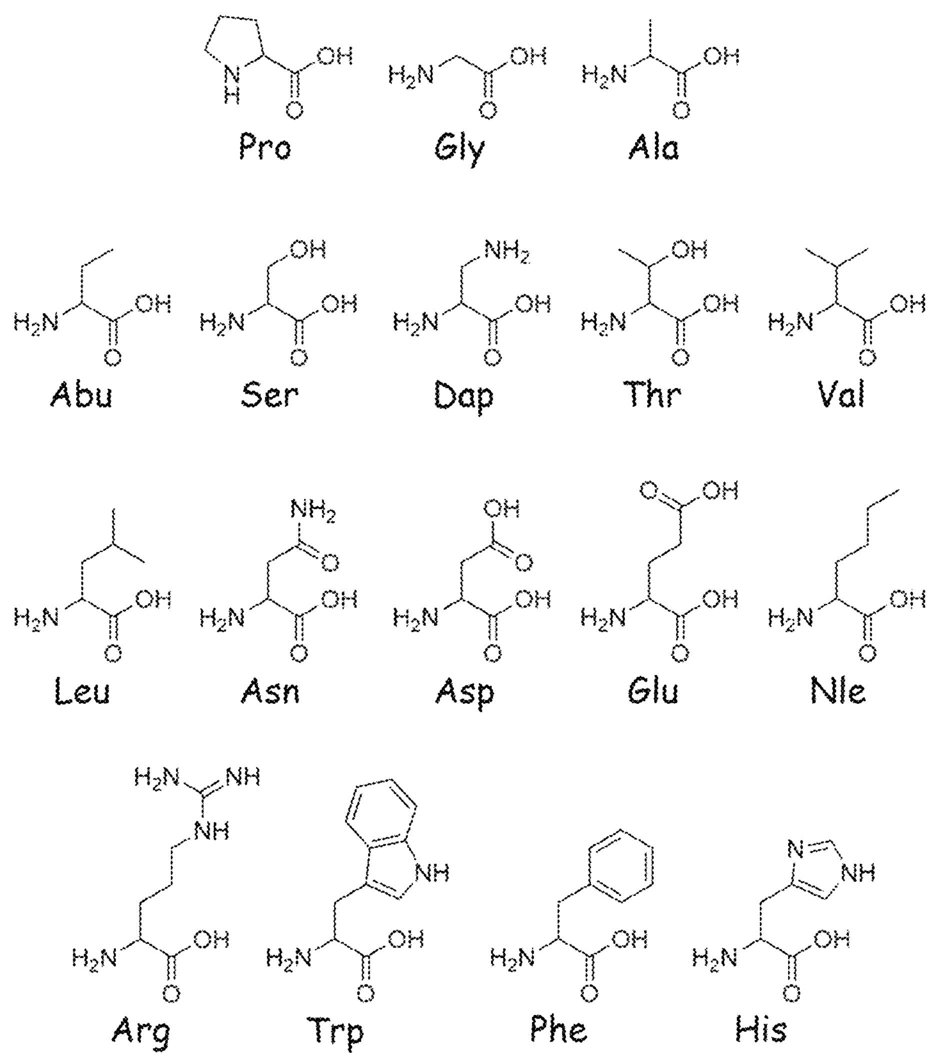

FIG. 2. Structures of the amino acids used in this study.

Figure 3:
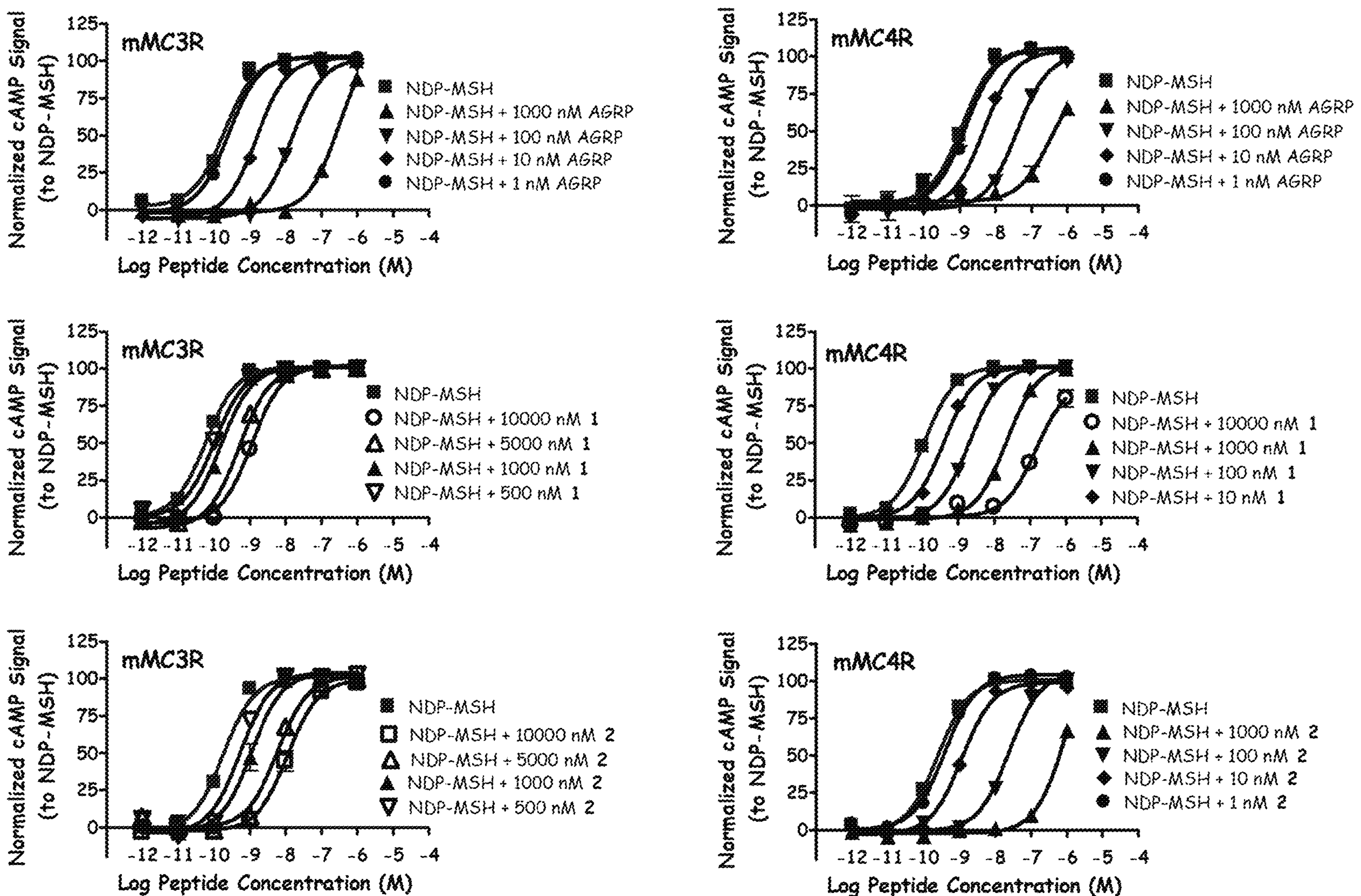
Figure 3:
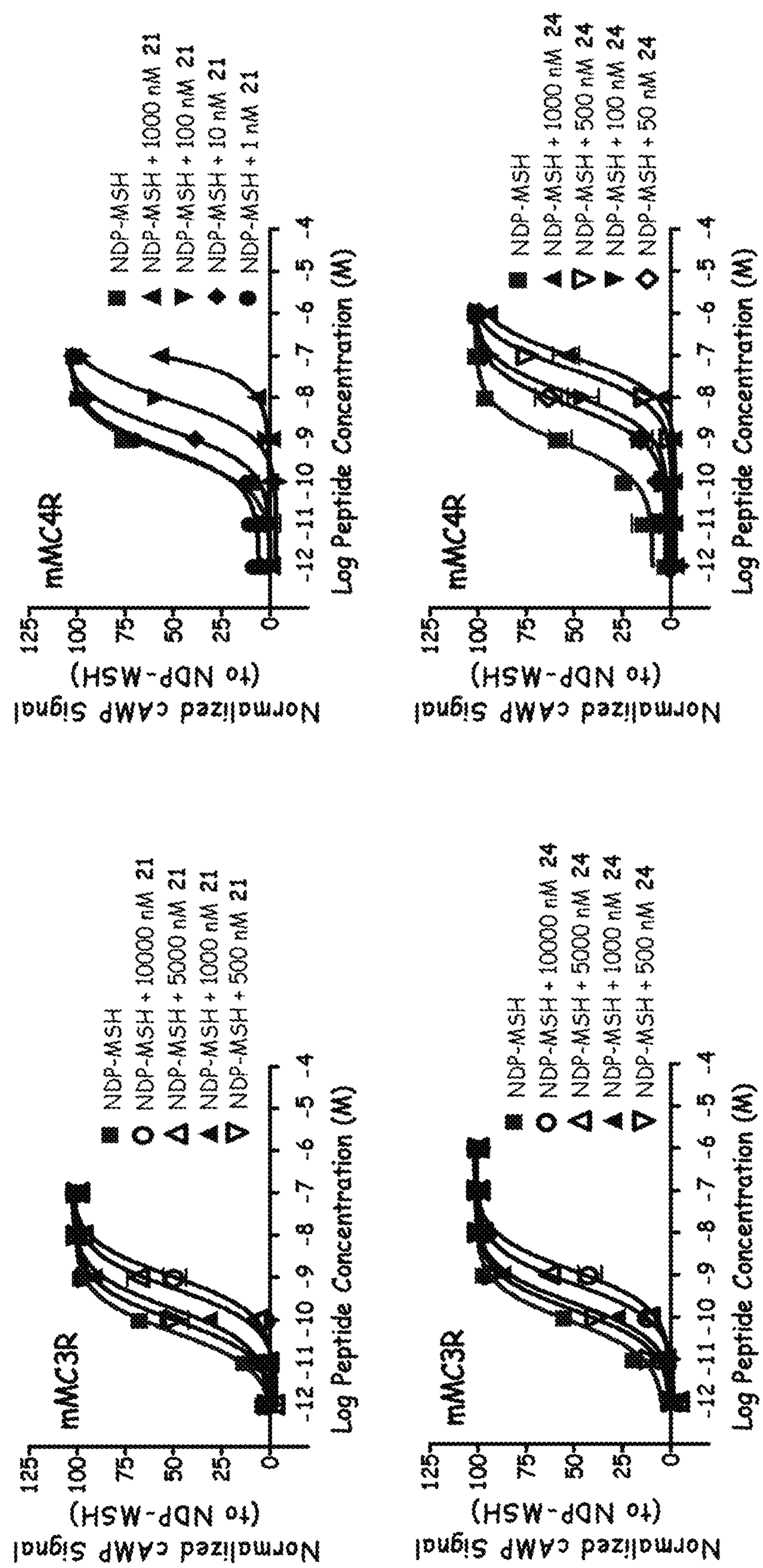

FIG. 3. Illustration of the antagonist pharmacology at the mMC3R and mMC4R for AGRP, 1, 2, 21, and 24, as described in Example 1.

Figure 4:
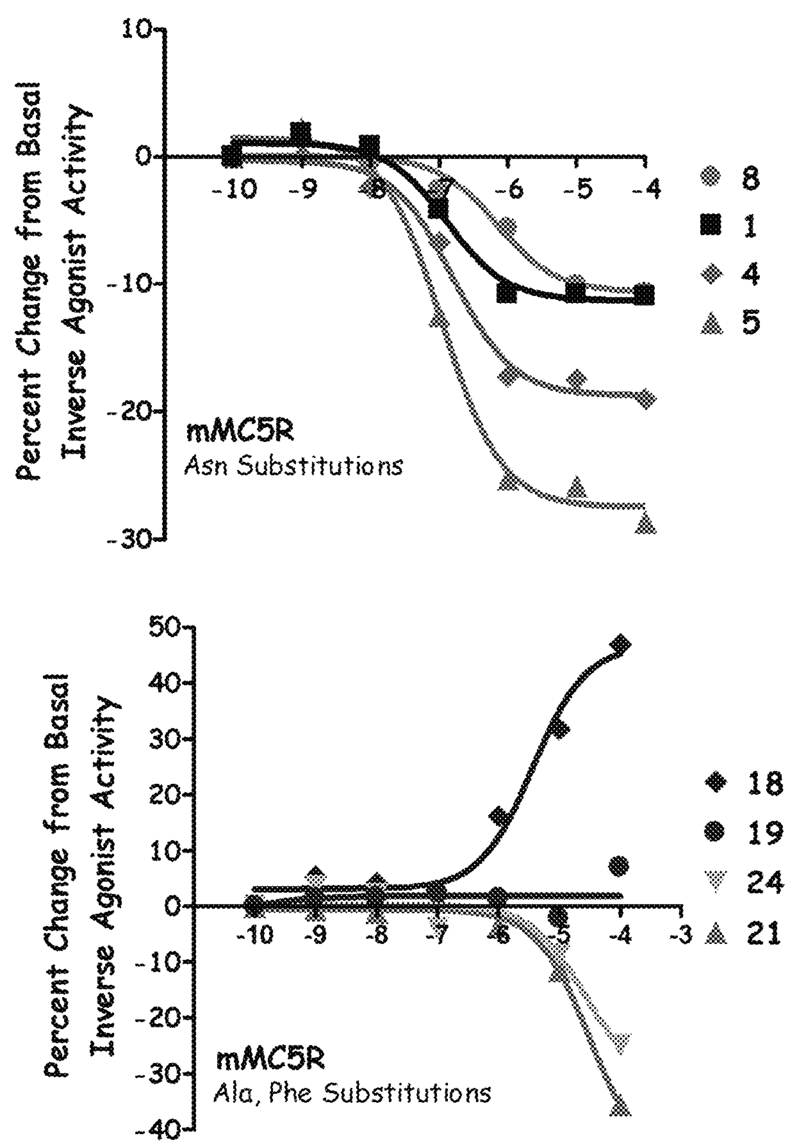

FIG. 4. Illustration of the pharmacology at the MC5R for 1, 4, 5, 8, 18, 19, 21, and 24, as described in Example 1.

Figure 5:
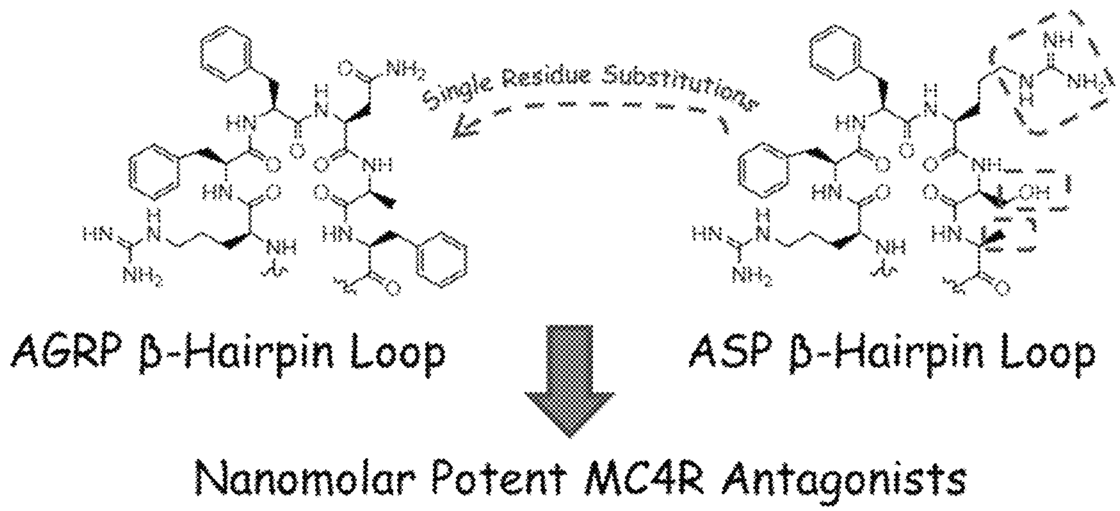

FIG. 5. Scheme for generating nanomolar potent MC4R antagonists.

Figure 6:
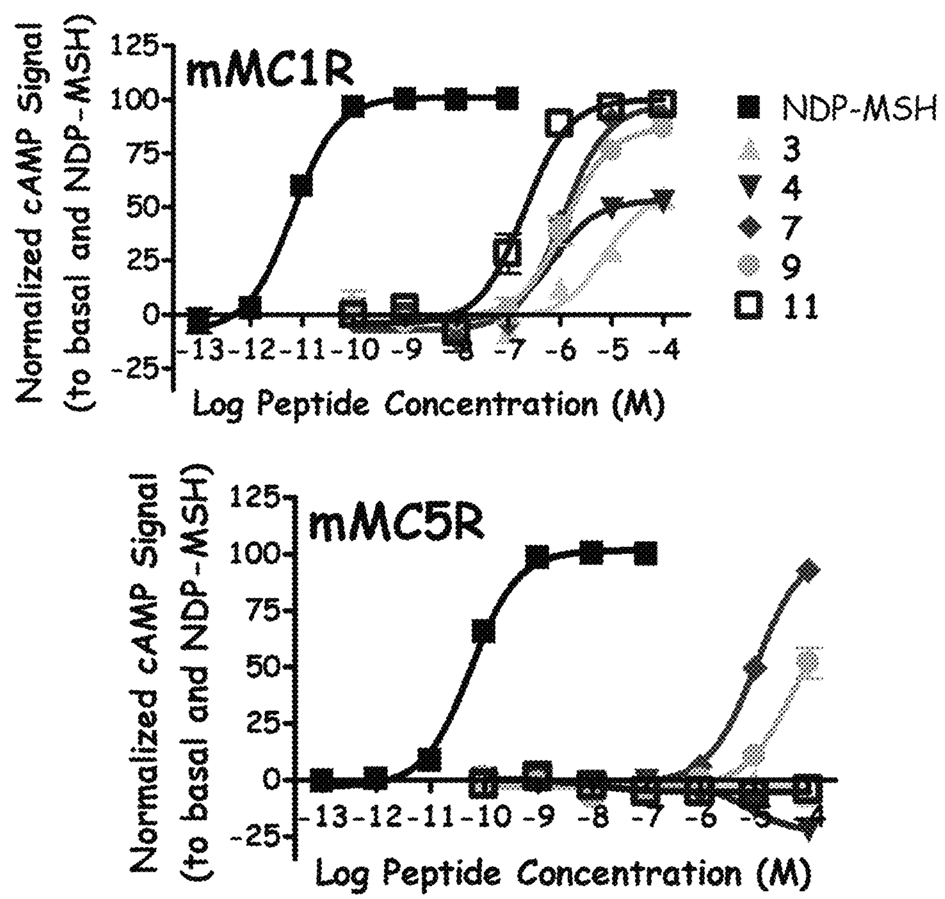

FIG. 6. Illustration of the normalized pharmacology of NDP-MSH and macrocyclic peptides 3, 4, 7, 9, and 11 at the mMC1R and MC5R (see, Example 2).

Figure 7:
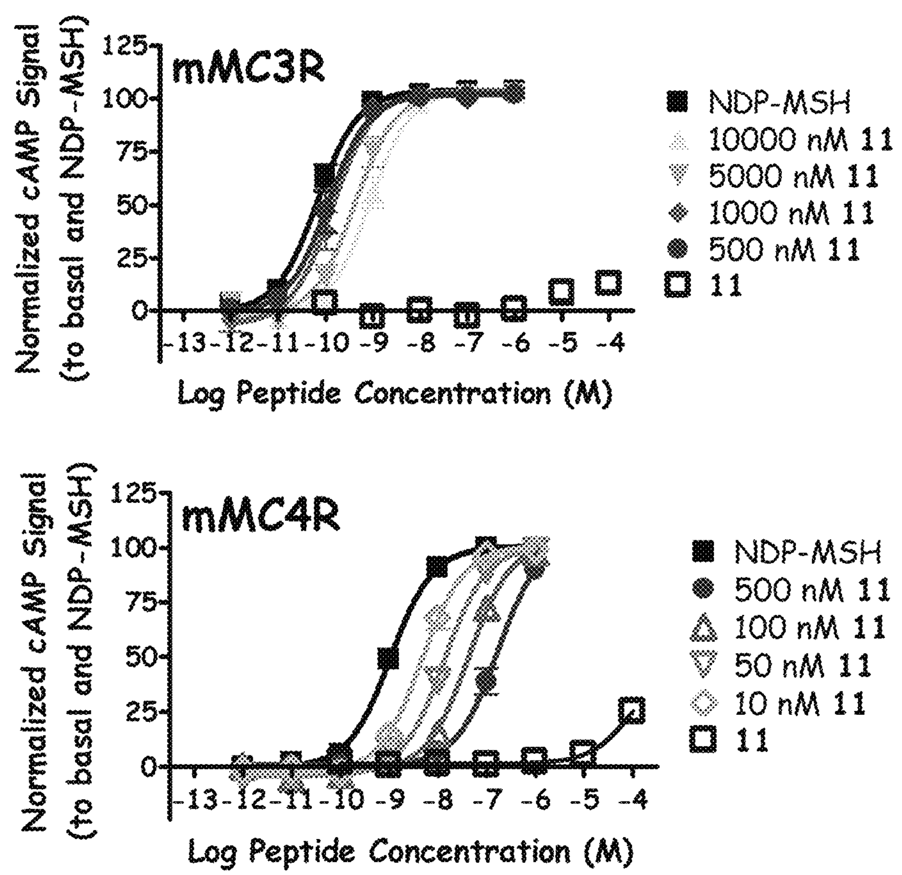

FIG. 7. Illustration of the normalized antagonist pharmacology of 11 at the mMC3R and mMC4R (see, Example 2).

FIG. 8. Normalized cAMP Signal.

Figure 9:
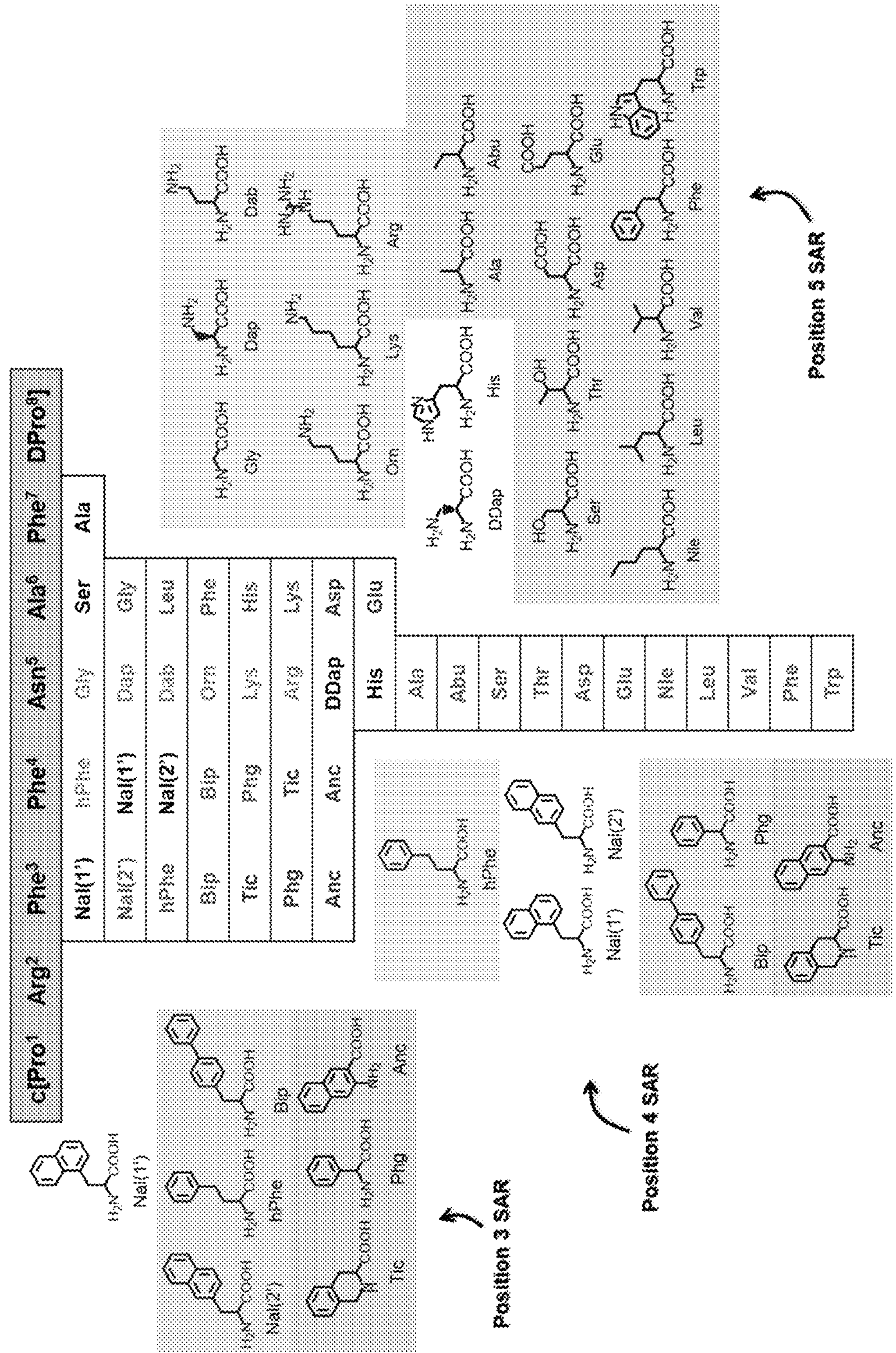

FIG. 9. Summary of the structure-activity relationship observed for this octapeptide scaffold at the mMC4R (see, Ericson, et al. (2015) J. Med. Chem. 58, 4638-4647; Ericson, et al. (2017) J. Med. Chem. 60, 8103-8114). In this figure, the sequence of the scaffold is shown in the bar at the top. Below each position is a listing of the different substitutions that have been tested at that position. The studies examining the $Phe^3$, $Phe^4$, and $Asn^5$ positions utilize unnatural amino acids, and the structures of the amino acids are provided. FIG. 9 discloses SEQ ID NO: 160.

Figure 10:
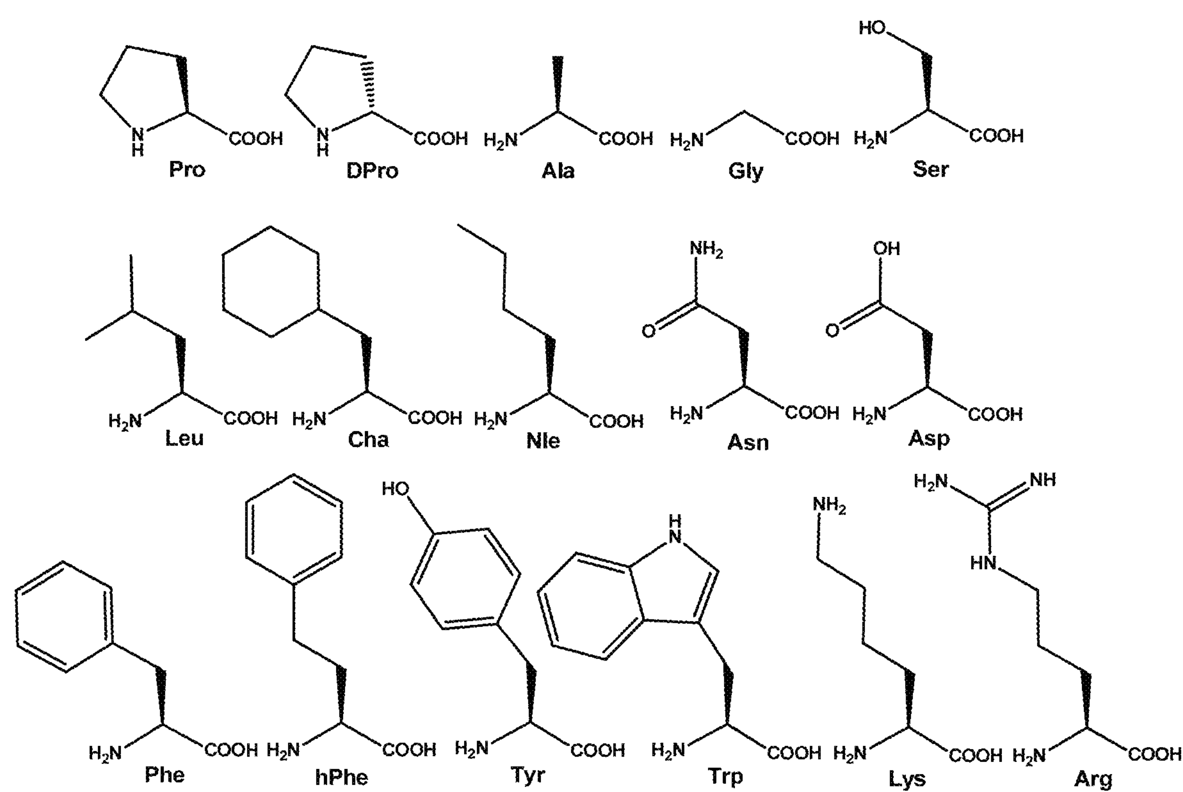

FIG. 10. Structures of the amino acids used in this study with three-letter amino acid abbreviations. The three-letter abbreviations for unnatural or uncommon amino acids are shown.

Figure 11:
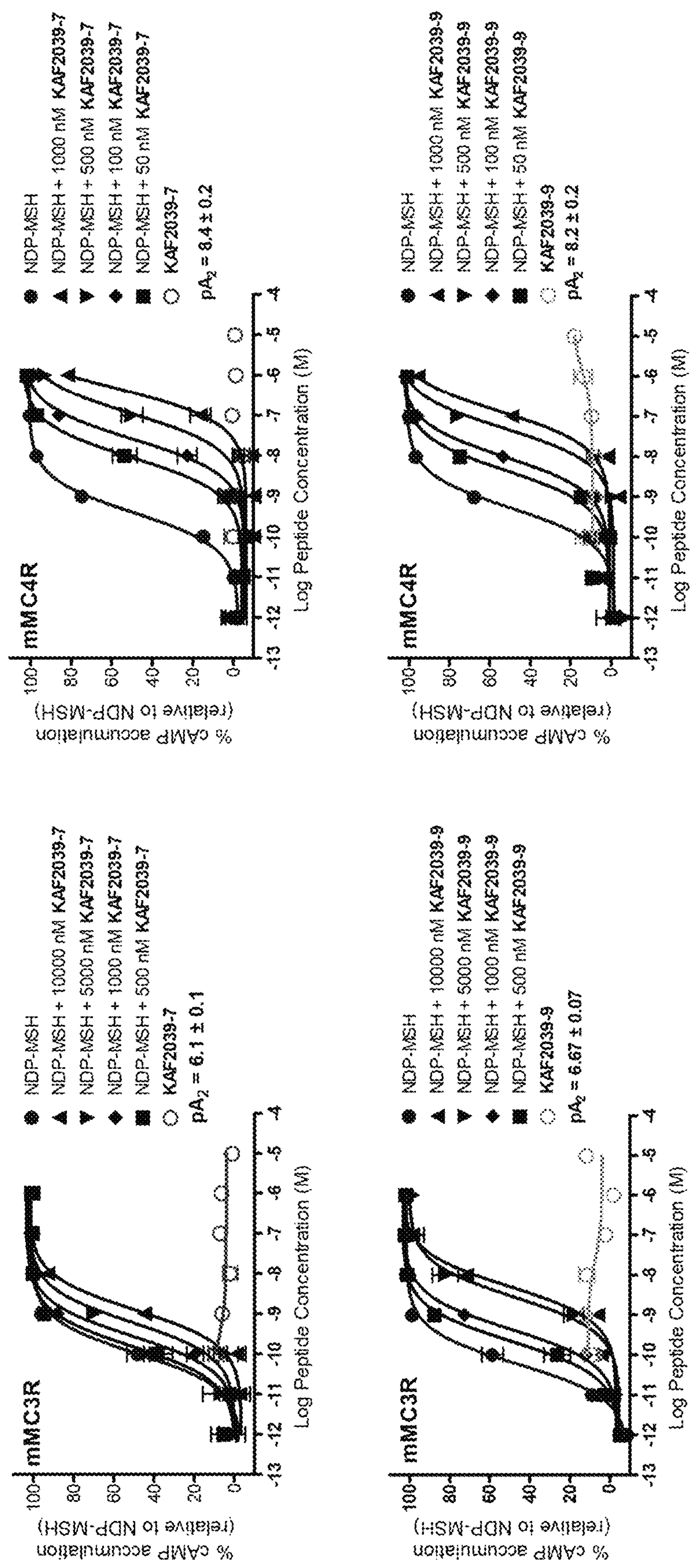
Figure 11:
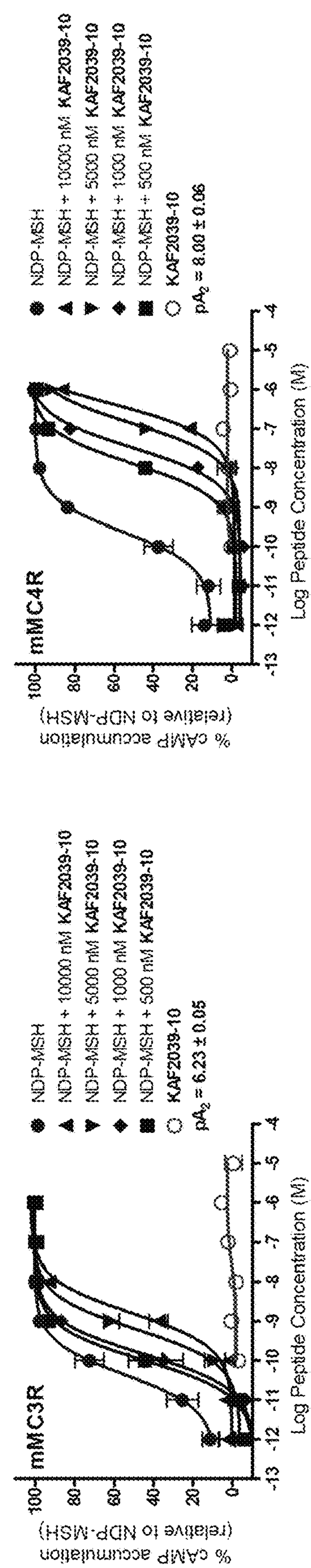

FIG. 11. Illustrations of the in vitro antagonist (mMC3R, mMC4R) pharmacology of 7, 8, and 9 (see. Example 3). A Schild antagonist experimental strategy was implemented using the agonist NDP-MSH. Data were normalized to an NDP-MSH response as previously described (Singh, et al. (2015) ACS Med. Chem. Lett. 6, 568-572; Ericson, et al. (2015) Bioorg. Med. Chem. Lett. 25, 5306-5308; Lensing, et al. (2016) J. Med. Chem. 59, 3112-3128).

Figure 12:
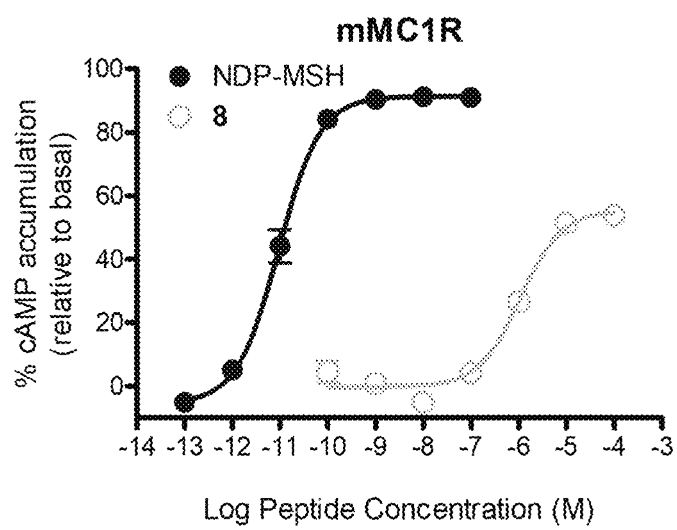

FIG. 12. Illustration of the in vitro partial agonist pharmacology of 8 at the mMC1R (see. Example 3). These data were normalized to an NDP-MSH response as previously described ((Singh, et al. (2015) ACS Med. Chem. Lett. 6, 568-572; Ericson, et al. (2015) Bioorg. Med. Chem. Lett. 25, 5306-5308; Lensing, et al. (2016) J. Med. Chem. 59, 3112-3128).

Figure 13:
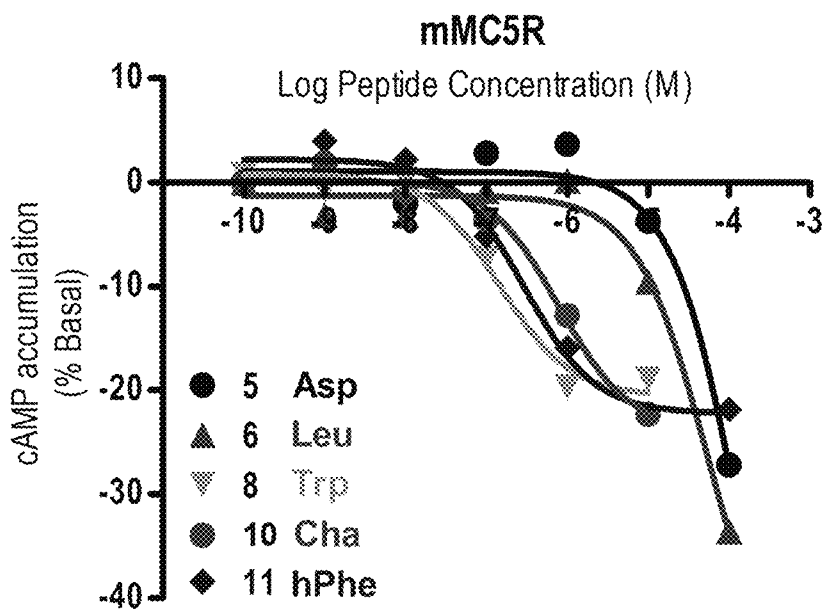

FIG. 13. Illustration of the in vitro inverse agonist pharmacology of 5, 6, 8, 10, 11 at the mMC5R (see. Example 3). The three-letter amino acid abbreviation for the amino acid in the $Phe^7$ position is provided. Two different pharmacological results were obtained from these studies. For some compounds, a sigmoidal dose-response curve was observed from which an apparent potency and percent cAMP accumulation change from basal can be calculated. Other compounds did not plateau, and for these compounds a percent cAMP accumulation change from basal at 100 μM concentrations is listed.

Figures 14A, 14B:
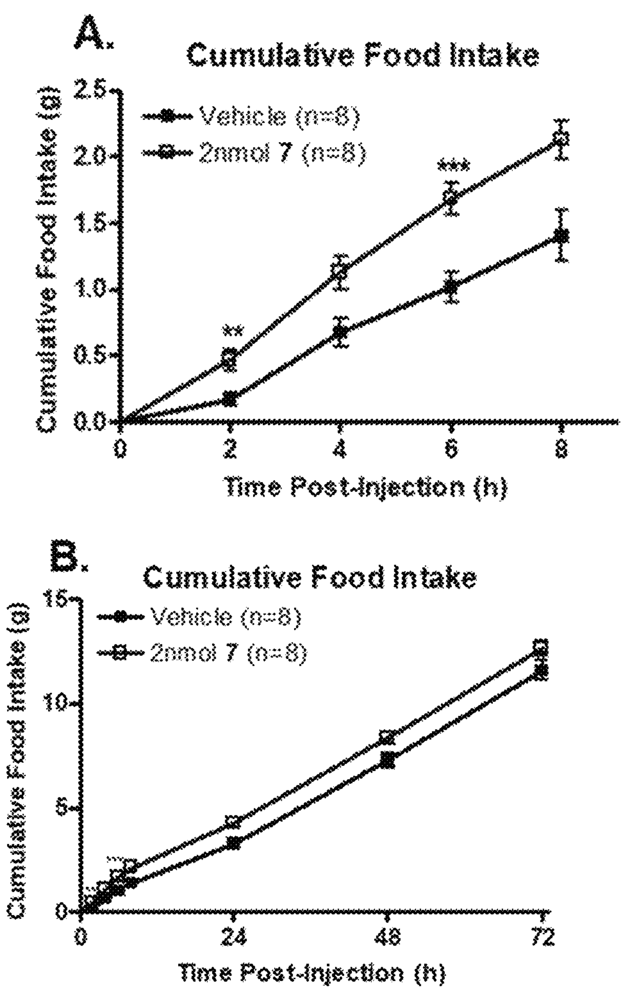

FIGS. 14A-14B. A stock of 7 was prepared using a 20% solutol solution (final concentration of 10 nmol/μL) (see, Example 3). On days of experimentation, the 7 stock was diluted using sterile $ddH_2O$ to the desired concentration of 2 nmol/5 μL. FIG. 14A. Cumulative food intake of male WT mice receiving 2 nmol 7 in 5 μL $ddH_2O$ vs. 5 μL of vehicle via IT injection. Male mice injected IT with 7 ate significantly more food t=2 h and 6 h post-injection than male mice injected with vehicle; p<0.01, *p<0.001. Data shown as mean±SEM. FIG. 14B. Cumulative food intake of male WT mice receiving 2 nmol 7 in 5 μL $ddH_2O$ vs. 5 μL of vehicle via cannula. Data shown as mean±SEM.

Figure 15:
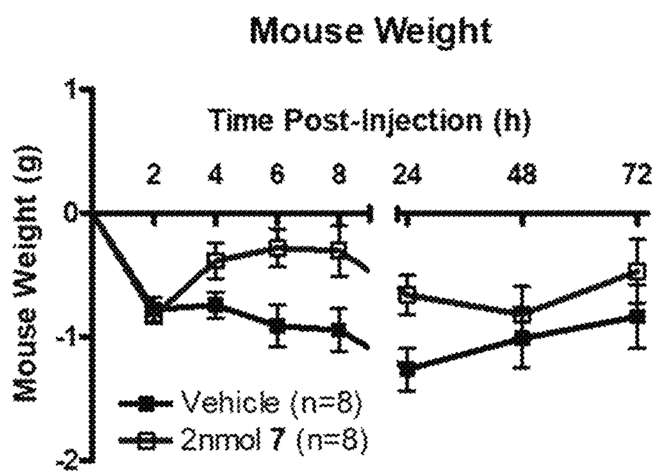

FIG. 15. A stock of 7 was prepared in 20% solutol to a final concentration of 10 nmol/μL (see, Example 3). On days of experimentation, the 7 stock was diluted using sterile $ddH_2O$ to the desired concentration of 2 nmol/5 μL. Difference in mouse weight from t=0 h of male WT mice receiving 2 nmol 7 in 5 μL $ddH_2O$ vs. 5 μL of vehicle via cannula. Data shown as mean±SEM.

Figure 16:
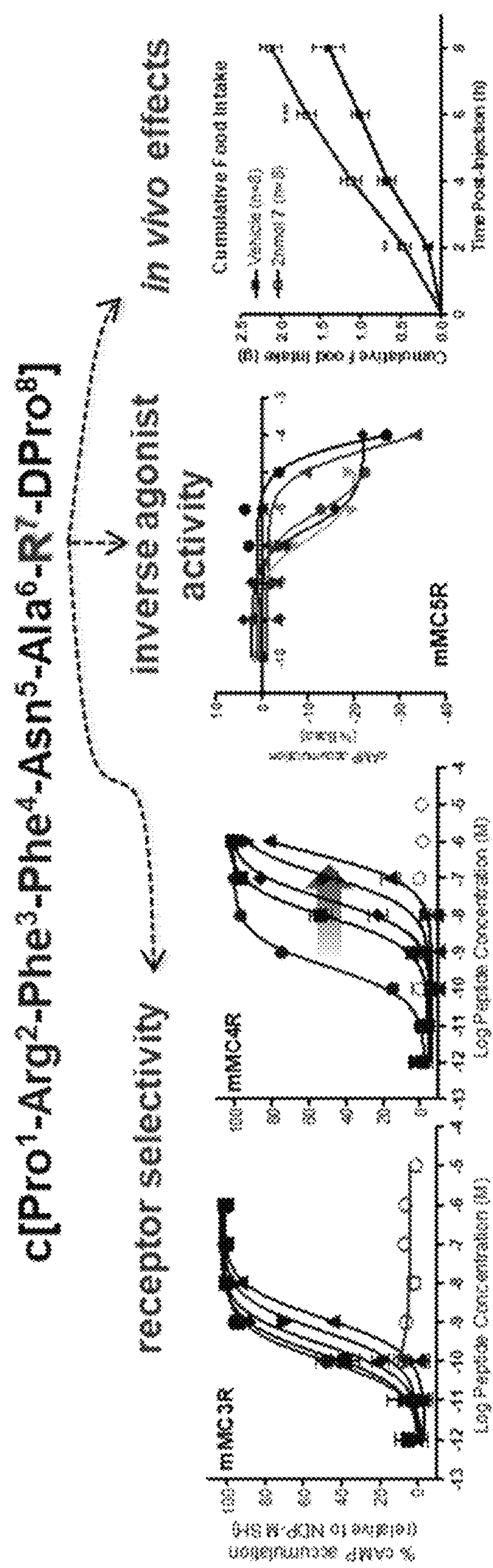

FIG. 16. Receptor selectivity, inverse agonist activity and in vivo effects. FIG. 16 discloses SEQ ID NO: 161.

Figure 17:
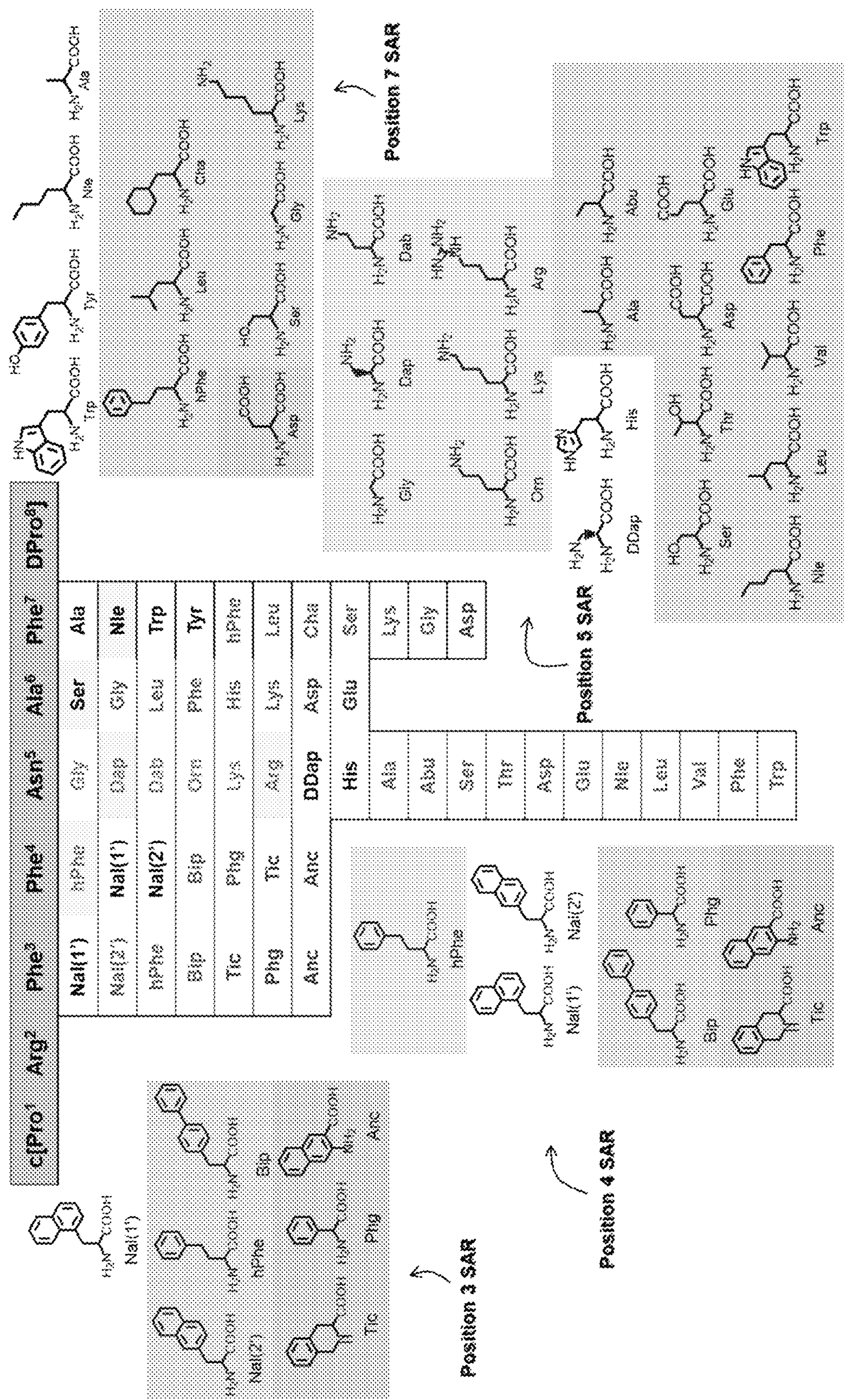

FIG. 17. Summary of the SAR observed for this macrocyclic peptide at mMC4R (Ericson, et al. J. Med. Chem. 2015, 58, 46384647; Ericson, et al. J. Med. Chem. 2017, 60, 8103-8114).[41-42] The core molecular scaffold is shown in the bar at the top, possessing the native AGRP active-loop sequence cyclized through a DPro-Pro motif Below each amino acid in the template is listed the individual substitutions that have been examined. The studies that examine the $Phe^3$, $Phe^4$, $Asn^5$, and $Phe^7$ positions utilize many unnatural amino acids, and the structures of the amino acids are provided. FIG. 17 discloses SEQ ID NO: 162.

Figure 18A:
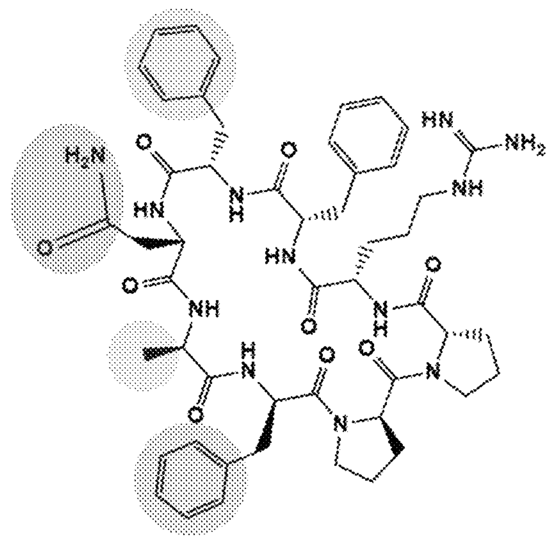
Figure 18B:
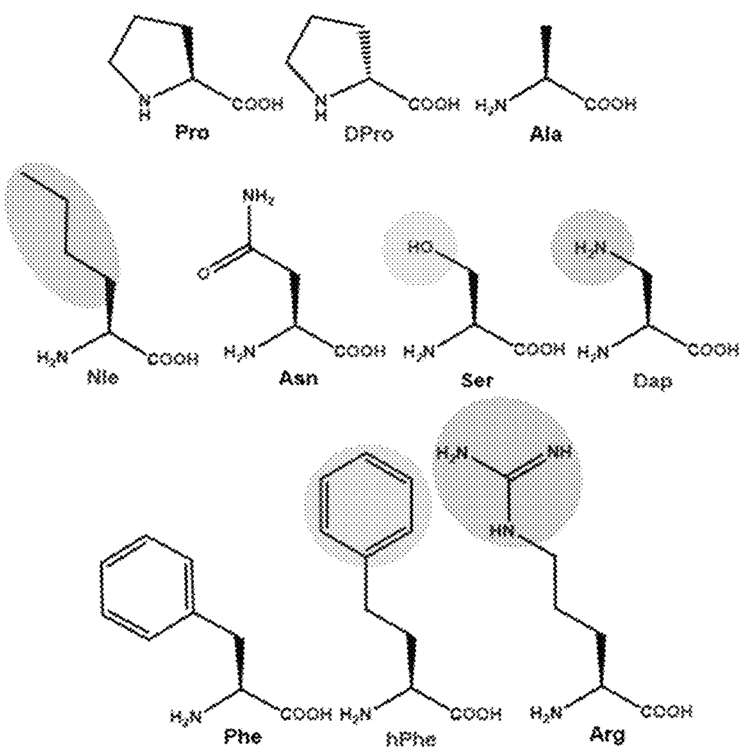

FIGS. 18A-18B. FIG. 18A) Structure of the core molecular scaffold used in these studies, c[Pro-Arg-Phe-Phe-Asn-Ala-Phe-DPro] (SEQ ID NO: 1). The positions modified in this study are highlighted by shading the side chains. FIG. 18B) Structures of the amino acids used in these studies. The abbreviations are listed below the structures of their corresponding amino acids, and the three letter abbreviations of unnatural amino acids are shown.

Figure 20:
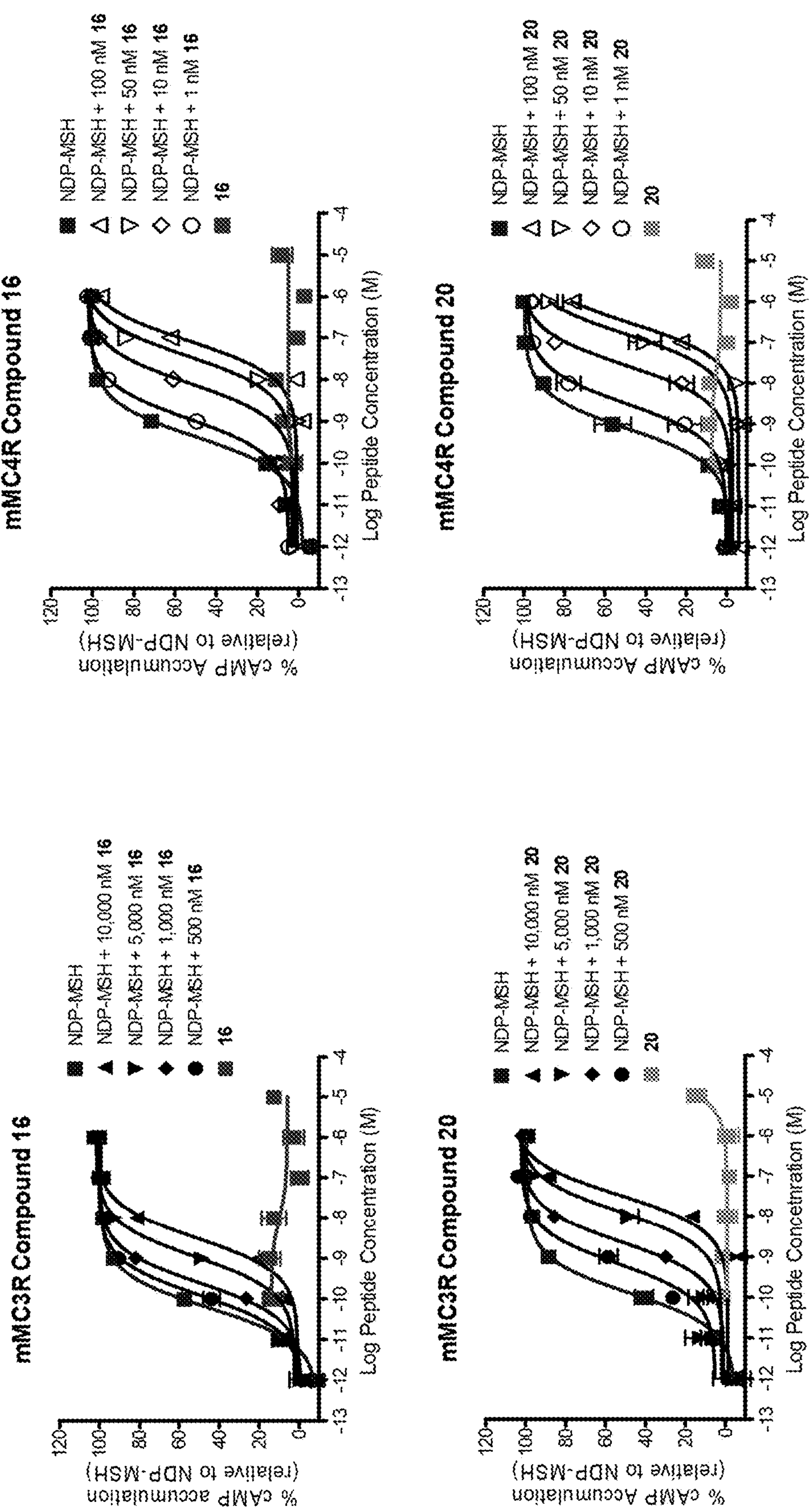
Figure 20:
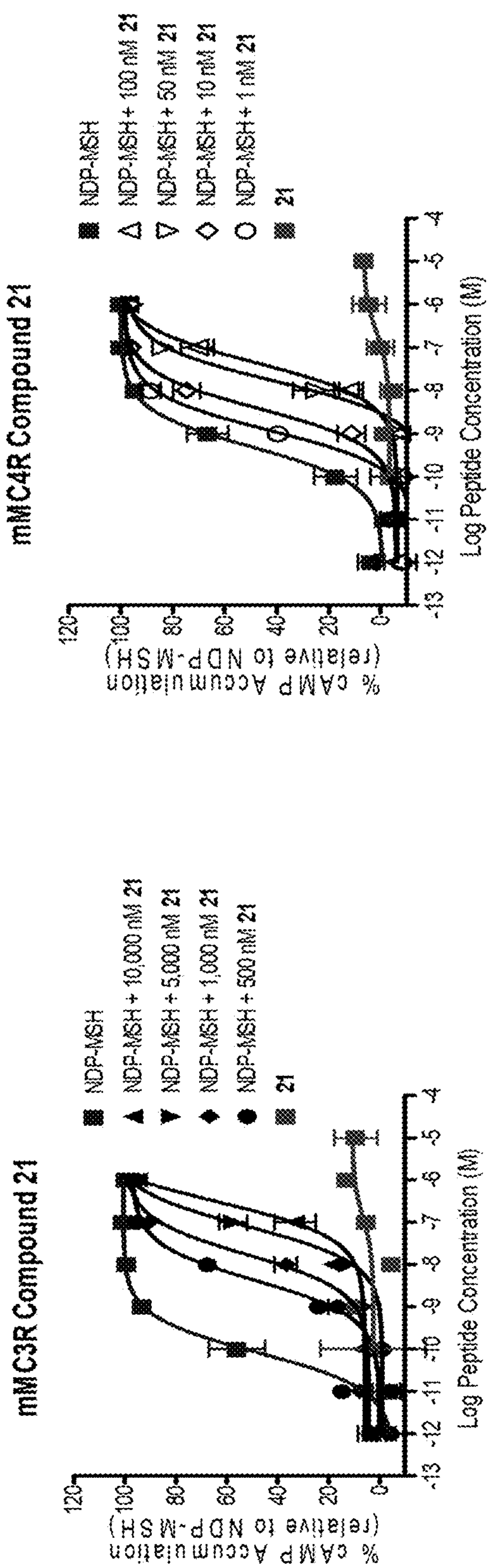

FIGS. 19A-19E. Structure activity relationship trends observed in the library discussed herein. FIG. 19A) Compound sequences and heat map of mMC3R potency. Changes from the core molecular scaffold are shown in grey. The most potent compounds are listed on top, and the least potent compounds are listed on the bottom. Trends observed in this set include the $hPhe^4/Arg^5$ motif, which increases mMC3R potency. FIG. 19A discloses SEQ ID NOS 65, 68, 67, 66, 55, 54, 2, 63, 51, 56, 61, 57, 52, 62, 64, 50, 45, 53, 59, 1, 60, 58, 22 and 3, respectively, in order of appearance. FIG. 19B) Compound sequences and heat map of mMC4R potency. Changes from the core molecular scaffold are shaded. The most potent compounds are listed on top, and the least potent compounds are listed on the bottom. Trends observed in this set include the high abundance of the $Ser^6/Nle^7$ motif in the most potent compounds in this set, and the increased prevalence of $hPhe^4$ in the most potent mMC4R compounds. Notably, the $hPhe^4/Arg^5$ motif is not grouped in this data set, indicating that while this motif increases mMC3R potency, it likely does not do so at the expense of mMC4R potency. FIG. 19B discloses SEQ ID NOS 57, 64, 68, 60, 63, 53, 55, 61, 62, 52, 51, 56, 65, 45, 2, 67, 66, 54, 58, 59, 50, 3, 1 and 22, respectively, in order of appearance. FIG. 19C) Compound sequences and heat map of mMC4R selectivity (calculated using antagonist $K_i$ values; $pA_2=-\log[K_i]$). Changes from the core molecular scaffold are shaded. The most selective compounds are listed on top, and the least selective compounds are listed on the bottom. Trends observed in this data set are that the $Nle^7$ substitution causes an increase in mMC4R selectivity, especially when combined with $Ser^6$. The compounds possessing the $Arg^5$ substitution are almost entirely grouped in the least selective compounds, as are compounds possessing the $hPhe^4/Arg^5$ motif, as discussed in the text. FIG. 19C discloses SEQ ID NOS 60, 64, 3, 53, 57, 62, 58, 45, 52, 59, 63, 61, 22, 51, 56, 50, 1, 2, 55, 68, 54, 66, 67 and 65, respectively, in order of appearance. FIG. 19D) Radar plot depicting the pharmacological profiles of compounds 16, 20, and 21 compared to 1 at the melanocortin receptors (see. Example 4). To fit these data on one chart, a log scale was used for potency values and the fold-selectivity for the mMC4R over the mMC3R was divided by 100. FIG. 19E) Radar plot depicting the pharmacological activity of compounds 16, 20, and 21 compared to 1 at the mMC3R and mMC4R. In this graph, $pA_2$ values were converted to nanomolar antagonist $K_i$ values ($pA_2$=−log[K]), and fold-selectivity for the mMC4R over the mMC3R is calculated using the $K_i$ values. FIG. 20. Illustrations of the in vitro antagonist (mMC3R, mMC4R) pharmacology of 16, 20, and 21 (see. Example 4). A Schild antagonist experimental strategy was implemented, using the agonist NDP-MSH (Schild, et al. Br. J. Pharmacol. Chemother. 1947, 120, 29-46). Data were normalized to NDP-MSH response, as previously described (Singh, et al. ACS Med. Chem. Lett. 2015, 6, 568-572; Ericson, et al. Bioorg. Med. Chem. Lett. 2015, 25, 5306-5308; Lensing, et al. J. Med. Chem. 2016, 59, 3112-3128).

Figure 21:
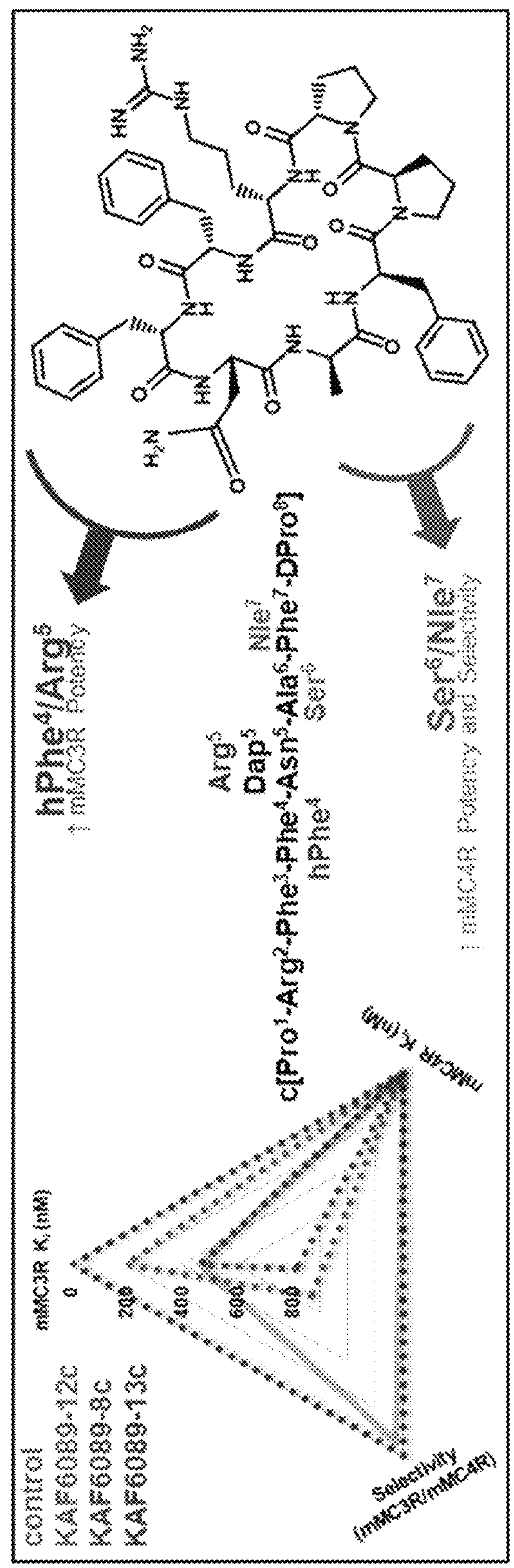

FIG. 21. Schematic showing mMC4R and mMC3R potency and selectivity. FIG. 21 discloses SEQ ID NO: 163.

Figure 22A:
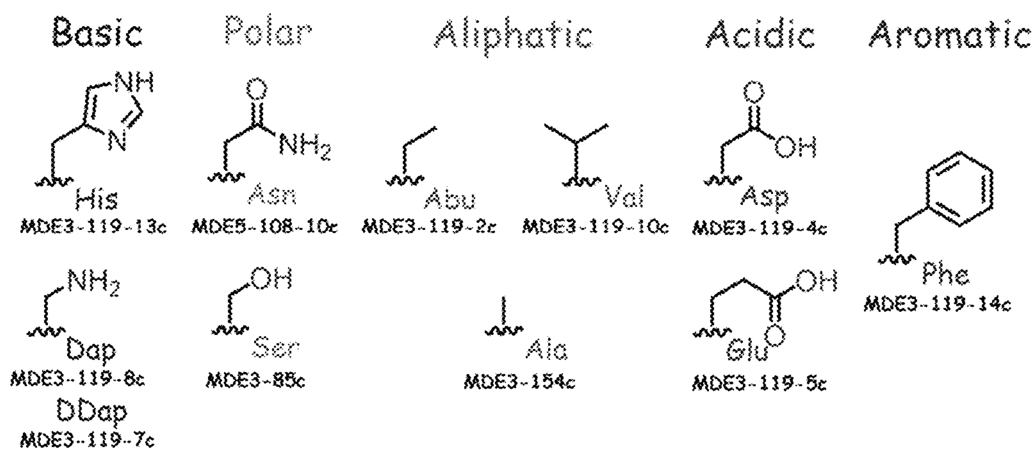
Figure 22B:
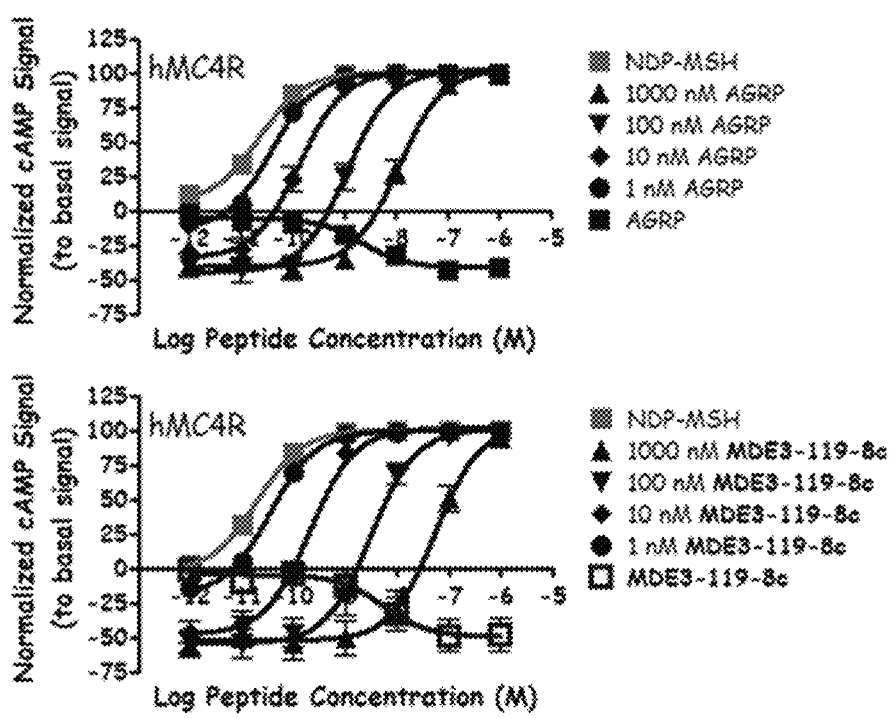
Figure 22C:
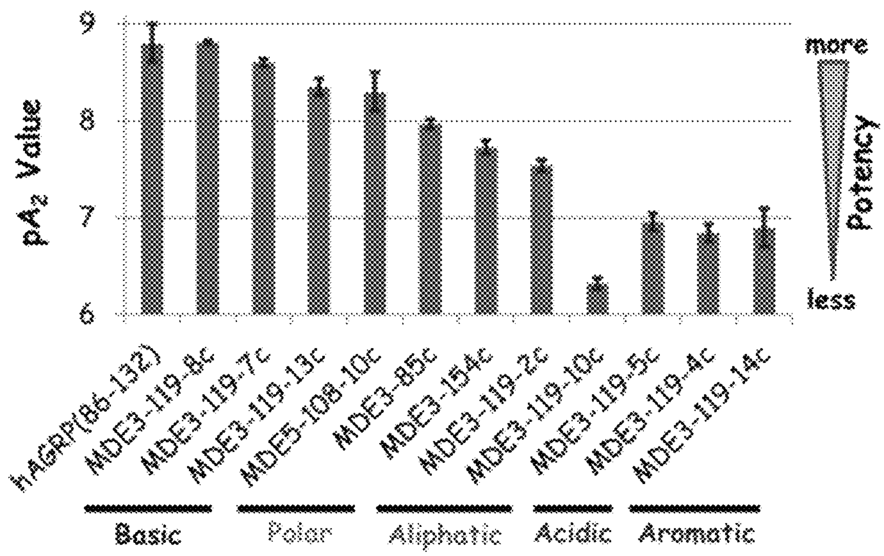

FIGS. 22A-22C. FIG. 22A) Structures of the amino acid side chains and corresponding compound number. FIG. 22B) Illustration of the antagonist and inverse agonist pharmacology for hAGRP(86-132) and MDE3-119-8c at the hMC4R. FIG. 22C) Antagonist potencies ($pA_2$ values) of ligands at the hMC4R. Error bars are SEM.

Figures 23A, 23B:
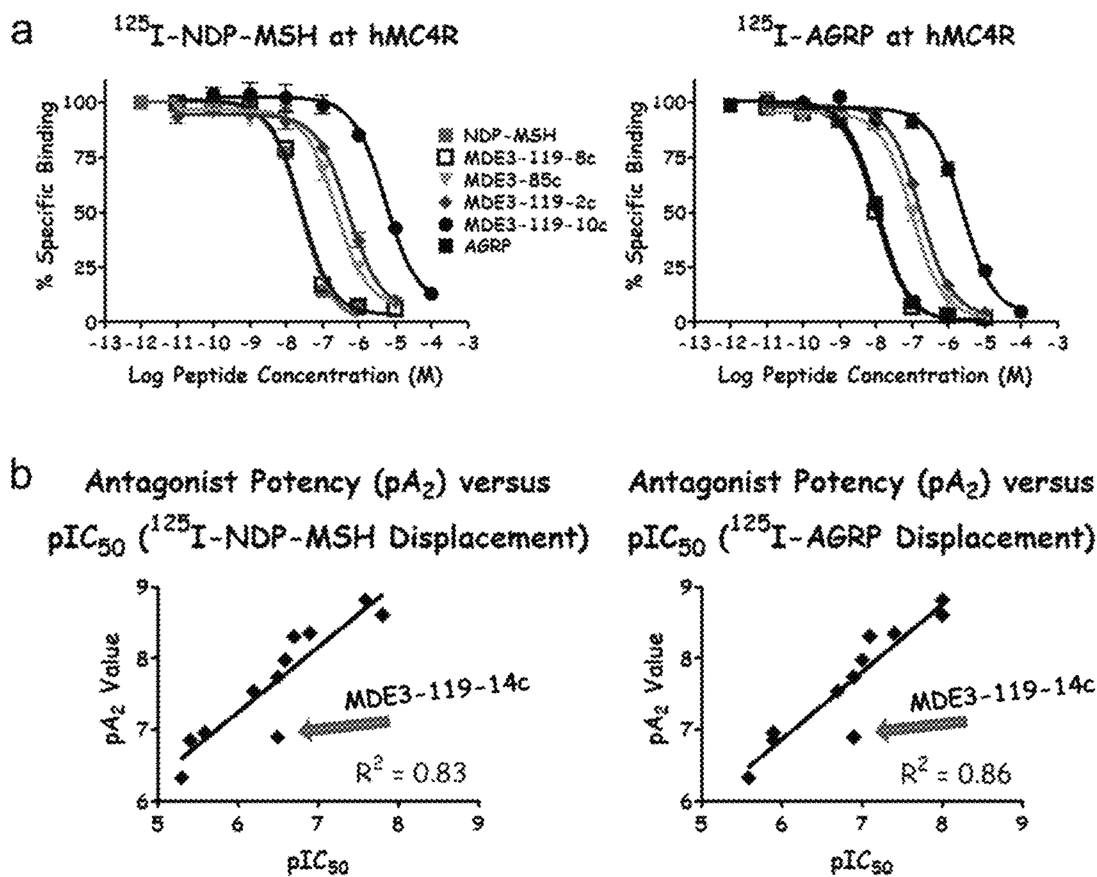

FIGS. 23A-23B. FIG. 23A) Illustration of radiolabeled displacement curves for NDP-MSH, AGRP, MDE3-119-8c, MDE3-85c, MDE3-119-2c, and MDE3-119-10c at the hMC4R. FIG. 23B) Correlation of $pIC_{50}$ (displacing $^{125}$I-NDP-MSH or $^{125}$I-AGRP) values versus $pA_2$ values for AGRP-derived macrocyclic ligands at the hMC4R. The arrows indicate ligand MDE3-119-14c.

Figures 24A, 24B:
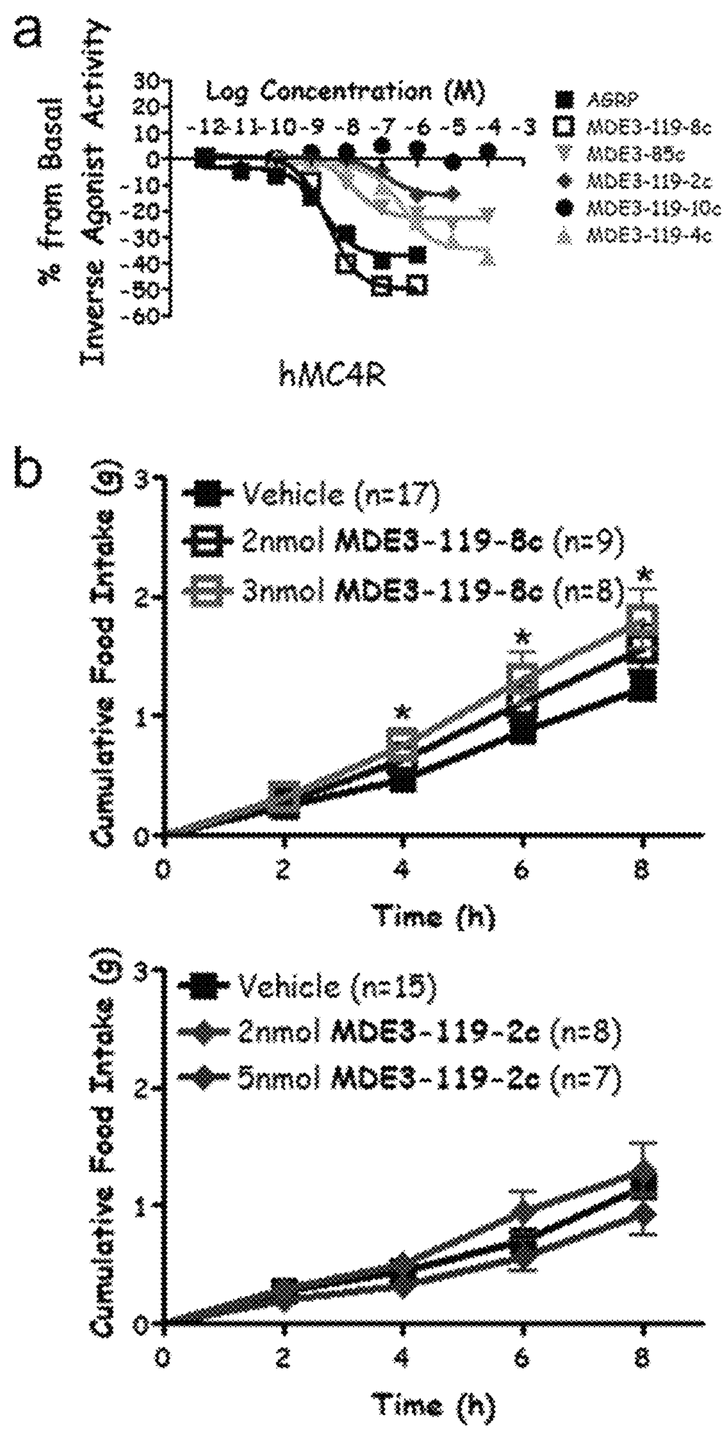

FIGS. 24A-24B. FIG. 24A) Illustration of the inverse agonist pharmacology for select ligands at the hMC4R FIG. 24B) Summary of acute food intake in free-feeding male mice following ICV administration of MDE3-119-8c and MDE3-119-2c. Mice ate significantly more food (* $p<0.05$) following 3 nmol dose of MDE3-119-8c ($pA_2$=8.8; inverse agonist efficacy=−50%) at 4, 6, and 8 h post-injection than vehicle treated mice. Administration of up to 5 nmol MDE3-119-2c ($pA_2$=7.5; inverse agonist efficacy=−15%) did not significantly affect food intake. Data are shown as mean±SEM.

FIGS. 25A-25B. FIG. 25A) Summary of the antagonist $K_i$ values derived from the cAMP AlphaScreen assay at the hMC4R [$pA_2$=−log($K_i$)], apparent potencies of the hMC4R-Kir7. (M125R) thallium flux assay, and the functional selectivity between the AlphaScreen cAMP assay and the hMC4R-Kir7.1(M125R) thallium flux assay. The Kir7.1 (M125R) variant was previously used due to the higher unitary conductance compared to the native channel (Ghamari-Langroudi, et al. Nature 2015, 520 (7545), 94-U223). FIG. 25B) Summary of food intake in free-feeding mice following ICV or IT administration of 10 nmol MDE3-119-10c. Following ICV administration, mice (male n=8, female=11) consumed significantly less food at 4, 6, 8, 24, 48, and 72 h post-injection than vehicle treated mice ( $p<0.01$; * $p<0.001$). No difference in cumulative food intake was observed following IT administration of 10 nmol MDE3-119-10c (male n=6, female n=5). Data are shown as mean±SEM.

Figure 26:
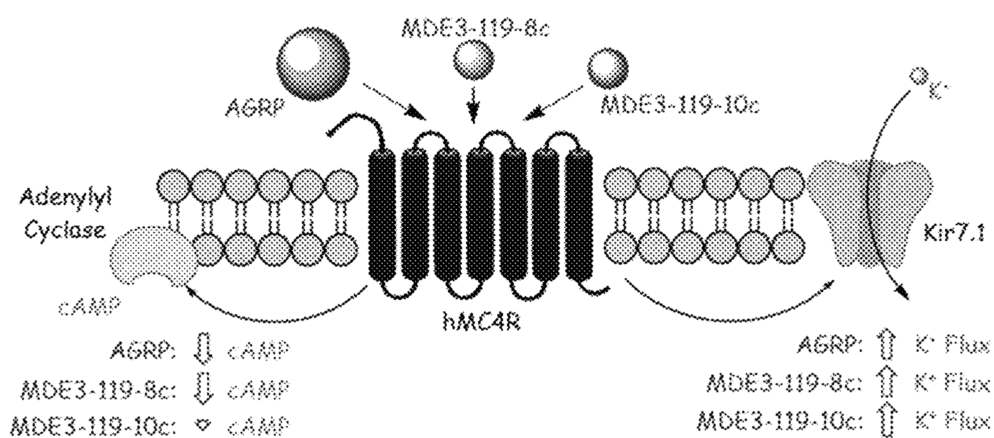

FIG. 26. Schematic.

DETAILED DESCRIPTION

Certain embodiments of the invention provide a cyclic compound of formula I:

I

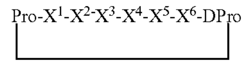

wherein:

Pro is a residue of L-proline, wherein the pyrrolidinyl ring is optionally substituted with one or more halo groups, $(C_1\text{-}C_4)$alkyl, —O$(C_1\text{-}C_4)$alkyl, $(C_1\text{-}C_4)$haloalkyl, or —O$(C_1\text{-}C_4)$haloalkyl;

$X^1$ is a residue of Arg or DArg:

$X^2$ is a residue of Phe or DPhe;

$X^3$ is a residue of Phe, DPhe or hPhe;

$X^4$ is a residue of a natural or unnatural amino acid:

$X^5$ is a residue of Ala, Asp, Glu, Lys, His, Phe, Ser, Leu or Gly;

$X^6$ is a residue of Phe, Ala, Gly, Ser, Lys, Asp, Leu, Nle. Trp, Tyr, Cha or hPhe; and DPro is a residue of D-proline, wherein the pyrrolidinyl ring is optionally substituted with one or more halo groups, $(C_1\text{-}C_4)$alkyl, —O$(C_1\text{-}C_4)$alkyl, $(C_1\text{-}C_4)$haloalkyl, or —O$(C_1\text{-}C_4)$haloalkyl;

or a salt thereof.

Certain embodiments of the invention provide a cyclic compound of formula I:

I

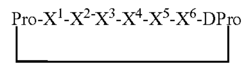

wherein:

Pro is a residue of L-proline;

$X^1$ is a residue of Arg or DArg;

$X^2$ is a residue of Phe or DPhe;

$X^3$ is a residue of Phe, DPhe or hPhe;

$X^4$ is a residue a natural or unnatural amino acid;

$X^5$ is a residue of Ala, Asp, Glu, Lys, His, Phe, Ser, Leu or Gly;

$X^6$ is a residue of Phe, Ala, Gly, Ser, Lys, Asp, Leu. Nle, Trp, Tyr. Cha or hPhe; and DPro is a residue of D-proline;

or a salt thereof.

Certain embodiments of the invention provide a cyclic compound of formula I:

I

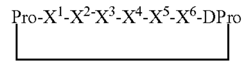

wherein:

Pro is a residue of L-proline;

$X^1$ is a residue of Arg or DArg:

$X^2$ is a residue of Phe or DPhe;

$X^3$ is a residue of Phe, DPhe or hPhe;

$X^4$ is a residue of Asn, Dap, Ala, Abu, Ser, Thr, Asp, Glu, DDap, His, Nle, Leu, Val, Phe, Trp or Arg;

$X^5$ is a residue of Ala, Asp, Glu, Lys, His, Phe, Ser, Leu or Gly;

$X^6$ is a residue of Phe, Ala, Gly, Ser, Lys, Asp, Leu, Nle, Trp, Tyr, Cha or hPhe; and DPro is a residue of D-proline; or a salt thereof.

In certain embodiments, the compound of formula I is not c[Pro-Arg-Phe-Phe-Asn-Ala-Phe-DPro] (SEQ ID NO: 1), c[Pro-Arg-Phe-Phe-Dap-Ala-Phe-DPro] (SEQ ID NO:2) or c[Pro-Arg-Phe-hPhe-Asn-Ala-Phe-DPro] (SEQ ID NO:3).

In certain embodiments, the compound of formula I is not c[Pro-Arg-Phe-Phe-Asn-Ala-Phe-DPro] (SEQ ID NO: 1), c[Pro-Arg-Phe-Phe-Dap-Ala-Phe-DPro] (SEQ ID NO:2), c[Pro-Arg-Phe-hPhe-Asn-Ala-Phe-DPro] (SEQ ID NO:3) or c[Pro-Arg-Phe-Phe-Arg-Ala-Phe-DPro](SEQ ID NO:54).

Thus, certain embodiments provide cyclic compound of formula I:

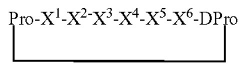

I wherein:

Pro is a residue of L-proline;

$X^1$ is a residue of Arg or DArg;

$X^2$ is a residue of Phe or DPhe;

$X^3$ is a residue of Phe, DPhe or hPhe;

$X^4$ is a residue of Asn, Dap, Ala, Abu, Ser, Thr, Asp, Glu, DDap, His, Nle, Leu, Val, Phe, Trp or Arg;

$X^5$ is a residue of Ala, Asp, Glu, Lys, His, Phe, Ser, Leu or Gly;

$X^6$ is a residue of Phe, Ala, Gly, Ser, Lys, Asp, Leu. Nle, Trp, Tyr, Cha or hPhe; and DPro is a residue of D-proline;

or a salt thereof, provided the compound of formula I is not c[Pro-Arg-Phe-Phe-Asn-Ala-Phe-DPro] (SEQ ID NO: 1), c[Pro-Arg-Phe-Phe-Dap-Ala-Phe-DPro] (SEQ ID NO:2), c[Pro-Arg-Phe-hPhe-Asn-Ala-Phe-DPro] (SEQ ID NO:3) or c[Pro-Arg-Phe-Phe-Arg-Ala-Phe-DPro] (SEQ ID NO:54).

In one embodiment, Pro is a residue of L-proline. In one embodiment, Pro is a residue of L-proline, wherein the pyrrolidinyl ring is substituted with one or more halo groups, $(C_1-C_4)$alkyl, $—O(C_1-C_4)$alkyl, $(C_1-C_4)$haloalkyl, or $—O(C_1-C_4)$haloalkyl.

In one embodiment, DPro is a residue of D-proline. In one embodiment, DPro is a residue of D-proline, wherein the pyrrolidinyl ring is substituted with one or more halo groups, $(C_1-C_4)$alkyl, $—O(C_1-C_4)$alkyl, $(C_1-C_4)$haloalkyl, or $—O(C_1-C_4)$haloalkyl.

In one embodiment. Pro is a residue of L-proline and DPro is a residue of D-proline.

In one embodiment, $X^1$ is a residue of Arg. In one embodiment, $X^1$ is a residue of DArg.

In one embodiment, $X^2$ is a residue of Phe. In one embodiment, $X^2$ is a residue of DPhe. In certain embodiments, $X^2$ is not a residue of Arg. In certain embodiments, $X^2$ is not a residue of Phe.

In one embodiment, $X^3$ is a residue of Phe. In one embodiment, $X^3$ is a residue of DPhe.

In one embodiment, $X^3$ is a residue of hPhe. In one embodiment, $X^3$ is not a residue of Phe. In one embodiment, $X^3$ is not a residue of hPhe.

In one embodiment, $X^4$ is a residue of a natural amino acid. In one embodiment, $X^4$ is a residue of an unnatural amino acid. In one embodiment, $X^4$ is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (31)Tyr. In one embodiment, $X^4$ is a residue of Asn, Dap, Ala, Abu, Ser, Thr, Asp, Glu, DDap, His, Nle, Leu, Val, Phe, Trp or Arg. In one embodiment, $X^4$ is a residue of DDap, Ser, Abu, Asp or Val. In one embodiment, $X^4$ is a residue of Asn. In one embodiment, $X^4$ is a residue of Dap. In one embodiment, $X^4$ is a residue of Ala. In one embodiment, $X^4$ is a residue of Abu. In one embodiment, $X^4$ is a residue of Ser. In one embodiment, $X^4$ is a residue of Thr. In one embodiment, $X^4$ is a residue of Asp. In one embodiment, $X^4$ is a residue of Glu. In one embodiment, $X^4$ is a residue of DDap. In one embodiment. $X^4$ is a residue of His. In one embodiment, $X^4$ is a residue of Nle. In one embodiment, $X^4$ is a residue of Leu. In one embodiment, $X^4$ is a residue of Val. In one embodiment, $X^4$ is a residue of Phe. In one embodiment, $X^4$ is a residue of Trp. In one embodiment, $X^4$ is a residue of Arg. In certain embodiments, $X^4$ is not a residue of Dap. In certain embodiments, $X^4$ is not a residue of Asn. In certain embodiments, $X^4$ is not a residue of Arg.

In one embodiment, $X^5$ is a residue of Ala. In one embodiment, $X^5$ is a residue of Asp. In one embodiment, $X^5$ is a residue of Glu. In one embodiment, $X^5$ is a residue of Lys. In one embodiment, $X^5$ is a residue of His. In one embodiment, $X^5$ is a residue of Phe. In one embodiment, $X^5$ is a residue of Ser. In one embodiment, $X^5$ is a residue of Leu. In one embodiment, $X^5$ is a residue of Gly. In one embodiment, $X^5$ is not a residue of Ala.

In one embodiment, $X^6$ is a residue of Phe. In one embodiment, $X^6$ is a residue of Ala. In one embodiment, $X^6$ is a residue of Gly. In one embodiment, $X^6$ is a residue of Ser. In one embodiment, $X^6$ is a residue of Lys. In one embodiment, $X^6$ is a residue of Asp. In one embodiment, $X^6$ is a residue of Leu. In one embodiment, $X^6$ is a residue of Nle. In one embodiment, $X^6$ is a residue of Trp. In one embodiment, $X^6$ is a residue of Tyr. In one embodiment, $X^6$ is a residue of Cha. In one embodiment, $X^6$ is a residue of hPhe. In one embodiment, $X^6$ is not a residue of Phe.

In one embodiment, $X^1$ is Arg; $X^2$ is Phe; $X^3$ is Phe; $X^4$ is DDap, Ser, Abu, Phe or Val; $X^5$ is Ala; and $X^6$ is Phe.

In one embodiment, $X^1$ is Arg; $X^2$ is Phe; $X^3$ is Phe; $X^4$ is DDap, Ser, Abu, Asp or Val; $X^5$ is Ala; and $X^6$ is Phe.

In one embodiment, the compound of invention is selected from the group consisting of:

```
                                    (SEQ ID NO: 4)
c[Pro-Arg-Phe-Phe-Ala-Ala-Phe-DPro]

                                    (SEQ ID NO: 5)
c[Pro-Arg-Phe-Phe-Abu-Ala-Phe-DPro]

                                    (SEQ ID NO: 6)
c[Pro-Arg-Phe-Phe-Ser-Ala-Phe-DPro]

                                    (SEQ ID NO: 7)
c[Pro-Arg-Phe-Phe-Thr-Ala-Phe-DPro]
```

-continued (SEQ ID NO: 8)
c[Pro-Arg-Phe-Phe-Asp-Ala-Phe-DPro]

(SEQ ID NO: 9)
c[Pro-Arg-Phe-Phe-Glu-Ala-Phe-DPro]

(SEQ ID NO: 10)
c[Pro-Arg-Phe-Phe-DDap-Ala-Phe-DPro]

(SEQ ID NO: 11)
c[Pro-Arg-Phe-Phe-His-Ala-Phe-DPro]

(SEQ ID NO: 12)
c[Pro-Arg-Phe-Phe-Nle-Ala-Phe-DPro]

(SEQ ID NO: 13)
c[Pro-Arg-Phe-Phe-Leu-Ala-Phe-DPro]

(SEQ ID NO: 14)
c[Pro-Arg-Phe-Phe-Val-Ala-Phe-DPro]

(SEQ ID NO: 15)
c[Pro-Arg-Phe-Phe-Phe-Ala-Phe-DPro]

(SEQ ID NO: 16)
c[Pro-Arg-Phe-Phe-Trp-Ala-Phe-DPro]

(SEQ ID NO: 17)
c[Pro-Arg-Phe-Phe-Asn-Asp-Phe-DPro]

(SEQ ID NO: 18)
c[Pro-Arg-Phe-Phe-Asn-Glu-Phe-DPro]

(SEQ ID NO: 19)
c[Pro-Arg-Phe-Phe-Asn-Lys-Phe-DPro]

(SEQ ID NO: 20)
c[Pro-Arg-Phe-Phe-Asn-His-Phe-DPro]

(SEQ ID NO: 21)
c[Pro-Arg-Phe-Phe-Asn-Phe-Phe-DPro]

(SEQ ID NO: 22)
c[Pro-Arg-Phe-Phe-Asn-Ser-Phe-DPro]

(SEQ ID NO: 23)
c[Pro-Arg-Phe-Phe-Asn-Leu-Phe-DPro]

(SEQ ID NO: 24)
c[Pro-Arg-Phe-Phe-Asn-Gly-Phe-DPro]

(SEQ ID NO: 25)
c[Pro-Arg-Phe-Phe-Asn-Ala-Ala-DPro]

(SEQ ID NO: 26)
c[Pro-DArg-Phe-Phe-Asn-Ala-Phe-DPro]

(SEQ ID NO: 27)
c[Pro-Arg-DPhe-Phe-Asn-Ala-Phe-DPro]

(SEQ ID NO: 28)
c[Pro-Arg-Phe-DPhe-Asn-Ala-Phe-DPro]

(SEQ ID NO: 29)
c[Pro-DArg-DPhe-Phe-Asn-Ala-Phe-DPro]

(SEQ ID NO: 30)
c[Pro-DArg-Phe-DPhe-Asn-Ala-Phe-DPro]

(SEQ ID NO: 31)
c[Pro-Arg-DPhe-DPhe-Asn-Ala-Phe-DPro]

(SEQ ID NO: 32)
c[Pro-DArg-DPhe-DPhe-Asn-Ala-Phe-DPro]

(SEQ ID NO: 33)
c[Pro-DArg-Phe-Phe-Dap-Ala-Phe-DPro]

(SEQ ID NO: 34)
c[Pro-Arg-DPhe-Phe-Dap-Ala-Phe-DPro]

-continued (SEQ ID NO: 35)
c[Pro-Arg-Phe-DPhe-Dap-Ala-Phe-DPro]

(SEQ ID NO: 36)
c[Pro-DArg-DPhe-Phe-Dap-Ala-Phe-DPro]

(SEQ ID NO: 37)
c[Pro-DArg-Phe-DPhe-Dap-Ala-Phe-DPro]

(SEQ ID NO: 38)
c[Pro-Arg-DPhe-DPhe-Dap-Ala-Phe-DPro]

(SEQ ID NO: 39)
c[Pro-DArg-DPhe-DPhe-Dap-Ala-Phe-DPro]

(SEQ ID NO: 40)
c[Pro-Arg-Phe-Phe-Asn-Ala-Gly-DPro]

(SEQ ID NO: 41)
c[Pro-Arg-Phe-Phe-Asn-Ala-Ser-DPro]

(SEQ ID NO: 42)
c[Pro-Arg-Phe-Phe-Asn-Ala-Lys-DPro]

(SEQ ID NO: 43)
c[Pro-Arg-Phe-Phe-Asn-Ala-Asp-DPro]

(SEQ ID NO: 44)
c[Pro-Arg-Phe-Phe-Asn-Ala-Leu-DPro]

(SEQ ID NO: 45)
c[Pro-Arg-Phe-Phe-Asn-Ala-Nle-DPro]

(SEQ ID NO: 46)
c[Pro-Arg-Phe-Phe-Asn-Ala-Trp-DPro]

(SEQ ID NO: 47)
c[Pro-Arg-Phe-Phe-Asn-Ala-Tyr-DPro]

(SEQ ID NO: 48)
c[Pro-Arg-Phe-Phe-Asn-Ala-Cha-DPro]

(SEQ ID NO: 49)
c[Pro-Arg-Phe-Phe-Asn-Ala-hPhe-DPro]

(SEQ ID NO: 50)
c[Pro-Arg-Phe-Phe-Asn-Ser-Nle-DPro]

(SEQ ID NO: 51)
c[Pro-Arg-Phe-Phe-Dap-Ala-Nle-DPro]

(SEQ ID NO: 52)
c[Pro-Arg-Phe-Phe-Dap-Ser-Phe-DPro]

(SEQ ID NO: 53)
c[Pro-Arg-Phe-Phe-Dap-Ser-Nle-DPro]

(SEQ ID NO: 55)
c[Pro-Arg-Phe-Phe-Arg-Ala-Nle-DPro]

(SEQ ID NO: 56)
c[Pro-Arg-Phe-Phe-Arg-Ser-Phe-DPro]

(SEQ ID NO: 57)
c[Pro-Arg-Phe-Phe-Arg-Ser-Nle-DPro]

(SEQ ID NO: 58)
c[Pro-Arg-Phe-hPhe-Asn-Ala-Nle-DPro]

(SEQ ID NO: 59)
c[Pro-Arg-Phe-hPhe-Asn-Ser-Phe-DPro]

(SEQ ID NO: 60)
c[Pro-Arg-Phe-hPhe-Asn-Ser-Nle-DPro]

(SEQ ID NO: 61)
c[Pro-Arg-Phe-hPhe-Dap-Ala-Phe-DPro]

(SEQ ID NO: 62)
c[Pro-Arg-Phe-hPhe-Dap-Ala-Nle-DPro]

-continued (SEQ ID NO: 63)
c[Pro-Arg-Phe-hPhe-Dap-Ser-Phe-DPro]

(SEQ ID NO: 64)
c[Pro-Arg-Phe-hPhe-Dap-Ser-Nle-DPro]

(SEQ ID NO: 65)
c[Pro-Arg-Phe-hPhe-Arg-Ala-Phe-DPro]

(SEQ ID NO: 66)
c[Pro-Arg-Phe-hPhe-Arg-Ala-Nle-DPro]

(SEQ ID NO: 67)
c[Pro-Arg-Phe-hPhe-Arg-Ser-Phe-DPro]

(SEQ ID NO: 68)
c[Pro-Arg-Phe-hPhe-Arg-Ser-Nle-DPro]

and salts thereof.

In one embodiment, the compound of invention is selected from the group consisting of:

(SEQ ID NO: 10)
c[Pro-Arg-Phe-Phe-DDap-Ala-Phe-DPro (SEQ ID NO: 6)
c[Pro-Arg-Phe-Phe-Ser-Ala-Phe-DPro (SEQ ID NO: 5)
c[Pro-Arg-Phe-Phe-Abu-Ala-Phe-DPro (SEQ ID NO: 8)
c[Pro-Arg-Phe-Phe-Asp-Ala-Phe-DPro (SEQ ID NO: 14)
c[Pro-Arg-Phe-Phe-Val-Ala-Phe-DPro and salts thereof.

In one embodiment, the compound of invention is c[Pro-Arg-Phe-Phe-DDap-Ala-Phe-DPro] (SEQ ID NO: 10), or a salt thereof.

In one embodiment, the compound of invention is c[Pro-Arg-Phe-Phe-Ser-Ala-Phe-DPro] (SEQ ID NO:6), or a salt thereof.

In one embodiment, the compound of invention is c[Pro-Arg-Phe-Phe-Abu-Ala-Phe-DPro] (SEQ ID NO:5), or a salt thereof.

In one embodiment, the compound of invention is c[Pro-Arg-Phe-Phe-Asp-Ala-Phe-DPro] (SEQ ID NO:8), or a salt thereof.

In one embodiment, the compound of invention is c[Pro-Arg-Phe-Phe-Val-Ala-Phe-DPro] (SEQ ID NO: 14), or a salt thereof.

In one embodiment, the compound of invention is a cyclic peptide, comprising an amino acid sequence having at least 80% sequence identity to:

(SEQ ID NO: 4)
Pro-Arg-Phe-Phe-Ala-Ala-Phe-DPro (SEQ ID NO: 69)
Pro-Arg-Phe-Phe-Abu-Ala-Phe-DPro (SEQ ID NO: 70)
Pro-Arg-Phe-Phe-Ser-Ala-Phe-DPro (SEQ ID NO: 71)
Pro-Arg-Phe-Phe-Thr-Ala-Phe-DPro (SEQ ID NO: 72)
Pro-Arg-Phe-Phe-Asp-Ala-Phe-DPro

-continued (SEQ ID NO: 73)
Pro-Arg-Phe-Phe-Glu-Ala-Phe-DPro (SEQ ID NO: 74)
Pro-Arg-Phe-Phe-DDap-Ala-Phe-DPro (SEQ ID NO: 75)
Pro-Arg-Phe-Phe-His-Ala-Phe-DPro (SEQ ID NO: 76)
Pro-Arg-Phe-Phe-Nle-Ala-Phe-DPro (SEQ ID NO: 77)
Pro-Arg-Phe-Phe-Leu-Ala-Phe-DPro (SEQ ID NO: 78)
Pro-Arg-Phe-Phe-Val-Ala-Phe-DPro (SEQ ID NO: 79)
Pro-Arg-Phe-Phe-Phe-Ala-Phe-DPro (SEQ ID NO: 80)
Pro-Arg-Phe-Phe-Trp-Ala-Phe-DPro (SEQ ID NO: 81)
Pro-Arg-Phe-Phe-Asn-Asp-Phe-DPro (SEQ ID NO: 82)
Pro-Arg-Phe-Phe-Asn-Glu-Phe-DPro (SEQ ID NO: 83)
Pro-Arg-Phe-Phe-Asn-Lys-Phe-DPro (SEQ ID NO: 84)
Pro-Arg-Phe-Phe-Asn-His-Phe-DPro (SEQ ID NO: 85)
Pro-Arg-Phe-Phe-Asn-Phe-Phe-DPro (SEQ ID NO: 86)
Pro-Arg-Phe-Phe-Asn-Ser-Phe-DPro (SEQ ID NO: 87)
Pro-Arg-Phe-Phe-Asn-Leu-Phe-DPro (SEQ ID NO: 88)
Pro-Arg-Phe-Phe-Asn-Gly-Phe-DPro (SEQ ID NO: 89)
Pro-Arg-Phe-Phe-Asn-Ala-Ala-DPro (SEQ ID NO: 90)
Pro-DArg-Phe-Phe-Asn-Ala-Phe-DPro (SEQ ID NO: 91)
Pro-Arg-DPhe-Phe-Asn-Ala-Phe-DPro (SEQ ID NO: 92)
Pro-Arg-Phe-DPhe-Asn-Ala-Phe-DPro (SEQ ID NO: 93)
Pro-DArg-DPhe-Phe-Asn-Ala-Phe-DPro (SEQ ID NO: 94)
Pro-DArg-Phe-DPhe-Asn-Ala-Phe-DPro (SEQ ID NO: 95)
Pro-Arg-DPhe-DPhe-Asn-Ala-Phe-DPro (SEQ ID NO: 96)
Pro-DArg-DPhe-DPhe-Asn-Ala-Phe-DPro (SEQ ID NO: 97)
Pro-DArg-Phe-Phe-Dap-Ala-Phe-DPro (SEQ ID NO: 98)
Pro-Ara-DPhe-Phe-Dap-Ala-Phe-DPro (SEQ ID NO: 99)
Pro-Arg-Phe-DPhe-Dap-Ala-Phe-DPro -continued

```
(SEQ ID NO: 100)
Pro-DArg-DPhe-Phe-Dap-Ala-Phe-DPro

(SEQ ID NO: 101)
Pro-DArg-Phe-DPhe-Dap-Ala-Phe-DPro

(SEQ ID NO: 102)
Pro-Arg-DPhe-DPhe-Dap-Ala-Phe-DPro

(SEQ ID NO: 103)
Pro-DArg-DPhe-DPhe-Dap-Ala-Phe-DPro

(SEQ ID NO: 104)
Pro-Arg-Phe-Phe-Asn-Ala-Gly-DPro

(SEQ ID NO: 105)
Pro-Ara-Phe-Phe-Asn-Ala-Ser-DPro

(SEQ ID NO: 106)
Pro-Arg-Phe-Phe-Asn-Ala-Lys-DPro

(SEQ ID NO: 107)
Pro-Arg-Phe-Phe-Asn-Ala-Asp-DPro

(SEQ ID NO: 108)
Pro-Arg-Phe-Phe-Asn-Ala-Leu-DPro

(SEQ ID NO: 109)
Pro-Arg-Phe-Phe-Asn-Ala-Nle-DPro

(SEQ ID NO: 110)
Pro-Arg-Phe-Phe-Asn-Ala-Trp-DPro

(SEQ ID NO: 111)
Pro-Arg-Phe-Phe-Asn-Ala-Tyr-DPro

(SEQ ID NO: 112)
Pro-Arg-Phe-Phe-Asn-Ala-Cha-DPro

(SEQ ID NO: 113)
Pro-Arg-Phe-Phe-Asn-Ala-hPhe-DPro

(SEQ ID NO: 114)
Pro-Arg-Phe-Phe-Asn-Ser-Nle-DPro

(SEQ ID NO: 115)
Pro-Arg-Phe-Phe-Dap-Ala-Nle-DPro

(SEQ ID NO: 116)
Pro-Arg-Phe-Phe-Dap-Ser-Phe-DPro

(SEQ ID NO: 117)
Pro-Arg-Phe-Phe-Dap-Ser-Nle-DPro

(SEQ ID NO: 119)
Pro-Arg-Phe-Phe-Arg-Ala-Nle-DPro

(SEQ ID NO: 120)
Pro-Ara-Phe-Phe-Arg-Ser-Phe-DPro

(SEQ ID NO: 121)
Pro-Arg-Phe-Phe-Arg-Ser-Nle-DPro

(SEQ ID NO: 122)
Pro-Arg-Phe-hPhe-Asn-Ala-Nle-DPro

(SEQ ID NO: 123)
Pro-Arg-Phe-hPhe-Asn-Ser-Phe-DPro

(SEQ ID NO: 124)
Pro-Arg-Phe-hPhe-Asn-Ser-Nle-DPro

(SEQ ID NO: 125)
Pro-Arg-Phe-hPhe-Dap-Ala-Phe-DPro

(SEQ ID NO: 126)
Pro-Arg-Phe-hPhe-Dap-Ala-Nle-DPro

(SEQ ID NO: 127)
Pro-Arg-Phe-hPhe-Dap-Ser-Phe-DPro
```

-continued

```
(SEQ ID NO: 128)
Pro-Arg-Phe-hPhe-Dap-Ser-Nle-DPro

(SEQ ID NO: 129)
Pro-Arg-Phe-hPhe-Arg-Ala-Phe-DPro

(SEQ ID NO: 130)
Pro-Arg-Phe-hPhe-Arg-Ala-Nle-DPro

(SEQ ID NO: 131)
Pro-Arg-Phe-hPhe-Arg-Ser-Phe-DPro;
or

(SEQ ID NO: 132)
Pro-Arg-Phe-hPhe-Arg-Ser-Nle-DPro.
```

In one embodiment, the compound of invention is a cyclic peptide, comprising an amino acid sequence having at least 81%, 82%, 83%, 84%, 85%, 86%, 87%, 88%, 89%, 900%, 91%, 92%, 93%, 94%, 95%, 96%, 97%, 98%, 99% or 100% sequence identity to SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; SEQ ID NO:87; SEQ ID NO:88; SEQ ID NO:89; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO:109; SEQ ID NO:110; SEQ ID NO: 111; SEQ ID NO: 112; SEQ ID NO: 113; SEQ ID NO: 114; SEQ ID NO: 115; SEQ ID NO: 116; SEQ ID NO:117; SEQ ID NO: 119; SEQ ID NO: 120; SEQ ID NO:121; SEQ ID NO:122; SEQ ID NO: 123; SEQ ID NO: 124. SEQ ID NO: 125; SEQ ID NO: 126; SEQ ID NO: 127; SEQ ID NO: 128; SEQ ID NO: 129; SEQ ID NO: 130; SEQ ID NO: 131); or SEQ ID NO: 132.

In one embodiment, the compound of invention is a cyclic peptide, comprising an amino acid sequence having at least 90% sequence identity to SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; SEQ ID NO:87; SEQ ID NO:88; SEQ ID NO:89; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO:109; SEQ ID NO: 110; SEQ ID NO:111; SEQ ID NO: 112; SEQ ID NO:113; SEQ ID NO:114; SEQ ID NO: 115; SEQ ID NO: 116; SEQ ID NO: 117; SEQ ID NO: 119; SEQ ID NO:120; SEQ ID NO: 121. SEQ ID NO: 122; SEQ ID NO:123; SEQ ID NO:124; SEQ ID NO: 125; SEQ ID NO: 126; SEQ ID NO: 127; SEQ ID NO: 128; SEQ ID NO: 129; SEQ ID NO: 130; SEQ ID NO:131); or SEQ ID NO: 132.

In one embodiment, the compound of invention is a cyclic peptide, comprising an amino acid sequence having at least 99% sequence identity to SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83;

SEQ ID NO:84; SEQ ID NO:85; SEQ ID NO:86; SEQ ID NO:87; SEQ ID NO:88; SEQ ID NO:89; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO: 100; SEQ ID NO:101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO:109; SEQ ID NO: 110; SEQ ID NO:111; SEQ ID NO: 112; SEQ ID NO:113; SEQ ID NO:114; SEQ ID NO:115; SEQ ID NO: 116; SEQ ID NO: 117; SEQ ID NO: 119; SEQ ID NO: 120; SEQ ID NO: 121; SEQ ID NO: 122; SEQ ID NO: 123; SEQ ID NO: 124; SEQ ID NO: 125; SEQ ID NO: 126, SEQ ID NO: 127; SEQ ID NO: 128; SEQ ID NO: 129; SEQ ID NO: 130; SEQ ID NO:131); or SEQ ID NO: 132.

In one embodiment, the compound of invention is a cyclic peptide, comprising an amino acid sequence having at least 80% sequence identity to:

```
                                  (SEQ ID NO: 74)
Pro-Arg-Phe-Phe-DDap-Ala-Phe-DPro

                                  (SEQ ID NO: 70)
Pro-Arg-Phe-Phe-Ser-Ala-Phe-DPro

                                  (SEQ ID NO: 69)
Pro-Arg-Phe-Phe-Abu-Ala-Phe-DPro

                                  (SEQ ID NO: 72)
Pro-Arg-Phe-Phe-Asp-Ala-Phe-DPro;
or

                                  (SEQ ID NO: 78)
Pro-Arg-Phe-Phe-Val-Ala-Phe-DPro.
```

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:74, SEQ ID NO:70, SEQ ID NO:69, SEQ ID NO:72 or SEQ ID NO:78. In one embodiment, the compound of invention is a cyclic peptide, consisting of an amino acid sequence having at least 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:74, SEQ ID NO:70, SEQ ID NO:69, SEQ ID NO:72 or SEQ ID NO:78.

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:74. In one embodiment, the compound of invention is a cyclic peptide, consisting of an amino acid sequence having at least 81%, 82%, 83%, 84%, 85%, 86%6, 87%, 88%, 89%, 90%, 91%, 92%, 93%, 94%, 95%, 96%, 97%, 98%, 99% or 100% sequence identity to SEQ ID NO:74. In certain embodiments, the cyclic peptide consists of SEQ ID NO:74.

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:70. In one embodiment, the compound of invention is a cyclic peptide, consisting of an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:70. In certain embodiments, the cyclic peptide consists of SEQ ID NO:70.

In one embodiment, the compound of invention is a cyclic peptide, comprising an amino acid sequence having at least 81%, 82%, 83%, 84%, 85%6, 86%, 87%, 88%, 89%, 90%, 91° %, 92%, 93%, 94%, 95%, 96%, 97%, 98%, 99% or 100% sequence identity to SEQ ID NO:69. In one embodiment, the compound of invention is a cyclic peptide, consisting of an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:69. In certain embodiments, the cyclic peptide consists of SEQ ID NO:69.

In one embodiment, the compound of invention is a cyclic peptide, comprising an amino acid sequence having at least 81%, 82%, 83%, 84%, 85%6, 86%, 87%, 88%, 89%, 90%, 91%, 92%, 93%, 94%, 95%, 96%, 97%, 98%, 99% or 100% sequence identity to SEQ ID NO:72. In one embodiment, the compound of invention is a cyclic peptide, consisting of an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:72. In certain embodiments, the cyclic peptide consists of SEQ ID NO:72.

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:78. In one embodiment, the compound of invention is a cyclic peptide, consisting of an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:78. In certain embodiments, the cyclic peptide consists of SEQ ID NO:78.

In certain embodiments, the cyclic peptide is between about 5 to about 13 amino acids in length. In certain embodiments, the cyclic peptide is about 5, 6, 7, 8, 9, 10, 11, 12 or 13 amino acids in length. In certain embodiments, the cyclic peptide is 8 amino acids in length.

In one embodiment, the compound of invention is a ligand for MC1R, MC3R, MC4R or MC5R. In one embodiment, the compound of invention is a ligand for MC4R or MC5R. In one embodiment, the compound of invention is a ligand for MC4R. In one embodiment, the compound of invention is a ligand for MC5R. In one embodiment, a compound of the invention is a ligand for Kir7.1.

In one embodiment, the compound of invention binds to MC1R, MC3R, MC4R or MC5R. In one embodiment, the compound of invention binds to Kir7.1. In one embodiment, the compound of invention selectively binds to MC1R, MC3R, MC4R or MC5R. In one embodiment, the compound of invention selectively binds to Kir7.1. For example, a compound of the invention may be at least 5, at least 10, at least 50, at least 100, at least 500, or at least 1,000 fold selective for a given melanocortin receptor (e.g., MC1R, MC3R, MC4R and/or MC5R) over another melanocortin receptor(s) in a selected assay (e.g., an assay described in the Examples herein). In one embodiment, a compound of the invention is a selective ligand for the melanocortin-4 receptor/Kir7.1 K+ ion channel pathway.

In one embodiment, a compound of the invention is capable of modulating the activity or function of MC1R, MC3R, MC4R or MC5R. In one embodiment, a compound of the invention is capable of modulating the activity or function of Kir7.1.

One embodiment of the invention provides a composition (e.g., a pharmaceutical composition) comprising a compound described herein or compound of formula I, or a pharmaceutically acceptable salt thereof, and a pharmaceutically acceptable carrier.

One embodiment of the invention provides a dietary supplement comprising a compound described herein or compound of formula I, or a salt thereof.

Another embodiment of the invention provides a prodrug of a compound of formula I or a salt thereof. As used herein the term "prodrug" refers to a biologically inactive compound that can be metabolized in the body to produce a biologically active form of the compound.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound of formula I herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

In cases where compounds are sufficiently basic or acidic, a salt of a compound of formula (I) can be useful as an intermediate for isolating or purifying a compound of formula (I). Additionally, administration of a compound of formula (I) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Certain Methods of the Invention

The invention also provides a method for treating obesity or a disease associated with obesity in an animal (e.g., a mammal, such as a human) comprising administering a compound described herein or compound of formula I or a pharmaceutically acceptable salt thereof to the animal. For example, in certain embodiments, the compound of formula I is a Kir7.1 selective compound. In certain embodiments, the compound of formula I is c[Pro-Arg-Phe-Phe-Val-Ala-Phe-DPro] (SEQ ID NO: 14). In certain embodiments, the compound of formula I is c[Pro-Arg-Phe-Phe-Abu-Ala-Phe-DPro] (SEQ ID NO:5). In certain embodiments, the compound of formula 1 is c[Pro-Arg-Phe-Phe-Asp-Ala-Phe-DPro] (SEQ ID NO:8).

The invention also provides a compound described herein or a compound of formula I or a pharmaceutically acceptable salt thereof for the prophylactic or therapeutic treatment of obesity or a disease associated with obesity.

The invention also provides the use of a compound described herein or a compound of formula I or a pharmaceutically acceptable salt thereof to prepare a medicament for treating obesity or a disease associated with obesity.

In one embodiment, the disease associated with obesity is diabetes, cardiovascular disease or hypertension.

The invention also provides a method for treating cachaxia or a disease associated with cachaxia in an animal (e.g., a mammal, such as a human) comprising administering a compound described herein or compound of formula I or a pharmaceutically acceptable salt thereof to the animal. For example, in certain embodiments, the compound of formula I is a MC4R antagonist. In certain embodiments, the compound of formula I is c[Pro-Arg-Phe-Phe-DDap-Ala-Phe-DPro] (SEQ ID NO: 10). In certain embodiments, the compound of formula I is c[Pro-Arg-Phe-Phe-Ser-Ala-Phe-DPro] (SEQ ID NO:6). In certain embodiments, the compound of formula I is c[Pro-Arg-Phe-Phe-Dap-Ala-Phe-DPro] (SEQ ID NO:2).

The invention also provides a compound described herein or a compound of formula I or a pharmaceutically acceptable salt thereof for the prophylactic or therapeutic treatment of cachaxia or a disease associated with cachaxia.

The invention also provides the use of a compound described herein or a compound of formula I or a pharmaceutically acceptable salt thereof to prepare a medicament for treating cachaxia or a disease associated with cachaxia.

In one embodiment, the disease associated with cachaxia is cancer, congestive heart failure or chronic kidney disease.

The invention also provides a compound described herein or a compound of formula I or a pharmaceutically acceptable salt thereof for use in medical therapy.

One embodiment of the invention provides a method of modulating (e.g., increasing or decreasing) the activity/function of a melanocortin receptor or Kir7.1 in vitro or in vivo comprising contacting the receptor/ion channel with an effective amount of a compound described herein or a compound of formula I, or a pharmaceutically acceptable salt thereof. In certain embodiments, such a method comprises contacting a cell comprising the melanocortin receptor or Kir7.1. In certain embodiments, the cell is in a mammal. In certain embodiments, the cell is contacted by administering the compound described herein or the compound of formula (I) or a salt thereof (e.g., a pharmaceutically acceptable salt thereof) to the mammal. In certain embodiments, the compound described herein or the compound of formula (I) or a salt thereof, increases the activity of the melanocortin receptor or the Kir7.1 ion channel (e.g., as compared to a control). In certain embodiments, a compound described herein or the compound of formula (I) or a salt thereof, decreases the activity of the melanocortin receptor or the Kir7.1 ion channel (e.g., as compared to a control).

One embodiment of the invention provides a compound described herein or a compound of formula I, or a pharmaceutically acceptable salt thereof for use in modulating (e.g., increasing or decreasing) the activity/function of a melanocortin receptor or a Kir7.1 ion channel in vitro or in vivo.

One embodiment of the invention provides the use of a compound described herein or a compound of formula I, or a pharmaceutically acceptable salt thereof for the manufacture of a medicament for modulating (e.g., increasing or decreasing) the activity/function of a melanocortin receptor or the Kir7.1 ion channel in vitro or in vivo.

In one embodiment, the melanocortin receptor is MC1R, MC3R, MC4R or MC5R.

In one embodiment, the melanocortin receptor is MC4R.

In one embodiment, the activity/function of Kir7.1 is modulated. For example, in certain embodiments, the compound described herein for modulating Kir7.1 is c[Pro-Arg-Phe-Phe-DDap-Ala-Phe-DPro] (SEQ ID NO: 10), c[Pro-Arg-Phe-Phe-Ser-Ala-Phe-DPro] (SEQ ID NO:6), c[Pro-Arg-Phe-Phe-Abu-Ala-Phe-DPro] (SEQ ID NO:5), c[Pro-Arg-Phe-Phe-Asp-Ala-Phe-DPro] (SEQ ID NO:8), c[Pro-Arg-Phe-Phe-Val-Ala-Phe-DPro] (SEQ ID NO: 14) or a salt thereof. In certain other embodiments, a compound for modulating Kir7.1 is c[Pro-Arg-Phe-Phe-Dap-Ala-Phe-DPro] (SEQ ID NO:2).

Another embodiment of the invention provides a method of modulating (e.g., increasing or decreasing) metabolic activity in an animal in need thereof, comprising administering an effective amount of a compound described herein or a compound of formula I, or a pharmaceutically acceptable salt thereof, to the animal.

Another embodiment of the invention provides a compound described herein or a compound of formula I, or a pharmaceutically acceptable salt thereof for use in modulating (e.g., increasing or decreasing) metabolic activity.

Another embodiment of the invention provides the use of a compound described herein or a compound of formula I, or a pharmaceutically acceptable salt thereof for the manufacture of a medicament for modulating (e.g., increasing or decreasing) metabolic activity in an animal in need thereof.

Another embodiment of the invention provides a compound described herein or a method of modulating (e.g., increasing or decreasing) appetite in an animal in need thereof, comprising administering an effective amount of a compound of formula I, or a pharmaceutically acceptable salt thereof, to the animal.

Another embodiment of the invention provides a compound described herein or a compound of formula I, or a pharmaceutically acceptable salt thereof for use in modulating (e.g., increasing or decreasing) appetite.

Another embodiment of the invention provides the use of a compound described herein or a compound of formula I, or a pharmaceutically acceptable salt thereof for the manufacture of a medicament for modulating (e.g., increasing or decreasing) appetite in an animal in need thereof.

The ability of a compound described herein or a compound of formula (I) to, e.g., modulate appetite, modulate metabolic activity or to treat obesity or diseases associated with obesity (e.g., diabetes, cardiovascular disease or hypertension) may be tested using an assay known in the art or described in the Examples.

In certain embodiments, the animal is a mammal. In certain embodiments, the mammal is a human.

Administration

Compounds described herein and compounds of formula (I) (including salts and prodrugs thereof) can be formulated as pharmaceutical compositions and administered to a mammalian host, such as a human patient in a variety of forms adapted to the chosen route of administration, i.e., orally or parenterally, by intravenous, intramuscular, intrathecal, topical, nasal, inhalation, suppository, sub dermal osmotic pump, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously, intrathecally or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form. i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds described herein to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents. For example, compounds of the invention (e.g., compounds of formula (I)), or salts thereof, may be administered with other agents that are useful for modulating appetite (i.e., increasing or decreasing), modulating metabolic activity, treating obesity or diseases associated with obesity (e.g., diabetes, cardiovascular disease or hypertension), inducing weight loss, or increasing or decreasing weight gain. Accordingly, in one embodiment the invention also provides a composition comprising a compound described herein (e.g., compound of formula (I)), or a pharmaceutically acceptable salt thereof, at least one other therapeutic agent, and a pharmaceutically acceptable diluent or carrier. The invention also provides a kit comprising a compound described herein (e.g, a compound of formula (I)), or a pharmaceutically acceptable salt thereof, at least one other therapeutic agent, packaging material, and instructions for administering a compound described herein (e.g., a compound of formula (I)) or the pharmaceutically acceptable salt thereof and the other therapeutic agent or agents to an animal to modulate appetite, modulate metabolic activity, treat obesity or diseases associated with obesity (e.g., diabetes, cardiovascular disease or hypertension), induce weight loss, increase weight gain, or decrease weight gain.

Certain Definitions

The term "alkyl", by itself or as part of another substituent, means, unless otherwise stated, a straight or branched chain hydrocarbon radical, having the number of carbon atoms designated (i.e., $C_{1-4}$ means one to four carbons). Non limiting examples of"alkyl" include methyl, ethyl, propyl, isopropyl, butyl, iso-butyl, sec-butyl.

The term "halo" means fluoro, chloro, bromo, or iodo.

The term "haloalkyl" means an alkyl that is optionally substituted with one or more (e.g., 1, 2, 3, 4, or 5) halo. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl 2,2-difluoroethyl and pentafluoroethyl.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. Dap, PyrAla, ThiAla, (pCl)Phe, $(pNO_2)$Phe, ε-Aminocaproic acid, Met$[O_2]$, dehydPro, (31)Tyr, norleucine (Nle), para-1-phenylalanine ((pI)Phe), 2-napthylalanine (2-Nal), β-cyclohexylalanine (Cha), β-alanine (β-Ala), phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid (Tic), penicillamine, ornithine, citruline, α-methyl-alanine, para-benzoylphenylalanine, phenylglycine, propargylglycine, sarcosine, and tert-butylglycine) in D or L form. The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T.W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine. An amino acid specifically recited herein refers to its L-form, unless specified otherwise.

The term "peptide" describes a sequence of 2 to 25 amino acids (e.g. as defined hereinabove) or peptidyl residues. The sequence may be linear or cyclic. For example, a cyclic peptide can be prepared or may result from the formation of amide bonds or disulfide bridges between two cysteine residues in a sequence. When a peptide is cyclic, it can be illustrated as "c[peptide sequence]". A peptide can be linked to the remainder of a compound of formula I through the carboxy terminus, the amino terminus, or through any other convenient point of attachment, such as, for example, through the sulfur of a cysteine. In certain embodiments, a peptide comprises 3 to 10, or 4 to 8 amino acids. In certain embodiments, a peptide comprises 5 to 13 amino acids, or 5 to 9 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right. The term "dipeptide" refers to a peptide comprising two amino acids joined through an amide bond. The term "tripeptide" means a peptide comprising three amino acids joined through two amide bonds. The terms "protein," "peptide" and "polypeptide" are used interchangeably herein.

As used herein, the term "compound" includes peptides and cyclic peptides described herein (e.g., compounds of formula I).

As used herein, the term "residue of an amino acid" means a portion of an amino acid. For example, variables $X^1$, $X^2$, $X^3$, $X^4$, $X^5$ and $X^6$ may be residues of an amino acid, wherein certain atoms (e.g., H or OH) have been removed to link the amino acids via a peptide bond.

The following terms are used to describe the sequence relationships between two or more sequences (e.g., polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length peptide sequence or the complete peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA. 85:2444; the algorithm of Karlin and Altschul, (1990) Proc. Natl. Acad. Sci. USA, 87:2264, modified as in Karlin and Altschul. (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive. Madison, Wis., USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm-.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes. Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics. Mountain View. Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The terms "treat" and "treatment" refer to both therapeutic treatment and prophylactic or preventative measures, wherein the object is to prevent or decrease an undesired physiological change or disorder, such as a metabolic disorder (e.g., obesity) or a disease associated with the metabolic disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to, e.g., humans, higher non-human primates, rodents, domestic, cows, horses, pigs, sheep, dogs and cats. In one embodiment, the mammal is a human.

The invention will now be illustrated by the following non-limiting Examples.

Example 1. Structure-Activity Relationship Studies on a Macrocyclic Agouti-Related Protein (AGRP) Scaffold Reveal Agouti Signaling Protein (ASP) Residue Substitutions Maintain Melanocortin-4 Receptor Antagonist Potency and Result in Inverse Agonist Pharmacology at the Melanocortin-5 Receptor Abstract:

The melanocortin system consists of five reported receptors, agonists from the proopiomelanocortin gene transcript, and two antagonists, agouti-signaling protein (ASP) and agouti-related protein (AGRP). For both ASP and AGRP, the hypothesized Arg-Phe-Phe pharmacophores are on exposed β-hairpin loops. In this study, the Asn and Ala positions of a reported AGRP macrocyclic scaffold (c[Pro-Arg-Phe-Phe-Asn-Ala-Phe-DPro] (SEQ ID NO: 1)) were explored with 14-compound and 8-compound libraries, respectively, to generate more potent, selective melanocortin receptor antagonists. Substituting diaminopropionic acid (Dap). DDap, and His at the Asn position yielded potent MC4R ligands, while replacing Ala with Ser maintained MC4R potency. Since these substitutions correlate to ASP loop residues, an additional Phe to Ala substitution was synthesized and observed to maintain MC4R potency. Seventeen compounds also possessed inverse agonist activity at the MC5R, the first report of this pharmacology. These findings are useful in developing molecular probes to study negative energy balance conditions and unidentified functions of the MC5R.

Introduction:

The melanocortin system has been implicated in many biological pathways. To date, five melanocortin G protein-coupled receptors (GPCRs) have been identified. The melanocortin-1 receptor (MC1R) plays an important role in pigmentation.[1,2] The melanocortin-2 receptor (MC2R) is linked to steroidogenesis.[2] and is only stimulated by the endogenous adrenocorticotropic hormone (ACTH).[3] The centrally expressed melanocortin-3 and -4 receptors (MC3R and MC4R) have been associated with food intake and energy homeostasis.[4-11] Dysregulation or single nucleotide polymorphisms (SNPs) of the MC3R may predispose an individual to obesity,[12] while SNPs in the MC4R have been demonstrated to result in an obese phenotype.[13] The melanocortin-5 receptor (MC5R) is expressed widely throughout the body with its physiological role less characterized,[14,15] although it has been linked to exocrine function in mice.[16] These melanocortin receptors (MCRs) are stimulated by endogenous agonists derived from the proopiomelanocortin gene transcript,[17] which is processed into α-MSH, β-MSH, γ-MSH, and ACTH among other peptide products, as previously reviewed.[18,19] The melanocortin system also possesses naturally occurring antagonists, agouti-signaling protein (ASP)[20,21] and agouti-related protein (AGRP).[22-24] Overexpression of ASP or AGRP in transgenic mice results in an obese phenotype, with the expression level of either protein correlating to weight gain.[25,26] Transgenic mice overexpressing ASP recapitulate the lethal yellow ($A^y$) mouse strain, characterized by ectopic ASP expression,[21,27] a yellow coat color (presumably due to MC1R antagonism),[28] and an obese phenotype (originally hypothesized to be due to MC4R antagonism, but may also involve MC3R antagonism).[28,29] While a yellow coat color is not observed (implying a lack of MC1R antagonism), ectopic expression of AGRP increases weight gain,[26] similar to the dose-dependent increase in food intake with icy administration of AGRP.[10,30] The AGRP-mediated increased consumption is observed in both MC3R and MC4R knockout mice, implying AGRP antagonism of both receptors may be responsible for the observed phenotype.[10] Developing probes from ASP and AGRP may therefore be important in investigating the origins and potential therapeutics for obesity. Additionally, as potent orexigenic (appetite-inducing) compounds, ligands developed from ASP and AGRP may be useful in the treatment of negative energy balance disorders, including cachexia, aneroxia, and failure to thrive in infants.[31-33]

Full length ASP is 132 amino acids (FIG. 1A), with the active form ASP(23-132) resulting from the cleavage of a 22-residue signal sequence.[34-36] Recombinant mouse (m)ASP was reported to impair α-MSH mediated cAMP production at the mMC1R[28,37,38] and the human (h) MC4R,[28] but did not at the rat (r)MC3R.[28] The C-terminal domain of recombinant mASP is equipotent to ASP(23-132) in *Xenopus* melanophores[35] and in murine Bl6F10 cells (both presumably express the MC1R),[38] indicating this region possessing 5 disulfide bonds is responsible for the observed antagonist activity. Although recombinant mASP was purportedly not able to antagonize the rMC3R,[28] later work with the recombinant hASP indicated this homolog was an antagonist at the hMC3R, with decreased potency relative to the hMC1R and hMC4R.[39] The authors reported seeing a similar trend for recombinant mASP at the human receptors, but did not show these data.[39] This functional activity correlated with a subsequent binding study which demonstrated that mASP was able to displace radiolabeled NDP-MSH at the mMC1R, mMC3R, and mMC4R with $K_{i\ app}$ of 2.6, 190, and 54 nM, respectively.[40] In the same report, an alanine positional scan of the C-terminal domain of mASP indicated that replacing the $Arg^{116}$ and $Phe^{118}$ residues of mASP decreased affinity at the mMC1R, mMC3R, and mMC4R; additionally, substituting Ala at the $Phe^{117}$ of mASP decreased affinity at the mMC4R.[40] To generate sufficient quantities of the hASP C-terminal domain for NMR analysis, a synthetic approach was explored.[29] Although synthesis of the 53 residue C-terminal domain of hASP resulted in poor yields due to misfolded products, substitution of two residues (Q115Y, S124Y, corresponding to equivalent residues in AGRP) resulted in one major observed product that possessed the correct molecular mass for the properly folded protein.[29] The synthetic hASP-YY possessed nanomolar antagonist potency at the hMC1R and hMC3R, and sub-nanomolar potency at the hMC4R.[29] Within the C-terminal domain of ASP-YY, the C-terminal loop (residues $Arg^{126}$-$Asn^{131}$) has been implicated as necessary for potent MC1R binding.[41]

Agouti-related protein, AGRP, was first identified due to sequence homology and the Cys-spacing pattern with ASP (FIG. 1A).[22-24] Described as agouti-related protein,[23] agouti-related peptide,[42,43] or agouti-related transcript,[22,24,26] AGRP possesses nanomolar antagonist pharmacology at the centrally expressed MC3R and MC4R,[22,23] as well as inverse agonist activity at the MC4R.[44,45] The biologically active form of AGRP has been hypothesized to be AGRP(83-132) following processing by proprotein convertase 1.[46] The C-terminal domain of synthetic[47,48] and recombinant AGRP[23] has been demonstrated to be equipotent to longer AGRP variants.[23,48] Like ASP, the C-terminal domain of AGRP possesses an Arg-Phe-Phe tripeptide sequence important for binding and antagonist activity (FIG. 1B).[49] Solution NMR structural studies of ASP-YY,[29] the C-terminal domain of AGRP,[50,51] and a shortened "mini-AGRP"[52] have all indicated that the hypothesized Arg-Phe-Phe pharmacophores are located on similar solvent-exposed 3-hairpin loops (FIG. 1C). Truncation studies of hAGRP, mASP, and hASP indicated that cyclic octapeptide fragments based upon the active loops of these molecules (c[Cys-Arg-Phe-Phe-Asn-Ala-Phe-Cys] (SEQ ID NO:139), c[Cys-Arg-Phe-Phe-Gly-Ser-Ala-Cys] (SEQ ID NO: 140), and c[Cys-Arg-Phe-Phe-Arg-Ser-Ala-Cys] (SEQ ID NO:141), respectively) were the minimal required sequences for MC4R binding affinity, with the hASP octapeptide also possessing affinity at the MC3R.[49] While mASP was not further explored, elongation of hAGRP by two Tyr residues, H-Tyr-c[Cys-Arg-Phe-Phe-Asn-Ala-Phe-Cys]-Tyr-OH (SEQ ID NO: 142), was necessary for binding affinity at the MC3R and sub-micromolar functional activity at the MC4R.[49] An additional four residues were required for functional antagonism at the MC3R, indicating the importance of amino acids outside the 3-hairpin loop for MC3R potency.[53] Although dodecapeptide and tetradecapeptides possess antagonist activity at the MC3R and MC4R the potencies of truncated AGRP peptides are lower compared to AGRP.

Previously, it was hypothesized that inducing a 3-hairpin structure in small AGRP-derived peptides containing the postulated Arg-Phe-Phe pharmacophore may result in more potent antagonists.[54] A macrocyclic scaffold containing the active hexapeptide loop of ARGP cyclized through a DPro-Pro motif, c[Pro-Arg-Phe-Phe-Asn-Ala-Phe-DPro] (SEQ ID NO: 1), was 50-fold less potent at the MC4R compared to AGRP.[54] Further structure-activity relationship studies at the Asn position indicated basic residues (diaminopropionic acid [Dap], diaminobutyric acid [Dab], Orn, Lys, Arg) or Gly increased MC4R potency. The most potent substitution, the Asn to Dap replacement, resulted in a sub-nanomolar potent MC4R antagonist that was 160-fold selective for the MC4R over the MC3R, induced partial MC1R activation at 100 μM concentrations, and did not possess agonist activity at the MC5R.[54] To further investigate this scaffold, a series of truncated macrocycles were synthesized containing either the Asn or Dap residues and replacing the Arg-Phe-Phe tripeptide antagonist sequence with the melanocortin agonist tetrapeptide His-DPhe-Arg-Trp (SEQ ID NO: 133) or tripeptide DPhe-Arg-Trp sequences.[55] This study examined if the AGRP DPro-Pro loop scaffold was amendable to substitutions that may result in melanocortin agonist activity as weight-management therapeutic compounds. Two macrocycles were identified that possessed nanomolar agonist potencies at the MC4R, nanomolar to sub-nanomolar potencies at the MC1R and MC5R, and 30-40 nanomolar potencies at the MC3R, c[Pro-His-DPhe-Arg-Trp-Asn-Ala-Phe-DPro] (SEQ ID NO: 134) and c[Pro-His-DPhe-Arg-Trp-Dap-Ala-DPro] (SEQ ID NO: 135).[55]

Due to the increased ligand potency for basic and Gly substitutions at the Asn position in the octapeptide macrocyclic scaffold, an additional SAR study was performed at the Asn position. To explore the ligand-receptor interface, substitutions at the Asn position with basic, acidic, polar, non-polar, and aromatic groups were assayed at the mouse MCRs. A similar series of substitutions explored the Ala position. From these two series, a substitution pattern was observed that substitution of the equivalent residue type in the exposed loop of ASP maintained MC4R potency in this AGRP scaffold while other substitutions decreased potency. Therefore, the non-pharmacophore Phe residue was replaced with an Ala found in the active loops of both hASP and mASP to examine if insertion of ASP residues into an AGRP scaffold would maintain MC4R potency.

Results & Discussion:

Peptide Synthesis and Characterization:

Peptides were synthesized manually or using an automated peptide synthesizer with standard fluorenylmethoxycarbonyl (Fmoc) chemistry.[56,57] The macrocyclization chemistry to form the amide bond between the Arg and Pro residues using BOP and HOBt has previously been reported.[54,55] Following cyclization and side-chain deprotection, peptides were purified by semi-preparative reverse-phase high pressure liquid chromatography (RP-HPLC). Peptides were assessed for purity (>95%) by analytical RP-HPLC in two solvent systems (Table 1), and the correct molecular mass was confirmed through matrix-assisted laser desorption/ionization mass spectrometry (MALDI-MS, University of Minnesota Mass Spectrometry Laboratory).

In Vitro AlphaScreen cAMP Assay:

The compounds were assayed using the AlphaScreen cAMP assay in HEK293 cells stably expressing the mouse melanocortin 1, 3, 4, and 5 receptors according to the manufacturer's instructions and as previously reported.[58-60] The MC2R is only stimulated by ACTH and was therefore excluded from this study. Compounds were first assayed for agonist activity at the MCRs; ligands that did not possess full agonist activity at the MC3R and MC4R were then assayed for antagonist activity using a Schild paradigm[61] and NDP-MSH as the agonist. Since the AlphaScreen assay is a competition assay (higher concentrations of ligand result in lower signal), concentration-activity curves were normalized to baseline and maximal NDP-MSH signal for illustrative purposes as previously described.[58,59] Due to the inherent error associated with the assay in our laboratory, compounds that were within a 3-fold potency range were considered equipotent.

Asn Position Substitutions:

Previously, the AGRP-derived macrocyclic octapeptide c[Pro-Arg-Phe-Phe-Asn-Ala-Phe-DPro] (SEQ ID NO: 1) was found to possess sub-micromolar antagonist potency at the MC4R ($pA_2$=7.7), and substitution at the Asn position with basic residues or Gly further increased potency ($pA_2$ values ranged from 8.3 to 9.1).[54] The most potent substitution, Asn to diaminopropionic acid (Dap), resulted in a ligand that was equipotent to the C-terminal domain of AGRP at the MC4R.[54] It was previously hypothesized that the active loop Asn residue in AGRP may be in close proximity to an Asp residue in the MC4R ($Asp^{189}$), and that inc orporation of basic residues into AGRP analogues at this position might form a novel salt bridge with the MC4R.[47] While the increased potency observed for basic substitutions supported the postulated salt bridge, the increased potency for Gly suggested other residues might also be incorporated without diminishing potency. Therefore, an additional SAR study was performed at the Asn position to explore the side-chain requirements for antagonist potency and to further examine the hypothesized salt-bridge interaction. Short aliphatic residues (Ala and Abu) were utilized to mimic the steric space of Dap without the charge. Residues were included that could mimic the hydrogen bond donor and acceptor potential of Dap without the positive charge (Ser and Thr). The negatively charged Asp and Glu were incorporated to reverse the charge while varying side-chain length. Additional basic residues were also explored by inverting the stereochemistry (DDap) and incorporating a small charged heterocycle (His). Longer and/or branched aliphatic side chains Nle, Leu, and Val were integrated to examine the functional consequence of expanding the uncharged side chain, as were the aromatic side chains in Phe and Trp. The Dap substitution was synthesized as a control, and the C-terminal domain of AGRP [AGRP(86-132)] was run in parallel as an antagonist at the MC3R and MC4R using the AlphaScreen assay as an additional known ligand. All amino acid structures can found in FIG. 2.

In the present study, AGRP(86-132) possessed identical $pA_2$ values of 8.7 at both the MC3R and MC4R, similar to previous reported nanomolar potencies at these receptors (Table 2, FIG. 3).[22,23,41,46,48,53] The native sequence of the exposed D-hairpin loop (1) partially stimulated the MC1R at 100 μM concentrations (25% of the maximal NDP-MSH signal) and did not possess agonist activity at the MC3R or MC4R up to 100 μM. This peptide possessed sub-micromolar antagonist potency at the MC3R ($pA_2$=6.3) and nanomolar potency at the MC4R ($pA_2$=8.2; FIG. 3). These values are comparable to a previous report where this peptide possessed micromolar agonist activity at the MC1R, and was an antagonist at the MC3R ($pA_2$=6.4) and MC4R ($pA_2$=7.7) using a β-galactatosidase reporter gene assay.[54] Insertion of the Dap residue (2) resulted in partial activation of the MC1R (30% NDP-MSH maximal signal) and did not stimulate cAMP production at the MC3R or MC4R up to 100 μM concentrations. Peptide 2 possessed antagonist activity at the MC3R ($pA_2$=6.5) and MC4R ($pA_2$=8.7; FIG. 3), similar to the previously reported $pA_2$ values of 6.9 and 9.1, respectively (2 also was reported to partially activate the MC1R to 75% NDP-MSH at 100 μM).[54] In both the previous and present study, 2 was an equipotent antagonist to AGRP(86-132) at the MC4R, and was over 100-fold selective for the MC4R over the MC3R despite using two different cAMP reporter assays.[54]

While similar activity was observed for 1 and 2 at the MC1R, MC3R, and MC4R, a difference was observed at the MC5R. Previously, these compounds were reported to possess no activity at the MC5R at 100 μM concentrations using a β-galactosidase assay.[54] In the present study, a decrease in normalized signal from basal activity was observed (Table 2, FIG. 4), correlating to decreased levels of cAMP and suggesting an inverse agonist response for these ligands at the MC5R. From basal activity, a 10% and 15% dose-response difference in signal were observed for 1 (FIG. 4) and 2, respectively. Since a sigmoidal curve was observed, 1 and 2 possessed apparent potencies (the inflection point on the curve) of 130 nM and 60 nM, respectively. This activity was only observed at the MC5R, and not the other MCRs in the present study. Since the MCRs are all stably expressed in HEK293 cells, if another factor such as cellular toxicity or signaling through an alternative receptor was responsible, the decreased signal would be expected at additional melanocortin receptors. It therefore appears that the observed decreased levels of cAMP may be the result of inverse agonist activity at the MC5R. While many ligands displayed a similar sigmoidal dose-response compared to 1 and 2 (FIGS. 4, 4, 5, and 8 as examples), some ligands decreased cAMP levels at the MC5R without plateauing at 100 μM concentrations (FIGS. 4, 21 and 24 as examples). The inverse agonist response of these compounds is reported as the percent decreased from basal at 100 μM concentrations.

Substitution of the short aliphatic Ala (3) or Abu (4) residues at the Asn position resulted in ligands that were unable to stimulate any receptor tested. At the MC5R, 3 and 4 (FIG. 4) decreased from basal signal 20% and had apparent potencies of 250 nM and 160 nM, respectively. Both peptides did not possess antagonist activity at the MC3R, and were 8-fold less potent at the MC4R compared to 1 ($pA_2$=7.3 for both). No agonist activity was observed when Asn was replaced with the polar amino acids Ser (5) or Thr (6) at the MC1R, MC3R, or MC4R. These peptides produced inverse agonist activity of 25% (with an apparent potency of 140 nM) and 20% (50 nM) for 5 (FIG. 4) and 6, respectively. Peptide 5 possessed antagonist potency at the MC3R ($pA_2$=5.9) and MC4R ($pA_2$=7.7), similar to the response of 6 ($pA_2$=6.4 and 7.8 at the MC3R and MC4R). When Asn was substituted with the acidic Asp residue (7), no agonist activity was observed for the MC1R, MC3R, and MC4R, while a 25% inverse agonist response was observed at 100 μM concentrations at the MC5R. This peptide did not possess antagonist activity at the MC3R, and was 25-fold less potent at the MC4R compared to 1. Elongating the acidic side chain by one methylene unit, 8, resulted in the only peptide in this study with full MC1R agonist activity ($EC_{50}$=20.5 μM). This Glu substitution did not result in measurable activity at the MC3R, had a 10% inverse agonist response (apparent potency=700 nM) at the MC5R, and was a 16-fold less potent antagonist at the MC4R compared to 1. When substituting the basic residues DDap or His (9 or 10, respectively), no agonist activity was observed at the MC1R, MC3R, and MC4R up to 100 μM concentrations. Similar 10% inverse agonist responses were observed at the MC5R, with apparent potencies of 110 nM (9) and 10 nM (10). Both substitutions possessed sub-micromolar antagonist potencies at the MC3R ($pA_2$ values of 6.7, and 6.5) and nanomolar antagonist potencies at the MC4R ($pA_2$ values of 8.6, and 8.3). For the longer and/or branched aliphatic substitutions Nle, Leu, and Val (11, 12, and 13), the Val substituted 13 stimulated the MC1R to 55% the maximal signal of NDP-MSH at 100 μM. These three ligands did not produce an agonist response at any other MCR. At the MC5R, 12 and 13 decreased the basal signal 20% and 25%, respectively, with apparent potencies of 110 nM and 510 nM. Peptide 12 was the only ligand of the three to possess micromolar antagonist potency at the MC3R ($pA_2$=5.7). These aliphatic substitutions possessed a range of potencies at the MC4R ($pA_2$=6.9, 7.3, and 5.9 for 11, 12, and 13, respectively), and were at least 8-fold less potent than 1. When substituting the aromatic amino acid Phe (14), only antagonist activity at the MC4R was observed ($pA_2$=6.6). Incorporation of Trp, 15, resulted in a ligand that partially stimulated the MC1R, MC3R, and MC4R (80%, 40%, and 50% maximal NDP-MSH signal) at 100 μM concentrations. This substitution resulted in a 20% inverse agonist response with an apparent potency of 150 nM at the MC5R, and antagonist activity at the MC3R and MC4R ($pA_2$=5.7 and 6.8, respectively).

Certain potency trends at the MC4R were observed when grouping these AGRP-derived macrocycles varied at the Asn position by side-chain type. Residues containing basic side chains (Dap, DDap, and His) possessed the highest MC4R potency, similar to the previous report.[54] These results support a potential salt-bridge between this position and the acidic residue $Asp^{189}$ of the MC4R, as previously hypothesized.[47] Interestingly, the stereochemistry of the basic charge did not appear significant, as the Dap ($pA_2$=8.7) and DDap ($pA_2$=8.6) were equipotent at the MC4R. Amino acids with side chains capable of donating and accepting hydrogen bonds (Ser, Thr, and Asn) possessed slightly lower potency at the MC4R compared to basic substitutions. Aliphatic substitutions of similar size to Dap (Ala and Abu) or Asn (Leu) possessed similar potencies, less than the hydrogen bond donor capable side-chains. Substitution of Asn with Asp, replacing an amide with a carboxylic acid, decreased potency more than 10-fold, indicating a negative charge adversely impacted activity. The remaining acidic, aliphatic, and aromatic substitutions all possessed similar potency at the MC4R, with $pA_2 \leq 7$. The Val substituted ligand (13) was the only compound with micromolar or higher potency at the MC4R ($pA_2=5.9$). Although Val is similar in structure to Thr (both possess a branched side chain and differ by a methyl versus hydroxyl substitution), the Thr substituted 6 was 70-fold more potent compared to 13. At the MC5R, no trends in percent inverse agonist activity of apparent potency were observed.

Ala Position Substitutions:

While SAR studies for the Asn and two pharmacophore Phe positions have been reported on this scaffold,[54] the Ala position has not previously been studied. One structural model of AGRP interacting with the MC4R indicated that this Ala position of AGRP may be in close proximity to the $His^{264}$ (TMH6) residue of the MC4R.[62] Therefore, it was hypothesized that incorporating an acidic amino acid into the corresponding Ala position in the truncated AGRP macrocycle may result in the formation of a new salt bridge and increase potency. A library of 8 compounds varied at the Ala position were synthesized and assayed at the mMCRs. To probe for a potential salt bridge with $His^{264}$, the acidic residues Asp and Glu were included. Additional residues were incorporated to begin to probe the ligand requirements at this position for potent melanocortin receptor activity including the basic Lys and His, aromatic Phe, hydrogen bond donor and acceptor Ser, aliphatic Leu, and small Gly.

While the Ala position in the active loop of AGRP was previously hypothesized to be in close proximity to $His^{264}$, substitution of Asp (16) or Glu (17) did not result in observable agonist or antagonist activity at the MC3R and MC4R. Both peptides partially stimulated the MC1R at 100 μM concentrations (65% and 60% for 16 and 17, respectively) and 16 produced an inverse agonist response at the MC5R (25% at 100 μM). Incorporation of a basic Lys (18) resulted in a ligand that partially stimulated the MC1R (60%), MC3R (45%), and MC5R (45%; FIG. 4), and possessed sub-micromolar antagonist potency at the MC4R ($pA_2=6.1$). Identical antagonist potency at the MC4R was observed for a His substitution (19, $pA_2=6.1$) compared to 18, while a partial agonist response was observed at the MC1R (40% NDP-MSH efficacy with an $EC_{50}=3{,}000$ nM). This compound did not possess activity at the MC5R (FIG. 4). Substitution of an aromatic Phe (20) resulted in partial stimulation of all the MCRs assayed at 100 μM concentrations (70%, 35%, 35%, and 25% of the maximal NDP-MSH signal at the MC1R, MC3R, MC4R. and MC5R, respectively), as well as micromolar antagonist potencies at the MC3R and MC4R ($pA_2=5.7$ for both receptors). Incorporating the polar Ser capable of donating and accepting hydrogen bonds resulted in peptide 21, which did not possess agonist activity at the MC1R, MC3R, and MC4R up to 100 μM concentrations, and generated an inverse agonist response at the MC5R (FIG. 4, 30% at 100 μM). Peptide 21 possessed sub-micromolar antagonist potency at the MC3R ($pA_2=6.2$), and was the only ligand in the Ala substitution series that was equipotent to 1 at the MC4R ($pA_2=8.2$; FIG. 3). The aliphatic Leu substitution (22) induced a partial agonist response at the MC1R, MC3R, and MC4R (80%, 25%, and 25%, respectively), and was a sub-micromolar antagonist at the MC4R ($pA_2=6.2$). Incorporating the small Gly residue (23) resulted in a ligand that possessed inverse agonist activity at the MC5R (35% at 100 μM concentrations) and sub-micromolar antagonist potency at the MC4R ($pA_2=6.1$).

The Ala position had previously been postulated to be near the $His^{264}$ residue in the MC4R,[62] and it was therefore hypothesized that incorporating a negatively charged residue may result in the formation of a novel salt bridge. If correct, replacement of the Ala with two acidic amino acids (Asp and Glu) might be expected to increase antagonist potency. However, both 16 and 17 did not possess antagonist activity at the MC3R or MC4R. While the current study does not support the postulated Ala-$His^{264}$ proximity, it is possible that a longer form of AGRP orients this position in a different conformation that may result in a productive interaction. Altering the side chain stereochemistry, elongating/shortening a side chain possessing a negative charge, or utilizing longer AGRP substituted derivatives could be utilized to further examine this hypothesis.

Phe Position Substitution:

Unlike substitutions at the Asn position, which resulted in a range of MC4R potencies, only one ligand substituted at the Ala position (Ser, 21) was equipotent to the parent macrocycle 1 ($pA_2=8.2$ for both compounds). All other substitutions decreased potency more than 100-fold ($pA_2<6.2$) relative to 1, perhaps indicating a more stringent structural requirement for ligand-receptor interactions at this position. While attempting to rationalize why Ser might be tolerated at the Ala position, it was observed that the equivalent loop position in both mouse and human ASP is a Ser (FIG. 1B). Another compelling observation was that the equivalent position of Asn in the active loop of AGRP was either a basic Arg (human) or Gly (mouse) residue in ASP, a substitution pattern described herein and previously as possessing potent MC4R antagonism.[54] To extend these observations, it was hypothesized that substitution of the non-pharmacophore Phe position in the AGRP loop with Ala (found in the equivalent ASP position) would maintain MC4R antagonist potency. The resulting Phe to Ala substitution, 24, possessed equipotent MC4R antagonist potency ($pA_2=8.2$; FIG. 3) compared to the parent macrocycle 1, supporting the observations that ASP loop residues substituted onto an AGRP macrocyclic template maintain MC4R antagonist potency. This peptide possessed sub-micromolar antagonist potency at the MC3R ($pA_2=6.1$), no agonist activity at the MC1R up to 100 μM concentrations, and resulted in inverse agonist activity at the MC5R (25% at 100 μM, FIG. 4).

Thus, single substitutions of ASP active loop residues into a macrocyclic AGRP-derived peptide result in the maintenance of MC4R antagonist potency and approximately 100-fold decrease in MC3R antagonist potency, a similar decrease to the parent ligand. In the current study, AGRP was shown to be equipotent at the MC3R and MC4R ($pA_2=8.7$ at both receptors), in agreement with prior reports of nanomolar potencies at both receptors.[22,23,53]. The decreased MC3R potency has been observed in many AGRP truncated analogs, and was described by Tota et al. who found the minimal fragment needed to bind to the MC4R (H-c[Cys-Arg-Phe-Phe-Asn-Ala-Phe-Cys]-OH (SEQ ID NO: 154)) was unable to bind the MC3R.[49] Acetylating the N-terminal and amidating the C-terminal of this octapeptide was sufficient to achieve micromolar MC4R antagonist potency.[49] Further elongation by adding Tyr residues to both terminals was required to achieve MC3R binding and resulted in sub-micromolar potency at the MC4R.[49,53] Two residues added to both the N- and C-terminals (Thr-Ala-Tyr-c[Cs-Arg-Phe-Phe-Asn-Ala-Phe-Cys]-Tyr-Ala-Arg-$NH_2$) (SEQ ID NO: 143) or four residues added to the C-terminal (Tyr-c[Cys-Arg-Phe-Phe-Asn-Ala-Phe-Cys]-Tyr-Ala-Arg-Lys-Leu-$NH_2$) (SEQ ID NO: 144) were required for sub-micromolar potency at the MC3R.[53] The prior study with DPro-Pro cyclized AGRP macrocycles also resulted in more potent antagonism at the MC4R relative to the MC3R.[54] Therefore, a common trend of truncated AGRP analogs is decreased potency at the MC3R, perhaps indicating that additional residues outside of the active loop are necessary for potent interaction at the MC3R.

While decreased MC3R potency is observed in many AGRP truncation studies, ASP was first described to interfere with α-MSH stimulation of the MC1R and MC4R, and not affect the MC3R and MC5R.[28] One interpretation of the current data, assuming ASP is an antagonist at the MC1R and MC4R while AGRP antagonizes the MC3R and MC4R, is that replacement of AGRP residues in the active loop sequence with ASP residues would be expected to maintain MC4R antagonism while decreasing and/or minimizing MC3R potency. However, such an interpretation would ignore subsequent publications indicating ASP was capable of binding[40] and functionally antagonizing[39] the MC3R. Throughout all of these conflicting reports, a recombinant ASP (expressed using a baculovirus construct in insect cells) was utilized, potentially resulting in varying degrees of ASP purity and difficulty in accurately assessing the concentration of ASP.

To generate a pure ASP for functional characterization and NMR studies, McNulty et al. attempted to chemically synthesize the C-terminal domain of ASP,[29] previously shown to be as active as the full-length construct.[35] However, when attempting to cyclize the 53-residue fragment, less than 10% of the linear peptide folded with the correct disulfide bond pairing, with greater than 90% of the observed products resulting from incorrect disulfide bond formation.[29] This is unlike the chemical synthesis of the C-terminal domain of AGRP, which correctly folds to the proper disulfide bonding when put under oxidative conditions.[48,50] In order to generate sufficient quantities of chemically synthesized ASP, two Tyr residues of AGRP were incorporated into the ASP synthesis (Ala115Tyr and Ser124Tyr) to generate a double-substituted form of ASP that properly folded under oxidative conditions.[29] This ASP-YY ligand was shown to possess potent antagonism at the MC3R (2.6 nM) as well as the MC1R (3.9 nM) and MC4R (0.5 nM), and incorporation of the two Tyr residues was crucial in yielding sufficient product for NMR studies. However, the addition of these Tyr amino acids confounds the activity of ASP at the MC3R, since it is impossible to discern if ASP-YY without the Tyr would retain the same activity, if the Tyr residues induce an altered conformation of the ligand, or if the Tyr amino acids result in novel ligand-receptor interactions. Despite these limitations, the in vitro pharmacological profile of ASP-YY at the MC1R, MC3R, and MC4R is similar to purified forms of recombinant ASP,[39,40] supporting the hypothesis that ASP can interact at the MC3R.

In addition to being found in the active loop of ASP, select residue types in the current study are also found in species variants of AGRP. A PubMed BLASTp search of the sequence Cys-Arg-Phe-Phe-Lys-Ala-Phe-Cys (SEQ ID NO: 145) (Asn to Lys) found this sequence to be in the AGRP precursor peptide of *Carassius auratus* (goldfish) and *Danio rerio* (zebrafish), indicating some species possess a basic residue in this position of the active loop of AGRP. Similarly, searching Cys-Arg-Phe-Phe-Asn-Ser-Phe-Cys (SEQ ID NO: 146) (Ala to Ser) and Cys-Arg-Phe-Phe-Asn-Thr-Phe-Cys (SEQ ID NO: 147) (Ala to Thr) found these sequences to be in the predicted AGRP of *Sarcophilus harrisii* (Tasmanian devil) and the precursor AGRP of *Rattus norvegicus* (rat), respectively. The observed residues types in the current study that maintained or increased MC4R potency (replacing Asn with basic residues, replacing Ala with hydroxyl-containing Ser) can also be found in naturally occurring AGRP orthologs, and may explain why these substitutions are tolerated at the MC4R.

An additional discovery from these structure-activity relationship studies was the apparent inverse agonism of several ligands at the MC5R. While the MC5R was previously reported to be constitutively active,[45] to the best of the authors' knowledge, no ligand to date has previously been shown to decrease cAMP through interaction with the MC5R. Twelve compounds (1, 2, 3, 4, 5, 6, 8, 9, 10, 12, 13, and 15) decreased the basal-normalized signal in a sigmoidal dose-response curve. This set of compounds decreased the observed response 10-25% that of the basal response, with apparent potencies (the inflection point of the sigmoidal dose-response) ranging from 10 to 700 nM. All compounds with the sigmoidal dose-response MC5R inverse agonist activity were substituted at the Asn position within the scaffold. An additional 5 ligands (7, 16, 21, 23, and 24) decreased the response from basal 25-35%, although this activity did not plateau at high concentrations. This scaffold did not uniformly result in MC5R inverse agonism, as five ligands possessed no activity at the MC5R (11, 14, 17, 19, and 22), while two more compounds partially stimulated the MC5R (18 and 20). The variable MC5R activities suggest this is not an artifact due to the ligand scaffold, since a uniform response to all ligands was not observed. Additional structure-activity relationship studies on this scaffold at the MC5R, coupled with mutagenesis and docking studies, may help elucidate the putative ligand-receptor interactions between this class of ligands and the MC5R to explain the variable inverse agonist activity and how to improve the apparent potency and percent change from basal activity.

Conclusions:

The present SAR study investigated the Asn and Ala positions within an AGRP-derived macrocyclic scaffold, c[Pro-Arg-Phe-Phe-Asn-Ala-Phe-DPro] (SEQ ID NO: 1), in attempts to generate more potent and/or selective MCR antagonists. Similar to a prior SAR study, basic substitutions at the Asn position increased MC4R potency. Substitution of Ser at the Ala position maintained MC4R potency, while all other substitutions at the Ala position decreased MC4R antagonist potency. The same trends were observed at the MC3R, though ligands were approximately 100-fold less potent at this receptor compared to the MC4R. Observing that the potent MC4R substitutions were also found in the active loop of ASP, a final Phe to Ala substitution was synthesized and assayed, which was equipotent at the MC4R compared to the core scaffold. These results indicated that the equivalent β-hairpin active loop positions of ASP could be inserted into this AGRP scaffold and resulted in similar or increased MC4R potency. From the increased knowledge of structural requirements for AGRP-derived ligand at the MC4R, this study may be important in the development of MC4R selective probes and molecules for potential weight gain therapeutics. Additionally, the observed MC5R inverse agonism from these SAR studies are useful in designing ligands and probes to clarify the role of the ubiquitously expressed MC5R in vivo.

Methods:

Peptide Synthesis:

All peptides were synthesized using standard Fmoc chemistry.[56,57] The coupling reagents 2-(1-H-benzotriazol-1-yl)-1,1,3,3-tetramethyluronium hexafluorophosphate (HBTU), benzotriazol-1-yl-oxy-tris(dimethylamino) phosphonium hexafluorophosphate (BOP) and 1-hydroxybenzotriazole (HOBt), the H-Pro-2-chlorotrityl resin, amino acids Fmoc-DPro, Fmoc-Phe. Fmoc-Ala, Fmoc-Abu (aminobutyric acid). Fmoc-Thr(tBu), Fmoc-Asp(tBu), Fmoc-Glu(tBu), Fmoc-Dap(Boc) (Diaminopropionic acid), Fmoc-Nle, Fmoc-Val, Fmoc-Leu. Fmoc-Trp(Boc), Fmoc-His(Trt), Fmoc-Gly, Fmoc-Ser(tBu), Fmoc-Lys(Boc), and Fmoc-Asn (Trt), and the agouti-related protein (AGRP86-132) were purchased from Peptides International (Louisville, Ky.). Amino acid Fmoc-D-Dap(Boc) was purchased from Bachem (Torrance, Calif.). Dichloromethane (DCM), methanol (MeOH), acetonitrile (ACN), dimethylformamide (DMF) and anhydrous ethyl ether were purchased from Fisher (Fairlawn, N.J.). Trifluoroacetic acid (TFA), dimethyl sulfoxide (DMSO), piperidine, triisopropylsilane (TIS), and N,N-diisopropylethylamine (DIEA) were purchased from Sigma-Aldrich (St. Louis, Mo.). All reagents and chemicals were ACS grade or better and were used without further purification.

Peptides were synthesized on a 0.05 mmol scale using H-Pro-2-chlorotrityl resin (0.68 to 0.76 meq/g substitution) in a 96-well block with an automated (Vantage Automated Parallel Peptide Synthesizer; Advanced ChemTech, Louisville, Ky.) or a semi-automated (LabTech I; Advanced ChemTech, Louisville, Ky.) instrument. Parallel syntheses consisted of two repeated steps separated by DMF washes: (i) removal of the Fmoc group with 20% piperidine in DMF (1× at rt for 5 min, 1× at rt for 20 min), and (ii) double coupling of the incoming Fmoc-protected amino acid (3.1 eq) with HBTU (3 eq) and DIEA (5 eq) in DMF at rt for 45 min. After completion of the syntheses, peptides were cleaved with a 99:1 DCM:TFA solution for 6 min. The cleavage solutions were concentrated and the side-chain protected linear peptides were precipitated using ice-cold ethyl ether. Peptides were cyclized in DCM with BOP (3 eq) and HOBt (3 eq) overnight using a peptide concentration of 1 mg/mL, and the DCM was removed under vacuum. Without further purification, the cyclized peptides were side-chain deprotected using a 95:2.5:2.5 TFA:TIS:$H_2O$ solution for 2 h. The solution was concentrated and cyclic peptides precipitated with ice-cold ethyl ether.

Crude peptides were purified by RP-HPLC using a Shimadzu system with a UV detector and a semi-preparative RP-HPLC C18 bonded silica column (Vydac 218TP1010, 1×25 cm). Assayed peptides were at least 95% pure as assessed by analytical RP-HPLC utilizing a Shimadzu system with a photodiode array detector and an analytical C18 silica column (Vydac 218TP104, 0.46×25 cm) in two diverse solvent systems and had the correct average molecular mass by MALDI-MS (Applied Biosystems-Sciex 5800 MALDI/TOF/TOF-MS, University of Minnesota Mass Spectrometry Lab).

cAMP AlphaScreen® Bioassay:

Cyclized peptides were dissolved in DMSO (NDP-MSH and AGRP in $H_2O$) at a stock concentration of $10^{-2}$M and were characterized pharmacologically using HEK293 cells stably expressing the mouse MC1R, MC3-5R by the cAMP AlphaScreen® assay (PerkinElmer) according to the manufacturer's instructions and as previously described.[58,60]

Briefly, cells 70-90% confluent were dislodged with Versene (Gibco®) at 37° C., and plated 10,000 cells/well in a 384-well plate (Optiplate™) with 10 μL freshly prepared stimulation buffer (1×HBSS, 5 mM HEPES, 0.5 mM IBMX, 0.1% BSA, pH=7.4) with 0.5 μg anti-cAMP acceptor beads per well. The cells were stimulated with the addition of 5 μL stimulation buffer containing peptide (concentrations from $10^{-4}$ to $10^{-13}$ M, determined by ligand potency) or forskolin ($10^{-4}$ M) and incubated in the dark at room temperature for 2 hr.

Following stimulation, streptavidin donor beads (0.5 μg) and biotinylated-cAMP (0.62 μmol) were added to the wells in a green light environment with 10 μL lysis buffer (5 mM HEPES, 0.3% Tween-20, 0.1% BSA, pH=7.4) and the plates were incubated in the dark at room temperature for an additional 2 hr. Plates were read on a Enspire (PerkinElmer) Alpha-plate reader using a pre-normalized assay protocol (set by the manufacturer).

Data Analysis.

The $EC_{50}$ and $pA_2$ values represent the mean of duplicate replicates performed in at least three independent experiments. The $EC_{50}$ and $pA_2$ estimates and associated standard errors (SEM) were determined by fitting the data to a nonlinear least-squares analysis using the PRISM program (v4.0, GraphPad Inc.). When analyzing the inverse agonist activity at the MC5R, each replicate was normalized to the replicate signal at $10^{-10}$ M to observe change from basal activity. The percent inverse agonist activity was calculated from the normalized signal of three independent experiments. When a sigmoidal dose-response was observed, the percent inverse agonist activity reported was the change from basal to the plateau signal at high ligand concentrations; in these instances, the apparent potency was reported to be the inflection point of the sigmoidal curve. When inverse agonist activity was observed without a plateau at high concentrations, the percent inverse activity reported was the percent change from basal to signal at 100 μM concentrations. The ligands were assayed as TFA salts and not corrected for peptide context.

Abbreviations

ACTH, adrenocorticotropin hormone; Fmoc, 9-fluorenylmethoxycarbonyl; AGRP, agouti-related protein; GPCR, G protein-coupled receptor; cAMP, cyclic 5'-adenosine monophosphate; MC1R, melanocortin-1 receptor; MC2R, melanocortin-2 receptor; MC3R, melanocortin-3 receptor; MC4R, melanocortin-4 receptor; MC5R, melanocortin-5 receptor; MCR, melanocortin receptor; MSH, melanocyte stimulating hormone; POMC, proopiomelanocortin; α-MSH, alpha-melanocyte stimulating hormone; β-MSH, beta-melanocyte stimulating hormone; γ-MSH, gamma-melanocyte stimulating hormone; μM, micromolar; NDP-MSH (4-Norleucine-7-D-Phenylalanine), Ac-Ser-Tyr-Ser-Nle-Glu-His-DPhe-Arg-Trp-Gly-Lys-Pro-Val-$NH_2$ (SEQ ID NO:136); Nle, norleucine; Dap, diaminopropioinic acid; RP-HPLC, reverse-phase high-pressure liquid chromatography; SAR, structure-activity relationships; SNPs, single nucleotide polymorphisms.

Documents Cited in Example 1

(1) Chhajlani, et al. FEBS Lett. 1992, 309, 417-420.
(2) Mountjoy, et al. Science 1992, 257, 1248-1251.
(3) Schioth, et al. Life Sci. 1996, 59, 797-801.
(4) Gantz, et al. J. Biol. Chem. 1993, 268, 8246-8250.
(5) Gantz, et al. J. Biol. Chem. 1993, 268, 15174-15179.
(6) Chen, et al. Nat. Genet. 2000, 26, 97-102.
(7) Huszar, et al. Cell 1997, 88, 131-141.
(8) Roselli-Rehfuss, et al. Proc. Natl. Acad. Sci. U.S.A. 1993, 90, 8856-8860.
(9) Butler, et al. Endocrinology 2000, 141, 3518-3521.
(10) Irani, et al. Eur. J. Pharmacol. 2011, 660, 80-87.
(11) Mountjoy, et al. Mol. Endocrinol. 1994, 8, 1298-1308.
(12) Yang, et al. Prog. Mol. Biol. Transl. Sci. 2016, 140, 97-129.
(13) Farooqi, et al. N. Engl. J. Med. 2003, 348, 1085-1095.

(14) Gantz, et al. Biochem. Biophys. Res. Commun. 1994, 200, 1214-1220.
(15) Griffon, et al. Biochem. Biophys. Res. Commun. 1994, 200, 1007-1014.
(16) Chen, et al. Cell 1997, 91, 789-798.
(17) Nakanishi, et al. Nature 1979, 278, 423-427.
(18) Eipper, et al. Endocr. Rev. 1980, 1, 1-27.
(19) Smith, et al. Endocr. Rev. 1988, 9, 159-179.
(20) Miller, et al. Genes Dev. 1993, 7, 454-467.
(21) Bultman, et al. Cell 1992, 71, 1195-1204.
(22) Fong, et al. Biochem. Biophys. Res. Commun. 1997, 237, 629-631.
(23) Ollmann, et al. Science 1997, 278, 135-138.
(24) Shutter, et al. Genes Dev. 1997, 11, 593-602.
(25) Klebig, et al. Proc. Natl. Acad. Sci. U.S.A. 1995, 92, 4728-4732.
(26) Graham, et al. Nat. Genet. 1997, 17, 273-274.
(27) Duhl, et al. Nat. Genet. 1994, 8, 59-65.
(28) Lu, et al. Nature 1994, 371, 799-802.
(29) McNulty, et al. J. Mol. Biol. 2005, 346, 1059-1070.
(30) Ebihara, et al. Diabetes 1999, 48, 2028-2033.
(31) Adan, et al. Ann. N.Y. Acad. Sci. 2003, 994, 267-274.
(32) Ge, et al. Brain Res. 2002, 957, 42-45.
(33) Kas, et al. Mol. Psychiatry 2003, 8, 235-240.
(34) He, et al. Nat. Genet. 2001, 27, 40-47.
(35) Ollmann, et al. J. Biol. Chem. 1999, 274, 15837-15846.
(36) Ollmann, et al. Genes Dev. 1998, 12, 316-330.
(37) Blanchard, et al. Biochemistry 1995, 34, 10406-10411.
(38) Willard, et al. Biochemistry 1995, 34, 12341-12346.
(39) Yang, et al. Mol. Endocrinol. 1997, 11, 274-280.
(40) Kiefer, et al. Biochemistry 1998, 37, 991-997.
(41) Patel, et al. J. Mol. Biol. 2010, 404, 45-55.
(42) Stanley, et al. Endocrinology 1999, 140, 5459-5462.
(43) Mizuno, et al. Endocrinology 1999, 140, 4551-4557.
(44) Haskell-Luevano, et al. Regul. Pept. 2001, 99, 1-7.
(45) Nijenhuis, et al. Mol. Endocrinol. 2001, 15, 164-171.
(46) Creemers, et al. Endocrinology 2006, 147, 1621-1631.
(47) Wilczynski, et al. J. Med. Chem. 2004, 47, 2194-2207.
(48) Yang, et al. Mol. Endocrinol. 1999, 13, 148-155.
(49) Tota, et al. Biochemistry 1999, 38, 897-904.
(50) Bolin, et al. FEBS Lett. 1999, 451, 125-131.
(51) McNulty, et al. Biochemistry 2001, 40, 15520-15527.
(52) Jackson, et al. Biochemistry 2002, 41, 7565-7572.
(53) Joseph, et al. Peptides 2003, 24, 263-270.
(54) Ericson, et al. J. Med. Chem. 2015, 58, 4638-4647.
(55) Ericson, et al. J. Med. Chem. 2017, 60, 805-813.
(56) Carpino, et al. J. Am. Chem. Soc. 1970, 92, 5748-5749.
(57) Carpino, et al. J. Org. Chem. 1972, 37, 3404-3409.
(58) Ericson, et al. Bioorg. Med. Chem. Lett. 2015, 25, 5306-5308.
(59) Lensing, et al. J. Med. Chem. 2016, 59, 3112-3128.
(60) Singh, et al. ACS Med. Chem. Lett. 2015, 6, 568-572.
(61) Schild, et al. Br. J. Pharmacol. Chemother. 1947, 2, 189-206.
(62) Chai, et al. Biochemistry 2005, 44, 3418-3431.

TABLE 1

Analytical Data for Peptides Synthesized in this Study.

| Peptide | Sequence | Retention Time (min)[a] system 1 | Retention Time (min)[a] system 2 | M (calc) | mass spectral analysis (M + 1) | purity % |
|---|---|---|---|---|---|---|
| 1 | c[Pro-Arg-Phe-Phe-Asn-Ala-Phe-DPro] (SEQ ID NO: 1) | 18.1 | 26.8 | 976.5 | 977.5 | >99 |
| 2 | c[Pro-Arg-Phe-Phe-**Dap**-Ala-Phe-DPro] (SEQ ID NO: 2) | 18.0 | 29.3 | 948.5 | 949.4 | >98 |
| 3 | c[Pro-Arg-Phe-Phe-**Ala**-Ala-Phe-DPro] (SEQ ID NO: 4) | 18.9 | 28.7 | 933.5 | 934.3 | >99 |
| 4 | c[Pro-Arg-Phe-Phe-**Abu**-Ala-Phe-DPro] (SEQ ID NO: 5) | 19.5 | 29.4 | 947.5 | 948.5 | >98 |
| 5 | c[Pro-Arg-Phe-Phe-**Ser**-Ala-Phe-DPro] (SEQ ID NO: 6) | 18.8 | 29.2 | 949.5 | 950.3 | >99 |
| 6 | c[Pro-Arg-Phe-Phe-**Thr**-Ala-Phe-DPro] (SEQ ID NO: 7) | 19.5 | 29.9 | 963.5 | 964.2 | >99 |
| 7 | c[Pro-Arg-Phe-Phe-**Asp**-Ala-Phe-DPro] (SEQ ID NO: 8) | 18.4 | 28.5 | 977.5 | 978.5 | >99 |
| 8 | c[Pro-Arg-Phe-Phe-**Glu**-Ala-Phe-DPro] (SEQ ID NO: 9) | 18.3 | 28.1 | 991.5 | 992.2 | >99 |
| 9 | c[Pro-Arg-Phe-Phe-**DDap**-Ala-Phe-DPro] (SEQ ID NO: 10) | 18.1 | 29.4 | 948.5 | 949.4 | >95 |
| 10 | c[Pro-Arg-Phe-Phe-**His**-Ala-Phe-DPro] (SEQ ID NO: 11) | 18.0 | 29.1 | 999.5 | 1000.2 | >96 |
| 11 | c[Pro-Arg-Phe-Phe-**Nle**-Ala-Phe-DPro] (SEQ ID NO: 12) | 21.2 | 31.0 | 975.5 | 976.3 | >99 |
| 12 | c[Pro-Arg-Phe-Phe-**Leu**-Ala-Phe-DPro] (SEQ ID NO: 13) | 21.0 | 30.8 | 975.5 | 976.3 | >99 |

TABLE 1-continued

Analytical Data for Peptides Synthesized in this Study.

| Peptide | Sequence | Retention Time (min)[a] system 1 | Retention Time (min)[a] system 2 | M (calc) | mass spectral analysis (M + 1) | purity % |
|---|---|---|---|---|---|---|
| 13 | c[Pro-Arg-Phe-Phe-**Val**-Ala-Phe-DPro] (SEQ ID NO: 14) | 20.4 | 30.8 | 961.5 | 962.2 | >99 |
| 14 | c[Pro-Arg-Phe-Phe-**Phe**-Ala-Phe-DPro] (SEQ ID NO: 15) | 21.6 | 31.6 | 1009.5 | 1010.3 | >98 |
| 15 | c[Pro-Arg-Phe-Phe-**Trp**-Ala-Phe-DPro] (SEQ ID NO: 16) | 23.2 | 30.7 | 1048.5 | 1049.2 | >97 |
| 16 | c[Pro-Arg-Phe-Phe-Asn-**Asp**-Phe-DPro] (SEQ ID NO: 17) | 17.7 | 26.6 | 1020.5 | 1021.6 | >99 |
| 17 | c[Pro-Arg-Phe-Phe-Asn-**Glu**-Phe-DPro] (SEQ ID NO: 18) | 17.4 | 26.7 | 1034.5 | 1035.6 | >98 |
| 18 | c[Pro-Arg-Phe-Phe-Asn-**Lys**-Phe-DPro] (SEQ ID NO: 19) | 16.0 | 25.2 | 1033.6 | 1034.6 | >99 |
| 19 | c[Pro-Arg-Ptie-Phe-Asn-**His**-Phe-DPro] (SEQ ID NO: 20) | 16.2 | 25.4 | 1042.5 | 1043.6 | >99 |
| 20 | c[Pro-Arg-Phe-Phe-Asn-**Phe**-The-DPro] (SEQ ID NO: 21) | 21.4 | 32.4 | 1052.5 | 1053.7 | >97 |
| 21 | c[Pro-Arg-Phe-Phe-Asa-**Ser**-Phe-DPro] (SEQ ID NO: 22) | 17.7 | 27.2 | 992.5 | 993.6 | >96 |
| 22 | c[Pro-Arg-Phe-Phe-Asn-**Leu**-Phe-DPro] (SEQ ID NO: 23) | 21.2 | 32.8 | 1018.5 | 1019.6 | >98 |
| 23 | c[Pro-Arg-Ine-Ine-Asn-**Gly**-Phe-DPro] (SEQ ID NO: 24) | 17.6 | 26.5 | 962.5 | 963.5 | >96 |
| 14 | c[Pro-Arg-Phe-Phe-Asn-Ala-**Ala**-DPro] (SEQ ID NO: 25) | 15.4 | 25.0 | 900.5 | 901.8 | >97 |

[a]Peptide retention times(min) are reported for solvent system 1 (10% acetonitrile in 0.1% trifluoroacetic acid/water and a gradient to 90% acetonitrile over 35 min) and solvent system 2 (10% methanol in 0.1% trifluoroacetic acidlwater and a gradient to 90% methanol over 35 mm).
An analytical Vydac C18 column (Vydac 218TP104) was used with a flow rate of 1.5 mL/min.
The peptide purity was determined by HPLC at a wavelength of 214 nm.

TABLE 2

Pharmacology of AGRP Loop Analogues at the Mouse Melanocortin Receptors.[a]

| Peptide | Sequence | mMC1R $EC_{50}$ (nM) | mMC3R $EC_{50}$ (nM) | mMC3R $pA_2$ | mMC4R $EC_{50}$ (nM) | mMC4R $pA_2$ | mMC5R $EC_{50}$ (nM) |
|---|---|---|---|---|---|---|---|
| NDP-MSH | | 0.021 ± 0.002 | 0.19 ± 0.02 | | 0.41 ± 0.03 | | 0.18 ± 0.02 |
| hAGRP (86-132) | | N.D. | | 8.7 ± 0.1 | | 8.7 ± 0.2 | N.D. |
| 1 | c[Pro-Arg-Phe-Phe-Asn-Ala-Phe-DPro] (SEQ ID NO: 1) | 25% @ 100 µM | >100,000 | 6.3 ± 0.1 | >100,000 | 8.2 ± 0.1 | Inverse Agonist -10%, 130 nM |
| 2 | c[Pro-Arg-Phe-Phe-**Dap**-Ala-Phe-DPro] (SEQ ID NO: 2) | 30% @ 100 µM | >100,000 | 6.52 ± 0.09 | >100,000 | 8.7 ± 0.1 | Inverse Agonist -15%, 60 nM |
| 3 | c[Pro-Arg-Phe-Phe-**Ala**-Ala-Phe-DPro] (SEQ ID NO: 4) | >100,000 | >100,000 | <5.5 | >100,000 | 7.32 ± 0.09 | Inverse Agonist -20%, 250 nM |

TABLE 2-continued

Pharmacology of AGRP Loop Analogues at the Mouse Melanocortin Receptors.[a]

| Peptide | Sequence | mMC1R EC$_{50}$ (nM) | mMC3R EC$_{50}$ (nM) | mMC3R pA$_2$ | mMC4R EC$_{50}$ (nM) | mMC4R pA$_2$ | mMC5R EC$_{50}$ (nM) |
|---|---|---|---|---|---|---|---|
| 4 | c[Pro-Arg-Phe-Phe-**Abu**-Ala-Phe-DPro] (SEQ ID NO: 5) | >100,000 | >100,000 | <5.5 | >100,000 | 7.3 ± 0.2 | Inverse Agonist -20%, 160 nM |
| 5 | c[Pro-Arg-Phe-Phe-**Ser**-Ala-Phe-DPro] (SEQ ID NO: 6) | >100,000 | >100,000 | 5.9 ± 0.2 | >100,000 | 7.7 ± 0.3 | Inverse Agonist -25%, 140 nM |
| 6 | c[Pro-Arg-Phe-Phe-**Thr**-Ala-Phe-DPro] (SEQ ID NO: 7) | >100,000 | >100,000 | 6.4 ± 0.2 | >100,000 | 7.76 ± 0.07 | Inverse Agonist -20%, 50 nM |
| 7 | c[Pro-Arg-Phe-Phe-**Asp**-Ala-Phe-DPro] (SEQ ID NO: 8) | >100,000 | >100,000 | <5.5 | >100,000 | 6.79 ± 0.07 | Inverse Agonist -25% @ 100 µM |
| 8 | c[Pro-Arg-Phe-Phe-**Glu**-Ala-Phe-DPro] (SEQ ID NO: 9) | 20,500 ± 500 | >100,000 | <5.5 | >100,000 | 7.00 ± 0.09 | Inverse Agonist -10%, 700 nM |
| 9 | c[Pro-Arg-Phe-Phe-**DDap**-Ala-Phe-DPro] (SEQ ID NO: 10) | >100,000 | >100,000 | 6.7 ± 0.2 | >100,000 | 8.58 ± 0.04 | Inverse Agonist -10%, 110 nM |
| 10 | c[Pro-Arg-Phe-Phe-**His**-Ala-Phe-DPro] (SEQ ID NO: 11) | >100,000 | >100,000 | 6.46 ± 0.07 | >100,000 | 8.3 ± 0.1 | Inverse Agonist -15%, 10 nM |
| 11 | c[Pro-Arg-Phe-Phe-**Nle**-Ala-Phe-DPro] (SEQ ID NO: 12) | >100,000 | >100,000 | <5.5 | >100,000 | 6.9 ± 0.1 | >100,000 |
| 12 | c[Pro-Arg-Phe-Phe-**Leu**-Ala-Phe-DPro] (SEQ ID NO: 13) | >100,000 | >100,000 | 5.7 ± 0.2 | >100,000 | 7.34 ± 0.04 | Inverse Agonist -20%, 110 nM |
| 13 | c[Pro-Arg-Phe-Phe-**Val**-Ala-Phe-DPro] (SEQ ID NO: 14) | 55% @ 100 µM | >100,000 | <5.5 | >100,000 | 5.9 ± 0.1 | Inverse Agonist -25%, 510 nM |
| 14 | c[Pro-Arg-Phe-Phe-**Phe**-Ala-Phe-DPro] (SEQ ID NO: 15) | >100,000 | >100,000 | <5.5 | >100,000 | 6.63 ± 0.09 | >100,000 |
| 15 | c[Pro-Arg-Phe-Phe-**Trp**-Ala-Phe-DPro] (SEQ ID NO: 16) | 80% @ 100 µM | 40% @ 100 µM | 5.70 ± 0.08 | 50% @ 100 µM | 6.81 ± 0.08 | Inverse Agonist -20%, 150 nM |
| 16 | c[Pro-Arg-Phe-Phe-Asn-**Asp**-Phe-DPro] (SEQ ID NO: 17) | 65% @ 100 µM | >100,000 | <5.5 | >100,000 | <5.5 | Inverse Agonist -25% @ 100 µM |
| 17 | c[Pro-Arg-Phe-Phe-Asn-**Glu**-Phe-DPro] (SEQ ID NO: 18) | 60% @ 100 µM | >100,000 | <5.5 | >100,000 | <5.5 | >100,000 |
| 18 | c[Pro-Arg-Phe-Phe-Asn-**Lys**-Phe-DPro] (SEQ ID NO: 19) | 60% @ 100 µM | 45% @ 100 µM | <5.5 | >100,000 | 6.11 ± 0.01 | 45% @ 100 µM |

TABLE 2-continued

Pharmacology of AGRP Loop Analogues at the Mouse Melanocortin Receptors.[a]

| | | mMC1R | mMC3R | | mMC4R | | mMC5R |
|---|---|---|---|---|---|---|---|
| Peptide | Sequence | $EC_{50}$ (nM) | $EC_{50}$ (nM) | $pA_2$ | $EC_{50}$ (nM) | $pA_2$ | $EC_{50}$ (nM) |
| 19 | c[Pro-Arg-Phe-Phe-Asn-**His**-Phe-DPro] (SEQ ID NO: 20) | Partial Agonist 40% NDP (2,600 ± 1,200) | >100,000 | <5.5 | >100,000 | 6.07 ± 0.09 | >100,000 |
| 20 | c[Pro-Arg-Phe-Phe-Asn-**Phe**-Phe-DPro] (SEQ ID NO: 21) | 70% @ 100 µM | 35% @ 100 µM | 5.72 ± 0.08 | 35% @ 100 µM | 5.71 ± 0.03 | 25% @ 100 µM |
| 21 | c[Pro-Arg-Phe-Phe-Asn-**Ser**-Phe-DPro] (SEQ ID NO: 22) | >100,000 | >100,000 | 6.2 ± 0.1 | >100,000 | 8.2 ± 0.2 | Inverse Agonist -30% @ 100 µM |
| 22 | c[Pro-Arg-Phe-Phe-Asn-**Leu**-Phe-DPro] (SEQ ID NO: 23) | 80% @ 100 µM | 25% @ 100 µM | <5.5 | 25% @ 100 µM | 6.18 ± 0.05 | >100,000 |
| 23 | c[Pro-Arg-Phe-Phe-Asn-**Gly**-Phe-DPro] (SEQ ID NO: 24) | >100,000 | >100,000 | <5.5 | >100,000 | 6.1 ± 0.3 | Inverse Agonist -35% @ 100 µM |
| 24 | c[Pro-Arg-Phe-Phe-Asn-Ala-**Ala**-DPro] (SEQ ID NO: 25) | >100,000 | >100,000 | 6.1 ± 0.2 | >100,000 | 8.16 ± 0.08 | Inverse Agonist -25% @ 100 µM |

[a]The indicated errors represent the standard error of the mean determined from at least three independent experiments. The antagonistic $pA_2$ values were determined using the Schild analysis and the agonist NDP-MSH. The use of >100,000 indicates that the compound was examined but lacked agonist activity at up to 100 µM concentrations. A percentage denotes the percent maximal stimulatory response observed at 100 µM concentrations but not enough stimulation was observed to determine an $EC_{50}$ value. N.D. indicates values not determined. The use of <5.5 indicates that no antagonist potency was observed in the highest concentration ranged assayed (10,000, 5,000, 1,000, and 500 nM). Partial agonist indicates partial agonist activity was observed, along with the percentage of activation relative to NDP-MSH and the $EC_{50}$. Inverse agonist indicates that inverse agonist pharmacology was observed with the percent decrease from basal indicated. For inverse agonists, an apparent potency is indicated for the inflection point on sigmoidal dose-response curves; if a decrease in cAMP signal was observed without a sigmoidal dose-response curve, the percent change from basal at 100 µM concentrations is indicated.

Example 2. Arg-Phe-Phe D-Amino Acid Stereochemistry Scan in the Macrocyclic Agouti-Related Protein Antagonist Scaffold c[Pro-Arg-Phe-Phe-Xaa-Ala-Phe-DPro] (SEQ ID NO: 137) Results in Unanticipated Melanocortin-1 Receptor Agonist Profiles Abstract The melanocortin-3 and melanocortin-4 receptors (MC3R and MC4R), endogenous agonists derived from the proopiomelanocortin gene transcript, and naturally-occurring antagonists agouti and agouti-related protein (AGRP) have been linked to biological pathways associated with energy homeostasis. The active tripeptide sequence of AGRP, Arg111-Phe112-Phe113, is located on a hypothesized β-hairpin loop. Herein, stereochemical modifications of the Arg-Phe-Phe sequence were examined in the octapeptide AGRP-derived macrocyclic scaffold c[Pro-Arg-Phe-Phe-Xaa-Ala-Phe-DPro] (SEQ ID NO: 137), where Xaa was Asn or diaminopropionic acid (Dap). Macrocyclic peptides were synthesized with one, two, or three residues of the Arg-Phe-Phe sequence substituted with the corresponding D-isomer(s), generating a 14 compound library. While L-to-D inversions of the Arg-Phe-Phe sequence in a 20-residue AGRP-derived ligand previously resulted in agonist activity at the MC1R, MC3R, MC4R, and MC5R, only the MC1R was consistently stimulated by the macrocyclic ligands in the present study, with varying ligand potencies and efficacies observed at the MC1R. A general trend of increased MC4R antagonist potency was observed for Dap-containing compounds, while MC5R inverse agonist activity was observed for select ligands. It was observed that stereochemical modification of the Arg-Phe-Phe active tripeptide sequence was insufficient to convert melanocortin antagonist into agonists. Overall, these observations are important in the design of melanocortin ligands possessing potent and selective agonist and antagonist activities.

Introduction

The five melanocortin receptors (MCRs),[1-8] discovered to date, are members of the G protein-coupled receptor (GPCR) superfamily. These receptors have been implicated in numerous physiological functions, including skin pigmentation (MC1R),[1,2] steroidogenesis (MC2R),[1,9] and energy homeostasis (MC3R and MC4R).[10-13] The MCRs are stimulated by agonists derived from the proopiomelanocortin (POMC) gene transcript,[14] and include α-MSH, β-MSH, γ-MSH, and ACTH. Common to these melanocortin agonists is a His-Phe-Arg-Trp (SEQ ID NO: 148) tetrapeptide sequence. Due to the role of the MC3R and MC4R in energy homeostasis,[10-13,15] agonist compounds that decrease feeding have been advanced to clinical trials in humans, including several peptides and small molecules as previously reviewed.[16] While MC4R-selective ligands decrease food intake, side-effects including increased blood pressure,[17] increased erectile activity,[18] and skin darkening[19,20] have been reported. New ligands that possess unique scaffolds may bypass some of these effects, illustrated by the use of setmelanotide in patients deficient in POMC to lower body weight without an accompanied increase in blood pressure.[19]

Unique to the melanocortin receptor family is the presence of two endogenous antagonists, agouti-signaling protein (ASP)[21,22] and agouti-related protein (AGRP).[23-25] Common to both antagonists is a highly structured C-terminal domain possessing 5 disulfide bonds and a tripeptide Arg-Phe-Phe sequence that has been demonstrated to be critical for receptor affinity and antagonist potency.[26,27] While originally described as an antagonist at the MC1R and MC4R[28] subsequent work with a synthetic derivative of ASP (ASP-YY) demonstrated that ASP may also possess antagonist pharmacology at the MC3R.[29] Pharmacological characterization of AGRP demonstrated that AGRP is an antagonist at the MC3R and MC4R,[23,24] as well as an inverse agonist at the MC4R.[30,31] Truncation studies involving AGRP indicated that the decapeptide H-Tyr-c[Cys-Arg-Phe-Phe-Asn-Ala-Phe-Cys]-Tyr-OH (SEQ ID NO: 142) was the minimal sequence required for sub-micromolar functional potency at the MC4R,[27] and further extension of four terminal residues was required to achieve functional potency at the MC3R.[32] Although α-MSH stimulation of the MC1R was not antagonized by AGRP,[24] the decapeptide H-Tyr-c[Cys-Arg-Phe-Phe-Asn-Ala-Phe-Cys]-Tyr-OH (SEQ ID NO: 142) possessed micromolar affinity and functional agonist potency at the MC1R.[33] Replacing the disulfide bond with a lactam bridge by substituting Asp and diaminopropioinic acid (Dap) for Cys resulted in a ligand (H-Tyr-c[Dap-Arg-Phe-Phe-Asn-Ala-Phe-Asp]-Tyr-$NH_2$ (SEQ ID NO: 149)) that retained micromolar agonist potency at the MC1R.[34] These data suggest that although AGRP does not antagonize the MC1R, small peptides based upon the active loop of AGRP may be MC1R agonists.

Utilizing a 20 amino acid derivative of AGRP possessing the active loop sequence (AGRP[103-122]1 H-Asp-Pro-Ala-Ala-Thr-Ala-Tyr-c[Cys-Arg-Phe-Phe-Asn-Ala-Phe-Cys]-Tyr-Ala-Arg-Lys-Leu-OH (SEQ ID NO: 138), with Cys105Ala, Cys108Ala, and Cys119Ala substitutions), Joseph et al. systemically replaced the Arg111, Phe112, and Phe113 residues with the corresponding D-isomers in single, double, and triple substitutions.[35] Although the all L-isomer was an antagonist at the MC3R and MC4R, a sub-micromolar agonist at the MC1R, and possessed no activity at the MC5R, agonist activity was observed for every D-substitution at the MC1R, MC3R, MC4R, and MC5R.[35] Additionally, replacing the DPhe-Arg-Trp tripeptide sequence of the potent, synthetic melanocortin agonists NDP-MSH[36] and MTII[37,38] with the Arg-Phe-Phe sequence also resulted in melanocortin agonist activity at the MC1R, MC3R, MC4R, and MC5R when the equivalent Phe112 was replaced with the D-isomer (Arg-DPhe-Phe) in both scaffolds.[39] Both reports indicate that MC3R and MC4R agonist activity may result from stereochemical modification of the Arg-Phe-Phe tripeptide sequence in the absence of the His-Phe-Arg-Trp (SEQ ID NO: 148) tetrapeptide sequence common to the POMC-derived melanocortin agonists.

One approach to generate melanocortin antagonists has been to cyclize the Arg-Phe-Phe-Asn-Ala-Phe (SEQ ID NO: 150) hexapeptide residues of AGRP (residues 111-116) head-to-tail through a DPro-Pro motif, resulting in the octapeptide c[Pro-Arg-Phe-Phe-Asn-Ala-Phe-DPro](SEQ ID NO: 1) macrocycle that was 50-fold less potent than AGRP at the MC4R.[40] Additional structure-activity relationship (SAR) studies at the Asn 114 position indicated that substitution with Gly or basic amino acids increased antagonist potency relative to Asn.[40,41] Substitution of Asn with Dap resulted in the most potent macrocyclic ligand at the MC4R, which was equipotent to AGRP.[40,41] Further substitutions at the Ala115 and non-pharmacophore Phe116 positions indicated that Ser could replace Ala and norleucine (Nle), Trp, Tyr, and Ala could replace Phe and maintain potency relative to the native sequence at the MC4R.[41,42] These macrocyclic ligands possessed >100-fold decreased antagonist potency at the MC3R compared to AGRP, micromolar agonist potency or higher at the MC1R, and select compounds were apparent inverse agonists at the MC5R.[40-42]

Prior studies have reported that AGRP-derived ligands possess MC1R agonist activity, and the stereochemical modification of Arg-Phe-Phe domain can generate MCR agonist activity across different receptors. It was hypothesized that stereochemical modifications of the Arg-Phe-Phe region in the potent c[Pro-Arg-Phe-Phe-Xaa-Ala-Phe-DPro] (SEQ ID NO: 137) scaffold (where Xaa is Asn or Dap) would also generate MCR agonist activity. Furthermore, since this scaffold is more potent at the MC4R compared to the previously used 20 amino acid template, it was hypothesized that the resulting MCR agonist potency may also be increased, generating potent MCR agonists without the His-Phe-Arg-Trp (SEQ ID NO: 148) pharmacophore. To test this hypothesis, systematic stereochemical modification of the Arg-Phe-Phe tripeptide sequence in both the Asn and Dap octapeptide macrocyclic scaffolds was performed, generating a 14 compound library that was assessed for activity at the MC1R, MC3R, MC4R, and MC5R.

Results

Peptide Synthesis and Characterization:

Peptides were synthesized manually using a semi-automated synthesizer or a microwave-assisted synthesizer using standard fluorenylmethoxycarbonyl (Fmoc) techniques.[43,44] Following cleavage from the resin while retaining amino acid side chains, the amide bond between the Arg and Pro was formed using BOP and HOBt to generate the peptide macrocycle as previously described.[40-42,45] After side-chain deprotection, peptides were purified to >95% by semi-preparative reverse-phase high pressure liquid chromatography (RP-HPLC). Peptides were assessed for purity using analytical RP-HPLC in two solvent systems (Table 3), and the correct molecular mass was confirmed through matrix-assisted laser desorption/ionization mass spectrometry (MALDI-MS; University of Minnesota Mass Spectrometry Laboratory).

In Vitro AlphaScreen cAMP Assay:

Macrocyclic peptides were assayed using HEK293 stably expressing the mouse MC1R, MC3R, MC4R and MC5R, according to the manufacturer's instructions and as previously described.[46,47] The MC2R is only stimulated by the ACTH and was therefore not studied. Ligands were first examined for agonist activity at the MCRs. Compounds that did not result in a full agonist signal at the MC3R and MC4R were then assayed for antagonist activity using a Schild paradigm[48] and the synthetic melanocortin agonist NDP-MSH.[36] The AlphaScreen cAMP signal was normalized to NDP-MSH and basal activity for illustrative purposes as previously described since it is a competition assay and results in lower signal at higher concentrations.[40,49] Compounds that were within a 3-fold range were considered equipotent due to the inherent error in the assay.

Arg-Phe-Phe D-Amino Acid Scan, Asn-Substituted Macrocycle:

Compound 1, comprised of the native sequence of the hypothesized active loop of AGRP cyclized through a DPro-Pro motif (c[Pro-Arg-Phe-Phe-Asn-Ala-Phe-DPro] (SEQ ID NO: 1)), was previously reported to partially stimulate the MC1R (25% of maximal NDP-MSH signal at 100 μM concentrations; Table 4), not stimulate the MC3R or MC4R, and possessed inverse agonist activity at the MC5R (−10% signal from basal activity, with an apparent potency of $EC_{50}$=130 nM corresponding to the inflection point of a sigmoidal dose-response curve).[41] This peptide was an antagonist at the MC3R and MC4R, with $pA_2$ values of 6.3 and 8.2, respectively.[41] Substitution of DArg into this scaffold (5) resulted in partial stimulation of the MC1R (50% at 100 μM; FIG. 6), and loss of agonist and antagonist activities in the concentrations assayed at the MC3R, MC4R, and MC5R. A DPhe substitution at the Phe112 position (4) produced a peptide with partial agonist efficacy at the MC1R (55% maximal NDP-MSH stimulation, $EC_{50}$=700 nM; FIG. 6), equipotent antagonist potency within experimental error at the MC3R and MC4R ($pA_2$=5.8 and 7.7, respectively) compared to 1, and decreased cAMP production 25% from basal levels at the MC5R at 100 μM concentrations (FIG. 6). Replacement of the Phe113 position with DPhe, 5, yielded a peptide that partially stimulated the MC1R (50% NDP-MSH maximal signal at 100 μM) and possessed micromolar antagonist potency at the MC4R ($pA_2$=5.9). No activity was observed for 5 at the MC3R or MC5R.

Replacing both the Arg111 and Phe112 positions with the D-isomers resulted in peptide 6, which was a partial agonist at the MC1R (90% NDP-MSH maximal signal, $EC_{50}$=500 nM) and partially activated the MC5R at 100 μM concentrations (55% NDP-MSH maximal signal). No activity was observed for 6 at the MC3R or MC4R. The peptide 7, possessing DArg and DPhe at positions Arg111 and Phe113, was a full agonist at the MC1R (1,200 nM) and MC5R (10,000 nM; FIG. 6), and partially stimulated the MC3R at 100 μM concentrations (35%). The substitutions of DPhe at both positions Phe112 and Phe113 resulted in peptide 8, a partial agonist at the MC1R (85% NDP-MSH maximal signal, $EC_{50}$=800 nM) and micromolar antagonist at the MC4R ($pA_2$=5.9). The replacement of Arg111, Phe112, and Phe113 with their D-isomers, 9, resulted in similar partial agonist efficacy at the MC1R (85% NDP-MSH signal, $EC_{50}$=1,300 nM) compared to 8, while partially activating the MC5R at 100 μM concentrations (55% NDP-MSH signal; FIG. 6). No agonist or antagonist activity was observed for 9 at the MC3R or MC4R at the concentrations assayed.

Arg-Phe-Phe D-Amino Acid Scan, Dap-Substituted Macrocycle:

Replacement of the Asn residue with a diaminopropionic acid (Dap) has previously been shown to increase the potency of the octapeptide macrocyclic scaffold, and is an equipotent antagonist at the MC4R compared to AGRP.[40,41] This peptide (2, c[Pro-Arg-Phe-Phe-Dap-Ala-Phe-DPro] (SEQ ID NO:2)) has previously been shown to partially stimulate the MC1R at 100 μM concentrations (30% NDP-MSH signal), possess antagonist activity at the MC3R and MC4R ($pA_2$=6.5 and 8.7, respectively), and was an apparent inverse agonist at the MC5R (15% decreased cAMP levels from basal, $EC_{50}$=60 nM).[41] Replacement of Arg111 in the scaffold with DArg, 10, resulted in a peptide that partially activated the MC1R, MC3R and MC4R at 100 μM concentrations (25%) while no activity was observed at the MC5R. Peptide 10 also possessed antagonist activity at the MC3R and MC4R, with $pA_2$ values of 5.7 and 6.8, respectively. The substitution of Phe112 with DPhe resulted in 11, the most potent full agonist at the MC1R in this study ($EC_{50}$=230 nM; FIG. 6). No agonist activity was observed for 11 at the MC3R and MC5R up to 100 μM concentrations, while this peptide partially activated the MC4R at 100 μM (20% NDP-MSH maximal signal). This peptide possessed equipotent MC4R antagonist potency compared to 2 at the MC4R ($pA_2$=8.4; FIG. 7), and was a micromolar antagonist at the MC3R ($pA_2$=5.9). Replacement of Phe113 with DPhe, 12, resulted in a peptide that was a partial agonist at the MC1R (75% NDP-MSH maximum signal, $EC_{50}$=800 nM) and was an antagonist at the MC4R ($pA_2$=7.3). No activity was observed for 12 at the MC3R or MC5R at the concentrations assayed.

Double substitution at the Arg111 and Phe112 positions with their D-isomers resulted in 13, which possessed partial agonist efficacy at the MC1R (70% NDP-MSH, $EC_{50}$=800 nM), antagonist activity at the MC3R and MC4R ($pA_2$=6.0 and 5.5, respectively), and decreased cAMP at the MC5R by 30% from basal levels at the MC5R at 100 μM concentrations. A similar activity trend to 13 was observed when positions Arg111 and Phe113 were substituted with the corresponding D-amino acids, resulting in peptide 14. This peptide (14) was a partial agonist at the MC1R (70% NDP-MSH, $EC_{50}$=450 nM), possessed antagonist potency at the MC3R and MC4R ($pA_2$=5.7 and 6.8, respectively), and decreased cAMP signal by 20% from basal activity at the MC5R. Replacement of both Phe112 and Phe113 with DPhe, 15, generated a full agonist at the MC1R ($EC_{50}$=700 nM), an antagonist at the MC3R ($pA_2$=5.7) and MC4R ($pA_2$=7.4), and no activity was observed at the MC5R at concentrations up to 100 μM. The triple substitution of Arg111, Phe112, and Phe113 with the corresponding D-isomers (16) resulted in a partial agonist at the MC1R (60%/o NDP-MSH maximal signal, $EC_{50}$=2,200 nM), no activity at the MC3R, a micromolar potent MC4R antagonist ($pA_2$=5.8), and a peptide that decreased cAMP production 15% from basal activity at 100 μM concentrations.

Discussion

Select stereochemical inversion combinations of the Arg-Phe-Phe tripeptide domain in a twenty residue AGRP-derived cyclic structure was previously shown to result in agonist activity at the MC1R, MC3R, MC4R, and MC5R, without the His-Phe-Arg-Trp (SEQ ID NO: 148) agonist sequence.[35] The two octapeptide macrocyclic scaffolds utilized in this study, c[Pro-Arg-Phe-Phe-Xaa-Ala-Phe-DPro] (SEQ ID NO: 137) (where Xaa is Asn or Dap), are more potent MC4R antagonists than the previously reported twenty residue fragments, with $pA_2$ values at the MC4R of 8.2 (Asn octapeptide)[41] and 8.7 (Dap octapeptide)[41] compared to 6.9 (20 residue peptide).[35] Due to the increased antagonist potency at the MC4R, it was hypothesized that stereochemical modifications of either macrocyclic scaffold may result in melanocortin agonist ligands with increased potency at the MC1R, MC3R, MC4R, and MC5R, compared to the twenty residue AGRP derivative previously reported. However, only three compounds (7, 11, and 15) possessed full agonist efficacy at the MC1R and one compound (7) was a full agonist at the MC5R (Table 4). The MC3R and MC4R were at most stimulated to 35% and 25% the maximal signal of NDP-MSH at 100 μM concentrations, perhaps suggesting that additional AGRP residues outside the hexapeptide sequence are required for consistent MCR agonism when inverting the stereochemical of the Arg-Phe-Phe tripeptide sequence of AGRP-derived ligands.

While previously AGRP-derived peptides have been reported to possess agonist potencies of 2.89 μM (H-Tyr-c[Cys-Arg-Phe-Phe-Asn-Ala-Phe-Cys]-Tyr-OH) (SEQ ID NO: 142),[33] 28.1 μM (H-Tyr-c[Dap-Arg-Phe-Phe-Asn-Ala-Phe-Asp]-Tyr-$NH_2$) (SEQ ID NO: 149),[34] and 960 nM (H-Asp-Pro-Ala-Ala-Thr-Ala-Tyr-c[Cys-Arg-Phe-Phe-Asn-Ala-Phe-Cys]-Tyr-Ala-Arg-Lys-Leu-OH) (SEQ ID NO: 138),[35] the identified macrocycles for the present study were only able to partially stimulate the MC1R at 100 μM concentrations (25% and 30% for 1 and 2, respectively). Two of the macrocycles (11 and 15) from the present study possess sub-micromolar agonist potency and full efficacy at the MC1R, representing >1,000-fold potency increase compared to the starting ligand 2. Several additional macrocyclic ligands possessed sub-maximal agonist efficacy or partially stimulated the MC1R at 100 μM concentrations. The broad range of agonist activities suggests that the macrocyclic scaffold may be tunable for MC1R potency and efficacy. The two most potent ligands for MC4R antagonist potency (2 and 11 with $pA_2$=8.7 and 8.4, respectively) possess MC1R agonist activities of 30% maximal NDP-MSH stimulation at 100 μM (2) and full agonist efficacy with an $EC_{50}$=230 nM (11). One off-target effect of MC4R agonist compounds in clinical development has been skin darkening/altered pigmentation in humans, presumably due to MC1R agonism.[19, 20] Due to the differential activities at the MC1R while retaining MC4R potency, the present macrocyclic scaffold may be able to modulate the potential risk of altering pigmentation, suggesting a benefit to the AGRP-derived macrocycles.

In the 20-residue AGRP fragment, the two most potent MC1R agonist involved the DPhe112 and DPhe112/DPhe113 stereochemical modifications,[35] the same inversion patterns found in the most potent MC1R full agonists in the present study (11 and 15). The equivalent DPhe112 substitution also resulted in the most potent MC1R agonists when the Arg-Phe-Phe tripeptide sequence replaced the DPhe-Arg-Trp of NDP-MSH and MTII.[39] While these substitutions increased potency with retained efficacy in different scaffolds, the same stereochemical inversions in the Asn-containing macrocycle resulted in partial agonists possessing 55% (4) and 85% (8) the maximal signal of NDP-MSH. These results indicate that DPhe112 and DPhe112/DPhe113 stereochemical inversions are not sufficient alone to generate full MC1R agonist ligands.

It has previously been reported that the Dap substitution increased MC4R antagonist potency compared to the native sequence Asn residue.[40,41] Stereochemically inverted residues within the Arg-Phe-Phe tripeptide sequence also resulted in a similar trend, with Dap-substituted macrocycles possessing increased MC4R antagonist potency compared to the Asn-containing peptides. The four macrocycles that did not possess antagonist activity at the highest assayed concentrations (3, 6, 7, and 9) all contained an Asn substitution. The equivalent Dap substituted peptides (10, 13, 14, and 16) possess antagonist potencies of 6.8, 5.5, 6.8, and 5.8, respectively. Two Asn-containing macrocycles possess micromolar MC4R antagonist potencies (5 and 8; $pA_2$=5.9 for both). The equivalent DPhe113 and DPhe112/DPhe113 Dap substituted peptides (12 and 15) possessed sub-micromolar MC4R antagonist potencies ($pA_2$=7.3 and 7.4, respectively). The most potent Asn antagonist at the MC4R (4, $pA_2$=7.7) contained the DPhe112 stereo-inversion. The same DPhe112 substitution in the Dap scaffold (11) resulted in an antagonist ligand with a $pA_2$=8.4. These data reflect the trend that Dap-substituted macrocycles were more potent antagonists at the MC4R, mirroring the prior observation that Dap substitution results in a more potent MC4R antagonist compared to Asn.

Ligands 1 and 2 possess inverse agonist activity at the MC5R,[41] as do other compounds based upon the AGRP-derived macrocyclic scaffold.[42] In this report, four additional compounds possessed apparent inverse agonist activity at the MC5R (decreased cAMP levels from basal at increased compound concentrations). These four peptides (4, 13, 14, and 16) resulted in decreased cAMP signals at 100 μM concentrations, although the signal did not plateau in a sigmoidal dose-response curve. There is not a clear structure-activity relationship trend to explain this activity, as one of the ligands is based upon the Asn scaffold (4) while three contain the Dap residue (13, 14, and 16), and different D-residues with the Arg-Phe-Phe tripeptide sequence are present in each macrocycle. Efforts to further develop MC5R inverse agonist probes may be useful to clarify the role of this receptor in vivo.

Conclusions

The present study examined the functional effects of stereochemically modifying the Arg-Phe-Phe antagonist active sequence of AGRP-derived octapeptide macrocyclic ligands possessing either an Asn or Dap substitution. Unlike a previously report using a 20-residue AGRP scaffold, stereochemical modification with the octapeptide scaffolds did not result in agonist activity at all the melanocortin receptors assayed. While all the ligands in the present study were able to partially or fully stimulate the MC1R, no ligands were able to fully stimulate the MC3R or MC4R, while one compound fully activated the MC5R. Thus, stereochemical inversion of the AGRP Arg-Phe-Phe tripeptide sequence does not necessarily result in melanocortin agonist activity. A tunable agonist response at the MC1R was observed for these macrocycles, from partial receptor stimulation at 100 μM to full agonist efficacy and a potency of 230 nM. This study also demonstrated that ligands possessing Dap substitutions possessed increased MC4R antagonist potencies compared to the native Asn residue. Stereochemical modification of the Phe112 position was also found to retain the highest MC4R antagonist potency in both scaffolds examined. These observations will be important in the design of future ligands to possess increased MC4R antagonist potency for potential treatment of states of negative energy balance, including anorexia and cachexia with minimal effects on skin pigmentation.

EXPERIMENTAL

Peptide Synthesis: Peptide Synthesis:

All peptides were synthesized using standard Fmoc chemistry.[43,44] The coupling reagents 2-(1-H-benzotriazol-1-yl)-1,1,3,3-tetramethyluronium hexafluorophosphate (HBTU), benzotriazol-1-yl-oxy-tris(dimethylamino) phosphonium hexafluorophosphate (BOP) and 1-hydroxybenzotriazole (HOBt), the H-Pro-2-chlorotrityl resin, and amino acids were purchased from Peptides International (Louisville, Ky.). Dichloromethane (DCM), methanol (MeOH), acetonitrile (ACN), dimethylformamide (DMF) and anhydrous ethyl ether were purchased from Fisher (Fairlawn, N.J.). Trifluoroacetic acid (TFA), dimethyl sulfoxide (DMSO), piperidine, triisopropylsilane (TIS), and N,N-diisopropylethylamine (DIEA) were purchased from Sigma-Aldrich (St. Louis. Mo.). All reagents and chemicals were ACS grade or better and were used without further purification.

Peptides were synthesized on a 0.05 mmol scale using H-Pro-2-chlorotrityl resin (0.76 meq/g substitution) in parallel using a 96-well block (LabTech I; Advanced ChemTech, Louisville, Ky.) or individually with a manual microwave synthesizer (CEM Discover SPS, Matthews, N.C.). Parallel syntheses consisted of two repeated steps separated by DMF washes: (i) removal of the Fmoc group with 20% piperidine in DMF (1× at rt for 5 min, 1× at rt for 20 min), and (ii) double coupling of the incoming Fmoc-protected amino acid (3.1 eq) with HBTU (3 eq) and DIEA (5 eq) in DMF at rt from 45 min. Individual syntheses consisted of two repeated steps separated by DMF washes:

(i) removal of the Fmoc group with 20% piperidine (1× at rt for 2 min, lx using microwave irradiation for 4 min at 75° C. with 30 W), and (ii) single coupling of the incoming Fmoc-protected amino acid (3 eq) with HBTU (3 eq) and DIPEA (5 eq) in DMF using microwave irradiation (75° C., 5 min, 30 W). The Arg coupling utilized more Arg (5 eq), HBTU (5 eq), and DIPEA (7 eq), and a longer irradiation time (10 min). After completion of the syntheses, peptides were cleaved with a 99:1 DCM:TFA solution for 6 min. The cleavage solutions were concentrated and the side-chain protected linear peptides were precipitated using ice-cold ethyl ether. Peptides were cyclized through amide bond formation between the Arg and Pro residues in DCM with BOP (3 eq) and HOBt (3 eq) overnight using a peptide concentration of 1 mg/mL, and the DCM was removed under vacuum. Without further purification, the side chain protecting groups of the cyclized peptides were removed with a 95:2.5:2.5 TFA:TIS:$H_2O$ solution for 2 h. The solution was concentrated and cyclic peptides precipitated with ice-cold ethyl ether.

Crude peptides were purified by RP-HPLC using a Shimadzu system with a UV detector and a semi-preparative RP-HPLC $C_{18}$ bonded silica column (Vydac 218TP1010, 1×25 cm).

Assayed peptides were at least 95% pure as assessed by analytical RP-HPLC utilizing a Shimadzu system with a photodiode array detector and an analytical C18 silica column (Vydac 218TP104, 0.46×25 cm) in two diverse solvent systems and had the correct average molecular mass by MALDI-MS (Applied Biosystems-Sciex 5800 MALDI/TOF/TOF-MS, University of Minnesota Mass Spectrometry Lab).

cAMP AlphaScreen® Bioassay:

Cyclized peptides were dissolved in DMSO (NDP-MSH in $H_2O$) at a stock concentration of $10^{-2}$ M and were pharmacologically characterized using HEK293 cells stably expressing the mouse MC1R, MC3R, MC4R, and MC5R by the cAMP AlphaScreen® assay (PerkinElmer) according to the manufacturer's instructions and as previously described.[46,47]

Briefly, cells 70-90% confluent were dislodged with Versene (Gibco®) at 37° C. and plated 10,000 cells/well in a 384-well plate (Optiplate™) with 10 μL freshly prepared stimulation buffer (1×HBSS, 5 mM HEPES, 0.5 mM IBMX, 0.1% BSA, pH=7.4) with 0.5 μg anti-cAMP acceptor beads per well. The cells were stimulated with the addition of 5 μL stimulation buffer containing peptide (concentrations from $10^{-4}$ to $10^{-13}$ M, determined by ligand potency) or forskolin ($10^{-4}$ M) and incubated in the dark at room temperature for 2 hr.

Following stimulation, streptavidin donor beads (0.5 μg) and biotinylated-cAMP (0.62 μmol) were added to the wells in a green light environment with 10 μL lysis buffer (5 mM HEPES, 0.3% Tween-20, 0.1% BSA, pH=7.4) and the plates were incubated in the dark at room temperature for an additional 2 hr. Plates were read on a Enspire (PerkinElmer) Alpha-plate reader using a pre-normalized assay protocol (set by the manufacturer).

Data Analysis:

The $EC_{50}$ and $pA_2$ values represent the mean of duplicate replicates performed in at least three independent experiments. Compounds that did not possess agonist activity in two independent experiments and did not produce a shift in the agonist curve when assayed as an antagonist at 10,000, 5,000, 1,000, and 500 nM concentrations in an initial experiments were not further assayed. The $EC_{50}$ and $pA_2$ estimates and associated standard errors (SEM) were determined by fitting the data to a nonlinear least-squares analysis using the PRISM program (v4.0, GraphPad Inc.). When analyzing the inverse agonist activity at the MC5R, each replicate was normalized to the replicate signal at $10^{-10}$ M to observe change from basal activity. The percent inverse agonist activity was calculated from the normalized signal of three independent experiments. As no compound produced a sigmoidal dose-response curve, the percent inverse activity reported was the percent change from basal to signal at 100 μM concentrations. The ligands were assayed as TFA salts and not corrected for peptide content.

Abbreviations Used

ACTH, Adrenocorticotropin hormone; Fmoc, 9-fluorenylmethoxycarbonyl; AGRP, Agouti-Related Protein; GPCR, G Protein-Coupled Receptor; cAMP, cyclic 5'-adenosine monophosphate; MC1R, Melanocortin-1 Receptor; MC2R, Melanocortin-2 Receptor; MC3R, Melanocortin-3 Receptor; MC4R, Melanocortin-4 Receptor; MC5R, Melanocortin-5 Receptor; MCR, Melanocortin Receptor; MSH, Melanocyte Stimulating Hormone; POMC, Proopiomelanocortin; α-MSH, Alpha-Melanocyte Stimulating Hormone; β-MSH, Beta-Melanocyte Stimulating Hormone; γ-MSH, Gamma-Melanocyte Stimulating Hormone; μM, Micromolar; NDP-MSH (4-Norleucine-7-D-Phenylalanine), Ac-Ser-Tyr-Ser-Nle-Glu-His-DPhe-Arg-Trp-Gly-Lys-Pro-Val-$NH_2$ (SEQ ID NO: 136); Nle, norleucine; RP-HPLC, reverse-phase high-pressure liquid chromatography; SAR, structure-activity relationships; SEM, standard error of the mean.

Example 2, Documents Cited

1. Mountjoy, et al (1992) Science 257, 1248-1251.
2. Chhajlani, et al (1992) FEBS Lett. 309, 417-420.
3. Gantz, et al (1993) J. Biol. Chem. 268, 8246-8250.
4. Gantz, et al (1993) J. Biol. Chem. 268, 15174-15179.
5. Roselli-Rehfuss, et al (1993) Proc. Natl. Acad. Sci. U.S.A. 90, 8856-8860.
6. Gantz, et al (1994) Biochem. Biophys. Res. Commun. 200, 1214-1220.
7. Griffon, et al (1994) Biochem. Biophys. Res. Commun. 200, 1007-1014.
8. Chhajlani, et al (1993) Biochem. Biophys. Res. Commun. 195, 866-873.
9. Haynes, et al (1957) J. Biol. Chem. 225, 115-124.
10. Chen, et al (2000) Nat. Genet. 26, 97-102.
11. Huszar, et al (1997) Cell 88, 131-141.
12. Butler, et al (2000) Endocrinology 141, 3518-3521.
13. Irani, et al (2011) Eur. J. Pharmacol. 660, 80-87.
14. Nakanishi, et al (1979) Nature 278, 423-427.
15. Fan, et al (1997) Nature 385, 165-168.
16. Ericson, et al (2017) Biochim. Biophys. Acta, Mol. Basis Dis. 1863, 2414-2435.
17. Greenfield, et al (2009) N. Engl. J. Med. 360, 44-52.
18. Dorr, et al (1996) Life Sci. 58, 1777-1784.
19. Kuhnen, et al (2016) N. Engl. J. Med. 375, 240-246.
20. Clement, et al. (2018) Nat. Med. 24, 551-555.
21. Bultman, et al (1992) Cell 71, 1195-1204.
22. Miller, et al (1993) Genes Dev. 7, 454-467.
23. Fong, et al (1997) Biochem. Biophys. Res. Commun. 237, 629-631.
24. Ollmann, et al (1997) Science 278, 135-138.
25. Shutter, et al (1997) Genes Dev. 11, 593-602.
26. Kiefer, et al (1998) Biochemistry 37, 991-997.
27. Tota, et al (1999) Biochemistry 38, 897-904.
28. Lu, et al (1994) Nature 371, 799-802.

29. McNulty, et al (2005) J. Mol. Biol. 346, 1059-1070.
30. Nijenhuis, et al (2001) Mol. Endocrinol. 15, 164-171.
31. Haskell-Luevano, et al (2001) Regul. Pept. 99, 1-7.
32. Joseph, et al (2003) Peptides 24, 263-270.
33. Haskell-Luevano, et al (2000) Peptides 21, 683-689.
34. Thirumoorthy, et al (2001) J. Med. Chem. 44, 4114-4124.
35. Joseph, et al (2004) J. Med. Chem. 47, 6702-6710.
36. Sawyer, et al (1980) Proc. Natl. Acad. Sci. U.S.A. 77, 5754-5758.
37. Al-Obeidi, et al (1989) J. Med. Chem. 32, 2555-2561.
38. Al-Obeidi, et al (1989) J. Am. Chem. Soc. 111, 3413-3416.
39. Joseph, et al. (2003) Peptides 24, 1899-1908.
40. Ericson, et al (2015) J. Med. Chem. 58, 4638-4647.
41. Ericson, et al (2017) J. Med. Chem. 60, 8103-8114.
42. Fleming, et al (2018) ACS Chem. Neurosci., published online Jan. 25, 2017. DOI: 2010.1021/acschemneuro.2017b00495.
43. Carpino, et al (1970) J. Am. Chem. Soc. 92, 5748-5749.
44. Carpino, et al (1972) J. Org. Chem. 37, 3404-3409.
45. Ericson, et al (2015) J. Med. Chem. 60, 805-813.
46. Ericson, et al (2015) Bioorg. Med. Chem. Lett. 25, 5306-5308.
47. Singh, et al (2015) ACS Med. Chem. Lett. 6, 568-572.
48. Schild, et al (1947) Br. J. Pharmacol. Chemother. 2, 189-206.
49. Lensing, et al (2016) J. Med. Chem. 59, 3112-3128.

TABLE 3

Analytical Data for Peptides Synthesized in this Study.

| Peptide | Sequence | Retention Time (min)[a] System 1 | Retention Time (min)[a] System 2 | M (calc) | mass spectral analysis (M + 1) | Purity % |
|---|---|---|---|---|---|---|
| 3 | c[Pro-**DArg**-Phe-Phe-Asn-Ala-Phe-DPro] (SEQ ID NO: 26) | 20.3 | 30.2 | 976.5 | 977.5 | >97% |
| 4 | c[Pro-Arg-**DPhe**-Phe-Asn-Ala-Phe-DPro] (SEQ ID NO: 27) | 17.2 | 27.8 | 976.5 | 977.5 | >99% |
| 5 | c[Pro-Arg-Phe-**DPhe**-Asn-Ala-Phe-DPro] (SEQ ID NO: 28) | 17.3 | 27.4 | 976.5 | 977.5 | >99% |
| 6 | c[Pro-**DArg**-**DPhe**-Phe-Asn-Ala-Phe-DPro] (SEQ ID NO: 29) | 17.3 | 26.9 | 976.5 | 977.6 | >96% |
| 7 | c[Pro-**DArg**-Phe-**DPhe**-Asn-Ala-Phe-DPro] (SEQ ID NO: 30) | 19.3 | 29.0 | 976.5 | 977.6 | >99% |
| 8 | c[Pro-Arg-**DPhe**-**DPhe**-Asn-Ala-Phe-DPro] (SEQ ID NO: 31) | 16.8 | 26.4 | 976.5 | 977.5 | >98% |
| 9 | c[Pro-**DArg**-**DPhe**-**DPhe**-Asn-Ala-Phe-DPro] (SEQ ID NO: 32) | 17.2 | 26.5 | 976.5 | 977.5 | >99% |
| 10 | c[Pro-**DArg**-Phe-Phe-*Dap*-Ala-Phe-DPro] (SEQ ID NO: 33) | 19.0 | 28.5 | 948.5 | 949.6 | >95% |
| 11 | c[Pro-Arg-**DPhe**-Phe-*Dap*-Ala-Phe-DPro] (SEQ ID NO: 34) | 17.2 | 27.9 | 948.5 | 949.5 | >99% |
| 12 | c[Pro-Arg-Phe-**DPhe**-*Dap*-Ala-Phe-DPro] (SEQ ID NO: 35) | 16.8 | 26.8 | 948.5 | 949.6 | >99% |
| 13 | c[Pro-**DArg**-**DPhe**-Phe-*Dap*-Ala-Phe-DPro] (SEQ ID NO: 36) | 16.4 | 25.5 | 948.5 | 949.6 | >99% |
| 14 | c[Pro-**DArg**-Phe-**DPhe**-*Dap*-Ala-Phe-DPro] (SEQ ID NO: 37) | 17.9 | 27.1 | 948.5 | 949.5 | >99% |

TABLE 3-continued

Analytical Data for Peptides Synthesized in this Study.

| Peptide | Sequence | Retention Time (min)[a] System 1 | Retention Time (min)[a] System 2 | M (calc) | mass spectral analysis (M + 1) | Purity % |
|---|---|---|---|---|---|---|
| 15 | c[Pro-Arg-**DPhe**-**DPhe**-*Dap*-Ala-Phe-DPro] (SEQ ID NO: 38) | 16.8 | 26.2 | 948.5 | 949.5 | >99% |
| 16 | c[Pro-**DArg**-**DPhe**-**DPhe**-*Dap*-Ala-Phe-DPro] (SEQ ID NO: 39) | 16.4 | 25.3 | 948.5 | 949.6 | >99% |

[a]Peptide retention times (min) are reported for solvent system 1 (10% acetonitrile in 0.1% trifluoroacetic acid/water and a gradient to 90% acetonitrile over 35 min) and solvent system 2 (10% methanol in 0.1% trifluoroacetic acid/water and a gradient to 90% methanol over 35 min). An analytical Vydac C18 column (Vydac 218TP104) was used with a flow rate of 1.5 mL/min. The peptide purity was determined by HPLC at a wavelength of 214 nm.

TABLE 4

Pharmacology of AGRP Macrocyclic Analogues at the Mouse Melanocortin Receptors.[a]

| Peptide | Sequence | mMC1R | mMC3R | | mMC4R | | mMC5R |
|---|---|---|---|---|---|---|---|
| | | $EC_{50}$ (nM) | $EC_{50}$ (nM) | $pA_2$ | $EC_{50}$ (nM) | $pA_2$ | $EC_{50}$ (nM) |
| NDP-MSH | | 0.007 ± 0.001 | 0.069 ± 0.009 | | 0.9 ± 0.1 | | 0.056 ± 0.009 |
| 1* | c[Pro-Arg-Phe-Phe-Asn-Ala-Phe-DPro] (SEQ ID NO: 1) | 25% @ 100 µM | >100,000 | 6.3 ± 0.1 | >100,000 | 8.2 ± 0.1 | Inverse Agonist, -10%, 130 nM |
| 3 | c[Pro-**DArg**-Phe-Phe-Asn-Ala-Phe-DPro] (SEQ ID NO: 26) | 50% @ 100 µM | >100,000 | <5.5 | >100,000 | <5.5 | >100,000 |
| 4 | c[Pro-Arg-**DPhe**-Phe-Asn-Ala-Phe-DPro] (SEQ ID NO: 27) | Partial Agonist 55% NDP-MSH (700 ± 200) | >100,000 | 5.8 ± 0.2 | >100,000 | 7.7 ± 0.2 | Inverse Agonist -25% @ 100 µM |
| 5 | c[Pro-Arg-Phe-**DPhe**-Asn-Ala-Phe-DPro] (SEQ ID NO: 28) | 50% @ 100 µM | >100,000 | <5.5 | >100,000 | 5.9 ± 0.1 | >100,000 |
| 6 | c[Pro-**DArg**-**DPhe**-Phe-Asn-Ala-Phe-DPro] (SEQ ID NO: 29) | Partial Agonist 90% NDP-MSH (500 ± 100) | >100,000 | <5.5 | >100,000 | <5.5 | 55% @ 100 µM |
| 7 | c[Pro-**DArg**-Phe-**DPhe**-Asn-Ala-Phe-DPro] (SEQ ID NO: 30) | 1200 ± 300 | 35% @ 100 µM | <5.5 | >100,000 | <5.5 | 10,000 ± 3,000 |
| 8 | c[Pro-Arg-**DPhe**-**DPhe**-Asn-Ala-Phe-DPro] (SEQ ID NO: 31) | Partial Agonist 85% NDP-MSH (800 ± 200) | >100,000 | <5.5 | >100,000 | 5.9 ± 0.2 | >100,000 |
| 9 | c[Pro-**DArg**-**DPhe**-**DPhe**-Asn-Ala-Phe-DPro] (SEQ ID NO: 32) | Partial Agonist 85% NDP-MSH (1300 ± 300) | >100,000 | <5.5 | >100,000 | <5.5 | 55% @ 100 µM |
| 2* | c[Pro-Arg-Phe-Phe-*Dap*-Ala-Phe-DPro] (SEQ ID NO: 2) | 30% @ 100 µM | >100,000 | 6.52 ± 0.09 | >100,000 | 8.7 ± 0.1 | Inverse Agonist -15%, 60 nM |
| 10 | c[Pro-**DArg**-Phe-Phe-*Dap*-Ala-Phe-DPro] (SEQ ID NO: 33) | 25% @ 100 µM | 25% @ 100 µM | 5.7 ± 0.2 | 25% @ 100 µM | 6.77 ± 0.05 | >100,000 |

TABLE 4-continued

Pharmacology of AGRP Macrocyclic Analogues at the Mouse Melanocortin Receptors.[a]

| Peptide | Sequence | mMC1R EC$_{50}$ (nM) | mMC3R EC$_{50}$ (nM) | mMC3R pA$_2$ | mMC4R EC$_{50}$ (nM) | mMC4R pA$_2$ | mMC5R EC$_{50}$ (nM) |
|---|---|---|---|---|---|---|---|
| 11 | c[Pro-Arg-**DPhe**-Phe-*Dap*-Ala-Phe-DPro] (SEQ ID NO: 34) | 230 ± 80 | >100,000 | 5.92 ± 0.05 | 20% @ 100 µM | 8.4 ± 0.1 | >100,000 |
| 12 | c[Pro-Arg-Phe-**DPhe**-*Dap*-Ala-Phe-DPro] (SEQ ID NO: 35) | Partial Agonist 75% NDP-MSH (800 ± 200) | >100,000 | <5.5 | >100,000 | 7.34 ± 0.08 | >100,000 |
| 13 | c[Pro-**DArg**-**DPhe**-Phe-*Dap*-Ala-Phe-DPro] (SEQ ID NO: 36) | Partial Agonist 70% NDP-MSH (800 ± 300) | >100,000 | 6.0 ± 0.1 | >100,000 | 5.5 ± 0.2 | Inverse Agonist -30% @ 100 µM |
| 14 | c[Pro-**DArg**-Phe-**DPhe**-*Dap*-Ala-Phe-DPro] (SEQ ID NO: 37) | Partial Agonist 70% NDP-MSH (450 ± 60) | >100,000 | 5.7 ± 0.2 | >100,000 | 6.82 ± 0.06 | Inverse Agonist -20% @ 100 µM |
| 15 | c[Pro-Arg-**DPhe**-**DPhe**-*Dap*-Ala-Phe-DPro] (SEQ ID NO: 38) | 700 ± 300 | >100,000 | 5.7 ± 0.1 | >100,000 | 7.4 ± 0.1 | >100,000 |
| 16 | c[Pro-**DArg**-**DPhe**-**DPhe**-*Dap*-Ala-Phe-DPro] (SEQ ID NO: 39) | Partial Agonist 60% NDP-MSH (2200 ± 800) | >100,000 | <5.5 | >100,000 | 5.8 ± 0.2 | Inverse Agonist -15% @ 100 µM |

[a]The indicated errors represent the standard error of the mean determined from at least three independent experiments. The antagonistic pA$_2$ values were determined using the Schild analysis and the agonist NDP-MSH. The use of >100,000 indicates that the compound was examined but lacked agonist activity at up to 100 µM concentrations. A percentage denotes the percent maximal stimulatory response observed at 100 µM concentrations but not enough stimulation was observed to determine an EC$_{50}$ value. The use of <5.5 indicates that no antagonist potency was observed in the highest concentration ranged assayed (10,000, 5,000, 1,000, and 500 nM). Partial agonist indicates partial agonist activity was observed, along with the percentage of activation relative to NDP-MSH and the EC$_{50}$ (compounds were considered full agonist if >90% maximal NDP-MSH signal was observed). Inverse agonist indicates that inverse agonist pharmacology was observed with the percent decrease from basal indicated. For inverse agonists, if a decrease in cAMP signal was observed without a sigmoidal dose-response curve, the percent change from basal at 100 µM concentrations is indicated.

*The pharmacology for 1 and 2 is described in (Ericson, et al (2017) J. Med. Chem. 60, 8103-8114).

Example 3. Structure-Activity Relationship Studies of a Macrocyclic AGRP-Mimetic Scaffold c[Pro-Arg-Phe-Phe-Asn-Ala-Phe-DPro] (SEQ ID NO: 1) Yield Potent and Selective Melanocortin-4 Receptor Antagonists and Melanocortin-5 Receptor Inverse Agonists that Increase Food Intake in Mice Abstract The melanocortin system has five receptors and antagonists of the central melanocortin receptors (MC3R, MC4R) are postulated to be viable therapeutics for disorders of negative energy balance such as anorexia, cachexia, and failure to thrive. Agouti-related protein (AGRP) is an antagonist of the MC3R and an antagonist/inverse agonist of the MC4R. Biophysical NMR based structural studies have demonstrated that the active sequence of this hormone, Arg-Phe-Phe, is located on an exposed β-hairpin loop. It has previously been demonstrated that the macrocyclic octapeptide scaffold c[Pro$^1$-Arg$^2$-Phe$^3$-Phe$^4$-Asn$^5$-Ala$^6$-Phe$^7$-DPro$^8$] (SEQ ID NO: 1) is 16-fold less potent than AGRP at the mMC4R. Herein, it was hypothesized that the Phe$^7$ position may be substituted to produce more potent and/or selective melanocortin receptor antagonist ligands based on this template. A ten-member library was synthesized that substituted small (Gly), polar (Ser), acidic (Asp), basic (Lys), aliphatic (Leu, Nle, and Cha), and aromatic (Trp, Tyr, hPhe) amino acids to explore potential modifications at the Phe$^7$ position. The most potent mMC4R antagonist contained a Nle$^7$ substitution, was equipotent to the ligand 1, 200-fold selective for the mMC4R over the mMC3R, and caused a significant increase in food intake when injected intrathecally (i.t.) into male mice. Three compounds possessed sigmoidal dose-response inverse agonist curves at the mMC5R, while the remaining seven decreased cAMP production from basal levels at 100 µM concentrations. These findings will add to the knowledge base towards the development of potent and selective probes to study the role of the melanocortin system in diseases of negative energy balance, and can be useful in the design of molecular probes to examine the physiological functions of the mMC5R.

Introduction

The melanocortin system is comprised of five G protein-coupled receptors (GPCRs, MC1-5R)[1-8] that have been associated with a wide range of physiological functions ranging from skin pigmentation[9] to energy homeostasis.[10-14] The melanocortin receptors couple to G proteins and signal primarily by stimulating the adenylate cyclase pathway, thereby increasing intracellular cyclic AMP (cAMP) upon stimulation by agonist compounds. Endogenous agonists for the melanocortin receptors include the adrenocorticotropic hormone (ACTH) and α-, β-, and γ-melanocyte stimulating hormones (MSHs). These peptides are produced via post-translational processing of the proopiomelanocortin (POMC) gene transcript.[15-17] Notably, this receptor system also contains naturally occurring antagonists: agouti signaling protein (ASP) and agouti-related protein (AGRP).[18-22]

The MC3R and MC4R have been investigated as promising targets for anti-obesity drugs due to their integral roles in regulating food intake and energy homeostasis.[10,14] Energy homeostasis is modulated by the MC3R,[10,13-14,23] MC4R.[11-12,24] POMC-derived agonists,[25,26] ASP,[11] and AGRP.[19] To date there have been numerous synthetic peptide and small molecule ligands developed for the study of the melanocortin system, as reviewed by Ericson et al.[27]

Transgenic mice overexpressing AGRP weigh more than wild type control mice,[28] and administration of AGRP via intracerebroventricular (icy) injection in mice increases food intake.[14,29] It has been proposed that self-starvation and physical hyperactivity in rats, induced via food restriction in the presence of running wheels, may be the result of insufficient suppression of central melanocortin receptor activity.[30] The effects of self-starvation in rats can be alleviated by central administration of AGRP.[30,31] A human single nucleotide polymorphism (SNP) in AGRP (A67T) has been identified in patients with anorexia nervosa.[32] Therefore diseases which produce a negative energy balance such as anorexia nervosa, cachexia, and failure to thrive in children may be alleviated through treatment with central melanocortin receptor antagonists.[30-31,33-35]

Using recombinant protein, human (h)AGRP was originally found to be a functional antagonist of endogenous agonist α-MSH at the human MC3R (hMC3R) and hMC4R, and did not have antagonist activity at the hMC1R.[19,21] It was later reported that a truncated version of human AGRP, hAGRP(83-132) possesses inverse agonist activity at the hMC4R as well as a mouse (m) MC4R mutated to possess constitutive activity.[36-37]

Studies utilizing recombinant human agouti first showed that hASP is a competitive antagonist of α-MSH activity at both the mouse and human MC1R, and the human MC4R.[38] Later studies were performed on a synthesized ASP variant, hASP(80-132, Q115Y,S124Y) (ASP-YY), which changed two residues from ASP to the homologous residues contained in AGRP to aid in proper folding.[39] In AGRP, these residues (Y109,Y118) are located within β-sheets that immediately flank the active loop sequence, and are hypothesized to confer stability to the protein through aromatic interactions, of which the ASP native residues (Q115,S124) are apparently incapable.[39] Agouti-YY was found to inhibit α-MSH activity at the hMC1R, hMC3R, and hMC4R with functional antagonist potencies of 4.0, 2.6, and 0.5 nM respectively. These functional potencies are similar to the binding affinities of ASP or other ASP variants, in which these peptides are >3-fold more potent binders at the MC4R than the MC3R.[40-42] Agouti (ASP) has also been shown to possess inverse agonist activity at the hMC4R.[43]

The decapeptide H-Tyr-c[Cys-Arg-Phe-Phe-Asn-Ala-Phe-Cys]-Tyr-OH (SEQ ID NO: 142) (AGRP[109-118]), containing the active loop sequence of AGRP, is a micromolar agonist at the MC1R ($EC_{50}$=3 μM), possesses an antagonist $pA_2$ value of 6.8 at the mMC4R. and does not possess an antagonist potency at the mMC3R that is quantifiable at the highest concentrations of antagonist assayed.[44] Truncations of H-Tyr-c[Cys-Arg-Phe-Phe-Asn-Ala-Phe-Cys]-Tyr-OH (SEQ ID NO: 142) to an octapeptide are therefore hypothesized to confer selectivity toward the MC4R as compared to the MC3R, with the caveat that some of these peptides may possess agonist activity at the MC1R.[45]

In the effort to create selective MC4R antagonist ligands that are equipotent or more potent than the native hormone AGRP, further structure-activity relationship (SAR) studies have been performed around the active loop sequence c[Cys-Arg-Phe-Phe-Asn-Ala-Phe-Cys] (SEQ ID NO: 151).[46] These studies provide important SAR information for the advancement of AGRP-based molecular probes and therapeutic design. The cyclic structure of this peptide is necessary for binding, as a linear derivative of this peptide containing serine isosteric replacements (H-Ser-Arg-Phe-Phe-Asn-Ala-Phe-Ser-OH) (SEQ ID NO: 152) was unable to bind the MC3R and MC4R at up to 20000 nM concentrations.[47] Previous studies have suggested that the Arg-Phe-Phe tripeptide sequence is important for potent antagonist ligands.[47-48] Structural studies of AGRP and "miniAGRP" have indicated that the active loop adopts a β-hairpin conformation, stabilized by five disulfide bonds.[49-51] The ability of heterochiral proline residues to induce β-hairpin turns in macrocyclic peptides has been previously established.[52-55] Previous studies on truncated AGRP macrocycles replacing Cys110 and Cys117 with a head-to-tail cyclized DPro-Pro motif have hypothesized that the resulting macrocyclic peptide may better mimic the β-hairpin loop contained in the native hormone, as these peptides show increased potency relative to H-Tyr-c[Cys-Arg-Phe-Phe-Asn-Ala-Phe-Cys]-Tyr-$NH_2$ (SEQ ID NO: 155) at the mMC4R (sequence=c[$Pro^1$-$Arg^2$-$Phe^3$-$Phe^4$-$Asn^5$-$Ala^6$-$Phe^7$-$DPro^8$] (SEQ ID NO: 1), 1, $pA_2$=7.7).[46]

SAR studies performed on this scaffold have focused on the $Phe^3$, $Phe^4$, $Asn^5$, and $Ala^6$ positions, and the results for these compounds assayed at the mMC4R are summarized in FIG. 9.[46,56] Replacing $Phe^3$ and $Phe^4$ in this macrocyclic template with other aromatic amino acid derivatives (including Bip, Phg, and hPhe) decreases or ablates potency at the mMC3R and the mMC4R with the exception of Nal(1'), which is equipotent to the compound 1.[46] Nearly all of these $Phe^3$- and $Phe^4$-substituted macrocycles are micromolar MC1R agonists, and are unable to stimulate the MC5R (with the exception of the $Anc^4$-substituted peptide, which is a micromolar agonist at the mMC5R). The SAR around the $Asn^5$ position suggests that this position is more amenable to change. In one study, replacing this residue with multiple different amino acids (Gly, Dap, Dab, Orn, Lys, Arg) resulted in ligands that were equipotent or more potent antagonists than the ligand 1 at the mMC3R and mMC4R.[46] Four of these substitutions possessed some agonist activity at the mMC1R at 100 μM concentrations, and all were unable to activate the MC5R.[46] A subsequent study has replaced $Asn^5$ with a larger variety of amino acids (Ala, Abu, Ser, Thr, Asp, Glu, DDap, His, Nle, Leu, Val, Phe, and Trp) in order to elaborate on the SAR around this position.[56] All of these peptides showed quantifiable antagonist potency at the mMC4R: two were more potent than the $Asn^5$ substitution (containing DDap and His substitutions), while the remainder possessed decreased potency. Notably, many of these ligands also possessed mMC5R inverse agonist activity, a novel pharmacology at this receptor.[56] This study also examined the $Ala^6$ position, replacing this residue with Asp, Glu, Lys, His, Phe, Ser, Leu, and Gly residues. All but one of these compounds, possessing a Ser substitution, resulted in decreased potency compared to the ligand 1 at the mMC4R. Many of these peptides also possessed inverse agonist activity at the mMC5R, though notably the $Lys^6$-substituted peptide possessed some agonist activity. During this study it was noted that the $Arg^5$ and $Ser^6$ substitutions corresponded to residues contained in the ASP active loop. Therefore, the $Phe^7$ was substituted with an Ala to elaborate on the hypothesis that ASP residues may be substituted into this macrocyclic octapeptide template to generate potent mMC4R antagonist ligands. Notably, this $Ala^7$-substituted peptide was also equipotent to the compound 1.[56]

Both $Ala^7$ and $Phe^7$ substitutions have been reported to possess equipotent mMC4R antagonist potency, despite the difference between the methyl side chain of Ala and the phenyl side chain of the Phe. Due to these differences, the present study focused on what properties of the Phe side chain were important for the observed antagonist potency. While Ala can be thought of as removal of a side chain, it is also the smallest side chain that may be considered aliphatic. It was hypothesized aliphatic or aromatic substitutions at the $Phe^7$ position may possess antagonist potency at the mMC4R, and that changing this residue to various aliphatic or aromatic amino acids will afford ligands that are more potent than the ligand 1 or have unique pharmacological profiles. The present study explores the SAR around the $Phe^7$ position of the macrocyclic template and tests this hypothesis through the synthesis and pharmacological screening of $Phe^7$-substituted macrocyclic ligands.

Results and Discussion

Peptide Synthesis and Characterization.

The peptides reported herein were synthesized in a semi- and fully automated fashion using standard fluorenylmethoxycarbonyl (Fmoc) methodology.[57-58] Following synthesis, peptides were purified using semi-preparative reverse phase high-pressure liquid chromatography (RP-HPLC). Purity was confirmed to be >95% via analytical RP-HPLC using two diverse solvent systems, and the peptide mass confirmed using matrix-assisted laser desorption ionization (MALDI) time of flight (TOF) mass spectrometry (University of Minnesota LeClaire-Dow Instrumentation Facility). Analytical characterization data for these peptides may be found in Table 5.

Compounds were first assayed as agonists in HEK293 cells stably expressing the mMC1R, mMC3R, mMC4R, or mMC5R using the AlphaScreen cAMP Assay.[59-61] None of the library compounds possessed agonist activity at the mMC3R or mMC4R at up to 100 μM concentrations, so antagonist potencies were measured. Competitive antagonist activity was measured using a Schild analysis at the mMC3R and mMC4R with the synthetic, non-selective, potent melanocortin agonist NDP-MSH.[62] Fold-change calculations were performed using the $K_i$ values derived from the Schild analysis $[pA_2=-\log(K_i)]$.

Library Design and Structure-Activity Relationship.

Herein, it was hypothesized that the possession of aliphatic or aromatic side chains in the 7 position of the macrocyclic template is important for MC4R antagonist activity of the peptide, and this was tested through removal of the side chain by replacing this residue with $Gly^7$ (KAF2039-1). This was also tested through replacing this residue with an Ala (KAF3094).[56] Additionally, to test this hypothesis, the $Phe^7$ residue was substituted with a hydrophilic amino acid (Ser) and charged amino acids (Lys and Asp) (KAF2039-3, KAF2039-4, and KAF2039-5). Due to the hydrophobic nature of the phenyl side chain in the peptide 1, it was hypothesized that these substitutions would decrease the potency compared to the ligand 1. Aliphatic amino acids Leu and Nle were used to replace the $Phe^7$ residue (KAF2039-6. KAF2039-7) to test the hypothesis that the $Ala^7$-substitution contributes to the activity of 1 through aliphatic interactions. The hypothesis that either aliphatic or aromatic amino acid substitutions could result in potent mMC4R antagonist ligands was tested further by replacing the $Phe^7$ residue with other aromatic amino acids such as Trp and Tyr (KAF2039-9, KAF2039-10), and by removing the aromaticity of this side chain through replacement of the $Phe^7$ residue with cyclohexylalanine (Cha) (KAF2039-11). Finally, to test the hypothesis that the side chain length of the $Phe^7$ residue is important for the activity of the ligand (1), the side chain of this residue was elongated by one methylene unit (hPhe) (KAF2039-13). The amino acids used in this study are illustrated in FIG. 10.

The pharmacological results for these experiments are summarized in Table 6. The pharmacology at the mMC3R and mMC4R of the three most potent compounds at the mMC4R are illustrated in FIG. 11. The $Gly^7$-substituted compound was 110-fold less potent at the mMC4R than 1, supporting the hypothesis that the possession of an aromatic or aliphatic sidechain is important for the activity of the ligand 1. Polar amino acids decreased antagonist potency at the mMC4R. The $Ser^7$-substituted compound was 10-fold less potent than 1, 40-fold decreased potency was observed for $Lys^7$, and the antagonist potency was not measurable for the $Asp^7$ substitution at the concentrations used in this study. These results support the hypothesis that the hydrophobic nature of the native $Phe^7$ sidechain in 1 is important for receptor activity. Lengthening the Phe residue by one methylene unit (KAF2039-13) produced a compound which is 8-fold less potent than 1 at the mMC4R. The aliphatic amino acids investigated in this study yielded different results. The $Nle^7$-substituted compound (KAF2039-7) was equipotent to 1 at the mMC4R, while KAF2039-6 was 15-fold less potent than 1 at the MC4R. The aromaticity of the $Phe^7$ ring in 1 is important, as substitution with a cyclohexyl ring ($Cha^7$) decreases potency 16-fold compared to the compound 1. Substitution of the $Phe^7$ side chain with $Tyr^7$ and $Trp^7$ (KAF2039-10, KAF2039-9) yielded compounds that were equipotent to the ligand 1 at the mMC4R.

The results obtained from this study support the hypothesis that the activity of the ligand c[Pro-Arg-Phe-Phe-Asn-Ala-Phe-DPro] (SEQ ID NO: 1) (1) at the MC4R as mediated through $Phe^7$ is due to aromatic interactions, but that aliphatic substitutions are also tolerated in this position. It is interesting that the $Leu^7$ and $Cha^7$ substitutions both resulted in approximately 15-fold decreased potency compared to the ligand 1, while the $Nle^7$ substitution was equipotent to 1. These two amino acids ($Leu^7$ and $Cha^7$) possess aliphatic sidechains that are branched on the γ-carbon, while the $Nle^7$ residue possesses a linear side chain. If the aliphatic interactions formed by the $Nle^7$ side chain are sufficient for producing antagonist activity, it might be expected that the interactions by $Leu^7$ and $Cha^7$ would be as well. It would therefore be anticipated that these compounds (KAF2039-6, KAF2039-11) would be equipotent to the $Nle^7$-substituted compound (KAF2039-7). However, this was not what was observed. Interestingly in ASP, the residue at the analogous 7 position is not a Phe, and is an Ala. The $Ala^7$-substituted compound (KAF3094) was also equipotent to 1 at the mMC4R. Therefore, it is possible that two distinct types of amino acids in the 7 position (aromatic, aliphatic) are equipotent the MC4R, and that branching at the γ-carbon may be unfavorable in forming putative ligand-receptor interactions for aliphatic substitutions.

Most of the substitutions examined in this study showed a reduced potency compared to ligand 1 at the MC3R. Antagonist activity was not observed for the $Gly^7$-, $Asp^7$-, or $Leu^7$-containing peptides (KAF2039-1. KAF2039-5, KAF2039-6) at the concentrations examined in this study at the mMC3R. The $Lys^7$- and $Cha^7$-containing peptides (KAF2039-4, KAF2039-11) resulted in decreased potency compared to 1 (4-fold and 3-fold, respectively), and $Nle^7$-, $Trp^7$-, $Tyr^7$-, and $hPhe^7$-containing peptides (KAF2039-7, KAF2039-9, KAF2039-10, KAF2039-13) were all equipotent to 1 at the mMC3R.

The ligand 1 is 80-fold more selective at the mMC4R than the mMC3R. Of the compounds that showed quantifiable potency at both the mMC3R and mMC4R, two possessed fold selectivities between 30 and 80. The $Tyr^7$-containing peptide was 60-fold more potent at the mMC4R than the mMC3R, and the Trp-containing peptide was 30-fold more potent at the mMC4R than the mMC3R. Notably, the $Nle^7$-substituted peptide was 200-fold more potent at the mMC4R than the mMC3R, an increase in selectivity compared to 1. Additionally, the $Ala^7$-substituted peptide (KAF3094) possesses 130-fold selectivity for the mMC4R over the mMC3R.[56] Above, it was postulated that two distinct types of amino acids at the 7 position of the macrocyclic template (linear aliphatic, aromatic) are capable of possessing equipotent antagonist activity at the mMC4R. These data suggest that the linear aliphatic substitutions may possess different pharmacological profiles compared to the aromatic substitutions. The active loop of ASP (sequence=-c[$Cys^1$-$Arg^2$-$Phe^3$-$Phe^4$-$Arg^5$-$Ser^6$-$Ala^7$-$Cys^8$]-) (SEQ ID NO: 141) contains an Ala residue in the 7 position, and studies on ASP-YY suggest that ASP is more selective for the MC4R (5-fold) than AGRP (equipotent).[39,48] It is possible that the linear aliphatic substitutions in this position, which are more ASP-like, may be used in order to increase mMC4R selectivity against the mMC3R as opposed to aromatic substitutions, which are more AGRP-like. The remainder of the macrocyclic peptides resulted in decreased mMC3R/mMC4R selectivity compared to the ligand 1; the $Ser^7$-containing peptide was 16-fold more potent at the mMC4R, the $Lys^7$-containing peptide was 8-fold more potent at the mMC4R, the $Cha^7$-containing peptide was 16-fold more potent at the mMC4R, and the $hPhe^7$-containing peptide was 6-fold more potent at the mMC4R.

Four of the ligand studied displayed agonist activity at the mMC1R. The $Gly^7$-, $Ser^7$-, and $Asp^7$-containing peptides (KAF2039-1, KAF2039-3, KAF2039-5) all were able to partially stimulate the MC1R at 100 μM concentrations. The $Trp^7$-containing peptide KAF2039-9 was a partial agonist at the mMC1R ($EC_{50}$=1,100±200 nM), and resulted in 50% receptor activation. The pharmacology of this peptide at the mMC1R is illustrated in FIG. 12.

All the $Phe^7$ side chain modifications examined in this study resulted in MC5R inverse agonist activity (Table 6, FIG. 13).[56] Three compounds (KAF2039-9, KAF2039-11, and KAF2039-13) appeared to generate sigmoidal dose-response curves with inverse agonist activities of 20%, which is shown in FIG. 13. The sigmoidal shape of these curves allowed the calculation of apparent inverse agonist potencies (the inflection point on the sigmoidal dose-response curve). The $Trp^7$- and $hPhe^7$-containing peptides were equipotent to each other, while the $Cha^7$-containing peptide was 5-fold less potent than the most potent inverse agonist at the mMC5R (KAF2039-9). Both the $Trp^7$ and $hPhe^7$-containing peptides possess aromatic moieties, and based on these results it appears that this functionality may be important for generating mMC5R inverse agonist ligands. Many ligands appeared to display inverse agonist efficacy, but did not plateau to generate a sigmoidal dose-response. These compounds are listed by the percent cAMP accumulation observed relative to basal at 100 μM. The two types of pharmacological results described above (apparent sigmoidal dose-response, and inverse agonist activity at 100 μM concentrations) observed for select compounds are illustrated in FIG. 13. The $Gly^7$- and $Asp^7$-containing peptides possessed similar percent decreases in cAMP accumulation (−25%) compared to KAF2039-9, KAF2039-11, and KAF2039-13. The $Leu^7$- and $Nle^7$-containing peptides possessed percent decreases in cAMP accumulation of −35% relative to basal. The $Ser^7$-, $Lys^7$-, and $Tyr^7$-containing peptides (KAF2039-3, KAF2039-4, and KAF2039-10) all showed the most prevalent MC5R inverse agonist pharmacology, with −55%, −40%, and −40% decreases in cAMP accumulation respectively. Interestingly, the ligands possessing the greatest decrease from basal levels at 100 μM concentrations at the mMC5R (KAF2039-3, KAF2039-4, and KAF2039-10) contain hydrogen bond donors. It may be speculated that the $Tyr^7$- and $Lys^7$-containing peptides orient a hydrogen bond donor-proton for a productive interaction, yielding an inverse agonist pharmacology of ~40%. A shorter hydrogen bond donor yields a greater inverse agonist response, as KAF2039-3 possessed a 55% inverse agonist pharmacology. This SAR, combined with the MC5R inverse agonism described in Ericson, et al (2017) J. Med. Chem. 60, 8103-8114, is a promising start in the development of MC5R inverse agonist peptides which are selective, potent, and possess percent decreases in cAMP from basal of >55%.[56] Such ligands could be used to study the activity of the MC5R by way of a pseudo conditional knockdown of MC5R activity.

Animal Studies.

As discussed above, MC1R agonism is commonly observed in MC4R antagonist ligands. There have been a few ligands reported in literature that are >100-fold selective for the MC4R over the MC3R but these ligands possess MC1R agonist activity as reviewed by Ericson et al.[27] One compound reported herein, KAF2039-7, possesses selectivity for the MC4R over the MC3R (200-fold) and does not possess MC1R agonist activity, thereby possessing a more selective pharmacological profile at the melanocortin receptors. Due to its potency at the mMC4R ($pA_2$=8.4±0.2) and selectivity for the mMC4R over the mMC3R (approximately 200-fold), KAF2039-7 was selected as a candidate for animal studies in mice to examine the potential in vive effects of this scaffold series (shown in FIGS. 14A-14B and FIG. 15). Intrathecal (IT) administration of melanocortin compounds into the spinal cord for the study of metabolic disorder is new to the field, and may provide some benefits as opposed to intracerebroventricular (ICV) injection into mice.[63] For example, it has been proposed that IT administration may result in a more sensitive in vivo response compared to ICV administration.[63] Male mice injected IT with 2 nmol KAF2039-7 showed a statistically significant increase in food intake at 2 and 6 hours post-injection, and exhibited a prolonged trend of increased food intake up to 72 hours post-injection (FIGS. 14A-14B). There was an overall effect of KAF2039-7 treatment on mouse body weight compared to vehicle control, with treated animals weighing more than control animals (FIG. 15).

Previously, it was demonstrated that IT administration of 2 nmol AGRP(86-132) statistically increased the average daily food intake for 2 days post-injection.[63] Mice treated with KAF2039-7 showed a strong trend in increased food intake for up to 72-hours. By fine-tuning the properties of these macrocyclic octapeptides, future AGRP-mimetics may be able to display the same potency and duration of action of AGRP(86-132) despite the truncation of 34 residues, an important step in the development of probes and therapeutic leads for the treatment of disease states with negative energy balance.

Conclusions

Overall, these studies advance the development of potent and selective antagonists at the melanocortin 4 receptors that lack MC1R agonism and identify a position in the macrocyclic template c[Pro-Arg-Phe-Phe-Asn-Ala-Phe-DPro]

(SEQ ID NO: 1) that can be modified to generate peptides possessing high nanomolar mMC5R inverse agonism. These ligands, and derivatives thereof, can make interesting probes for the investigation of the physiological role(s) of the MC5R. This study also produced one ligand (KAF2039-7) that was equipotent to the ligand (1), and was 200-fold more selective for the mMC4R over the mMC3R without possessing MC1R agonist activity. When injected IT into male mice, this peptide causes a significant increase in food intake at 2 and 6 hours post-injection, with a trend exhibited out until 72 hours post-injection. Potent and selective antagonists are useful pharmacological probes in understanding the differential roles of the mMC3R and mMC4R in body weight management and energy homeostasis, and afford a deeper understanding of the melanocortin system. The insights provided by these data will be useful in the future development of therapeutics to treat anorexia, cachexia, or other diseases of negative energy balance such as failure to thrive.

Experimental Section

Peptide Synthesis.

All peptides were synthesized using flourenyl-9-methoxycarbonyl (Fmoc) methodology on a H-Pro-CTC Resin (0.67 meqiv/g substitution) purchased from Peptides International (Louisville, Ky.).[57-58] Coupling reagents O-benzotriazol-1-yl-N,N,N',N'-tetramethyluronium hexafluorophosphate (HBTU), (benzotriazolyloxy)tris(dimethylamino)phosphonium hexafluorophosphate (BOP), and 1-hydroxybenzotriazole (HOBt) were purchased from Peptides International (Louisville, Ky.). Amino acids Fmoc-DPro, Fmoc-Gly, Fmoc-Ser(tBu), Fmoc-Lys(Boc), Fmoc-Asp(OtBu), Fmoc-Nle, Fmoc-DPhe, Fmoc-Trp(Boc), Fmoc-Tyr(tBu), Fmoc-cyclohexylalanine (Fmoc-Cha), Fmoc-Ala, Fmoc-Asn(Trt), Fmoc-Phe, and Fmoc-Arg(Pbf), which were purchased from Peptides International (Louisville, Ky.). The Fmoc-homophenylalanine (Fmoc-hPhe) was purchased from Synthetech (Albany, Oreg.). Dichloromethane (DCM), N,N-Dimethylformamide (DMF), methanol, acetonitrile, and anhydrous ethyl ether were purchased from Fisher (Fair Lawn, N.J.). Trifluoroacetic acid (TFA), piperidine, dimethyl sulfoxide (DMSO), N—N-Diisopropylethylamine (DIEA) and triisopropylsilane (TIS) were purchased from Sigma-Aldrich (St. Louis, Mo.). All reagents were ACS grade or better, and were used without purification.

Peptides were synthesized in parallel at a 0.075 mmol scale on a H-Pro-CTC-resin using a semi-automated synthesizer (LabTech 1, Advanced Chemtech, Lousiville, Ky.). Resin was swelled in dimethylformamide (DMF) for at least one hour prior to the first coupling. The first two amino acids (DPro, and variable) were coupled using the semi-automated synthesizer in a 16-well Teflon reaction block. Fmoc protected amino acid (3.1 eqiv), HBTU (3 equiv), and DIEA (5 equiv) were added, and the solution was agitated for 1 hour. The presence of a free secondary amine was monitored using a chloranil test.[64] This procedure was repeated if necessary. Next, the amino acid was deprotected with 20% piperidine in DMF (1×2 min, 1×18 min). Deprotection was monitored again using a chloranil test. The second amino acid was coupled using the same procedure as described above. Subsequent amino acids were coupled on an automated synthesizer (Vantage, Advanced Chemtech, Lousville, Ky.). The following procedure was used: (i) wash with DMF (4 mL for 2 min×3), (ii) deprotect with 20% piperidine in DMF (4 mL×5 min, 4 mL×20 min), (iii) wash with DMF (4 mL for 2 min×3), (iv) couple with Fmoc amino acid (3.1 equiv. dissolved in DMF), HBTU (3 equiv, dissolved in DMF), and DIEA (5 equiv) for 1 hr, (iv) empty well block and repeat coupling procedure, (v) proceed to coupling of next amino acid using steps i-iv. Following synthesis, the N-terminal Fmoc amines were deprotected with 20% piperidiene in DMF (2 mL/well, 1×2 min, 1×18 min) and dried in vacuo after washing with methanol.

Peptides were cleaved from solid support using 1% trifluoroacetic acid (TFA) in dichloromethane (DCM) by rinsing the resin 4 times with 2 mL of cleavage solution for 1.5 minutes. Peptides were precipitated with cold ether and pelleted via centrifugation (4,000 rpm at 4° C. for 4 minutes, ThermoScientific Sorvall Legend XTR). The supernatant was decanted, and the peptides were then dried in vacuo in the presence of desiccant overnight. For the coupling of the C-terminus ($Pro^1$ in the macrocyclic template) to the N-terminus ($Arg^2$ in the macrocyclic template) to create the macrocycle, peptides were dissolved in DCM (1 mM), and cyclized using BOP (3 equiv), HOBt (3 equiv), and DIEA (6 equiv), stirring the solution overnight at room temperature. The peptides were dried under reduced pressure for a minimum of 1 hour, and 5 mL of a 95:2.5:2.5 TFA:$H_2O$:TIS solution were added at room temperature for 2 hours. The peptides were then concentrated via evaporation under an increased pressure of $N_2$ (g) and precipitated with cold ether. Peptides were pelleted via centrifugation at 4,000 rpm at 4° C. for 4 minutes, and the supernatant was decanted. The final products were dried in vacuo in the presence of desiccant.

Peptides were purified via reverse phase high pressure liquid chromatography (RP-HPLC, Shimadzu) on a semi-preparative Cis column (Vydac 218TP1010, 1 cm×25 cm) using acetonitrile and 0.1% TFA in $H_2O$. Analytical data was then collected using an analytical Cis column (Vydac 218TP, 4.6 mm×250 mm) on a Shimadzu chromatography system equipped with a photodiode array detector in two different solvent systems: acetonitrile/0.1% TFA in $H_2O$, and methanol/0.1% TFA in $H_2O$ to confirm purity >95%. Molecular weights were then confirmed using matrix-assisted laser desorption ionization (MALDI) and time of flight (TOF) mass spectrometry analysis (AB-Sciex 5800 MALDI/TOF-MS, LeClaire-Dow Instrumentation Facility, University of Minnesota), using a cyano-4-hydroxycinnamic acid (CCA) matrix. Peptides were assayed as TFA salts.

AlphaScreen™ cAMP Functional Assay.

The AlphaScreen™ cAMP assay (PerkinElmer Life Sciences, Cat #6760625M) was used to measure the functional cAMP potencies of peptides at HEK293 cells stably expressing the individual melanocortin receptors (mMC1R, mMC3R, mMC4R, and mMC5R). The assay was performed according to manufacturer instructions, and as previously described.[59-61]

Cells were 70-90% confluent at the start of the assay. Growth medium was aspirated and cells were rinsed with 1 mL Gibco® Versene solution, then 1 mL fresh Versene solution was added. Cells were incubated at 37° C. until cells had detached from the plate, then pelleted via centrifugation (800 rpm, 5 minutes; Sorvall™ Legend™ XTR centrifuge, swinging bucket rotor). The medium was aspirated and the cell pellet was resuspended a second time in Dulbecco's phosphate buffered saline solution (DPBS 1× [-] without calcium and magnesium chloride. Gibco 9 Cat #14190-144). A 10 μL of each cell line was removed for counting, during which the remaining cells were centrifuged a second time as described above. Cells were counted by adding 10 μL Trypan blue dye (BioRad) and counted manually using a hemocytometer. After centrifugation, the DPBS was aspirated and the pellet was resuspended in a solution of freshly-made stimulation buffer [Hank's Balanced Salt Solution (HBSS 10× (-) sodium bicarbonate) and (-) phenol red, Gibco®), 0.5 mM isobutylmethylxanthine (IBMX), 5 mM HEPES buffer solution (1M, Gibco®), 0.1% bovine serum albumin (BSA) in Milli-Q water, pH=7.4] to a concentration of 10,000 cells per μL. An acceptor bead solution was created by diluting the acceptor bead stock solution (5 mg/mL anti-cAMP acceptor beads in stimulation buffer) to a concentration of 0.1 mg/mL in stimulation buffer. The acceptor bead solution was added to the cells such that there were 0.5 μg anti-cAMP acceptor beads in each cell line.

Next, 10 μL of the cell/acceptor bead solution per well was added to an Opti-384 plate using a 16 channel pipettor. This was repeated for each cell line. To each well 5 μL of compound was added so that, when diluted with the 10 μL cell/acceptor bead solution, the compound reached the desired concentration(s). Compounds were run in duplicate replicates, and each cell line had a positive control (10 μM forskolin) and negative control (plain stimulation buffer, instead of compound). The 384-well plate was sealed with a cover slip, covered with aluminum foil, and incubated at room temperature in a dark desk drawer for 2 hours. A biotinylated cAMP/Streptavidin-coated donor bead working solution was prepared by diluting the stock solution of donor beads (5 mg/mL) and cAMP biotinylated tracer (1 μL with 1×PBS 14190-144) in a freshly prepared lysis buffer [10% Tween-20, 5 mM HEPES buffer solution (1M, Gibco), 0.1% bovine serum albumin (BSA) in Milli-Q water, pH=7.4] such that the final solution contained 0.5 μg of donor beads and 0.62 μmol biotinylated cAMP. This donor bead/biotinylated cAMP solution was allowed to incubate in a dark desk drawer at room temperature for a minimum of 30 minutes.

After the incubation period for the cells/acceptor beads/compound solution was completed, 10 μL of the donor bead/biotinylated cAMP mixture was added to each well in a room containing a green light using a multichannel pipettor, mixing well. The plate was then re-sealed with the cover slip, covered in aluminum foil, and allowed to incubate in a dark desk drawer at room temperature for another 2 hours. Following the second incubation period, the plate was inserted into an Enspire™ Alpha plate reader and read using a pre-normalized assay protocol set by the manufacturer.

Cell Data Analysis.

The data collected were analyzed using PRISM software (v4.0, GraphPad Inc.). Agonist potency was evaluated by calculating the $EC_{50}$ values using non-linear regression analysis with the PRISM software. Antagonist potency was determined using a Schild analysis [$pA_2=-\log(K_i)$] and the agonist ligand NDP-MSH.[62] Because this assay is loss-of-function, mMC1R, mMC3R, and mMC4R data were normalized to represent a percent response relative to control ligand (NDP-MSH), as has been reported previously, unless otherwise specified.[59-61] For illustrative purposes, mMC1R partial agonist activity (seen in FIG. 12) was normalized to a basal response to yield a percent difference from basal activity. For illustrative and data analysis purposes, inverse agonist activity (seen in FIG. 13) for the mMC5R was also normalized to a basal response to yield a percent difference from basal activity.

Animals.

This study was conducted in accordance with the guidelines set up by the Institutional Animal Care and Use Committee (IACUC) at the University of Minnesota. Male Wildtype (WT) mice (mixed 129/Sv×C57BL/6J background) derived from an in house breeding colony were used throughout this experiment as previously reported in literature.[14,23,61,63,65] Each mouse was individually housed in standard polycarbonate conventional cages provided by the University of Minnesota's Research Animal Resources (RAR). Mice were singly housed in order to adequately measure food intake of individual mice during experiments. At the beginning of this experiment, mice were age-matched at 24 weeks old. Research lab staff performed weekly cage changes. Mice had ad libitum access to normal chow (Harlan Teklad 2018 Diet: 18.6% crude protein, 6.2% crude fat, 3.5% crude fiber, with energy density of 3.1 kcal/g) and water. Mice were maintained on a revered 12-hour light/dark cycle (lights off at 12:00 pm) and housed in a temperature-controlled room at 23°-25° C. Mice were monitored daily to assess health.

Mouse Feeding Studies.

All mouse feeding experiments were designed following a crossover, non-fasting (nocturnal) paradigm. Compound (KAF2039-7) or vehicle was administered IT in a single injection 2 hours before lights out (t=0 h). Intrathecal injections were performed as previously described.[63,66-68] Mouse body weight and food weight was recorded in 2, 4, 6, 8, 24, 48 and 72 hours post-injection following a single IT injection. Mice were given 7 days between treatments to re-establish pre-treatment feeding behavior and body weight. Eight male WT mice were used for the whole feeding study.

Compounds.

A stock of KAF2039-7 was prepared using a 20% solutol (Kolliphor HS 15; Sigma) solution (final concentration of 10 nmol/μL) and stored at −20° C. On days of experimentation, the KAF2039-7 stock was diluted using sterile dd$H_2O$ to the desired concentration of 2 nmol/5 μL. The vehicle was created using identical volumes of 20% solutol to sterile dd$H_2O$ as the experimental compound.

Animal Data Analysis.

Primary dependent variables were: (i) food intake; and (ii) body weight. Food intake and body weight was analyzed a two-factor within-subject Analysis of Variance (ANOVA) with between session variables of compound and the within-subject variable of time. To identify sources of significant interactions at specific time-points, follow-up independent sample t-tests with Bonferroni correction was performed. Graphpad Prism was used to graph data. Data was analyzed using Statistical Package for the Social Science Software (SPSS) and was represented as the mean±error with $p<0.05$ indicating significance.

Cumulative Food Intake Statistics.

To examine the effect of drug (7/Vehicle) on food intake during the first 72 hours post-injection, a two-factor repeated measures Analysis of Variance (ANOVA) was performed with drug as the between-subject factor and time as the within-subject factor. Results showed that there was a main effect of drug ($F_{1,14}=7.017$; $p=0.019$). A follow-up independent sample t-test with Bonferroni correction (to control for multiple comparisons) revealed that mice that were administered with 2 nmol of 7 ate significantly more 2 ($t_{14}=-3.145$; $p=0.007$) and 6 ($t_{14}=-4.030$; $p=0.001$) hours post-injection compared to vehicle controls.

Mouse Weight Statistics.

To analyze the effect of 2 nmol 7 on changes in mouse weight, a two-factor repeated measure ANOVA was performed, with drug as the between-subject factor and time as the within-subject factor. Results indicated that there was a main effect of time ($F_{6,84}=2.578$; $p=0.024$) and a main effect of drug ($F_{1,14}=2.938$; $p=0.045$). A follow-up independent sample t-test with Bonferroni correction did not show significance between treatment at specific time points.

Abbreviations

ACTH, adrenocorticotropin hormone; Fmoc, 9-fluorenylmethoxycarbonyl; AGRP, agouti-related protein; GPCR, G-protein coupled receptor; cAMP, cyclic 5'-adenosine monophosphate; MC1R, melanocortin-1 receptor; MC2R, melanocortin-2 receptor; MC3R, melanocortin-3 receptor; MC4R, melanocortin-4 receptor; MC5R, melanocortin-5 receptor; MSH, melanocyte stimulating hormone; POMC, proopiomelanocortin; α-MSH, alpha-melanocyte stimulating hormone; β-MSH, beta-melanocyte stimulating hormone; γ-MSH, gamma-melanocyte stimulating hormone; μM, micromolar; NDP-MSH (4-Norleucine-7-D-Phenylalanine), Ac-Ser-Tyr-Ser-Nle-Glu-His-DPhe-Arg-Trp-Gly-Lys-Pro-Val-$NH_2$ (SEQ ID NO: 136); Nle, norleucine; Cha, cyclohexylalanine; hPhe, homophenylalanine; RP-HPLC, reverse-phase high-pressure liquid chromatography; SAR, structure-activity relationships; SNP, single nucleotide polymorphism; IT, intrathecal

TABLE 5

Analytical characterization data for peptides.

| Compound ID | KAF# | Sequence | HPLC RT (system 1) | HPLC RT (system 2) | Purity % | M + 1 (calculated) | M + 1 (observed) |
|---|---|---|---|---|---|---|---|
| 2 | KAF2039-1 | c[Pro-Arg-Phe-Phe-Asn-Ala-**Gly**-DPro] (SEQ ID NO: 40) | 10.5 | 18.9 | >95% | 888.0 | 887.9 |
| 3 | KAF2039-3 | c[Pro-Arg-Phe-Phe-Asn-Ala-**Ser**-DPro] (SEQ ID NO: 41) | 14.8 | 24.3 | >98% | 918.0 | 918.7 |
| 4 | KAF2039-4 | c[Pro-Arg-Phe-Phe-Asn-Ala-**Lys**-DPro] (SEQ ID NO: 42) | 14.2 | 23.3 | >98% | 959.1 | 959.0 |
| 5 | KAF2039-5 | c[Pro-Arg-Phe-Phe-Asn-Ala-**Asp**-DPro] (SEQ ID NO: 43) | 15.1 | 25.3 | >95% | 946.1 | 946.9 |
| 6 | KAF2039-6 | c[Pro-Arg-Phe-Phe-Asn-Ala-**Leu**-DPro] (SEQ ID NO: 44) | 17.4 | 28.3 | >98% | 944.1 | 944.1 |
| 7 | KAF2039-7 | c[Pro-Arg-Phe-Phe-Asn-Ala-**Nle**-DPro] (SEQ ID NO: 45) | 17.4 | 28.7 | >95% | 944.1 | 944.5 |
| 8 | KAF2039-9 | c[Pro-Arg-Phe-Phe-Asn-Ala-**Trp**-DPro] (SEQ ID NO: 46) | 18.2 | 28.4 | >98% | 1017.2 | 1017.5 |
| 9 | KAF2039-10 | c[Pro-Arg-Phe-Phe-Asn-Ala-**Tyr**-DPro] (SEQ ID NO: 47) | 16.1 | 25.5 | >98% | 994.1 | 994.8 |
| 10 | KAF2039-11 | c[Pro-Arg-Phe-Phe-Asn-Ala-**Cha**-DPro] (SEQ ID NO: 48) | 19.1 | 30.6 | >98% | 984.2 | 984.5 |
| 11 | KAF2039-13 | c[Pro-Arg-Phe-Phe-Asn-Ala-**hPhe**-DPro] (SEQ ID NO: 49) | 18.3 | 29.4 | >98% | 992.2 | 992.9 |

HPLC RT = peptide retention time in solvent system 1 (10% acetonitrile in 0.1% trifluoroacetic acid in water and a gradient of 90% acetonitrile over 35 minutes) or solvent system 2 (10% methanol in 0.1% trifluoroacetic acid in water and a gradient of 90% methanol over 35 minutes). An analytical Vydac C18 column (Vydac 218TP104) was used with a flow rate of 1.5 mL/min. The peptide purity was determined by HPLC at a wavelength of 214 nm.

TABLE 6

Pharmacology of the macrocyclic AGRP-based peptides modified in the $Phe^7$ position [$Pro^1$-$Arg^2$-$Phe^3$-$Phe^4$-$Asn^5$-$Ala^6$-$Phe^7$-$DPro^8$] (SEQ ID NO: 1).

| | | | Agonist mMC1R | Antagonist mMC3R | | Antagonist mMC4R | | Inverse Agonist mMC5R |
|---|---|---|---|---|---|---|---|---|
| Compound ID | KAF# | R7 | Agonist $EC_{50}$ (nM) | $pA_2$ | Antagonist $K_i$ (nM) | $pA_2$ | Antagonist $K_i$ (nM) | Inverse Agonist $EC_{50}$ (nM) |
| NDP-MSH | | | 0.010 ± 0.003 | $EC_{50}$ = 0.06 ± 0.01 nM | | $EC_{50}$ = 0.35 ± 0.06 nM | | $EC_{50}$ = 0.10 ± 0.01 nM |
| hAGRP(87-132)[a] | | | >100,000 | 8.9 ± 0.2 | 1.3 | 9.4 ± 1.0 | 0.40 | >100,000 |
| 1[b] | MDE5108-10c | Phe | 25% @ 100 μM | 6.3 ± 0.1 | 500 | 8.2 ± 0.1 | 6.3 | 130 (−10%) |
| 2 | KAF2039-1 | Gly | 60% @ 100 μM | <5.5 | | 6.17 ± 0.04 | 680 | −25% @ 100 μM |

TABLE 6-continued

Pharmacology of the macrocyclic AGRP-based peptides modified in the $Phe^7$ position $[Pro^1\text{-}Arg^2\text{-}Phe^3\text{-}Phe^4\text{-}Asn^5\text{-}Ala^6\text{-}Phe^7\text{-}DPro^8]$ (SEQ ID NO: 1).

| | | | Agonist mMC1R | Antagonist mMC3R | | Antagonist mMC4R | | Inverse Agonist mMC5R |
|---|---|---|---|---|---|---|---|---|
| Compound ID | KAF# | R7 | Agonist $EC_{50}$ (nM) | $pA_2$ | Antagonist $K_i$ (nM) | $pA_2$ | Antagonist $K_i$ (nM) | Inverse Agonist $EC_{50}$ (nM) |
| 3 | KAF2039-3 | Ser | 35% @ 100 μM | 6.0 ± 0.2 | 1,000 | 7.2 ± 0.2 | 63 | −55% @ 100 μM |
| 4 | KAF2039-4 | Lys | >100,000 | 5.7 ± 0.1 | 2,000 | 6.60 ± 0.06 | 250 | −40% @ 100 μM |
| 5 | KAF2039-5 | Asp | 40% @ 100 μM | <5.5 | | <5.5 | | −25% @ 100 μM |
| 6 | KAF2039-6 | Leu | >100,000 | <5.5 | | 7.03 ± 0.09 | 93 | −35% @ 100 μM |
| 7 | KAF2039-7 | Nle | >100,000 | 6.1 ± 0.1 | 790 | 8.4 ± 0.2 | 4.0 | −35% @ 100 μM |
| 8 | KAF2039-9 | Trp | partial agonist 1,100 ± 200 (50%) | 6.67 ± 0.07 | 210 | 8.2 ± 0.2 | 6.3 | 150 (−20%) |
| 9 | KAF2039-10 | Tyr | >100,000 | 6.23 ± 0.05 | 590 | 8.00 ± 0.06 | 10 | −40% @ 100 μM |
| 10 | KAF2039-11 | Cha | >100,000 | 5.8 ± 0.2 | 1,600 | 7.0 ± 0.03 | 100 | 780 (−20%) |
| 11 | KAF2039-13 | hPhe | >100,000 | 6.5 ± 0.3 | 320 | 7.30 ± 0.06 | 50 | 290 (−20%) |
| 12[b] | KAF3094 | Ala | >100,000 | 6.1 ± 0.2 | 790 | 8.2 ± 0.1 | 6.3 | −25% @ 100 μM |

Compounds were assayed in duplicate replicates and values are expressed as the mean ± the standard error of the mean (SEM) of at least 3 independent experiments.

"Partial agonist": partial agonist activity, with a maximal percent activated listed in parenthesis.

"X% @ 100 μM": Compounds that partially stimulated the receptor but were unable to generate a sigmoidal dose-response at 100 μM concentrations are listed by their percent activation at 100 μM.

">100,000": Compounds which showed no agonist activity at 100 μM are listed as >100,000.

">5.5": The use of <5.5 indicates that no antagonist potency was observed in the highest concentrationranged assayed (10,000, 5,000, 1,000, and 500 nM).

"X (−X%)": For compounds that displayed inverse agonist activity and appeared to generate a sigmoidal dose-response, the average apparent potency at the inflection point and maximal decrease in basal activity at the plateau is listed.

"−X% @ 100 μM": For all other compounds with inverse agonist activity, the percent decrease observed in receptor activity compared to basal at 100 μM is provided.

The $pA_2$ values were determined using the Schild analysis with agonist NDP-MSH ($pA_2 = -\log[K_i]$).

[a]This peptide has been previously described in Wilczynski, et al (2004) J. Med. Chem. 47, 2194-2207.

[b]These peptides were described in Ericson, et al (2017) J. Med. Chem. 60, 8103-8114.

Example 3, Cited Documents

1. Chhajlani, et al. (1993) Biochem. Biophys. Res. Commun. 195, 866-873.
2. Chhajlani, et al. (1992) FEBS Lett. 309, 417-420.
3. Gantz, et al. (1993) J. Biol. Chem. 268, 8246-8250.
4. Gantz, et al. (1993) J. Biol. Chem. 268, 15174-15179.
5. Gantz, et al. (1994) Biochem. Biophys. Res. Commun. 200, 1214-1220.
6. Griffon, et al. (1994) Biochem. Biophys. Res. Commun. 200, 1007-1014.
7. Mountjoy, et al. (1992) Science. 257, 1248-1251.
8. Roselli-Rehfuss, et al. (1993) Proc. Natl. Acad. Sci. 90, 8856-8860.
9. Lerner, et al. (1961) Nature. 189, 176-179.
10. Chen, et al. (2000) Nat. Genet. 26, 97-102.
11. Fan, et al. (1997) Nature. 385, 165-168.
12. Huszar, et al. (1997) Cell. 88, 131-141.
13. Butler, et al. (2000) Endocrinology. 141, 3518-3521.
14. Irani, et al. (2011) Eur. J. Pharmacol. 660, 80-87.
15. Nakanishi, et al. (1979) Nature. 278, 423-427.
16. Eipper, et al. (1980) Endocr. Rev. 1, 1-27.
17. Smith, et al. (1988) Endocr. Rev. 9, 159-179.
18. Bultman, et al. (1992) Cell. 71, 1195-1204.
19. Ollmann, et al. (1997) Science. 278, 135-138.
20. Blanchard, et al. (1995) Biochemistry. 34, 10406-10411.
21. Fong, et al. (1997) Biochem. Biophys. Res. Commun. 237, 629-631.
22. Miller, et al. (1993) Genes Dev. 7, 454-467.
23. Rowland, et al. (2010) Peptides. 31, 2314-2317.
24. Farooqi, et al. (2003) N. Engl. J. Med. 348, 1085-1095.
25. Krude, et al. (1998) Nat. Genet. 19, 155-157.
26. Yaswen, et al. (1999) Nat. Med. 5, 1066-1070.
27. Ericson, et al. (2017) Biochim. Biophys. Acta, Mol. Basis Dis. 1863, 2414-2435.
28. Graham, et al. (1997) Nat. Genet. 17, 273-274.
29. Ebihara, et al. (1999) in Leptin Action. Diabetes. 48, 2028-2033.
30. Kas, et al. (2003) Mol. Psychiatry. 8, 235-240.
31. Adan, et al. (2003) Ann. N.Y. Acad. Sci. 994, 267-274.
32. Vink, et al. (2001) Mol. Psychiatry. 6, 325-328.
33. Ge, et al. (2002) Brain Res. 957, 42-45.
34. Marks, et al. (2003) Endocrinology. 144, 1513-1523.
35. Marks, et al. (2001) Cancer Res. 61, 1432-1438.
36. Haskell-Luevano, et al. (2001) Regul. Pept. 99, 1-7.
37. Nijenhuis, et al. (2001) Mol. Endocrinol. 15, 164-171.
38. Lu, et al. (1994) Nature. 371, 799-802.
39. McNulty, et al. (2005) J. Mol. Biol. 346, 1059-1070.
40. Kiefer, et al. (1998) Biochemistry. 37, 991-997.
41. Yang, et al. (1999) J. Biol. Chem. 274, 14100-14106.
42. Yang, et al. (1999) Mol. Endocrinol. 13, 148-155.
43. Chai, et al. (2003) Peptides. 24, 603-609.
44. Haskell-CLuevano, et al. (2000) Peptides. 21, 683-689.
45. Patel, et al. (2010) J. Mol. Biol. 404, 45-55.
46. Ericson, et al. (2015) J. Med. Chem. 58, 4638-4647.
47. Tota, et al. (1999) Biochemistry. 38, 897-904.
48. Wilczynski, et al. (2004) J. Med. Chem. 47, 2194-2207.
49. McNulty, et al. (2001) Biochemistry. 40, 15520-15527.
50. Bolin, et al. (1999) FEBS Lett. 451, 125-131.
51. Jackson, et al. (2002) Biochemistry. 41, 7565-7572.
52. Spath, et al. (1998) Helv. Chim. Acta. 81, 1726-1738.
53. Favre, et al. (1999) J. Am. Chem. Soc. 121, 2679-2685.
54. Jiang, et al. (2000) Helv. Chim. Acta. 83, 3097-3112.
55. Robinson, et al. (2008) Acc. Chem. Res. 41, 1278-1288.
56. Ericson, et al. (2017) J. Med. Chem. 60, 8103-8114.
57. Carpino, et al. (1970) J. Am. Chem. Soc. 92, 5748-5749.
58. Carpino, et al. (1972) J. Org. Chem. 37, 3404-3409.
59. Singh, et al. (2015) ACS Med. Chem. Lett. 6, 568-572.
60. Ericson, et al. (2015) Bioorg. Med. Chem. Lett. 25, 5306-5308.
61. Lensing, et al. (2016) J. Med. Chem. 59, 3112-3128.
62. Schild, et al. (1997) Br. J. Pharmacol. Chemother. 120, 29-46.
63. Adank, et al. (2017) ACS Chem. Neurosci.
64. Christensen, et al. (1979) Acta Chem. Scand., Ser. B. 33, 763-766.

65. Lensing, et al. (2016) ACS Chem. Neurosci. 7, 1283-1291.
66. Le Naour, et al. (2012) J. Med. Chem. 55, 670-677.
67. Lunzer, et al. (2007) J. Pharmacol. Exp. Ther. 322, 166-171.
68. Hylden, et al. (1980) Eur. J. Pharmacol. 67, 313-316.

Example 4. Synergistic Multi-Residue Substitutions of a Macrocyclic c[Pro-Arg-Phe-Phe-Asn-Ala-Phe-DPro] (SEQ ID NO: 1) Agouti-Related Protein (AGRP) Scaffold Yield Potent and S600-Fold MC4R Versus MC3R Selective Melanocortin Receptor Antagonists Abstract Antagonist ligands of the melanocortin-3 and -4 receptors (MC3R, MC4R), including agouti-related protein (AGRP), are postulated to be targets for the treatment of diseases of negative energy balance. Previous studies reported the macrocyclic MC3R/MC4R antagonist c[Pro$^1$-Arg$^2$-Phe$^3$-Phe$^4$-Asn$^5$-Ala$^6$-Phe$^7$-DPro$^8$] (SEQ ID NO: 1), which is 250-fold less potent at the mouse (m) mMC3R and 3-fold less potent at the mMC4R than AGRP. Previous studies explored the structure-activity relationships around individual positions in this template. Herein, a multiresidue substitution strategy is utilized, combining the core scaffold (SEQ ID NO: 1) with hPhe$^4$, Dap$^5$, Arg$^5$, Ser$^6$, and Nle$^7$ substitutions. Two compounds from this study (16, 20) contain an hPhe$^4$/Ser$^6$/Nle$^7$ substitution pattern, are 3-6 fold more potent than AGRP at the mMC4R, and are 600-800 fold selective for the mMC4R over the mMC3R. Another compound (21), possessing the hPhe$^4$/Arg$^5$ substitutions, is only 5-fold less potent than AGRP at the mMC3R and is equipotent to AGRP at the mMC4R.

Introduction

There have been five G protein-coupled melanocortin receptors (GPCRs, MC1-5R)[1-8] discovered to date. Following stimulation by agonist ligands, these receptors couple to stimulatory G-proteins (producing an increase in intracellular cyclic AMP [cAMP]) and to β-Arrestin (resulting in receptor internalization).[9-11] Naturally occurring agonists for these receptors, produced after posttranslational processing of the proopiomelanocortin (POMC) gene transcript, include the adrenocorticotropic hormone (ACTH) and the α-, β-, and γ-melanocyte stimulating hormones (MSHs).[12-14] Endogenous antagonists for this receptor include agouti signaling protein (ASP) and agouti-related protein (AGRP).[15-19] Many components of the melanocortin system have been found to play roles in energy homeostasis, including the MC3R,[20-23] MC4R,[24-26] POMC-derived agonists,[27-28] ASP,[24] and AGRP.[16] There have been numerous peptide and small molecule melanocortin ligands discovered to date, as reviewed by Ericson et al.[29] Agonist ligands for these receptors have made attractive targets for diseases like metabolic syndrome, while antagonist ligands are postulated to be treatments for diseases of negative energy balance due to their ability to increase food intake.[29-35]

In rat models of anorexia, self-starvation can be induced by restriction of food in the presence of running wheels.[30] It has been proposed that insufficient central melanocortin receptor suppression may be the cause of this phenotype, which can be alleviated by central administration of AGRP.[30-31] In transgenic mouse models, mice overexpressing AGRP weigh more than wild type control mice.[36] Additionally, administration of AGRP increases food intake in mice.[22,37-38] It has been thought that melanocortin receptor antagonist ligands may be viable therapeutics for the treatment of diseases in which an increase in food intake is desired, such as anorexia nervosa, cachexia, and failure to thrive in children.[30-34]

Studies using recombinant human (h)AGRP demonstrated that AGRP is an antagonist of the endogenous agonist α-MSH at the hMC3R and hMC4R, and does not have antagonist activity at the hMC1R.[16,18] At the constitutively active hMC4R and at a mutated mouse (m)MC4R that is constitutively active, the active C-terminal domain of AGRP [AGRP(83-132)] has been reported to possess inverse agonist activity.[39-40] The active loop of AGRP possesses the sequence c[Cys-Arg-Phe-Phe-Asn-Ala-Phe-Cys] (SEQ ID NO: 139), containing the hypothesized Arg-Phe-Phe tripeptide antagonist sequence. Structure-activity relationship (SAR) studies have investigated this core scaffold.[41-45] Notably, the decapeptide containing the active loop sequence H-Tyr-c[Cys-Arg-Phe-Phe-Asn-Ala-Phe-Cys]-Tyr-OH (SEQ ID NO: 142) (AGRP[109-118]) is a micromolar agonist at the MC1R ($EC_{50}$=3 μM), and does not possess quantifiable antagonist potency at the mMC3R at up to 10 μM concentrations.[46] However, Schild analysis of antagonist potency has indicated that AGRP(109-118) possesses submicromolar antagonist potency at the MC4R.[46-47] Many subsequent studies have observed similar melanocortin receptor pharmacology, including agonist activity at the mMC1R, micromolar potency at the mMC3R, and a range of potencies at the mMC4R (generally ranging from micromolar to nanomolar).[41-43]

NMR structural studies performed on AGRP have demonstrated that the active loop sequence of AGRP forms a 3-hairpin, stabilized by five disulfide bonds.[48-50] In macrocyclic peptides, it has been previously established that heterochiral proline residues can induce a β-hairpin turn conformation.[51-54] This rationale led to the development of the macrocyclic octapeptide c[Pro$^1$-Arg$^2$-Phe$^3$-Phe$^4$-Asn$^5$-Ala$^6$-Phe$^7$-DPro$^8$] (SEQ ID NO: 1), containing the active loop sequence of AGRP cyclized through a DPro-Pro motif rather than through a disulfide bond via the endogenous Cys residues. This motif was hypothesized to better allow the macrocycle to adopt a β-hairpin loop structure,[41] allowing it to better recapitulate the structure observed in the full-length hormone of the naturally occurring tripeptide antagonist sequence, and therefore increase potency. In comparison to the decapeptide discussed above, which possesses a $pA_2$ at the mMC4R of 6.8, this macrocyclic octapeptide (peptide 1 in this study) possesses a $pA_2$ of 7.7-8.1, depending on the cAMP assay utilized.[41,46] Although peptide 1 possessed increased potency compared to the disulfide cyclized peptide at the mMC4R, it still does not match the potency of the native hormone AGRP ($pA_2$=8.7-9.1).[42] Therefore, the SAR around this octapeptide scaffold has been explored in order to generate more potent and/or selective MC4R antagonists.[41-43] These SAR analyses have been performed on the Phe$^3$, Phe$^4$, Asn$^5$, Ala$^6$, and Phe$^7$ positions. The results of these studies at the mMC4R are summarized in FIG. 17.[41-43] One substitution in the Phe$^4$ position (hPhe$^4$) possessed increased potency compared to the core scaffold at the mMC4R.[41] Numerous substitutions were found to increase potency at the Asn$^5$ position.[41-42] One substitution at the Ala$^6$ position (Ser$^6$) was found to be equipotent to the core scaffold.[42] Two types of amino acids maintained MC4R antagonist potency at the Phe$^7$ position: aromatic (Trp$^7$, Tyr$^7$), and linear aliphatic (Ala$^7$, Nle$^7$).[42-43] In particular, it was noted that peptides possessing linear aliphatic amino acids in the 7 position displayed increased selectivity for the mMC4R over the mMC3R compared to the core scaffold.[43] While the mMC4R possesses a varied SAR based on the substitutions examined in these studies, with $pA_2$ values ranging from micromolar to nanomolar, most of these ligands possess micromolar antagonist activity at the mMC3R or no activity at all. Three substitutions examined possessed potency values of 7.0 or greater at the mMC3R. and these ligands possessed a $Gly^5$ substitution ($pA_2$=7.6), $Dab^5$ substitution ($pA_2$=7.0), and $Lys^5$ substitution ($pA_2$=7.0).[41] Some peptides examined in these studies have appeared to possess inverse agonist activity at the mMC5R, and contain a variety of substitutions to the $Asn^5$, $Ala^6$, and $Phe^7$ positions.[42-43]

Selective antagonist ligands for the mMC4R will make useful pharmacological probes, and can be used to understand the role of the melanocortin system in the etiology of diseases like anorexia, cachexia, and failure-to-thrive. Therefore, the development of potent and selective pharmacological probes is desired. Furthermore, selective mMC4R antagonist activity could potentially be desirable from a therapeutic perspective for certain patient populations. Mice deficient in the mMC3R have been shown to possess dysregulated fasted-related feeding behaviors such as food anticipatory activity, gorging, and motivational responses.[20,22,55-57] It is currently unknown if these behaviors in mice translate to behaviors in humans. It could be speculated that an mMC4R-selective antagonist may be a useful therapeutic for patients where an increase in food intake is desired, but the modulation of such MC3R-mediated feeding behaviors may be harmful and/or reduce patient compliance, such as in patients with anorexia. The current study expands upon previous reports by utilizing a multi-residue-substitution strategy in this core octapeptide macrocyclic template. By combining substitutions which increase mMC4R potency ($hPhe^4$, $Dap^5$, $Arg^5$), substitutions that are contained in ASP ($Arg^5$, $Ser^6$), and substitutions that increase selectivity for the mMC4R ($Nle^7$), it was hypothesized that the pharmacological properties of this peptide could be fine-tuned to generate potent and selective probes for the mMC4R.

Results

Peptide Synthesis and Characterization.

The peptides used in this study were synthesized with a semi-automated synthesizer using standard fluorenylmethoxycarbonyl (Fmoc) methodology.[58-59] The singly-substituted macrocyclic octapeptides that have been previously reported were resynthesized, characterized, and assayed for these studies.[41-43] The structures of the amino acids used are provided in FIGS. 18A-18B. The peptides reported herein were purified using semi-preparative reverse phase high-pressure liquid chromatography (RP-HPLC). The purity of the peptides was confirmed to be >95% via analytical RP-HPLC using two different solvent systems. The masses of the peptides were confirmed using matrix-assisted laser desorption ionization (MALDI) time of flight (TOF) mass spectrometry or electrospray ionization (ESI) time of flight (TOF) mass spectrometry (University of Minnesota LeClaire-Dow Instrumentation Facility).

Initially, compounds were assayed as agonists in HEK293 cells stably expressing the mMC1R, mMC3R, mMC4R, or mMC5R using the AlphaScreen cAMP Assay.[60-62] The results of these experiments for agonist activity at the mMC1R and inverse agonist activity at the mMC5R are summarized in Table 7. None of the library compounds possessed a greater than 20% agonist response at 100 μM concentrations at the mMC3R or mMC4R, so antagonist potencies were measured for these compounds. Competitive antagonist potencies of the macrocyclic peptides were measured using Schild analyses at the mMC3R and mMC4R with the synthetic, non-selective, potent melanocortin agonist NDP-MSH.[47] The results of these antagonist experiments at the mMC3R and mMC4R are summarized in Table 8. The fold-changes in potency discussed herein were calculated using the $K_i$ values derived from the Schild analysis [$pA_2=-\log(K_i)$].

Library Design.

In this study, individual substitutions to the macrocyclic octapeptide template were identified from previous reports.[41-43] The $hPhe^4$, $Ser^6$, and $Nle^7$ substitutions were chosen because of their decreased antagonist activity at the mMC3R while maintaining mMC4R antagonist potency.[41-43] The $Dap^5$ residue was chosen because it increased mMC4R antagonist potency ($Dap^5$).[41-42] Additionally, the $Arg^5$ and $Ser^6$ substitutions were chosen because these amino acids are present in the active loop of ASP, not AGRP, and it has been previously observed that the substitution of ASP active-loop residues into the AGRP-based macrocyclic template maintain mMC4R antagonist potency ($Arg^5$, $Ser^6$).[42] In the current study, it was hypothesized that combining multiple substitutions and perhaps a synergistic outcome of multiple substitutions would result in increased potency and selectivity at the mMC4R.

MC1R Activity.

Twenty-one of the 24 peptides examined in this study did not possess full agonist potency at the mMC1R. Of these peptides, seven possessed partial agonist activity wherein they did not stimulate the receptor up to 100% of NDP-MSH but were able to generate a sigmoidal dose response, five resulted in some agonist activity at 100 μM concentrations, and nine did not possess any agonist activity at up to 100 μM. The remaining three peptides resulted in full agonist activity at the mMC1R.

MC5R Activity.

Twenty-one of the 24 peptides examined in this study did not result in any receptor activation at up to 100 μM. Two peptides appeared to result in inverse agonist activity with an apparent sigmoidal dose-response, and one peptide resulted in some decrease in receptor activation at up to 100 μM relative to basal.

MC3R Activity.

All the peptides synthesized in these studies possessed antagonist activity at the mMC3R against agonist ligand NDP-MSH. One of these peptides possessed an antagonist $pA_2$ potency value between 5.5-6.0. Eleven of these peptides possessed an antagonist $pA_2$ potency value between 6.0-7.0. Eleven of these peptides possessed an antagonist $pA_2$ potency value between 7.0-8.0. One peptide possessed an antagonist $pA_2$ potency value of 8.0 or greater.

MC4R Activity.

All the peptides synthesized in these studies possessed antagonist activity at the mMC4R against agonist ligand NDP-MSH. Notably, none of the peptides synthesized and investigated as part of these studies possessed an antagonist $pA_2$ potency value of less than 8.0. Three of the peptides possessed an antagonist $pA_2$ potency value between 8.0-8.5. Nine of the peptides possessed an antagonist $pA_2$ potency value between 8.5-9.0. Nine of the peptides possessed an antagonist $pA_2$ potency value between 9.0-9.5. Three of the peptides possessed an antagonist $pA_2$ potency value of 9.5 or greater.

Discussion and Conclusions

MC1R Structure-Activity Relationship.

Many of these peptides possessed micromolar agonist activity at the mMC1R.[41-43] Most of the peptides that generated a sigmoidal dose-response and thus possessed quantifiable $EC_{50}$ values did not possess the $hPhe^4$ or $Arg^5$ substitutions. Generally, peptides possessing the $hPhe^4$ substitution did not possess agonist activity at the mMC1R at up to 100 μM concentrations (14, which possessed hPhe$^4$ in combination with Nle$^7$; 16, which possessed the hPhe$^4$, Ser$^6$, and Nle$^7$ substitutions; 22, which possessed the hPhe$^4$, Arg$^5$, and Nle$^7$ substitutions; 18, which possessed hPhe$^4$, Dap$^5$, and Nle$^7$ substitutions; and 20, which possessed hPhe$^4$, Dap$^5$, Ser$^6$, and Nle$^7$ substitutions). Two of the hPhe$^4$-substituted peptides resulted in partial MC1R activation between 20-30% at 100 μM concentrations (23, which possessed hPhe$^4$, Arg$^5$, and Ser$^6$ substitutions; and 21, which possessed hPhe$^4$ and Arg$^5$ substitutions), and three hPhe$^4$-substituted peptides produced an assay response between 30%-40% at 100 μM concentrations (13, possessing only the hPhe$^4$ substitution; 15, possessing the hPhe$^4$ and Ser$^6$ substitution; 19, possessing the hPhe$^4$, Dap$^5$, and Ser$^6$ substitutions). Two of the hPhe$^4$-substituted peptides were partial agonists: 17, possessing the hPhe$^4$ and Dap$^5$ substitutions ($EC_{50}$=580 nM, 70% receptor activation), and 24, which possessed the hPhe$^4$, Arg$^5$, Ser$^6$, and Nle$^7$ substitutions ($EC_{50}$=400 nM, 25% receptor activation).

MC5R Structure-Activity Relationship.

Some peptides derived from this macrocyclic template may result in some inverse agonist activity at the mMC5R.[42-43] In this library, inverse agonist activity was observed for three peptides. One of these compounds possessed the Nle$^7$-substitution (2), one of these possessed the Ser$^6$-substitution (3), and the last one possessed both the Ser$^6$ and Nle$^7$ substitutions (4). For the remainder of these peptides, inverse agonist activity was not observed at the mMC5R. Both the Nle$^7$-substituted peptide and the Ser$^6$-substituted peptide possess inverse agonist activity at the mMC5R.[42-43]

mMC3R Structure Activity Relationship.

Nearly all the compounds, except for 13 (the hPhe$^4$-substituted compound), were either approximately equipotent to or more potent than the compound 1 at the mMC3R. Notably, 6 compounds possessed increased potencies of greater than 10-fold at the mMC3R compared to 1. These compounds possessed the following substitutions: Arg$^5$ (9), Arg$^5$ and Nle$^7$ (10), or a combination of the hPhe$^4$ and Arg$^5$ substitution (21, 22, 23, and 24). Although by itself the hPhe$^4$-substitution reduced potency at the mMC3R 5-fold compared to 1, the macrocycles that possess this substitution combined with the Arg$^5$ substitution all possessed increased of potencies ranging from 16-fold to 47-fold. The combination of the hPhe$^4$ and Arg$^5$ substitutions appeared to result in a synergistic increase in mMC3R potency. The pharmacological results from combining these two substitutions were unexpected, as the singly-substituted hPhe$^4$ compound decreased mMC3R potency, and showed that the utilization of a multiresidue substitution strategy may lead to results that are counterintuitive to what may initially be speculated.

mMC4R Structure-Activity Relationship.

Nine peptides possessed 10-fold or greater increased potency at the mMC4R compared to 1. Many of these peptides possessed the Nle$^7$ substitution in combination with another substitution, including Dap$^5$, Ser$^6$, and Nle$^7$ (8), Arg$^5$ and Nle$^7$ (10), Arg$^5$, Ser$^6$, and Nle$^7$ (12), or hPhe$^4$, Ser$^6$, and Nle$^7$ (16). Neither the Nle$^7$ or Ser$^6$ individual (2 or 3) substitutions or the Nle$^7$/Ser$^6$ combination (4) increased potency greater than 10-fold. This Ser$^6$/Nle$^7$ motif appeared to have worked best when combined with other substitutions to synergistically result in at least a 10-fold increase in mMC4R activity compared to 1.

mMC4R Selectivity Structure-Activity Relationship.

Many of the individual substitutions were selected for their ability to potentiate selectivity for the mMC4R over the mMC3R. The structure-activity relationship of these compounds at the mMC3R and mMC4R can be found in FIGS. 19A-19E. Interestingly, one of the peptides in this study displayed a 7-fold decrease in mMC4R selectivity compared to 1. This peptide was 21, which possessed hPhe$^4$ and Arg$^5$ substitutions. The dose response curves of this compound at the mMC3R and mMC4R can be observed in FIG. 20. This peptide possessed the highest fold-increase in potency at the mMC3R (47-fold) and a 6-fold increase in potency at the mMC4R. As a result, it was 8-fold selective for the mMC4R over the mMC3R. It also possessed nanomolar antagonist potency at the mMC3R, which is unusual for peptides of this scaffold, as peptides containing the DPro-Pro macrocyclic scaffold used in this study have decreased mMC4R selectivity via maintaining micromolar antagonist activity at the mMC3R and possessing a decreased potency at the mMC4R compared to the core scaffold.[41-43] Instead, this peptide possessed $pA_2$ values of 8.0±0.3 and 8.9±0.3 at the mMC3R and mMC4R respectively. Additionally, this peptide nearly recapitulated the antagonist pharmacology observed in AGRP (despite its reduced size), which has previously been reported to possess $pA_2$ of 8.7 at both the mMC3R and mMC4R.[42] This indicates a promising direction in the development of peptides utilizing this scaffold that possess the same antagonist potency at both the MC3R and MC4R as the native hormone, despite the size difference between the C-terminal domain of AGRP and the 8-residue macrocycle.

Previous studies using a β-galactosidase reporter gene assay (compared to the cAMP accumulation assay utilized in this study) discovered that the hPhe$^4$-substituted peptide did not possess antagonist activity at the mMC3R and was 5-fold less potent than 1 at the mMC4R, therefore making it selective for the mMC4R.[41] Other reports, using the same assay as this study, found that the Nle$^7$-substituted peptide increased selectivity for the mMC4R over the mMC3R (albeit to a lesser extent than the hPhe$^4$-substituted peptide) while maintaining mMC4R antagonist potency.[43] In the present study, the hPhe$^4$-substituted peptide (13) possessed antagonist potency at the mMC3R ($pA_2$=5.6±0.2) and was equipotent to the core peptide scaffold at the mMC4R, making it approximately 500-fold selective for the mMC4R over the mMC3R. Overall, peptides that possessed the hPhe$^4$-substitution were more selective for the mMC4R over the mMC3R (excluding peptides that possessed both hPhe$^4$ and Arg$^5$ substitutions, which increased mMC3R antagonist potency, as discussed above). Interestingly, although hPhe$^4$ and Nle$^7$ substitutions were chosen due to their ability to increase mMC4R selectivity, the peptide that possessed both the hPhe$^4$ and Nle$^7$ substitution (14) resulted in decreased selectivity for the mMC4R as compared to the hPhe$^4$ substitution alone (13). Notably, this trend did not remain throughout the set of peptides, as the most selective peptides in this study possessed the combination of the two substitutions, including hPhe$^4$/Ser$^6$/Nle$^7$ (16, 800-fold more potent at the mMC4R than the mMC3R) and hPhe$^4$/Dap$^5$/Ser$^6$/Nle$^7$ (20, 600-fold more potent at the mMC4R than the mMC3R). The dose response curves of these two compounds are provided in FIG. 21. These peptides differed in the amino acid side chain at the 5 position (Asn for 16, and Dap for 20). The Dap$^5$ substitution increased potency at the mMC4R compared to the Asn$^5$ substitution. The peptide 16 was 13-fold more potent than the core scaffold compound at the mMC4R, and 20 was 25-fold more potent than the core scaffold compound at the mMC4R. Other than the peptides discussed above, three other peptides possessed >200-fold selectivity for the MC4R over the MC3R. The substitution pattern in these peptides were: Dap$^5$/Ser$^6$/Nle$^7$ (8, 430-fold selectivity), $Arg^5/Ser^6/Nle^7$ (12, 320-fold selectivity), and $hPhe^4/Dap^5/Nle^7$ (18, 250-fold selective). As discussed above, while the $Ser^6/Nle^7$ motif did not increase selectivity, the combination of this motif with many other substitutions utilized in this study resulted in a synergistic increase in selectivity compared to the individual substitutions alone. The exception to this is the combination of the $Ser^6/Nle^7$ motif with the $hPhe^4/Arg^5$ motif (24), which possessed a reduced selectivity for the mMC4R. This may be expected, given that the $hPhe^4/Arg^5$ motif resulted in a synergistic 47-fold increase in mMC3R potency, and therefore resulted in a reduced MC4R selectivity.

In conclusion, this study utilized a multiresidue substitution strategy to test the hypothesis that the pharmacological properties possessed by singly-substituted macrocyclic AGRP mimetics could be combined and amplified in order to generate ligands with increased potency and/or selectivity for the mMC4R over the mMC3R. Herein, it was found that peptides containing the $Ser^6/Nle^7$ motif, in combination with the $hPhe^4$ and/or $Dap^5$ substitutions, possessed increased potency at the mMC4R. It was also found that this $Ser^6/Nle^7$ motif appeared to work synergistically to generate peptides with enhanced selectivity for the mMC4R over the mMC3R, especially when used in combination with substitutions like $hPhe^4$, $Asn^5$, or $Dap^5$. Unexpectedly, one of the motifs examined in this study ($hPhe^4/Arg^5$) resulted in a synergistic increase in mMC3R potency, despite the $hPhe^4$-substituted peptide possessing the lowest $pA_2$ value at the mMC3R of all the peptides examined in this study (13, $pA_2$=5.6). As discussed above, peptides possessing the $Arg^5$ substitution largely increased mMC3R potency and thus decreased mMC4R selectivity, especially when used in combination with the $hPhe^4$ substitution.

This study produced three ligands with interesting pharmacological profiles. One of these ligands, 16 (containing $hPhe^4$, $Ser^6$, and $Nle^7$ substitutions), did not result in mMC1R stimulation, had a $pA_2$ of 6.33 at the mMC3R, had a $pA_2$ of 9.23 at the mMC4R, did not result in mMC5R stimulation, and was 800-fold selective for the mMC4R over the mMC3R. Another of these ligands, 20 (containing $hPhe^4$, $Dap^5$, $Ser^6$, and $Nle^7$ substitutions), did not result in mMC1R stimulation, had a $pA_2$ of 6.7 at the mMC3R had a $pA_2$ of 9.5 at the mMC4R, did not result in mMC5R stimulation, and was 630-fold selective for the mMC4R over the mMC3R. While this ligand was less selective for the mMC4R than 16, it was also more potent at the mMC4R than 16. The peptide 20 possesses potency greater than that of AGRP at the mMC4R ($pA_2$=8.7) and another antagonist ligand in the field, SHU9119 ($pA_2$=−9.2) in the cAMP assay used in the present study.[42,63] Finally, 21 (containing $hPhe^4$ and $Arg^5$ substitutions), resulted in 25% receptor stimulation at the mMC1R, had a $pA_2$ of 8.0 at the mMC3R, had a $pA_2$ of 8.9 at the mMC4R, and did not result in mMC5R stimulation. The octapeptide 21 possessed nearly equipotent antagonist activity to the active form of the native hormone AGRP at both receptors ($pA_2$ of AGRP at the mMC3R and mMC4R=8.7), and represents a promising start for the generation of dual antagonist ligands that are equipotent at both the mMC3R and mMC4R compared to AGRP.[42]

These three peptides possess dual antagonist pharmacology or selective antagonist pharmacology for the mMC3R and mMC4R. Importantly, they possess the same core scaffold, which will allow them to serve as more ideal candidate probes for future comparative in vivo studies as they should theoretically possess more similar pharmacokinetic properties than, for example, 20 (an octapeptide) as compared to AGRP (a 50-residue protein in the active form). Herein, three macrocyclic octapeptides were discovered using a multiresidue substitution strategy that will make useful pharmacological probes for understanding the role of the melanocortin system in diseases of negative energy balance such as anorexia, cachexia, and failure to thrive in children.

Experimental Section

Peptide Synthesis.

The peptides investigated in this study were synthesized using flourenyl-9-methoxycarbonyl (Fmoc) chemistry using a H-Pro-CTC Resin (0.67 meqiv/g substitution) purchased from Peptides International (Louisville, Ky.).[58-59] The amino acids Fmoc-DPro, Fmoc-Phe, Fmoc-Nle, Fmoc-Ser(tBu), Fmoc-Ala, Fmoc-Asn(Trt), Fmoc-Dap(Boc), and Fmoc-Arg(Pbf) were purchased from Peptides International (Louisville, Ky.). The amino acid Fmoc-homophenylalanine (Fmoc-hPhe) was purchased from Synthetech (Albany, Oreg.). The coupling reagents used in this study, O-benzotriazol-1-yl-N,N,N',N'-tetramethyluronium hexafluorophosphate (HBTU), (benzotriazolyloxy)tris(dimethylamino) phosphonium hexafluorophosphate (BOP), and 1-hydroxybenzotriazole (HOBt), were purchased from Peptides International (Louisville, Ky.). The solvents N,N-dimethylformamide (DMF), anhydrous ethyl ether, dichloromethane (DCM), methanol, and acetonitrile were purchased from Fisher (Fair Lawn, N.J.). Trifluoroacetic acid (TFA), piperidine, dimethyl sulfoxide (DMSO), N—N-diisopropylethylamine (DIEA) and triisopropylsilane (TIS) were purchased from Sigma-Aldrich (St. Louis, Mo.). All reagents were ACS grade or better, and were used without purification.

The peptides investigated in this study were synthesized in parallel using a semi-automated synthesizer (LabTech 1, Advanced Chemtech, Louisville, Ky.) at a 0.05 mmol scale on a H-Pro-CTC-resin. The H-Pro-CTC-resin was swelled in dimethylformamide (DMF) for at least one hour prior to the first coupling. The amino acid in the 8 position ($DPro^8$) and subsequent amino acids were coupled using the semi-automated synthesizer in a 40-well Teflon reaction block. For natural amino acids the following coupling conditions were used: Fmoc protected amino acid (3.1 eqiv), HBTU (3 equiv), and DIEA (5 equiv) were added, and the solution was agitated for 1 hour. For unnatural amino acids (e.g. DPro. Nle, Dap), the following coupling conditions were used: Fmoc protected amino acid (1.56 equiv), HBTU (1.5 equiv), HOBt (1.5 equiv), and DIEA (2.5 equiv) were added, and the solution was agitated for 1 hour. All amino acids were coupled using a double-couple strategy, so each well was rinsed with DMF and then the coupling procedure was repeated. The amino acids were Fmoc-deprotected with 20% piperidine in DMF (1×2 min, 1×20 min). Coupling and deprotection completeness was monitored via colorimetric assays, and the procedures repeated if necessary. A chloranil test was used to test for the presence of free secondary amines.[64] A Kaiser test was used to test for the presence of free primary amines.[65] Following synthesis, the N-terminal Fmoc amines were deprotected with 20% piperidiene in DMF (4 mL/well, 1×2 min, 1×20 min) and dried in vacuo after washing with methanol.

Peptides were cleaved from solid support using a cleavage cocktail composed of 1% trifluoroacetic acid (TFA) in dichloromethane (DCM). The peptides were washed three times with 2 mL of cleavage solution for 2 minutes. The peptide solutions were concentrated using nitrogen, precipitated with cold ether and pelleted via centrifugation (4,000 rpm at 4° C. for 4 minutes, ThermoScientific Sorvall Legend XTR). The supernatant was decanted, and the peptides were then dried in vacuo. For the coupling of the C-terminus ($Pro^1$) to the N-terminus ($Arg^2$) to create the macrocycles, the peptides were dissolved in DCM to a concentration of approximately 0.5 mM, and cyclized using BOP (3 equiv), HOBt (3 equiv), and DIEA (6 equiv), stirring the solution overnight at room temperature. The peptides were dried under reduced pressure for a minimum of 1 hour, and 5 mL of a deprotection solution composed of 95:2.5:2.5 TFA:$H_2O$:TIS were added at room temperature for 2 hours. The peptides were then concentrated using nitrogen and precipitated with cold ether. Peptides were pelleted via centrifugation at 4,000 rpm at 4° C. for 4 minutes, and the supernatant was decanted. The final products were dried in vacuo.

Peptides were purified via reverse phase high pressure liquid chromatography (RP-HPLC, Shimadzu) on a semi-preparative Cis column (Vydac 218TP1010, 1 cm×25 cm) using acetonitrile and 0.1% TFA in $H_2O$. Analytical data was then collected using an analytical Cis column (Vydac 218TP, 4.6 mm×250 mm) on a Shimadzu chromatography system equipped with a photodiode array detector in two different solvent systems: acetonitrile/0.1% TFA in $H_2O$, and methanol/0.1% TFA in $H_2O$ to confirm purity >95%. The peptide purity was determined by HPLC at a wavelength of 214 nm. The molecular weights of 1 through 8 were then confirmed using matrix-assisted laser desorption ionization (MALDI) and time of flight (TOF) mass spectrometry analysis (AB-Sciex 5800 MALDI/TOF-MS, LeClaire-Dow Instrumentation Facility, University of Minnesota), using a cyano-4-hydroxycinnamic acid (CCA) matrix. The molecular weights of remaining peptides were confirmed using electrospray ionization (ESI) time of flight (TOF) mass spectrometry (University of Minnesota LeClaire-Dow Instrumentation Facility). Peptides were assayed as TFA salts and not corrected for peptide content.

AlphaScreen™ cAMP Functional Assay.

The functional cAMP potencies of peptides at HEK293 cells stably expressing the individual melanocortin receptors (mMC1R, mMC3R, mMC4R, and mMC5R) were measured using the AlphaScreen™ cAMP assay (PerkinElmer Life Sciences, Cat #6760625M). The assay was performed according to manufacturer instructions, and as previously described.[60-62]

Cells were approximately 90% confluent at the start of the assay. Growth medium was aspirated, and cells were rinsed with 1 mL Gibco® Versene solution, then 1 mL fresh Versene solution was added. Cells were incubated at 37° C. until cells had detached from the plate, then pelleted via centrifugation (800 rpm, 5 minutes; Sorvall™ Legend™ XTR centrifuge, swinging bucket rotor). The medium was aspirated, and the cell pellet was resuspended a second time in Dulbecco's phosphate buffered saline solution (DPBS 1× [-] without calcium and magnesium chloride. Gibco 9 Cat #14190-144). A 10 μL aliquot of each cell line was removed for counting, during which the remaining cells were centrifuged a second time as described above. Cells were counted by adding 10 μL Trypan blue dye (BioRad) and counted manually using a hemocytometer. After centrifugation, the DPBS was aspirated and the pellet was resuspended in a solution of freshly-made stimulation buffer [Hank's Balanced Salt Solution (HBSS 10× (-) sodium bicarbonate) and (-) phenol red, Gibco®), 0.5 mM isobutylmethylxanthine (IBMX), 5 mM HEPES buffer solution (1M, Gibco®), 0.1% bovine serum albumin (BSA) in Milli-Q water, pH=7.4] to a concentration of 10,000 cells per μL. An acceptor bead solution was created by diluting the acceptor bead stock solution (5 mg/mL anti-cAMP acceptor beads in stimulation buffer) to a concentration of 0.1 mg/mL in stimulation buffer. The acceptor bead solution was added to the cells such that there were 0.5 μg anti-cAMP acceptor beads in each cell line.

Next, 10 μL of the cell/acceptor bead solution per well was added to an Opti-384 plate using a 16 channel pipettor. To each well 5 μL of compound was added. Compounds were run in duplicate replicates, and each cell line had a positive control ($10^{-4}$ M forskolin) and negative control (plain stimulation buffer). The 384-well plate was sealed with a cover slip, covered with aluminum foil, and incubated at room temperature in a dark desk drawer for 2 hours. A biotinylated cAMP/streptavidin-coated donor bead working solution was prepared by diluting the stock solution of donor beads (5 mg/mL) and cAMP biotinylated tracer (1 μL with 1×PBS 14190-144) in a freshly prepared lysis buffer [10% Tween-20, 5 mM HEPES buffer solution (1M, Gibco®), 0.1% bovine serum albumin (BSA) in Milli-Q water, pH=7.4] such that the final solution contained 0.5 μg of donor beads and 0.62 μmol biotinylated cAMP. This donor bead biotinylated cAMP solution was allowed to incubate in a dark desk drawer at room temperature for a minimum of 30 minutes.

After the incubation period for the cells/acceptor beads/compound solution was completed, 10 μL of the donor bead/biotinylated cAMP mixture was added to each well in a room containing a green light using a multichannel pipettor, mixing well. The plate was then re-sealed with the cover slip, covered in aluminum foil, and allowed to incubate in a dark desk drawer at room temperature for another 2 hours. Following the second incubation period, the plate was read by an Enspire™ Alpha plate reader using a pre-normalized assay protocol set by the manufacturer. Assays were run in duplicate wells in at least three independent experiments.

Cell Data Analysis.

The data collected were analyzed using PRISM software (v4.0, GraphPad Inc.). Agonist potency was evaluated by calculating the $EC_{50}$ values using non-linear regression analysis with the PRISM software. Antagonist potency was determined using a Schild analysis [$pA_2=-\log(K_i)$] and the agonist ligand NDP-MSH.[47] Because this assay is loss-of-function mMC3R, and mMC4R data were normalized to represent a percent response relative to control ligand (NDP-MSH) for illustrations, as has been reported previously.[60-62] Inverse agonist activity for the mMC5R was calculated by normalizing signal to a basal response, thus yielding a percent difference from basal activity.

Abbreviations

ACTH, adrenocorticotropin hormone; Fmoc, 9-fluorenylmethoxycarbonyl; AGRP, agouti-related protein; GPCR, G-protein coupled receptor; cAMP, cyclic 5'-adenosine monophosphate; MC1R, melanocortin-1 receptor; MC2R, melanocortin-2 receptor; MC3R, melanocortin-3 receptor; MC4R, melanocortin-4 receptor; MC5R, melanocortin-5 receptor; MSH, melanocyte stimulating hormone; POMC, proopiomelanocortin; α-MSH, alpha-melanocyte stimulating hormone; β-MSH, beta-melanocyte stimulating hormone; γ-MSH, gamma-melanocyte stimulating hormone; μM, micromolar; NDP-MSH (4-Norleucine-7-D-Phenylalanine), Ac-Ser-Tyr-Ser-Nle-Glu-His-DPhe-Arg-Trp-Gly-Lys-Pro-Val-$NH_2$ (SEQ ID NO: 136); Nle, norleucine; Dap, diaminopropionic acid; hPhe, homophenylalanine;

RP-HPLC, reverse-phase high-pressure liquid chromatography; SAR, structure-activity relationships Example 4, Cited Documents 1. Chhajlani, et al. Biochem. Biophys. Res. Commun. 1993, 195, 866-873.
2. Chhajlani, et al. FEBS Lett. 1992, 309, 417-420.
3. Gantz, et al. J. Biol. Chem. 1993, 268, 8246-8250.
4. Gantz, et al. J. Biol. Chem. 1993, 268, 15174-15179.
5. Gantz, et al. Biochem. Biophys. Res. Commun. 1994, 200, 1214-1220.
6. Griffon, et al. Biochem. Biophys. Res. Commun. 1994, 200, 1007-1014.
7. Mountjoy, et al. Science 1992, 257, 1248-1251.
8. Roselli-Rehfuss, et al. Proc. Natl. Acad. Sci. 1993, 90, 8856-8860.
9. Shinyama, et al. Endocrinology 2003, 144, 1301-1314.
10. Kroeze, et al. Nature Structural & Molecular Biology 2015, 22, 362-369.
11. Cai, et al. J. Am. Chem. Soc. 2004, 126, 7160-7161.
12. Nakanishi, et al. Nature 1979, 278, 423-427.
13. Eipper, et al. Endocr. Rev. 1980, 1, 1-27.
14. Smith, et al. Endocr. Rev. 1988, 9, 159-179.
15. Bultman, et al. Cell 1992, 71, 1195-1204.
16. Ollmann, et al. Science 1997, 278, 135-138.
17. Blanchard, et al. Biochemistry 1995, 34, 10406-10411.
18. Fong, et al. Biochem. Biophys. Res. Commun. 1997, 237, 629-631.
19. Miller, et al. Genes Dev. 1993, 7, 454-467.
20. Butler, et al. Endocrinology 2000, 141, 3518-3521.
21. Chen, et al. Nat. Genet. 2000, 26, 97-102.
22. Irani, et al. Eur. J. Pharmacol. 2011, 660, 80-87.
23. Rowland, et al. Peptides 2010, 31, 2314-2317.
24. Fan, et al. Nature 1997, 385, 165-168.
25. Huszar, et al. Cell 1997, 88, 131-141.
26. Farooqi, et al. N. Engl. J. Med. 2003, 348, 1085-1095.
27. Krude, et al. Nat. Genet. 1998, 19, 155-157.
28. Yaswen, et al. Nat. Med. 1999, 5, 1066-1070.
29. Ericson, et al 1954. Biochim. Biophys. Acta, Mol. Basis Dis. 2017, 1863, 2414-2435.
30. Kas, et al. Mol. Psychiatry 2003, 8, 235-240.
31. Adan, et al. Ann. N.Y. Acad. Sci. 2003, 994, 267-274.
32. Ge, et al. Brain Res. 2002, 957, 42-45.
33. Marks, et al. Endocrinology 2003, 144, 1513-1523.
34. Marks, et al. Cancer Res. 2001, 61, 1432-1438.
35. Goncalves, et al. Trends in Pharmacological Sciences 2018, 39, 402-423.
36. Graham, et al. Nat. Genet. 1997, 17, 273-274.
37. Ebihara, et al, in Leptin Action. Diabetes 1999, 48, 2028-2033.
38. Adank, et al. ACS Chem. Neurosci. 2017, 9, 320-327.
39. Haskell-Luevano, et al. Regul. Pept. 2001, 99, 1-7.
40. Nijenhuis, et al. Mol. Endocrinol. 2001, 15, 164-171.
41. Ericson, et al. J. Med. Chem. 2015, 58, 4638-4647.
42. Ericson, et al. J. Med. Chem. 2017, 60, 8103-8114.
43. Fleming, et al. ACS Chem. Neurosci. 2018, 9, 1141-1151.
44. Tota, et al. Biochemistry 1999, 38, 897-904.
45. Wilczynski, et al. J. Med. Chem. 2004, 47, 2194-2207.
46. Haskell-CLuevano, et al. Peptides 2000, 21, 683-689.
47. Schild, et al. Br. J. Pharmacol. Chemother. 1947, 120, 29-46.
48. McNulty, et al. Biochemistry 2001, 40, 15520-15527.
49. Bolin, et al. FEBS Lett. 1999, 451, 125-131.
50. Jackson, et al. Biochemistry 2002, 41, 7565-7572.
51. Spath, et al. Helv. Chim. Acta 1998, 81, 1726-1738.
52. Favre, et al. J. Am. Chem. Soc. 1999, 121, 2679-2685.
53. Jiang, et al. Helv. Chim. Acta 2000, 83, 3097-3112.
54. Robinson, et al. Acc. Chem. Res. 2008, 41, 1278-1288.
55. Renquist, et al. PNAS 2012, 109, E1489-E1498.
56. Girardet, et al. Scientific Reports 2017, 7, 44444.
57. Mavrikaki, et al. Molecular Metabolism 2016, 5, 566-579.
58. Carpino, et al. J. Am. Chem. Soc. 1970, 92, 5748-5749.
59. Carpino, et al. J. Org. Chem. 1972, 37, 3404-3409.
60. Singh, et al. ACS Med. Chem. Lett. 2015, 6, 568-572.
61. Ericson, et al. Bioorg. Med. Chem. Lett. 2015, 25, 5306-5308.
62. Lensing, et al. J. Med. Chem. 2016, 59, 3112-3128.
63. Tala, et al. Bioorg. Med. Chem. Lett. 2015, 25, 5708-5711.
64. Christensen, et al. Acta Chem. Scand., Ser. B 1979, 33, 763-766.
65. Kaiser, et al. Anal. Biochem. 1970, 34, 595-598.

TABLE 7

Pharmacology of the macrocyclic AGRP-based peptides at the mMC1R and mMC5R.

| Compound ID | Sequence | Agonist mMC1R $EC_{50}$ (nM) | Inverse Agonist mMC5R $EC_{50}$ (nM) |
|---|---|---|---|
| NDP-MSH | Ac-Ser-Tyr-Ser-Nle-Glu-His-DPhe-Arg-Trp-Gly-Lys-Pro-Val-$NH_2$ (SEQ ID NO: 136) | 0.010 ± 0.001 | $EC_{50}$ = 0.14 ± 0.01 |
| 1* | c[Pro Arg Phe Phe Asn Ala Phe DPro] (SEQ ID NO: 1) | 2800 ± 600 (80%) | >100,000 |
| 2* | c[Pro Arg Phe Phe Asn Ala **Nle** DPro] (SEQ ID NO: 45) | 1700 ± 300 (50%) | 10 ± 6 (-20%) |
| 3* | c[Pro Arg Phe Phe Asn **Ser** Phe DPro] (SEQ ID NO: 22) | 1200 ± 300 | 6 ± 3 (-14%) |
| 4 | c[Pro Arg Phe Phe Asn **Ser** **Nle** DPro] (SEQ ID NO: 50) | 2600 ± 300 (75%) | -35% @ 100 μM |
| 5* | c[Pro Arg Phe Phe **Dap** Ala Phe DPro] (SEQ ID NO: 2) | 1600 ± 400 (80%) | >100,000 |
| 6 | c[Pro Arg Phe Phe **Dap** Ala **Nle** DPro] (SEQ ID NO: 51) | 190 ± 60 | >100,000 |
| 7 | c[Pro Arg Phe Phe **Dap** **Ser** Phe DPro] (SEQ ID NO: 52) | 600 ± 100 (85%) | >100,000 |
| 8 | c[Pro Arg Phe Phe **Dap** **Ser** **Nle** DPro] (SEQ ID NO: 53) | >100,000 | >100,000 |

TABLE 7-continued

Pharmacology of the macrocyclic AGRP-based peptides at the mMC1R and mMC5R.

| Compound ID | Sequence | Agonist mMC1R $EC_{50}$ (nM) | Inverse Agonist mMC5R $EC_{50}$ (nM) |
|---|---|---|---|
| 9* | c[Pro Arg Phe Phe **Arg** Ala Phe DPro] (SEQ ID NO: 54) | 600 ± 200 (25%) | >100,000 |
| 10 | c[Pro Arg Phe Phe **Arg** Ala **Nle** DPro] (SEQ ID NO: 55) | >100,000 | >100,000 |
| 11 | c[Pro Arg Phe Phe **Arg** **Ser** Phe DPro] (SEQ ID NO: 56) | >100,000 | >100,000 |
| 12 | c[Pro Arg Phe Phe **Arg** **Ser** **Nle** DPro] (SEQ ID NO: 57) | >100,000 | >100,000 |
| 13* | c[Pro Arg Phe **hPhe** Asn Ala Phe DPro] (SEQ ID NO: 3) | 35% @ 100 μM | >100,000 |
| 14 | c[Pro Arg Phe **hPhe** Asn Ala **Nle** DPro] (SEQ ID NO: 58) | >100,000 | >100,000 |
| 15 | c[Pro Arg Phe **hPhe** Asn **Ser** Phe DPro] (SEQ ID NO: 59) | 40% @ 100 μM | >100,000 |
| 16 | c[Pro Arg Phe **hPhe** Asn **Ser** **Nle** DPro] (SEQ ID NO: 60) | >100,000 | >100,000 |
| 17 | c[Pro Arg Phe **hPhe** **Dap** Ala Phe DPro] (SEQ ID NO: 61) | 560 ± 80 (70%) | >100,000 |
| 18 | c[Pro Arg Phe **hPhe** **Dap** Ala **Nle** DPro] (SEQ ID NO: 62) | >100,000 | >100,000 |
| 19 | c[Pro Arg Phe **hPhe** **Dap** **Ser** Phe DPro] (SEQ ID NO: 63) | 40% @ 100 μM | >100,000 |
| 20 | c[Pro Arg Phe **hPhe** **Dap** **Ser** **Nle** DPro] (SEQ ID NO: 64) | >100,000 | >100,000 |
| 21 | c[Pro Arg Phe **hPhe** **Arg** Ala Phe DPro] (SEQ ID NO: 65) | 25% @ 100 μM | >100,000 |
| 22 | c[Pro Arg Phe **hPhe** **Arg** Ala **Nle** DPro] (SEQ ID NO: 66) | >100,000 | >100,000 |
| 23 | c[Pro Arg Phe **hPhe** **Arg** **Ser** Phe DPro] (SEQ ID NO: 67) | 30% @ 100 μM | >100,000 |
| 24 | c[ Pro Arg Phe **hPhe** **Arg** **Ser** **Nle** DPro] (SEQ ID NO: 68) | 400 ± 200 | >100,000 |

Compounds were assayed in duplicate replicates and values are expressed as the mean ± the standard error of the mean (SEM) of at least 3 independent experiments. The use of "(X%)" indicates that the compound possessed partial agonist activity and was able to stimulate the receptor to a given percent. The use of "X% @ 100 μM" indicates that the compound partially stimulated the receptor to a given percent, but did not generate a sigmoidal dose-response at 100 μM. The use of ">100,000" indicates that the compound did not stimulate the receptor greater than 20% at 100 μM. For mMC5R inverse agonist studies, the use of "X (-X%)" indicates that the compound displayed inverse agonist efficacy of X% relative to basal and appeared to generate a sigmoidal dose-response of potency X. The use of "-X% @ 100 μM" indicates that the compound displayed inverse agonist efficacy of X% at 100 μM, but did not generate a sigmoidal dose-response at up to 100 μM concentrations.
*These singly substituted macrocyclic octapeptides, described in Ericson, et al. J. Med. Chem. 2015, 58, 4638-4647; Ericson, et al. J. Med. Chem. 2017, 60, 8103-8114; Fleming, et al. ACS Chem. Neurosci. 2018, 9, 1141-1151, were resynthesized, re-characterized, and re-assayed herein as controls.

TABLE 8

Pharmacology of the macrocyclic AGRP-based peptides at the mMC3R and mMC4R.

| Compound ID | Sequence | Antagonist mMC3R $pA_2$ | Antagonist mMC4R $pA_2$ |
|---|---|---|---|
| AGRP[a] | | 8.7 ± 0.1 | 8.7 ± 0.2 |
| SHU9119[a] | Ac-Nle-c[Asp-His-DNal(2')-Arg-Trp-Lys]-$NH_2$ (SEQ ID NO: 153) | 8.7 ± 0.3 (partial agonist) | 9.2 ± 0.1 |
| NDP-MSH | Ac-Ser-Tyr-Ser-Nle-Glu-His-DPhe-Arg-Trp-Gly-Lys-Pro-Val-$NH_2$ (SEQ ID NO: 136) | $EC_{50}$ = 0.09 ± 0.01 | $EC_{50}$ = 0.64 ± 0.06 |
| hAGRP[a] (109-118) | Tyr-c[Cys-Arg-Phe-Phe-Asn-Ala-Phe-Cys]-Tyr (SEQ ID NO: 156) | No activity (Agonist or Antagonist) | 6.8 ± 0.4 |
| 1* | c[Pro Arg Phe Phe Asn Ala Phe DPro] (SEQ ID NO: 1) | 6.3 ± 0.03 | 8.1 ± 0.2 |
| 2* | c[Pro Arg Phe Phe Asn Ala **Nle** DPro] (SEO ID NO: 45) | 6.6 ± 0.03 | 8.9 ± 0.1 |
| 3* | c[Pro Arg Phe Phe Asn **Ser** Phe DPro] (SEQ ID NO: 22) | 6.1 ± 0.3 | 8.1 ± 0.2 |
| 4 | c[Pro Arg Phe Phe Asn **Ser** **Nle** DPro] (SEQ ID NO: 50) | 6.6 ± 0.2 | 8.5 ± 0.2 |
| 5* | c[Pro Arg Phe Phe **Dap** Ala Phe DPro] (SEQ ID NO: 2) | 7.2 ± 0.1 | 8.9 ± 0.1 |

TABLE 8-continued

Pharmacology of the macrocyclic AGRP-based peptides at the mMC3R and mMC4R.

| Compound ID | Sequence | Antagonist mMC3R $pA_2$ | Antagonist mMC4R $pA_2$ |
|---|---|---|---|
| 6 | c[Pro Arg Phe Phe **Dap** Ala **Nle** DPro] (SEQ ID NO: 51) | 7.1 ± 0.2 | 9.0 ± 0.2 |
| 7 | c[Pro Arg Phe Phe **Dap** **Ser** Phe DPro] (SEQ ID NO: 52) | 6.8 ± 0.03 | 9.1 ± 0.1 |
| 8 | c[Pro Arg Phe Phe **Dap** **Ser** **Nle** DPro] (SEQ ID NO: 53) | 6.5 ± 0.1 | 9.1 ± 0.03 |
| 9* | c[Pro Arg Phe Phe **Arg** Ala Phe DPro] (SEQ ID NO: 54) | 7.4 ± 0.1 | 8.7 ± 0.1 |
| 10 | c[Pro Arg Phe Phe **Arg** Ala **Nle** DPro] (SEQ ID NO: 55) | 7.5 ± 0.1 | 9.1 ± 0.03 |
| 11 | c[Pro Arg Phe Phe **Arg** **Ser** Phe DPro] (SEQ ID NO: 56) | 7.1 ± 0.1 | 9.0 ± 0.1 |
| 12 | c[Pro Arg Phe Phe **Arg** **Ser** **Nle** DPro] (SEQ ID NO: 57) | 7.1 ± 0.03 | 9.6 ± 0.1 |
| 13* | c[Pro Arg Phe **hPhe** Asn Ala Phe DPro] (SEQ ID NO: 3) | 5.6 ± 0.02 | 8.3 ± 0.2 |
| 14 | c[Pro Arg Phe **hPhe** Asn Ala **Nle** DPro] (SEQ ID NO: 58) | 6.2 ± 0.06 | 8.6 ± 0.1 |
| 15 | c[Pro Arg Phe **hPhe** Asn **Ser** Phe DPro] (SEQ ID NO: 59) | 6.5 ± 0.2 | 8.6 ± 0.2 |
| 16 | c[Pro Arg Phe **hPhe** Asn **Ser** **Nle** DPro] (SEQ ID NO: 60) | 6.3 ± 0.1 | 9.2 ± 0.1 |
| 17 | c[Pro Arg Phe **hPhe** **Dap** Ala Phe DPro] (SEQ ID NO: 61) | 7.1 ± 0.2 | 9.1 ± 0.1 |
| 18 | c[Pro Arg Phe **hPhe** **Dap** Ala **Nle** DPro] (SEQ ID NO: 62) | 6.7 ± 0.1 | 9.1 ± 0.1 |
| 19 | c[Pro Arg Phe **hPhe** **Dap** **Ser** Phe DPro] (SEQ ID NO: 63) | 7.2 ± 0.03 | 9.2 ± 0.03 |
| 20 | c[Pro Arg Phe **hPhe** **Dap** **Ser** **Nle** DPro] (SEQ ID NO: 64) | 6.7 ± 0.2 | 9.5 ± 0.2 |
| 21 | c[Pro Arg Phe **hPhe** **Arg** Ala Phe DPro] (SEQ ID NO: 65) | 8.0 ± 0.3 | 8.9 ± 0.3 |
| 22 | c[Pro Arg Phe **hPhe** **Arg** Ala **Nle** DPro] (SEQ ID NO: 66) | 7.5 ± 0.1 | 8.8 ± 0.1 |
| 23 | c[Pro Arg Phe **hPhe** **Arg** **Ser** Phe DPro] (SEQ ID NO: 67) | 7.7 ± 0.1 | 8.8 ± 0.03 |
| 24 | c[Pro Arg Phe **hPhe** **Arg** **Ser** **Nle** DPro] (SEQ ID NO: 68) | 7.9 ± 0.1 | 9.5 ± 0.2 |

Compounds were assayed in duplicate replicates and values are expressed as the mean ± the standard error of the mean (SEM) of at least 3 independent experiments. The $pA_2$ values were determined using the Schild analysis with agonist NDP-MSH ($pA_2 = -\log[K_i]$).[47]

[a]Pharmacological data for these peptides have been previously published.[42, 46, 63] The data for hAGRP(109-118) is from a cAMP β-galactosidase reporter gene bioassay[46] and different from the ALPHA assay reported herein.

*These singly substituted macrocyclic octapeptides, described in Ericson, et al, J. Med, Chem, 2015, 58, 4638-4647; Ericson, et al. J. Med. Chem. 2017, 60, 8103-8114; Fleming, et al. ACS Chem. Neurosci. 2018, 9, 1141-1151, were resynthesized, re-characterized, and re-assayed herein as controls.

Example 5. Characterization of an Agouti-Related Protein Macrocyclic Peptide (c[Pro-Arg-Phe-Phe-Val-Ala-Phe-DPro] (SEQ ID NO: 14)) In Vitro Results in a 4000-Fold Selective (Allosteric Kir7.1 Versus G Protein) Human Melanocortin-4 Receptor (hMC4R) Signaling Ligand with Differential Feeding Responses Following Intrathecal (IT) or Intracerebroventricular (ICV) Administration In Vivo Abstract Knock-out mouse and human polymorphism studies link the melanocortin-4 receptor (MC4R) to increased food intake and obesity. Therapeutics targeting the MC4R have focused on cAMP signaling, though the MC4R can utilize additional pathways. Novel probes are needed that are functionally selective for different MC4R-signaling pathways, to determine pathway-specific effects in vivo. In this report, an 11-member AGRP-derived macrocyclic library was examined at the human MC4R for antagonist and inverse agonist activity. Two ligands were evaluated in mice to explore the functional significance between MC4R antagonism and inverse agonism signaling. Additionally, six ligands were assayed and observed to activate G-protein-independent MC4R-Kir7.1 signaling. One ligand (c[Pro-Arg-Phe-Phe-Val-Ala-Phe-DPro] (SEQ ID NO: 14)) possessed 4,000-fold selective potency for MC4R-Kir7.1 signaling over cAMP antagonism (a first-in-class probe). This ligand decreased food intake when administered ICV but had no effect following IT dosing, suggesting that activation of specific MC4R signaling pathways may differentially affect a feeding response in vivo. These data will be useful in the development of novel melanocortin lead ligands to modulate appetite.

Introduction

The melanocortin system has been associated with many physiological functions, including skin pigmentation,[1-2] steroidogenesis,[3] and energy homeostasis.[4] Five melanocortin receptors have been identified to date that are members of the super-family of G protein-coupled receptors (GPCRs).[5-13] The melanocortin receptors couple to $G_{\alpha s}$ protein subunits and increase intracellular levels of cAMP following agonist stimulation.[14] Naturally occurring ligands for the receptor include peptide agonists derived from the proopiomelanocortin gene transcript[15] and two endogenous antagonists, agouti[16-18] and agouti-related protein (AGRP).[19-21] While both the melanocortin-3 receptor (MC3R) and melanocortin-4 receptor (MC4R) have been implicated in food intake and energy homeostasis in mice.[4,22-23] polymorphisms in the human MC4R have been directly linked to an obese phenotype.[24-25] With the world-wide rate of obesity doubling between 1980 and 2014,[26] investigating biological pathways such as the MC4R associated with food intake and energy homeostasis may result in new therapeutic leads for weight management.

Intracerebroventricular (ICV) administration of agonists to the centrally expressed MC3R and MC4R in rodents that increase intracellular cAMP levels, including MTII,[22-23] α-MSH,[27] and NDP-MSH,[28] have been demonstrated to decrease food intake. Similar administration of antagonists to the MC3R and MC4R, including SHU9119-[22-23] (which possesses partial agonist activity at the MC3R)[29] and AGRP,[23,30] that block agonist stimulation of cAMP production at these receptors, increase food intake in rodents. Additionally, AGRP has been demonstrated to possess inverse agonist activity at the MC4R,[31-32] decreasing intracellular cAMP concentration from basal levels in the absence of endogenous agonists. Since the observed in vivo feeding response in rodents has been well-documented to correlate to the in vitro cAMP pharmacological response, many ligands have been optimized for modulating cAMP signaling. Compounds selective for the MC4R have been advanced to clinical trials with varying success, as reviewed.[33] However, the MC4R has also been demonstrated to couple to other signaling pathways. Administration of the pertussis toxin has been reported to affect α-MSH and AGRP signaling of the MC4R, suggesting the MC4R may also couple with $G_{i/o}$ proteins.[34] The nonselective melanocortin ligand NDP-MSH[35] that potently stimulates cAMP production in the MC1R, MC3R, MC4R, and MC5R has also been reported to stimulate MAPK phosphorylation.[36-38] Compounds selective for the MC4R that act as antagonists/inverse agonists for cAMP signaling also act as agonists for MAPK signaling,[38] indicating the MC4R may differentially signal through these pathways (an antagonist in one pathway may be an agonist in another). The MC4R has been reported to G-protein-independently couple to the Kir7.1 inward rectifying potassium channel, with α-MSH depolarizing (indicating closure of Kir7.1 channels) and AGRP hyperpolarizing (suggesting opening of Kir7.1 channels) cells from the paraventricular nucleus of the hypothalamus and transfected HEK293 cells.[39] Thus, while MC4R-selective ligands are typically optimized for cAMP pharmacology, the MC4R can signal through other pathways which are not well-correlated with in vivo effects. A greater understanding of the physiological relevance of these other signaling pathways may discern if these pathways are involved in reported off-target effects of MC4R-selective ligands (erectile activity, increase blood pressure),[40-42] and may allow the development of new lead ligands with safer profiles. Therefore, molecular probes that selectively signal through different MC4R-linked pathways are needed.

Since the sequence of α-MSH was first reported in 1957,[43] numerous ligands have been synthesized based upon this peptide. However, not many novel melanocortin ligands have been developed from AGRP, perhaps in part because AGRP was first reported 40 years following α-MSH,[19-21] the large size of the proposed active form of AGRP in vivo (50 residues versus 13 residues in α-MSH),[44] and structural complexity of AGRP indicated by NMR studies (10 Cys forming 5 disulfide bridges).[45-46] Many truncated forms of AGRP also possess decreased MC4R antagonist potency.[47-49] One previously identified macrocyclic octapeptide scaffold based upon the hypothesized β-hairpin active loop of AGRP cyclized head-to-tail through a DPro-Pro motif (c[Pro-Arg-Phe-Phe-Asn-Ala-Phe-DPro] (SEQ ID NO: 1)) was 50-fold less potent at the mouse (m)MC4R (300-fold at the mMC3R) compared to AGRP.[50] Further structure-activity relationship (SAR) studies replacing the Asn with a diaminopropionic (Dap) acid residue resulted in an equipotent antagonist to AGRP at the mMC4R.[50] Replacement of the Arg-Phe-Phe purported antagonist pharmacophore with the agonist His-DPhe-Arg-Trp (SEQ ID NO: 133) tetrapeptide sequence resulted in nanomolar potent mMC4R agonists.[51] Further SAR studies at the mMC4R reported Dap, DDap, and His residues at the Asn position,[52] Ser at the Ala position,[52] and Ala, Nle, Trp, and Try at the non-pharmacophore Phe position[52-53] maintained mMC4R antagonist potency. This scaffold has also produced ligands that possessed inverse agonist pharmacology at the mMC5R,[52-53] a novel pharmacology that indicates the utility of developing melanocortin probes from this AGRP-derived scaffold.

Due to the potency observed for the AGRP-derived DPro-Pro macrocyclic scaffold at the mMC4R, a library of 11 ligands substituted at the Asn position was assessed at the human (h)MC4R. In addition to observing a range of hMC4R antagonist potencies, many ligands possessed inverse agonist activity at the hMC4R. To examine the functional consequence of antagonist potency versus inverse agonism, two compounds were centrally administered in mice and cumulative food intake was monitored. Six compounds were further assessed in HEK293 cells expressing both the hMC4R and Kir7.1 channel to explore if this scaffold could engage this signaling pathway. From this set of six, one ligand was studied in mice to begin to explore the biological effects of the MC4R-Kir7.1 signaling pathway in vivo.

Results

Experimental Rational and Peptide Synthesis:

Previous SAR studies using the macrocyclic scaffold from the AGRP β-hairpin active loop hexapeptide sequence cyclized through a DPro-Pro motif examined pharmacology at the mouse melanocortin receptors.[50-53] While studying the mouse melanocortin receptors is useful for advancing ligands for in vive studies in mice, species differences between $\gamma_2$-MSH agonist potency at the mouse and human MC5R have previously been reported.[54] To address potential species differences in this scaffold at the MC4R, 11 AGRP-derived macrocycles substituted at the Asn position were examined at the hMC4R. Previous SAR studies at the mouse receptor reported basic residues increased antagonist potency relative to Asn at the mMC4R, with a diaminopropionic (Dap) substitution resulting in the most potent antagonist.[50,52] Therefore the Dap (MDE3-119-8c), DDap (MDE3-119-7c), and His (MDE3-119-12c) substitutions were included (structures for all amino acids are reported in FIG. 22A). Polar residue substitutions decreased antagonist potency less than 10-fold compared to the Dap substitution at the mMC4R,[s2] leading to the incorporation of the Asn (MDE5-108-10c) and Ser (MDE3-85c) ligands. Also included were the short, aliphatic Ala (MDE3-154c) and Abu (MDE3-119-2c) residues and the branch aliphatic Val (MDE3-119-10c) residue, which decreased antagonist potencies 24-, 25-, and 630-fold, respectively, compared to the Dap substitution, at the mMC4R.[52] The acidic Asp (MDE3-119-4c) and Glu (MDE3-119-5c) amino acids and aromatic Phe (MDE3-119-14c) residue were also examined, which previously decreased antagonist potency 50-100 fold at the mMC4R.[52]

All peptides were synthesized manually using standard Fmoc chemistry,[55] as previously described.[52] Peptides were purified to greater than 95% purity using semi-preparative reverse-phase high pressure liquid chromatography (RP-HPLC) as analyzed by analytical RP-HPLC in two diverse systems (Table 9) and possessed the correct molecular mass as determined by MALDI-MS (University of Minnesota Mass Spectrometry Lab).

AlphaScreen cAMP Assay at Human Melanocortin-4 Receptor:

Compounds were assayed at the human MC4R using the AlphaScreen cAMP assay according to the manufacturer instructions and as previously described.[56-59] Compounds were assayed for antagonist activity using a Schild paradigm,[60] with NDP-MSH as the agonist. Since the AlphaScreen cAMP assay is a loss-of-signal assay (decreased signal at higher concentrations), dose-response curves were normalized to NDP-MSH as previously described for illustrative purposes.[56-57,61] Compounds within a 3-fold potency range were considered equipotent due to the inherent error of the assay in our laboratory.

The hAGRP (86-132) and the Dap substituted MDE3-119-8c possessed similar nanomolar antagonist potencies ($pA_2$=8.8 for both) at the hMC4R (FIGS. 22B and 22C, Table 10). Inversion of the Dap stereocenter to DDap, MDE3-119-7c, and substitution of His (MDE3-119-13c) also resulted in nanomolar antagonist potencies at the hMC4R ($pA_2$=8.6 and 8.4, respectively). The ligand containing Asn (MDE5-108-10c), representing the native loop sequence, was 3-fold less potent than MDE3-119-8c at the hMC4R, while insertion of another polar residue Ser decreased potency 7-fold relative to MDE3-119-8c. Inserting the aliphatic Ala (MDE3-154c) and Abu (MDE3-119-2c) further decreased antagonist potency 12-fold and 19-fold, respectively compared to MDE3-119-8c, while the branched aliphatic Val (MDE3-119-10c) decreased potency 310-fold. Substitution of the acidic Glu (MDE3-119-5c) and Asp (MDE3-119-4c) decreased antagonist potency 70- and 90-fold, respectively, while the aromatic Phe substitution (MDE3-119-14c) decreased antagonist potency 80-fold. Comparing these data to a prior study at the mMC4R,[52] the ligands were equipotent at the human and mouse MC4R. Ranking the ligands by antagonist potency resulted in the same order of ligands, indicating no difference in antagonist potency between the two species' MC4R. This difference is in contrast to the reported differences in activity for $\gamma_2$-MSH at the mouse and human melanocortin receptors.[54] Several ligands also were shown to possess inverse agonist activity at the hMC4R (FIG. 22B), vide infra.

Binding at the hMC4R:

The ligands' ability to displace radiolabeled $^{125}$I-NDP-MSH and $^{125}$I-AGRP were studied in HEK293 cells stabilizing expressing the hMC4R. Both NDP-MSH and AGRP utilize overlapping, but distinct binding sites on the MC4R.[62] Since the ligands in the present work were derived from the active loop of AGRP, it was hypothesized that the ligands might better occupy the binding site of AGRP, evident in greater displacement of $^{125}$I-AGRP than $^{125}$I-NDP-MSH. To examine this theory, both radiolabeled ligands were used.

Similar to previous studies, NDP-MSH displaced $^{125}$I-NDP-MSH at 26 nM and AGRP displaced $^{125}$I-AGRP at 12 nM concentrations (Table 10, FIG. 23A).[63-66] As a general trend, the most potent AGRP-based macrocyclic ligands also displaced the radiolabeled NDP-MSH and AGRP at the lowest concentrations. The Dap-containing MDE3-119-8c and DDap-substituted MDE3-119-7c compounds possessed equivalent binding affinities compared to NDP-MSH and AGRP. The other basic residue, His (MDE3-119-13c), possessed 5- and 4-fold decreased binding affinity compared to NDP-MSH and AGRP, respectively. The polar Asn (MDE5-108-10c) and Ser (MDE3-85c) decreased binding affinity 8- and 10-fold compared to NDP-MSH and 7- and 9-fold compared to AGRP. Binding affinities for the aliphatic Ala (MDE3-154c) and Abu (MDE3-119-2c) decreased 13- and 20-fold in relationship to NDP-MSH, and 10- and 16-fold to AGRP. Similar to the functional potency, the aliphatic Val residue (MDE3-119-10c) possessed the lowest binding affinity for the MC4R, with 200-fold decreased affinity compared to both NDP-MSH and AGRP. Substituting acidic residues Glu (MDE3-119-5c) and Asp (MDE3-119-4c) resulted in 90- and 130-fold decreased ability to displace $^{125}$I-NDP-MSH and 110- and 100-fold decreased displacement of $^{125}$I-AGRP. While the ligands described above followed the same trend observed in the antagonist functional data, the Phe substituted MDE3-119-14c possessed higher binding affinity than expected based upon the functional activity data. While MDE3-119-14c possessed an antagonist $pA_2$ value of 6.9, similar to MDE3-119-5c (7.0) and MDE3-119-4c (6.9), the ligand MDE3-119-14c displaced $^{125}$I-NDP-MSH at 320 nM (12-fold decrease) and $^{125}$I-AGRP at 115 nM (10-fold decrease) concentrations. This may be visual represented by plotting $pIC_{50}$ versus $pA_2$ values for each ligand (FIG. 23B). While an approximate linear relationship is observed for the majority of the ligands, the MDE3-119-14c compound (FIG. 23B, blue arrows) does not follow the same correlation. The Phe substituted MDE3-119-14c ligand possessed the longest retention time by HPLC (Table 9). The macrocyclic ligands were also observed to displace $^{125}$I-AGRP at 2-3 fold lower concentrations compared to $^{125}$I-NDP-MSH, supporting the hypothesis that the AGRP-derived ligands might better displace AGRP from the receptor binding pocket.

Inverse Agonism at the hMC4R:

Similar to AGRP, several AGRP-derived macrocycle ligands possessed inverse agonist activity at the hMC4R, including MDE3-119-8c (FIGS. 22B and 24A, Table 10). Ligands were considered to possess inverse agonist activity if a sigmoidal dose-response curve was observed in at least two independent experiments. To quantify the inverse agonist activity, ligand dose-response curves were normalized to the response at $10^{-12}$ M concentrations, representing a basal signal for each ligand. The apparent potencies were determined from the inflection point of the normalized sigmoidal dose-response curves. The percent decrease from basal signal was determined from the average decrease from basal signal (signal at $10^{-12}$ M concentration) from replicates observed to possess a sigmoidal dose-response curve.

At the hMC4R, AGRP decreased the cAMP signal 35% from basal levels and possessed an apparent potency of 2.4 nM (FIGS. 22B and 24A. Table 10). The nanomolar inverse agonist response was similar to the antagonist potency for AGRP observed during the Schild analysis (Table 10). A similar apparent inverse agonist potency was observed for the Dap-containing MDE3-119-8S peptide (3.4 nM; Table 10), with a greater decrease in cAMP (−50% from basal; FIG. 24A) compared to AGRP. Inverting the stereocenter to DDap (MDE3-119-7c) or replacing Dap with His (MDE3-119-13c) both resulted in nanomolar apparent potencies (4 and 8 nM, respectively), and both substitutions decreased cAMP from basal levels by 30%. The same decrease in basal signal (30%) was also observed in the Asn-substituted MDE5-108-10c ligand, with 14 nM apparent potency. Similar apparent potency (16 nM) and decreased cAMP signal from basal (−25%) were observed with the Ser substitution (MDE3-85c; FIG. 24A). Insertion of an aliphatic Ala (MDE3-154c) or Abu (MDE3-119-2c; FIG. 24A) resulted in apparent potencies of 50 and 22 nM respectively. The Ala substitution maintained an equivalent decreased signal (−35%) compared to AGRP, while a smaller response (−15%) was observed for the Abu substitution. Substitution of acidic residues resulted in diminished apparent inverse agonist potencies relative to AGRP. The Glu substituted MDE3-119-5c possessed 1,100 nM apparent potency with −35% decreased cAMP response from basal, while the Asp containing peptide MDE3-119-4c (FIG. 24A) possessed 2,000 nM apparent potency with 35% decreased cAMP response. Insertion of Phe (MDE3-119-14c) or Val (MDE3-119-10c; FIG. 24A) resulted in ligands that did not possess an inverse agonist response at the wildtype hMC4R at concentrations up to 100 μM concentrations.

The apparent potencies for the inverse agonist response at the wildtype hMC4R follow the same trend as the antagonist potencies previously described. Peptides containing basic residues (MDE3-119-8c, MDE3-119-7c, and MDE3-119-13c) were equipotent to AGRP. Substitution of polar residues (MDE5-108-10c and MDE3-85c) decreased the apparent potencies 6- and 7-fold relative to AGRP, while insertion of the aliphatic amino acids (MDE3-154c and MDE3-119-2c) resulted in further decreases in the apparent potencies (20- and 9-fold) relative to AGRP. Acidic substitutions (MDE3-119-5c and MDE3-119-4c) decreased apparent potencies 450- and 830-fold, while the branched aliphatic/aromatic substitutions (MDE3-119-14c and MDE3-119-10c) did not possess inverse agonist activity at concentrations up to 100 μM (>41,000-fold difference than AGRP). Thus, the apparent potencies of the inverse agonist response appear to correlate with antagonist function and follow a similar trend to ligand binding affinity. For ligands that possessed an inverse agonist response, the decrease from basal signal was in a similar range for most ligands (−25% to −35%), although one ligand (MDE3-119-8c) decreased cAMP signal 50% relative to basal, while the Abu substituted MDE3-119-2c signal decreased basal signal 15%. No immediate SAR trends were apparent in the decrease in basal signal for these ligands at the wildtype hMC4R.

In Vivo Administration of MDE3-119-8c and MDE3-119-2c:

In the present study, the signal decrease from basal levels (inverse agonist efficacy) and apparent potencies varied based upon substitutions in AGRP-derived macrocyclic ligands at the wildtype hMC4R (FIG. 24A). In attempts to distinguish the roles MC4R antagonism versus inverse agonism may have in the feeding response in vivo, two ligands were selected for ICV administration. The MDE3-119-8c ligand was an equipotent antagonist to AGRP at the mMC4R ($pA_2$=8.7)[52] and hMC4R ($pA_2$=8.8, Table 9), possessed similar inverse agonist apparent potency to AGRP (3.4 nM versus 2.4 nM for AGRP), and produced a greater decrease from basal levels of cAMP than AGRP (−50% versus −35%). Compound MDE3-119-2c possessed 18-fold decreased antagonist potency ($pA_2$=7.5) at the hMC4R, decreased apparent inverse agonist potency (22 nM, 10-fold), and a smaller (−15% versus −35%) decrease from basal signaling compared to AGRP. Previous ICV administration of another MC4R antagonist SKY2-23-7, with similar potency to MDE3-119-2c ($pA_2$=7.8 for SKY2-23-7),[67-68] increased food intake in mice, suggesting antagonist potency in this range is sufficient to generate an observable response. While other ligands in the present study did not produce an inverse agonist response at the hMC4R, their further decreased antagonist potency ($pA_2$<7) may be too weak to be observed in vivo.

When MDE3-119-8c was centrally administered into free feeding mice, a dose-dependent increase in food intake was observed for the first 8 h post-injection (FIG. 24B). The 3 nmol dose resulted in a significant increase in food intake at 4, 6, and 8 h compared to administration of the vehicle control. This difference between the 3 nmol dose and vehicle was of a similar magnitude at 8 h compared to a prior report of 2 nmol of AGRP versus saline at 8 h.[23] Unlike AGRP, which was shown to have a prolonged effect on cumulative food intake (greater than 7 days),[23] peptide MDE3-119-8c did not significantly alter cumulative food intake after 24 h.

Following 2 and 5 nmol doses of MDE3-119-2c, no significant food increase was observed by 8 h (FIG. 24B). The 5 nmol dose of MDE3-119-2c was observed to decrease food intake, a trend that did not achieve statistical significance. While decreased food intake could be the result of an adverse effect of the ligand on the health of the animal, no behavioral changes were observed in the mice following injection of MDE3-119-2c. Previously, a compound with similar antagonist potency (SKY2-23-7) increased food intake[67] suggesting MDE3-119-2c failure to stimulate food intake was not the result of antagonist potency.

One interpretation of these results would be that inverse agonist activity at the MC4R may be required for at least an immediate (8 h) increase in food intake. However, SHU9119 also increases murine food intake[22-23] and is devoid of inverse agonist activity at the MC4R. SHU9119 is also an antagonist and partial agonist at the MC3R, which has been implicated in the regulation of food intake,[23] so MC3R antagonism may compensate for the lack of MC4R inverse agonism. The two ligands (MDE3-119-8c and MDE3-119-2c) administered in the present study were also characterized as MC5R inverse agonist ligands,[52] a pharmacology that has not been characterized in vivo. As the MC5R is expressed in the brain,[5,10,13] to these ligands may also mediate effects through this receptor in addition to the MC4R with unknown physiological effects. While the current data suggest that inverse agonism at the MC4R may be more consequential than simple antagonism of the MC4R for a short-term feeding response in vivo, the lack of a truly selective molecule precludes a firm conclusion. The development of future probes with a more clean profile (activity at one receptor) will be necessary to more thoroughly investigate the correlation between in vitro pharmacology with in vivo functional effects.

Kir7.1 Thallium Flux Assay:

In addition to modulating cAMP levels, the MC4R has been linked to additionally signaling pathways, including G protein-independent coupling to the Kir7.1 potassium channel.[39] The endogenous α-MSH cAMP agonist was demonstrated to depolarize neuronal cells, reported to be through closure of the Kir7.1 channel, while the naturally occurring AGRP cAMP antagonist hyperpolarized membranes by activation of the Kir7.1 channel.[39] The MC4R coupling to the Kir7.1 channel may also be involved in the regulation of food intake. The MC4R ligand MC4-NN2-0453 possessed a cAMP agonist potency of 4.9 nM and inhibited thallium flux with an apparent potency of 0.45 nM, with a significant decrease in food intake up to 24 h compared to saline.[39] A truncated form of AGRP, miniAGRP (AGRP87-120, C105A) possesses similar binding affinity and cAMP antagonist potency to AGRP.[69-70] Following ICV administration into rats, mini-AGRP increased 24 h food intake by 21% above saline compared to 42% for AGRP(87-132) and 77% for AGRP(83-132).[71] Mini-AGRP did not affect thallium flux at concentrations up to 100 nM.[39] The lack of coupling to the Kir7.1 channel to the MC4R with the mini-AGRP ligand was postulated to correlate to the observed changes in food intake observed in rats.[39] While the MC4-NN2-0453 compound was reported to possess 10-fold selectivity for inhibiting thallium flux over stimulating cAMP production,[39] no ligands have been reported that selectively increase thallium flux through the MC4R.

Since AGRP was reported as a ligand for MC4R-Kir7.1 channel signaling, and the scaffold discussed herein is derived from the active loop of AGRP, it was hypothesized that this scaffold might increase thallium flux through MC4R-Kir7.1 signaling. Since various substitutions resulted in a range of cAMP antagonist potencies (Table 10), a subset of the library with varying potencies was assayed to explore if antagonist potency correlated with thallium flux. Included were the basic Dap (MDE3-119-8c) and DDap (MDE3-119-7c) substitutions that were the most potent antagonists, the polar Ser (MDE3-85c), aliphatic Abu (MDE3-119-2c), acidic Asp (MDE3-119-4c), and branched aliphatic Val (MDE3-119-10c) with 7-, 18-, 90-, and 310-fold decreased cAMP antagonist potencies compared to MDE3-119-8c. In this assay, the Kir7.1 (M125R) variant was used since it previously was reported to result in higher unitary conductance compared to the native channel.[39]

The six ligands were assayed using HEK293 cells co-expressing the MC4R and Kir7.1 channel while monitoring thallium flux with the thallium-sensitive dye Thallos, as previously described.[39] All compounds possessed nanomolar to sub-nanomolar apparent potencies in the thallium flux assay, in contrast to the 320-fold antagonist potency range observed for cAMP activity (FIG. 25A). The compound with the highest apparent potency. MDE3-119-10c (FIG. 25A), possessed 0.12 nM apparent potency in this assay. Decreased apparent potencies were observed for MDE3-119-8c (28-fold), MDE3-119-7c (80-fold), MDE3-85c (2-fold), MDE3-119-2c (5-fold), and MDE3-119-4c (2-fold) compared to MDE3-119-10c. No apparent trend was observed for correlating the type of amino acid substitution with Kir7.1 apparent potency.

To determine the functional selectivity of the AGRP-derived macrocyclic ligands for MC4R-Kir7.1 signaling over cAMP antagonism, the cAMP antagonist $pA_2$ values were converted to $K_i[pA_2=-\log(K_i)]$. The antagonist $K_i$ values were then divided by Kir7.1 apparent potencies to generate a fold selectivity for the Kir7.1 assay. Since the six ligands possessed similar Kir7.1 apparent potencies and a greater range of cAMP antagonist potencies, the most potent cAMP antagonist ligands were the least selective. The basic Dap (MDE3-119-8c), DDap (MDE3-119-7c), and AGRP ligands were 2-, 4-, and 2-fold selective for cAMP over Kir7.1 signaling, respectively. The polar Ser (MDE3-85c) and aliphatic Abu (MDE3-119-2c) substituted compounds were approximately 50-fold selective for Kir7.1 signaling, while the acidic Asp-substituted MDE3-119-4c was over 500-fold selective for Kir7.1 signaling compared to cAMP. The branched aliphatic Val (MDE3-119-10c), possessing the weakest cAMP antagonist potency and highest Kir7.1 apparent potency, was the most selective ligand assayed, with a 4,000-fold functional selectivity for Kir7, signaling. To the authors' knowledge, this ligand is the first compound to selectively increase thallium flux through the MC4R-Kir7.1 pathway, representing a first-in-class molecular probe.

ICV and IT In Vivo Administration of MDE3-119-10c:

In this study, one ligand (MDE3-119-10c) possessed sub-nanomolar potency in the hMC4R-Kir7.1 signaling assay and 480 nM antagonist potency in hMC4R cAMP signaling. To begin to examine the functional consequences of Kir7.1 signaling in vivo, the MDE3-119-10c compound was administered into mice. As the G-protein-independent MC4R-Kir7.1 signaling was originally demonstrated in neurons from the paraventricular nucleus of the hypothalamus (PVN),[39] MDE3-119-10c was directly injected via ICV administration. At the highest tolerated dose, 10 nmol MDE3-119-10c resulted in a significant, prolonged decrease in cumulative food intake at 4, 6, 8, 24, 48, and 72 h (FIG. 25B) compared to vehicle. These data are in contrast to the published results of MC4R cAMP antagonists administered ICV, which have been reported to increase food intake.[22-23, 30,67] As the MDE3-119-10c ligand is more potent and selective for Kir7.1 signaling, these results may suggest that hyperpolarization of neurons in the PVN due to opening of the Kir7.1 potassium ion channel may result in a decrease in food intake. Since AGRP and MDE3-119-8c also possess nanomolar Kir7.1 signaling (expected to decrease food intake based upon the results of MDE3-119-8c) and cAMP antagonist (expected to increase food intake) potencies, it may be further speculated that the cAMP antagonist may overwhelm the Kir7.1 signaling in vivo when non-selective ligands are used, since both compounds increase food intake when administered ICV. Attempts to use a higher dose of MDE3-119-10c was unsuccessful, as two mice dosed with 12 nmol MDE3-119-10c had apparent seizures and did not survive, suggesting a dose-limiting toxicity.

It has previously been demonstrated that IT administration of the melanocortin cAMP agonist MTII decreased food intake,[72] while IT administration of AGRP[72] or an AGRP-derived macrocycle[53] increased food intake, the same functional pattern for these compounds following ICV administration. This may suggest that IT administration of MC4R ligands that signal through Gas and modulate cAMP levels result in a similar feeding pattern to ICV administration. In contrast, when 10 nmol MDE3-119-10c was administered IT, there was no effect on food intake compared to vehicle (FIG. 25B). No seizure activity was observed following IT administration of MDE3-119-10c. Since the Kir7.1 neurons previously identified are located in the PVN,[39] and IT administration of $[^3H]$morphine results in minimally penetration of the forebrain (<2% after 20 min),[73] it may be rationalized that MDE3-119-10c did not have an effect on feeding following IT administration as it was unable to access the PVN in sufficient quantities for signaling. It could be further speculated that for Kir7.1 signaling to have a physiological effect on feeding, a ligand must be able to reach the PVN. Such a paradigm may allow for screening for new ligands that have Kir7.1 signaling by comparing the effects following IT and ICV administration. If a compound has an effect following ICV and IT administration, it would be expected to have cAMP activity and may additional signal through the Kir7.1 pathway. If activity is observed following ICV and not IT, the ligand may possess selective Kir7.1 signaling. Such an approach may be useful in the discovery of new hMC4R-Kir7.1 selective ligands.

Conclusions

Dysregulation of the MC4R has been linked to altered energy homeostasis, with many MC4R polymorphisms associated with obesity. While potential probes and therapeutics for this receptor have focused on optimizing cAMP signaling, the MC4R has been reported to signal through additional pathways. By developing probes for specific signaling pathways, the physiological function of the different pathways can be revealed. In this report, different MC4R signaling pathways were examined by an AGRP-derived macrocyclic library. By varying the Asn position from the active loop of AGRP in the macrocycle scaffold, basic substitutions were found to increase antagonist potency at the hMC4R. A range of inverse agonist apparent potencies and efficacies at the MC4R was also observed, following a similar trend to antagonist potencies. Two ligands (MDE3-119-8c and MDE3-119-2c) were examined in mice, to begin to explore the differential effects of antagonism versus inverse agonism. The MDE3-119-8c peptide was a more potent antagonist ($pA_2$=8.8), inverse agonist ($EC_{50}$=3.4 nM), and greater decrease from basal signal (−50%) compared to $pA_2$=7.5, inverse agonist $EC_{50}$=22 nM, and −15% decrease from basal for ligand MDE3-119-2c. An dose-dependent increase in food intake was observed for MDE3-119-8c, while a non-significant decrease in food intake was observed for MDE3-119-2c, perhaps indicating the inverse agonist response is important for a short-term increased food intake response. A subset of compounds was also examined using the hMC4R-Kir7.1 thallium flux assay to see if this molecular scaffold could signal through this pathway. All compounds assayed possessed nanomolar to sub-nanomolar potencies for this pathway. One compound, MDE3-119-10c possessed sub-nanomolar potency in the Kir7.1 flux assay and micromolar cAMP antagonist potency, representing the first ligand to be functionally selective for MC4R-mediated opening of this channel. Unlike MC4R cAMP antagonist compounds, this ligand decreased food intake when administered ICV and had no effect when administered IT, suggesting that selective MC4R-Kir7.1 signaling may decrease food intake. This suggest that developing ligands that increase cAMP levels and open the Kir7.1 potassium channel may be more potent anorexigenic ligands, and may aid in the development of future MC4R-based therapeutics that do not possess the side effects common to current MC4R lead molecules.

Methods

Peptide Synthesis:

The coupling reagents [2-(1-H-benzotriazol-1-yl)-1,1,3,3-tetramethyluronium hexafluorophosphate (HBTU), benzotriazol-1-yl-oxy-tris(dimethylamino) phosphonium hexafluorophosphate (BOP), and 1-hydroxybenzotriazole (HOBt)], amino acids (unless otherwise noted), and the H-Pro-2-chlorotrityl resin were purchased from Peptides International (Louisville, Ky.). The Fmoc-DDap(Boc)-OH amino acid was purchased from Bachem (Torrance, Calif.). N,N-Dimethylformamide (DMF), dichloromethane (DCM), methanol, acetonitrile, and anhydrous ethyl ether were purchased from Fisher (Fair Lawn, N.J.). Trifluoroacetic acid (TFA), dimethyl sulfoxide (DMSO), piperidine, and phenol were purchased from Sigma (St. Louis, Mo.). N,N-diisopropylethylamine (DIEA) and triisopropylsilane (TIS) were purchased from Aldrich (Milwaukee, Wis.). All reagents and chemicals were ACS grade or better and were used without further purification.

The peptides were synthesized manually using standard Fmoc methodology as previously described.[50,52,55] Briefly, the syntheses (0.05 mmol scale) consisted of the following steps on a preloaded H-Pro-2-chlorotrityl resin (0.68 mequiv/g substitution): (i) double-coupling of Fmoc-amino acid (3.1 equiv) with HBTU (3 equiv) and DIEA (5 equiv) in DMF for 1 h per coupling; (ii) removal of the N-Fmoc group by 20% piperidine in DMF (1×5 min, 1×20 min). Upon synthesis completion, peptides were cleaved from the resin with 1% TFA in DCM for 6 min. The solution was concentrated and the protected peptides were precipitated and washed with cold (4° C.) diethyl ether. Cyclization was performed overnight in DCM with a peptide concentration of 1 mg/mL using BOP (3 equiv), HOBt (3 equiv), and DIEA (6 equiv). The DCM was removed under reduced pressure, and the final side chain deprotection was performed in TFA:TIS:$H_2O$ (95:2.5:2.5) for 2 h. Cyclic, deprotected peptides were precipitated and washed in cold diethyl ether.

All peptides were purified by RP-HPLC using a Shimadzu chromatography system with a photodiode array detector and a semi-preparative RP-HPLC C18 bonded silica column (Vydac 218TP1010, 1.0×25 $cm^2$). The peptides were at least 95% pure as determined by analytical RP-HPLC in two diverse solvent systems and had the correct molecular mass by MALDI-MS (University of Minnesota Mass Spectrometry Lab).

cAMP AlphaScreen® Bioassay:

Peptide ligands were dissolved in DMSO at a stock concentration of $10^{-2}$ M and were pharmacological characterized using the cAMP AlphaScreen® assay (PerkinElmer) according to the manufacturer's instructions and as previously described.[56-59]

Briefly, cells 70-90% confluent were dislodged with Versene (Gibco®) at 37° C. and plated 10,000 cells/well in a 384-well plate (Optiplate™) with 10 μL freshly prepared stimulation buffer (1×HBSS, 5 mM HEPES, 0.5 mM IBMX, 0.1% BSA, pH=7.4) with 0.5 μg anti-cAMP acceptor beads per well. The cells were stimulated with the addition of 5 μL stimulation buffer containing peptide (a seven point dose-response curve was used starting at $10^{-4}$ to $10^{-7}$ M, determined by ligand potency) or forskolin ($10^{-4}$ M) and incubated in the dark at room temperature for 2 hr.

Following stimulation, streptavidin donor beads (0.5 μg) and biotinylated-cAMP (0.62 μmol) were added to the wells in a subdued light environment with 10 μL lysis buffer (5 mM HEPES, 0.3% Tween-20, 0.1% BSA, pH=7.4) and the plates were incubated in the dark at room temperature for an additional 2 hr. Plates were read on a Enspire (PerkinElmer) Alpha-plate reader using a pre-normalized assay protocol (set by the manufacturer).

In Vitro Data Analysis:

The $EC_{50}$ values represent the mean of duplicate replicates performed in at least three independent experiments. The $EC_{50}$ estimates and associated standard errors (SEM) were determined by fitting the data to a nonlinear least-squares analysis using the PRISM program (v4.0, GraphPad Inc.). The ligands were assayed as TFA salts and not corrected for peptide context.

Competitive Radioligand Binding Affinity Studies:

Human AGRP(86-132) or NDP-MSH were radiolabeled Dr. Robert Speth using $Na^{125}I$ using the chloramine-T method.[74] Monoradioiodinated peptide was purified from uniodinated or diradioioindated peptide by HPLC, eluted isocratically in a mobile phase of 24% acetonitrile and 76% trimethylamine phosphate (pH 3.0).

Competitive binding affinity experiments were performed on HEK-293 cells stably expressing the wildtype hMC4R. Cells were plated 1-2 days before the experiment in 12-well tissue-culture plates (cat #353043, Corning Life Sciences) and were grown to 90-100% confluency on the day of the assay. Media was gently aspirated and cells were treated with a freshly diluted aliquot of experimental non-labeled ligand at the appropriate concentration (a seven point dose-response curve starting at $10^{-4}$ to $10^{-6}$ M) in assay buffer (DMEM and 0.1% BSA) and a constant amount of $^{125}I$-NDP-MSH or $^{125}I$-AGRP (100,000 cpm/well) for 1 h at 37° C. The assay media was carefully aspirated and cells were washed once with assay buffer. Cell were lysed with 500 μL 0.1 M NaOH and 500 μL 1% Triton X-100 for a minimum of 10 min. The cell lysate was transferred to 12×75 mm polystyrene tubes (cat 14-961-13, Fisherbrand) and radioactivity quantified on a WIZARD² Automatic Gamma Counter (PerkinElmer). All experiments were performed with duplicate data points and in at least two independent experimental replicates. The non-specific values were defined as a signal from $10^{-6}$ M unlabeled NDP-MSH or AGRP(86-132), corresponding to the respective $^{125}$I-labeled peptide. Concentration-response curves and $IC_{50}$ values were generated and analyzed by the PRISM program (version 4.0. GraphPad Inc.) by a nonlinear regression method. The standard error of the mean (SEM) was derived from the $IC_{50}$ values from at least two independent experimental replicates.

Animals:

All studies were performed in accordance with the Institutional Animal Care and Use Committee (IACUC) of the University of Minnesota The mice use were wild-type male with a mixed genetic background from the C57BL/6J and 129/Sv inbred stains as previously described.[67,75-76] Mice were maintained on a 12 h light/dark cycle (lights off at 1100 h) in a temperature controlled room (23-25° C.) with free access to tap water and normal chow (Harlan Taklad 2018 Diet: 18.6% crude peptide, 6.2% crude fat, 3.5% crude fiber, with energy of 3.1 kcal/g). All studies were performed in standard mouse polycarbonate conventional cages provided by the University of Minnesota's Research Animal Resources (RAR), and were changed weekly by laboratory research staff.

Cannulation Surgery and Placement Validation:

Cannulation surgeries were performed to place a cannula into the lateral cerebral ventricle as previously reported.[23,67,76] Mice were anesthetized with a mixture of xylazine (5 mg/kg) and ketamine (100 mg/kg) administered intraperitoneal (IP) and placed in a stereotaxic apparatus (David Kopf Instruments) that was used to guide the cannula placement. A 26-guage cannula (cat #8IC315GS4SPC; PlasticsOne, Roanoke, Va.) was inserted into the lateral cerebral ventricle at the coordinates 1.0 mm lateral and 0.46 mm posterior to bregma and 2.3 mm ventral to the skull.[77] The cannula was secured to the skull using dental cement (C&B-Metabond Adhesive Cement Kit # S380) followed by Lang's Jet Denture Repair Kit (Jet Denture Repair Powder, ref #1220; Jet Liquid, ref #1403). After surgery, flunixin meglumine (FluMegluine, Clipper Distribution Company) and 0.5 mL of 0.9% saline (Hospira, Lake Forrest, Ill.) was administered subcutaneously to aid in recovery. Mice recovered for at least 7 days prior to cannula placement validation. Mice were housed individually after surgery and for the remainder of the experiments.

Cannula placement was validated by the feeding response after ICV administration of 2.5 μg of human (h)PYY3-36 (cat # H8585; Bachem), as described previously.[23,67,75-76] Mice received saline treatment and hPYY treatment on different days separated by a washout period of at least 3 days in a crossover design nocturnal feeding paradigm. In this paradigm, compound or saline is administered 2 h prior to lights out (t=0 h) and body weight and food are measured. Mice have free access to food and water. At 4 h post-administration, food is measured. A mouse with a validated properly placed cannula consumed at least 0.8 g more food after hPYY administration compared to saline administration at 4 h.

In Vivo Study Design:

All ICV and IT administration experiments utilized a crossover design with free access to standard chow. Mice were housed in RAR supplied conventional mouse cages. Compound MDE3-119-8e was dissolved in a stock solution of 10 nmols/μL in 3% v/v DMSO (Sigma Aldrich)/saline (0.9% sodium chloride, Hospira Inc., Lake Forest, Ill.). Ligands MDE3-119-2c and MDE3-119-10c were dissolved in 20% solutol (Sigma Aldrich). Matching vehicle controls (3% v/v DMSO in saline and 20% solutol) were prepared in parallel. The day of compound administration, an aliquot of stock solution was diluted with saline to the desired experimental dose in 3 μL, in parallel with vehicle control. For ICV administration, the desired experimental dose (3 μL) or vehicle control (3 μL) was delivered 2 h before lights out (t=0 h). For IT administration, the desired experimental dose (5 μL) or vehicle control (5 μL) was delivered 2 h before lights out (t=0 h). Food intake and mouse weight was manually measured at t=0, 2, 4, 6, 8, 24, 48, and 72 h post-injection. Mice recovered 6-7 days between treatments to reestablish pretreatment body weight and feeding patterns.

In Vivo Data Analysis:

For feeding results for compounds MDE3-119-8c and MDE3-119-2c, data were analyzed using the PRISM program (v4.0; GraphPad Inc.) by a two-way repeated measures ANOVA followed by a Bonferroni post-test in order to compare individual doses to saline administration at each time point. For feeding experiments with compound MDE3-119-10c, data were analyzed using the PRISM program (v4.0; GraphPad Inc.) by two-way ANOVA with a Sidak's multiple comparison post hoc test.

Kir7.1 Thallium Flux Assay:

HEK293 cells stably expressing the human MC4R and Kir7.1 (M125R) were grown in MEM medium with 10% FBS without antibiotics, suspended in medium plus 1 μg $ml^{-1}$ tetracycline (to induce expression of the transfected tet-sensitive Kir7.1 gene) and plated (20 μL) in 384-well poly-D-lysine coated optical bottom plates (BD Biosciences) at 20,000 cells per well. Plates were incubated overnight for 16-24 h in the cell incubator at 37° C., 5% $CO_2$. The following day, the media was removed and replaced with 50 μL dye solution in each well [a 100 μL aliquot containing 250 μg Thallos (TEFLabs) in 100 μL 6.7% pluronic acid, 26.3% DMSO, and 67% $H_2O$ was added to 200 mL 1×HBSS, 20 mM HEPES, pH 7.3]. Plates were incubated in the dark for 1 h at room temperature and dye solution was removed. Upon addition of 20 μL 1×HBSS buffer, a liquid handler added 20 μL of ligand solution to entire plate simultaneously (ligands were prepared by serial dilution in 1×HBSS, 20 mM HEPES, 0.1% BSA, pH 7.3). Plates were incubated in the dark for 20 min (unless otherwise indicated). After a baseline reading on a Thallos Plate-reader (Vanderbilt, Tenn.), 10 μL of a thallium solution (1×HBSS, 20 mM HEPES, 2 mM Tl, pH 7.3) was loaded and fluorescence generated by thallium influx was recorded for 10 min. The signal was normalized to an untreated control.

Example 5, Cited Documents

1. Smith, et al. Science 1916, 44 (1130), 280-282.
2. Allen, et al. Science 1916, 44 (1143), 755-758.
3. Haynes, et al. J. Biol. Chem. 1957, 225 (1), 115-124.
4. Huszar, et al. Cell 1997, 88 (1), 131-141.
5. Chhajlani, et al. Biochem. Biophys. Res. Commun. 1993, 195 (2), 866-873.
6. Chhajlani, et al. FEBS Lett. 1992, 309 (3), 417-420.
7. Chen, et al. Bioorg. Med. Chem. 2008, 16 (10), 5606-5618.
8. Gantz, et al. J. Biol. Chem. 1993, 268 (11), 8246-8250.
9. Gantz, et al. J. Biol. Chem. 1993, 268 (20), 15174-15179.
10. Gantz, et al. Biochem. Biophys. Res. Commun. 1994, 200 (3), 1214-1220.

11. Mountjoy, et al. Science 1992, 257 (5074), 1248-1251.
12. Roselli-Rehfuss, et al. Proc. Natl. Acad. Sci. U.S.A. 1993, 90 (19), 8856-8860.
13. Griffon, et al. Biochem. Biophys. Res. Commun. 1994, 200 (2), 1007-1014.
14. Haynes, et al. J. Biol. Chem. 1958, 233 ((5)), 1220-1222.
15. Nakanishi, et al. Nature 1979, 278 (5703), 423-427.
16. Bultman, et al. Cell 1992, 71 (7), 1195-1204.
17. Lu, et al. Nature 1994, 371 (6500), 799-802.
18. Miller, et al. Genes Dev. 1993, 7 (3), 454-467.
19. Ollmann, et al. Science 1997, 278 (5335), 135-138.
20. Fong, et al. Biochem. Biophys. Res. Commun. 1997, 237 (3), 629-631.
21. Shutter, et al. Genes Dev. 1997, 11 (5), 593-602.
22. Fan, et al. Nature 1997, 385 (6612), 165-168.
23. Irani, et al. Eur. J. Pharmacol. 2011, 660 (1), 80-87.
24. Farooqi, et al. N. Engl. J. Med. 2003, 348 (12), 1085-95.
25. Hinney, et al. Prog. Mol. Biol. Transl. Sci. 2013, 114, 147-191.
26. Organization, W. H. Obesity and overweight fact sheet. http://www.who.int/mediacentre/factsheets/fs311/en (accessed September 6).
27. Poggioli, et al. Peptides 1986, 7 (5), 843-8.
28. Brown, et al. Fos. Regul. Pept. 1998, 78 (1-3), 89-94.
29. Hruby, et al. J. Med. Chem. 1995, 38 (18), 3454-3461.
30. Ebihara, et al., in leptin action. Diabetes 1999, 48 (10), 2028-2033.
31. Haskell-Luevano, et al. Regul. Pept. 2001, 99 (1), 1-7.
32. Nijenhuis, et al. Mol. Endocrinol. 2001, 15 (1), 164-171.
33. Ericson, et al. 1954. Biochim. Biophys. Acta, Mol. Basis Dis. 2017, 1863 (10), 2414-2435.
34. Buch, et al. J. Biol. Chem. 2009, 284 (39), 26411-26420.
35. Sawyer, et al. Proc. Natl. Acad. Sci. U.S.A. 1980, 77 (10), 5754-5758.
36. Vongs, et al. Regul. Pept. 2004, 120 (1-3), 113-118.
37. Chai, et al. Peptides 2006, 27 (11), 2846-2857.
38. Mo, et al. Biochim. Biophys. Acta, Mol. Basis Dis. 2013, 1832 (12), 1939-1948.
39. Ghamari-Langroudi, et al. Nature 2015, 520 (7545), 94-U223.
40. Greenfield, et al. N. Engl. J. Med. 2009, 360 (1), 44-52.
41. Hadley, et al. Peptides 2005, 26 (10), 1687-1689.
42. Dorr, et al. Life Sci. 1996, 58 (20), 1777-1784.
43. Harris, et al. Nature 1957, 179 (4574), 1346-1347.
44. Creemers, et al. Endocrinology 2006, 147 (4), 1621-31.
45. Bolin, et al. FEBS Lett. 1999, 451 (2), 125-131.
46. McNulty, et al. Biochemistry 2001, 40 (51), 15520-15527.
47. Wilczynski, et al. J. Med. Chem. 2004, 47 (23), 5662-5673.
48. Tota, et al. Biochemistry 1999, 38 (3), 897-904.
49. Joseph, et al. Peptides 2003, 24 (2), 263-270.
50. Ericson, et al. J. Med. Chem. 2015, 58 (11), 4638-4647.
51. Ericson, et al. J. Med. Chem. 2017, 60 (2), 805-813.
52. Ericson, et al. J. Med. Chem. 2017, 60 (19), 8103-8114.
53. Fleming, et al. ACS Chem. Neurosci. 2018, published online Jan. 25, 2017. DOI: 10.1021/acschemneuro.7b00495.
54. Joseph, et al. Peptides 2010, 31 (12), 2304-2313.
55. Carpino, et al. J. Am. Chem. Soc. 1970, 92 (19), 5748-5749.
56. Ericson, et al. Bioorg. Med. Chem. Lett. 2015, 25 (22), 5306-5308.
57. Lensing, et al. J. Med. Chem. 2016, 59 (7), 3112-3128.
58. Singh, et al. ACS Med. Chem. Lett. 2015, 6 (5), 568-572.
59. Tala, et al. Bioorg. Med. Chem. Lett. 2015, 25 (24), 5708-5711.
60. Schild, et al. Br. J. Pharmacol. Chemother. 1947, 2 (3), 189-206.
61. Elster, et al. J. Biomol. Screening 2007, 12 (1), 41-49.
62. Haskell-Luevano, et al. Biochemistry 2001, 40 (20), 6164-6179.
63. Xiang, et al. Biochemistry 2006, 45 (23), 7277-7288.
64. Xiang, et al. Biochemistry 2010, 49 (22), 4583-4600.
65. Yang, et al. J. Biol. Chem. 1999, 274 (20), 14100-6.
66. Yang, et al. Mol. Endocrinol. 1999, 13 (1), 148-155.
67. Lensing, et al. ACS Chem. Neurosci. 2016, 7 (9), 1283-1291.
68. Doering, et al. ACS Med. Chem. Lett. 2015, 6 (2), 123-127.
69. Jackson, et al. Biochemistry 2002, 41 (24), 7565-7572.
70. Wilczynski, et al. J. Med. Chem. 2004, 47 (9), 2194-2207.
71. Madonna, et al. ACS Chem. Biol. 2012, 7 (2), 394-401.
72. Adank, et al. ACS Chem. Neurosci. 2017.
73. Hylden, et al. Eur. J. Pharmacol. 1980, 67 (2-3), 313-316.
74. Hunter, et al. Nature 1962, 194, 495-6.
75. Marsh, et al. Nat. Genet. 1999, 21 (1), 119-122.
76. Lensing, et al. ACS Chem. Neurosci., Jan. 27, 2017 ed.; 2017.
77. Franklin, et al. Academic Press: San Diego, 1997.

TABLE 9

Analytical Data for Peptides Synthesized in this Study.[a]

| Peptide | Sequence | Retention Time (min) system 1 | Retention Time (min) system 2 | M (calc) | mass spectral analysis (M + 1) | purity % |
|---|---|---|---|---|---|---|
| MDE5-108-10c | c[Pro-Arg-Phe-Phe-**Asn**-Ala-Phe-DPro] (SEQ ID NO: 1) | 18.1 | 26.8 | 976.5 | 977.5 | >99 |
| MDE3-154c | c[Pro-Arg-Phe-Phe-**Ala**-Ala-Phe-DPro] (SEQ ID NO: 4) | 18.9 | 28.7 | 933.5 | 934.3 | >99 |
| MDE3-85c | c[Pro-Arg-Phe-Phe-**Ser**-Ala-Phe-DPro] (SEQ ID NO: 6) | 18.8 | 29.2 | 949.5 | 950.3 | >99 |
| MDE3-119-2c | c[Pro-Arg-Phe-Phe-**Abu**-Ala-Phe-DPro] (SEQ ID NO: 5) | 19.5 | 29.4 | 947.5 | 948.5 | >98 |
| MDE3-119-4c | c[Pro-Arg-Phe-Phe-**Asp**-Ala-Phe-DPro] (SEQ ID NO: 8) | 18.4 | 28.5 | 977.5 | 978.5 | >99 |

TABLE 9-continued

Analytical Data for Peptides Synthesized in this Study.[a]

| Peptide | Sequence | Retention Time (min) system 1 | Retention Time (min) system 2 | M (calc) | mass spectral analysis (M + 1) | purity % |
|---|---|---|---|---|---|---|
| MDE3-119-5c | c[Pro-Arg-Phe-Phe-**Glu**-Ala-Phe-DPro] (SEQ ID NO: 9) | 18.3 | 28.1 | 991.5 | 992.2 | >99 |
| MDE3-119-7c | c[Pro-Arg-Phe-Phe-**DDap**-Ala-Phe-DPro] (SEQ ID NO: 10) | 18.1 | 29.4 | 948.5 | 949.4 | >95 |
| MDE3-119-8c | c[Pro-Arg-Phe-Phe-**Dap**-Ala-Phe-DPro] (SEQ ID NO: 2) | 18.0 | 29.3 | 948.5 | 949.4 | >98 |
| MDE3-119-10c | c[Pro-Arg-Phe-Phe-**Val**-Ala-Phe-DPro] (SEQ ID NO: 14) | 20.4 | 30.8 | 961.5 | 962.2 | >99 |
| MDE3-119-13c | c[Pro-Arg-Phe-Phe-**His**-Ala-Phe-DPro] (SEQ ID NO: 11) | 18.0 | 29.1 | 999.5 | 1000.2 | >96 |
| MDE3-119-14c | c[Pro-Arg-Phe-Phe-**Phe**-Ala-Phe-DPro] (SEQ ID NO: 15) | 21.6 | 31.6 | 1009.5 | 1010.3 | >98 |

[a]Peptide retention times (min) are reported for solvent system 1 (10% acetonitrile in 0.1% trifluoroacetic acid/water and a gradient to 90% acetonitrile over 35 min) and solvent system 2 (10% methanol in 0.1% trifluoroacetic acid/water and a gradient to 90% methanol over 35 min). An analytical Vydac C18 column (Vydac 218TP104) was used with a flow rate of 1.5 mL/min. The peptide purity was determined by HPLC at a wavelength of 214 nm.

TABLE 10

Peptide Antagonist Pharmacology, Inverse Agonist Activity, and Binding Affinity at the Human Melanocortin-4 Receptor.[a]

| | | hMC4R | | | |
|---|---|---|---|---|---|
| Peptide | Sequence | Antagonist $pA_2$ | Inverse Agonist $EC_{50}$ (nM) | $^{125}$I-NDP-MSH $IC_{50}$ (nM) | $^{125}$I-AGRP $IC_{50}$ (nM) |
| hAGRP(86-132) | | 8.8 ± 0.2 | 2.4 ± 0.5 (-35%) | 11 ± 1[b] | 12 ± 1 |
| MDE3-119-8c | c[Pro-Arg-Phe-Phe-**Dap**-Ala-Phe-DPro] (SEQ ID NO: 2) | 8.81 ± 0.02 | 3.4 ± 1.9 (-50%) | 26 ± 1 | 11 ± 1 |
| MDE3-119-7c | c[Pro-Arg-Phe-Phe-**DDap**-Ala-Phe-DPro] (SEQ ID NO: 10) | 8.60 ± 0.04 | 4 ± 2 (-30%) | 16 ± 1 | 11 ± 4 |
| MDE3-119-13c | c[Pro-Arg-Phe-Phe-**His**-Ala-Phe-DPro] (SEQ ID NO: 11) | 8.35 ± 0.09 | 8 ± 6 (-30%) | 120 ± 50 | 44 ± 7 |
| MDE5-108-10c | c[Pro-Arg-Phe-Phe-**Asn**-Ala-Phe-DPro] (SEQ ID NO: 1) | 8.3 ± 0.2 | 14 ± 3 (-30%) | 200 ± 30 | 78 ± 6 |
| MDE3-85c | c[Pro-Arg-Phe-Phe-**Ser**-Ala-Phe-DPro] (SEQ ID NO: 6) | 7.97 ± 0.05 | 16 ± 4 (-25%) | 260 ± 90 | 110 ± 20 |
| MDE3-154c | c[Pro-Arg-Phe-Phe-**Ala**-Ala-Phe-DPro] (SEQ ID NO: 4) | 7.73 ± 0.07 | 50 ± 20 (-35%) | 340 ± 40 | 120 ± 10 |
| MDE3-119-2c | c[Pro-Arg-Phe-Phe-**Abu**-Ala-Phe-DPro] (SEQ ID NO: 5) | 7.54 ± 0.06 | 22 ± 8 (-15%) | 600 ± 200 | 190 ± 20 |
| MDE3-119-5c | c[Pro-Arg-Phe-Phe-**Glu**-Ala-Phe-DPro] (SEQ ID NO: 9) | 6.96 ± 0.09 | 1,100 ± 800 (-35%) | 2,500 ± 900 | 1,400 ± 200 |

TABLE 10-continued

Peptide Antagonist Pharmacology, Inverse Agonist Activity, and Binding Affinity at the Human Melanocortin-4 Receptor.[a]

| | | hMC4R | | | |
|---|---|---|---|---|---|
| Peptide | Sequence | Antagonist $pA_2$ | Inverse Agonist $EC_{50}$ (nM) | $^{125}$I-NDP-MSH $IC_{50}$ (nM) | $^{125}$I-AGRP $IC_{50}$ (nM) |
| MDE3-119-14c | c[Pro-Arg-Phe-Phe-**Phe**-Ala-Phe-DPro] (SEQ ID NO: 15) | 6.9 ± 0.2 | none | 320 ± 50 | 115 ± 5 |
| MDE3-119-4c | c[Pro-Arg-Phe-Phe-**Asp**-Ala-Phe-DPro] (SEQ ID NO: 8) | 6.85 ± 0.09 | 2,000 ± 1,000 (-35%) | 3,600 ± 1,300 | 1,300 ± 100 |
| MDE3-119-10c | c[Pro-Arg-Phe-Phe-**Val**-Ala-Phe-DPro] (SEQ ID NO: 14) | 6.32 ± 0.06 | none | 5,400 ± 1,500 | 2,400 ± 600 |

[a]The indicated errors represent the standard error of the mean determined from at least two (binding) or three (antagonist/inverse agonist pharmacology) independent experiments. The antagonistic $pA_2$ values were determined using the Schild analysis and the agonist NDP-MSH. None indicates that no inverse agonist activity was observed. A percent for inverse agonist activity indicates the decrease from basal signal for the ligand.
[b]The displacement of $^{125}$I-NDP-MSH by AGRP(87-132) was previously reported by Jackson et al.[69]

All publications, patents, and patent documents are incorporated by reference herein, as though individually incorporated by reference, including the following documents and any associated supplementary materials: Ericson et al., J. Med. Chem., 2017, 60 (19), pp 8103-8114; Ericson et al., "Arg-Phe-Phe D-Amino Acid Stereochemistry Scan in the Macrocyclic Agouti-Related Protein Antagonist Scaffold c[Pro-Arg-Phe-Phe-Xaa-Ala-Phe-DPro] (SEQ ID NO:137) Results in Unanticipated Melanocortin-1 Receptor Agonist Profiles" ACS Chem Neurosci. 2018 Jul. 20. doi: 10.1021/acschemneuro.8b00218; Fleming et al., ACS Chem. Neurosci., 2018, 9 (5), pp 1141-1151; and Fleming et al., "Synergistic Multi-Residue Substitutions of a Macrocyclic c[Pro-Arg-Phe-Phe-Asn-Ala-Phe-DPro] (SEQ ID NO: 1) Agouti-Related Protein (AGRP) Scaffold Yield Potent and >600-Fold MC4R versus MC3R Selective Melanocortin Receptor Antagonists", J. Med. Chem., DOI: 10.1021/acs.jmedchem.8b00684, Jul. 23, 2018. The invention has been described with reference to various specific and preferred embodiments and techniques. However, it should be understood that many variations and modifications may be made while remaining within the spirit and scope of the invention.

What is claimed is:

1. A cyclic compound of formula I:

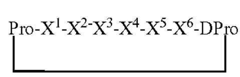

I wherein:

Pro is a residue of L-proline;

$X^1$ is a residue of Arg;

$X^2$ is a residue of Phe;

$X^3$ is a residue of Phe, or hPhe;

$X^4$ is a residue of Asn, Dap, Ala, Abu, Ser, Thr, Glu, DDap, His, Leu, Val, Trp or Arg;

$X^5$ is a residue of Ala, or Ser;

$X^6$ is a residue of Phe, Ala, Nle, Trp, Cha or hPhe; and

DPro is a residue of D-proline;

or a salt thereof, provided the compound of formula I is not c[Pro-Arg-Phe-Phe-Asn-Ala-Phe-DPro] (SEQ ID NO:1), c[Pro- Arg-Phe-Phe-Dap-Ala-Phe-DPro] (SEQ ID NO:2), c[Pro-Arg-Phe-hPhe-Asn-Ala-Phe-DPro] (SEQ ID NO:3) or c[Pro-Arg-Phe-Phe-Arg-Ala-Phe-DPro] (SEQ ID NO:54).

2. The compound of claim 1, wherein $X^6$ is a residue of Ala, Nle, Trp, Cha, or hPhe; and/or $X^5$ is a residue of Ser.

3. The compound of claim 1, wherein $X^6$ is a residue of Nle.

4. The compound of claim 1, wherein $X^5$ is a residue of Ser.

5. The compound of claim 1, wherein $X^5$ is a residue of Ser; and $X^6$ is a residue of Nle.

6. The compound of claim 1, wherein $X^5$ is a residue of Ala; and $X^6$ is a residue of Nle.

7. The compound of claim 1, wherein $X^6$ is a residue of Trp.

8. The compound of claim 1, wherein $X^1$ is a residue of Arg; $X^2$ is a residue of Phe; $X^3$ is a residue of Phe; $X^4$ is a residue of Thr or His; $X^5$ is a residue of Ala; and $X^6$ is a residue of Phe.

9. The compound of claim 1, which is selected from the group consisting of:

```
(SEQ ID NO: 4)
c[Pro-Arg-Phe-Phe-Ala-Ala-Phe-DPro]

(SEQ ID NO: 5)
c[Pro-Arg-Phe-Phe-Abu-Ala-Phe-DPro]

(SEQ ID NO: 6)
c[Pro-Arg-Phe-Phe-Ser-Ala-Phe-DPro]

(SEQ ID NO: 7)
c[Pro-Arg-Phe-Phe-Thr-Ala-Phe-DPro]

(SEQ ID NO: 9)
c[Pro-Arg-Phe-Phe-Glu-Ala-Phe-DPro]

(SEQ ID NO: 10)
c[Pro-Arg-Phe-Phe-DDap-Ala-Phe-DPro]

(SEQ ID NO: 11)
c[Pro-Arg-Phe-Phe-His-Ala-Phe-DPro]

(SEQ ID NO: 13)
c[Pro-Arg-Phe-Phe-Leu-Ala-Phe-DPro]

(SEQ ID NO: 14)
c[Pro-Arg-Phe-Phe-Val-Ala-Phe-DPro]

(SEQ ID NO: 16)
c[Pro-Arg-Phe-Phe-Trp-Ala-Phe-DPro]

(SEQ ID NO: 22)
c[Pro-Arg-Phe-Phe-Asn-Ser-Phe-DPro]

(SEQ ID NO: 25)
c[Pro-Arg-Phe-Phe-Asn-Ala-Ala-DPro]

(SEQ ID NO: 45)
c[Pro-Arg-Phe-Phe-Asn-Ala-Nle-DPro]

(SEQ ID NO: 46)
c[Pro-Arg-Phe-Phe-Asn-Ala-Trp-DPro]

(SEQ ID NO: 48)
c[Pro-Arg-Phe-Phe-Asn-Ala-Cha-DPro]

(SEQ ID NO: 49)
c[Pro-Arg-Phe-Phe-Asn-Ala-hPhe-DPro]

(SEQ ID NO: 50)
c[Pro-Arg-Phe-Phe-Asn-Ser-Nle-DPro]
```

-continued

```
(SEQ ID NO: 51)
c[Pro-Arg-Phe-Phe-Dap-Ala-Nle-DPro]

(SEQ ID NO: 52)
c[Pro-Arg-Phe-Phe-Dap-Ser-Phe-DPro]

(SEQ ID NO: 53)
c[Pro-Arg-Phe-Phe-Dap-Ser-Nle-DPro]

(SEQ ID NO: 55)
c[Pro-Arg-Phe-Phe-Arg-Ala-Nle-DPro]

(SEQ ID NO: 56)
c[Pro-Arg-Phe-Phe-Arg-Ser-Phe-DPro]

(SEQ ID NO: 57)
c[Pro-Arg-Phe-Phe-Arg-Ser-Nle-DPro]

(SEQ ID NO: 58)
c[Pro-Arg-Phe-hPhe-Asn-Ala-Nle-DPro]

(SEQ ID NO: 59)
c[Pro-Arg-Phe-hPhe-Asn-Ser-Phe-DPro]

(SEQ ID NO: 60)
c[Pro-Arg-Phe-hPhe-Asn-Ser-Nle-DPro]

(SEQ ID NO: 61)
c[Pro-Arg-Phe-hPhe-Dap-Ala-Phe-DPro]

(SEQ ID NO: 62)
c[Pro-Arg-Phe-hPhe-Dap-Ala-Nle-DPro]

(SEQ ID NO: 63)
c[Pro-Arg-Phe-hPhe-Dap-Ser-Phe-DPro]

(SEQ ID NO: 64)
c[Pro-Arg-Phe-hPhe-Dap-Ser-Nle-DPro]

(SEQ ID NO: 65)
c[Pro-Arg-Phe-hPhe-Arg-Ala-Phe-DPro]

(SEQ ID NO: 66)
c[Pro-Arg-Phe-hPhe-Arg-Ala-Nle-DPro]

(SEQ ID NO: 67)
c[Pro-Arg-Phe-hPhe-Arg-Ser-Phe-DPro]

(SEQ ID NO: 68)
c[Pro-Arg-Phe-hPhe-Arg-Ser-Nle-DPro]
```

and salts thereof.

10. The compound of claim 1, which is selected from the group consisting of:

```
(SEQ ID NO: 10)
c[Pro-Arg-Phe-Phe-DDap-Ala-Phe-DPro]

(SEQ ID NO: 6)
c[Pro-Arg-Phe-Phe-Ser-Ala-Phe-DPro]

(SEQ ID NO: 5)
c[Pro-Arg-Phe-Phe-Abu-Ala-Phe-DPro]

(SEQ ID NO: 14)
c[Pro-Arg-Phe-Phe-Val-Ala-Phe-DPro]
```

and salts thereof.

11. The compound of claim 1, which is:

```
(SEQ ID NO: 4)
c[Pro-Arg-Phe-Phe-Ala-Ala-Phe-DPro]

(SEQ ID NO: 5)
c[Pro-Arg-Phe-Phe-Abu-Ala-Phe-DPro]
```

-continued (SEQ ID NO: 6)
c[Pro-Arg-Phe-Phe-Ser-Ala-Phe-DPro]

(SEQ ID NO: 7)
c[Pro-Arg-Phe-Phe-Thr-Ala-Phe-DPro]

(SEQ ID NO: 9)
c[Pro-Arg-Phe-Phe-Glu-Ala-Phe-DPro]

(SEQ ID NO: 10)
c[Pro-Arg-Phe-Phe-DDap-Ala-Phe-DPro]

(SEQ ID NO: 11)
c[Pro-Arg-Phe-Phe-His-Ala-Phe-DPro]

(SEQ ID NO: 13)
c[Pro-Arg-Phe-Phe-Leu-Ala-Phe-DPro]

(SEQ ID NO: 14)
c[Pro-Arg-Phe-Phe-Val-Ala-Phe-DPro]

(SEQ ID NO: 16)
c[Pro-Arg-Phe-Phe-Trp-Ala-Phe-DPro]

(SEQ ID NO: 22)
c[Pro-Arg-Phe-Phe-Asn-Ser-Phe-DPro]

(SEQ ID NO: 45)
c[Pro-Arg-Phe-Phe-Asn-Ala-Nle-DPro]

(SEQ ID NO: 46)
c[Pro-Arg-Phe-Phe-Asn-Ala-Trp-DPro]

(SEQ ID NO: 48)
c[Pro-Arg-Phe-Phe-Asn-Ala-Cha-DPro]

(SEQ ID NO: 49)
c[Pro-Arg-Phe-Phe-Asn-Ala-hPhe-DPro]

or a salt thereof.

12. The compound of claim 1, which is:

(SEQ ID NO: 7)
c[Pro-Arg-Phe-Phe-Thr-Ala-Phe-DPro]

(SEQ ID NO: 11)
c[Pro-Arg-Phe-Phe-His-Ala-Phe-DPro]

(SEQ ID NO: 22)
c[Pro-Arg-Phe-Phe-Asn-Ser-Phe-DPro]

(SEQ ID NO: 45)
c[Pro-Arg-Phe-Phe-Asn-Ala-Nle-DPro]

(SEQ ID NO: 46)
c[Pro-Arg-Phe-Phe-Asn-Ala-Trp-DPro]

or a salt thereof.

13. The compound of claim 1, which is:

(SEQ ID NO: 22)
c[Pro-Arg-Phe-Phe-Asn-Ser-Phe-DPro]

(SEQ ID NO: 25)
c[Pro-Arg-Phe-Phe-Asn-Ala-Ala-DPro]

(SEQ ID NO: 45)
c[Pro-Arg-Phe-Phe-Asn-Ala-Nle-DPro]

(SEQ ID NO: 52)
c[Pro-Arg-Phe-Phe-Dap-Ser-Phe-DPro]

(SEQ ID NO: 53)
c[Pro-Arg-Phe-Phe-Dap-Ser-Nle-DPro]

-continued (SEQ ID NO: 57)
c[Pro-Arg-Phe-Phe-Arg-Ser-Nle-DPro]

(SEQ ID NO: 58)
c[Pro-Arg-Phe-hPhe-Asn-Ala-Nle-DPro]

(SEQ ID NO: 59)
c[Pro-Arg-Phe-hPhe-Asn-Ser-Phe-DPro]

(SEQ ID NO: 60)
c[Pro-Arg-Phe-hPhe-Asn-Ser-Nle-DPro]

(SEQ ID NO: 61)
c[Pro-Arg-Phe-hPhe-Dap-Ala-Phe-DPro]

(SEQ ID NO: 62)
c[Pro-Arg-Phe-hPhe-Dap-Ala-Nle-DPro]

(SEQ ID NO: 63)
c[Pro-Arg-Phe-hPhe-Dap-Ser-Phe-DPro]

(SEQ ID NO: 64)
c[Pro-Arg-Phe-hPhe-Dap-Ser-Nle-DPro]

or a salt thereof.

14. The compound of claim 1, which is:

(SEQ ID NO: 53)
c[Pro-Arg-Phe-Phe-Dap-Ser-Nle-DPro]

(SEQ ID NO: 57)
c[Pro-Arg-Phe-Phe-Arg-Ser-Nle-DPro]

(SEQ ID NO: 60)
c[Pro-Arg-Phe-hPhe-Asn-Ser-Nle-DPro]

(SEQ ID NO: 64)
c[Pro-Arg-Phe-hPhe-Dap-Ser-Nle-DPro]

or a salt thereof.

15. The compound of claim 1, which is:

(SEQ ID NO:11)
c[Pro-Arg-Phe-Phe-His-Ala-Phe-DPro]

or a salt thereof.

16. A pharmaceutical composition comprising a compound of formula I as described in claim 1, or a pharmaceutically acceptable salt thereof, and a pharmaceutically acceptable carrier.

17. The compound of claim 1, wherein $X^6$ is a residue of Ala, Nle, Trp, Cha, or hPhe.

18. The compound of claim 1, wherein $X^4$ is a residue of Ala, Abu, Ser, Thr, Glu, DDap, His, Leu, Val, Trp or Arg.

19. The compound of claim 1, which is:

(SEQ ID NO: 22)
c[Pro-Arg-Phe-Phe-Asn-Ser-Phe-DPro]

(SEQ ID NO: 25)
c[Pro-Arg-Phe-Phe-Asn-Ala-Ala-DPro]

(SEQ ID NO: 45)
c[Pro-Arg-Phe-Phe-Asn-Ala-Nle-DPro]

(SEQ ID NO: 46)
c[Pro-Arg-Phe-Phe-Asn-Ala-Trp-DPro]

(SEQ ID NO: 48)
c[Pro-Arg-Phe-Phe-Asn-Ala-Cha-DPro]

(SEQ ID NO: 49)
c[Pro-Arg-Phe-Phe-Asn-Ala-hPhe-DPro]

-continued (SEQ ID NO: 52)
c[Pro-Arg-Phe-Phe-Dap-Ser-Phe-DPro]

(SEQ ID NO: 53)
c[Pro-Arg-Phe-Phe-Dap-Ser-Nle-DPro]

(SEQ ID NO: 57)
c[Pro-Arg-Phe-Phe-Arg-Ser-Nle-DPro]

(SEQ ID NO: 58)
c[Pro-Arg-Phe-hPhe-Asn-Ala-Nle-DPro]

(SEQ ID NO: 59)
c[Pro-Arg-Phe-hPhe-Asn-Ser-Phe-DPro]

(SEQ ID NO: 60)
c[Pro-Arg-Phe-hPhe-Asn-Ser-Nle-DPro]

(SEQ ID NO: 62)
c[Pro-Arg-Phe-hPhe-Dap-Ala-Nle-DPro]

(SEQ ID NO: 63)
c[Pro-Arg-Phe-hPhe-Dap-Ser-Phe-DPro]

(SEQ ID NO: 64)
c[Pro-Arg-Phe-hPhe-Dap-Ser-Nle-DPro]

or a salt thereof.

20. The compound of claim 1, which is c[Pro-Arg-Phe-hPhe-Dap-Ala-Phe-DPro] (SEQ ID NO:61), or a salt thereof.

21. The compound of claim 1, which is:

(SEQ ID NO: 4)
c[Pro-Arg-Phe-Phe-Ala-Ala-Phe-DPro]

(SEQ ID NO: 5)
c[Pro-Arg-Phe-Phe-Abu-Ala-Phe-DPro]

(SEQ ID NO: 6)
c[Pro-Arg-Phe-Phe-Ser-Ala-Phe-DPro]

(SEQ ID NO: 7)
c[Pro-Arg-Phe-Phe-Thr-Ala-Phe-DPro]

(SEQ ID NO: 9)
c[Pro-Arg-Phe-Phe-Glu-Ala-Phe-DPro]

(SEQ ID NO: 10)
c[Pro-Arg-Phe-Phe-DDap-Ala-Phe-DPro]

(SEQ ID NO: 11)
c[Pro-Arg-Phe-Phe-His-Ala-Phe-DPro]

(SEQ ID NO: 13)
c[Pro-Arg-Phe-Phe-Leu-Ala-Phe-DPro]

(SEQ ID NO: 14)
c[Pro-Arg-Phe-Phe-Val-Ala-Phe-DPro]

(SEQ ID NO: 16)
c[Pro-Arg-Phe-Phe-Trp-Ala-Phe-DPro]

or a salt thereof.

* * * * *